US006921762B2

(12) United States Patent
Cai et al.

(10) Patent No.: US 6,921,762 B2
(45) Date of Patent: Jul. 26, 2005

(54) SUBSTITUTED INDOLIZINE-LIKE COMPOUNDS AND METHODS OF USE

(75) Inventors: Guolin Cai, Thousand Oaks, CA (US); Jennifer N. Chau, Santa Ana, CA (US); Celia Dominguez, Thousand Oaks, CA (US); Yuelie Lu, Thousand Oaks, CA (US); Gilbert M. Rishton, Malibu, CA (US)

(73) Assignee: Amgen Inc., Thousand Oaks, CA (US)

( * ) Notice: Subject to any disclaimer, the term of this patent is extended or adjusted under 35 U.S.C. 154(b) by 141 days.

(21) Appl. No.: 10/298,205

(22) Filed: Nov. 15, 2002

(65) Prior Publication Data

US 2003/0195221 A1 Oct. 16, 2003

Related U.S. Application Data

(60) Provisional application No. 60/332,447, filed on Nov. 16, 2001.

(51) Int. Cl.[7] .................... C07D 487/04; C07D 471/04; A61K 31/4188
(52) U.S. Cl. ............... 514/249; 514/252.16; 514/259.1; 514/259.5; 544/263; 544/281
(58) Field of Search ................................ 544/263, 281; 514/249, 252.16, 259.1, 259.5

(56) References Cited

U.S. PATENT DOCUMENTS

| | | | | |
|---|---|---|---|---|
| 5,229,519 A | 7/1993 | Zhang et al. | ................ | 546/250 |
| 5,624,935 A | 4/1997 | Fujita et al. | ................ | 514/303 |
| 5,714,495 A | 2/1998 | Viaud et al. | ................ | 514/300 |
| 6,096,753 A | 8/2000 | Spohr et al. | ................ | 514/269 |

FOREIGN PATENT DOCUMENTS

| | | |
|---|---|---|
| EP | 039 051 | 11/1881 |
| GB | 2306108 | 4/1997 |
| WO | WO 96/03387 | 2/1996 |
| WO | WO 97/16442 | 5/1997 |
| WO | WO 98/24780 | 6/1998 |
| WO | WO 98/24782 | 6/1998 |
| WO | WO 00/64065 | 10/2000 |
| WO | WO 01/00208 | 1/2001 |
| WO | WO 01/34603 | 5/2001 |
| WO | WO 01/34605 | 5/2001 |
| WO | WO 01/42241 | 6/2001 |

OTHER PUBLICATIONS

Damasio, Alzheimer's Disease and Related Dementias, Cecil Textbook of Medicine, 20th Edition, vol. 2, pp. 1992–1996, 1996.*

Freston, PubMed Abstract (Am J Med 107(6A):78S–88S; discussion 89S), Dec. 1999.*

Naesdal et al., PubMed Abstract (Eur J Gastroenterol Hepatol. 13(12):1401–6), Dec. 2001.*

Casanova et al., PubMed Abstract (Rev Neurol. 28(9):909–15), May 1999.*

* cited by examiner

*Primary Examiner*—Deepak Rao
(74) *Attorney, Agent, or Firm*—Richard V. Person

(57) ABSTRACT

Selected novel substituted indolizine-like compounds are effective for treatment of diseases, such as TNF-α, IL-1β, IL-6 and/or IL-8 mediated diseases, and other maladies, such as cancer, pain and diabetes. The invention encompasses novel compounds, analogs, prodrugs and pharmaceutically acceptable salts thereof, pharmaceutical compositions and methods for treatment of diseases and other maladies or conditions involving inflammation, cancer, pain, diabetes and the like. The subject invention also relates to processes for making such compounds as well as to intermediates useful in such processes.

21 Claims, No Drawings

SUBSTITUTED INDOLIZINE-LIKE COMPOUNDS AND METHODS OF USE

This application claims the benefit of U.S. Provisional Application No. 60/332,447, filed Nov. 16, 2001, which is hereby incorporated by reference.

BACKGROUND OF THE INVENTION

The present invention comprises a new class of substituted indolizine-like compounds useful in treating diseases, such as TNF-α, IL-1β, IL-6 and/or IL-8 mediated diseases and other maladies, such as pain, cancer, and diabetes. In particular, the compounds of the invention are useful for the treatment of diseases or conditions involving inflammation. This invention also relates to intermediates and processes useful in the preparation of such compounds.

Interleukin-1 (IL-1) and Tumor Necrosis Factor α (TNF-α) are pro-inflammatory cytokines secreted by a variety of cells, including monocytes and macrophages, in response to many inflammatory stimuli (e.g., lipopolysaccharide—LPS) or external cellular stress (e.g., osmotic shock and peroxide).

Elevated levels of TNF-α and/or IL-1 over basal levels have been implicated in mediating or exacerbating a number of disease states including rheumatoid arthritis; Pagets disease; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster are also exacerbated by TNF-α.

It has been reported that TNF-α plays a role in head trauma, stroke, and ischemia. For instance, in animal models of head trauma (rat), TNF-α levels increased in the contused hemisphere (Shohami et al., *J. Cereb. Blood Flow Metab.* 14, 615 (1994)). In a rat model of ischemia wherein the middle cerebral artery was occluded, the levels of TNF-α mRNA of TNF-α increased (Feurstein et al., *Neurosci. Lett.* 164, 125 (1993)). Administration of TNF-α into the rat cortex has been reported to result in significant neutrophil accumulation in capillaries and adherence in small blood vessels. TNF-α promotes the infiltration of other cytokines (IL-1β, IL-6) and also chemokines, which promote neutrophil infiltration into the infarct area (Feurstein, *Stroke* 25, 1481 (1994)). TNF-α has also been implicated to play a role in type II diabetes (Endocrinol. 130, 43–52, 1994; and Endocrinol. 136, 1474–1481, 1995).

TNF-α appears to play a role in promoting certain viral life cycles and disease states associated with them. For instance, TNF-α secreted by monocytes induced elevated levels of HIV expression in a chronically infected T cell clone (Clouse et al., *J. Immunol.* 142, 431 (1989)). Lahdevirta et al., (*Am. J. Med.* 85, 289 (1988)) discussed the role of TNF-α in the HIV associated states of cachexia and muscle degradation.

TNF-α is upstream in the cytokine cascade of inflammation. As a result, elevated levels of TNF-α may lead to elevated levels of other inflammatory and pro-inflamatory cytokines, such as IL-1, IL-6, and IL-8.

Elevated levels of IL-1 over basal levels have been implicated in mediating or exacerbating a number of disease states including rheumatoid arthritis; osteoarthritis; rheumatoid spondylitis; gouty arthritis; inflammatory bowel disease; adult respiratory distress syndrome (ARDS); psoriasis; Crohn's disease; ulcerative colitis; anaphylaxis; muscle degeneration; cachexia; Reiter's syndrome; type I and type II diabetes; bone resorption diseases; ischemia reperfusion injury; atherosclerosis; brain trauma; multiple sclerosis; sepsis; septic shock; and toxic shock syndrome. Viruses sensitive to TNF-α inhibition, e.g., HIV-1, HIV-2, HIV-3, are also affected by IL-1.

TNF-α and IL-1 appear to play a role in pancreatic β cell destruction and diabetes. Pancreatic β cells produce insulin which helps mediate blood glucose homeostasis. Deterioration of pancreatic β cells often accompanies type I diabetes. Pancreatic β cell functional abnormalities may occur in patients with type II diabetes. Type II diabetes is characterized by a functional resistance to insulin. Further, type II diabetes is also often accompanied by elevated levels of plasma glucagon and increased rates of hepatic glucose production. Glucagon is a regulatory hormone that attenuates liver gluconeogenesis inhibition by insulin. Glucagon receptors have been found in the liver, kidney and adipose tissue. Thus glucagon antagonists are useful for attenuating plasma glucose levels (WO 97/16442, incorporated herein by reference in its entirety). By antagonizing the glucagon receptors, it is thought that insulin responsiveness in the liver will improve, thereby decreasing gluconeogenesis and lowering the rate of hepatic glucose production.

In rheumatoid arthritis models in animals, multiple intra-articular injections of IL-1 have led to an acute and destructive form of arthritis (Chandrasekhar et al., *Clinical Immunol Immunopathol.* 55, 382 (1990)). In studies using cultured rheumatoid synovial cells, IL-1 is a more potent inducer of stromelysin than is TNF-α (Firestein, *Am. J. Pathol.* 140, 1309 (1992)). At sites of local injection, neutrophil, lymphocyte, and monocyte emigration has been observed. The emigration is attributed to the induction of chemokines (e.g., IL-8), and the up-regulation of adhesion molecules (Dinarello, *Eur. Cytokine Netw.* 5, 517–531 (1994)).

IL-1 also appears to play a role in promoting certain viral life cycles. For example, cytokine-induced increase of HIV expression in a chronically infected macrophage line has been associated with a concomitant and selective increase in IL-1 production (Folks et al., *J. Immunol.* 136, 40 (1986)). Beutler et al. (*J. Immunol.* 135, 3969 (1985)) discussed the role of IL-1 in cachexia. Baracos et al. (*New Eng. J. Med.* 308, 553 (1983)) discussed the role of IL-1 in muscle degeneration.

In rheumatoid arthritis, both IL-1 and TNF-α induce synoviocytes and chondrocytes to produce collagenase and neutral proteases, which leads to tissue destruction within the arthritic joints. In a model of arthritis (collagen-induced arthritis (CIA) in rats and mice), intra-articular administration of TNF-α either prior to or after the induction of CIA led to an accelerated onset of arthritis and a more severe course of the disease (Brahn et al., *Lymphokine Cytokine Res.* 11, 253 (1992); and Cooper, *Clin. Exp. Immunol.* 898, 244 (1992)).

IL-8 has been implicated in exacerbating and/or causing many disease states in which massive neutrophil infiltration into sites of inflammation or injury (e.g., ischemia) is mediated by the chemotactic nature of IL-8, including, but not limited to, the following: asthma, inflammatory bowel disease, psoriasis, adult respiratory distress syndrome, cardiac and renal reperfusion injury, thrombosis and glomerulonephritis. In addition to the chemotaxis effect on neutrophils, IL-8 also has the ability to activate neutrophils. Thus, reduction in IL-8 levels may lead to diminished neutrophil infiltration.

Several approaches have been taken to block the effect of TNF-α. One approach involves using soluble receptors for TNF-α (e.g., TNFR-55 or TNFR-75), which have demonstrated efficacy in animal models of TNF-α-mediated disease states. A second approach to neutralizing TNF-α using a monoclonal antibody specific to TNF-α, cA2, has demonstrated improvement in swollen joint count in a Phase II human trial of rheumatoid arthritis (Feldmann et al., *Immunological Reviews*, pp. 195–223 (1995)). These approaches block the effects of TNF-α and IL-1 by either protein sequestration or receptor antagonism.

GB 2,306,108, which is incorporated herein by reference in its entirety, describes imidazole derivatives which are Raf kinase antagonists useful in the treatment of cancer which is mediated by Raf and Raf-inducible proteins. Raf proteins are kinases activated in response to extracellular mitogenic stimuli such as PDGF, EGF, acidic FGF, thrombin, insulin or endothelin, and also in response to oncoproteins such as v-src, v-sis, and v-fms. Raf functions downstream of ras in signal transduction from the cellular membrane to the nucleus. Compounds may be oncolytics through the antagonism of Raf kinase. It has been reported that antisense constructs which reduce cellular levels of c-Raf and hence Raf activity inhibit the growth of rodent fibroblasts in soft agar, while exhibiting little or no general cytotoxicity. This inhibition of growth in soft agar is highly predictive of tumor responsiveness in whole animals. Moreover, Raf antisense constructs have shown efficacy in reducing tumor burden in animals. Examples of cancers where Raf kinase is implicated by overexpression include cancers of the brain, larynx, lung, lymphatic system, urinary tract and stomach, including hystocytic lymphoma, lung adenocarcinoma and small cell lung cancers. Other examples include cancers involving overexpression of upstream activators of Raf or Raf-activating oncogenes, including pancreatic and breast carcinoma.

U.S. Pat. No. 5,714,495 describes compounds of the formula

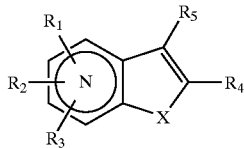

wherein X, $R_1$, $R_2$, $R_3$, $R_4$ and $R_5$ are as defined therein, useful as melatonin receptor ligands.

U.S. Pat. No. 5,624,935 describes compounds of the formula

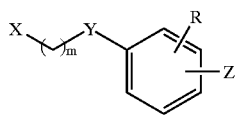

wherein X may represent among other things optionally substituted imidazo[1,2-a]pyridine and m, R, Y and Z are as defined therein, having hypoglycemic and anti-diabetic activities.

WO 01/34603 describes compounds of the formula

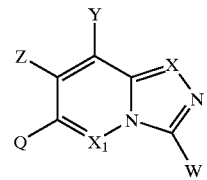

wherein Q, W, X, $X_1$, Y and Z are as defined therein, that bind to the benzodiazepine site of GABA$_A$ receptors.

WO 01/34605 describes substituted 2-aryl-3-(heteroaryl)-imidazo[1,2-a]pyrimidine compounds useful in the inhibition of the production of inflammatory cytokines, particularly TNF-α and IL-1β, and in the treatment of diseases mediated by p38, such as inflammation and the like.

WO 00/31065, which is incorporated herein by reference in its entirety, describes substituted heterocyclic compounds useful in the inhibition of the production of cytokines, such as TNF, IL-1, IL-6 and/or IL-8.

WO 01/00208, which is incorporated herein by reference in its entirety, describes substituted pyridone compounds useful in the inhibition of the production of cytokines, such as TNF, IL-1, IL-6 and/or IL-8.

WO 01/42241, which is incorporated herein by reference in its entirety, describes substituted pyridazine compounds useful in the inhibition of the production of cytokines, such as TNF, IL-1, IL-6 and/or IL-8.

U.S. Pat. No. 6,096,753, which is incorporated herein by reference in its entirety, describes substituted pyrimidinone and pyridone compounds and compositions useful for the prophylaxis and treatment of diseases, such as TNF-α, IL-1β, IL-6 and/or IL-8 mediated diseases, and other maladies, such as pain and diabetes, and processes of making such compounds.

BRIEF DESCRIPTION OF THE INVENTION

The present invention comprises a new class of compounds useful in the treatment of diseases, such as TNF-α, IL-1β, IL-6 and/or IL-8 mediated diseases and other maladies, such as pain, cancer and diabetes. In particular, the compounds of the invention are useful for the treatment of diseases or conditions involving inflammation. Accordingly, the invention also comprises pharmaceutical compositions comprising the compounds, methods for the treatment of TNF-α, IL-1β, IL-6 and/or IL-8 mediated diseases, such as inflammatory, pain and diabetes diseases, using the compounds and compositions of the invention, and intermediates and processes useful for the preparation of the compounds of the invention.

The compounds of the invention are represented by the following general structure

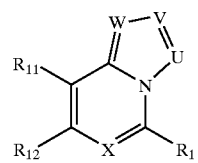

or a pharmaceutically acceptable salt thereof, wherein U, V, W, X, $R_1$, $R_{11}$ and $R_{12}$ are defined below.

The foregoing merely summarizes certain aspects of the invention and is not intended, nor should it be construed, as limiting the invention in any way. All patents, patent applications and other publications recited herein are hereby incorporated by reference in their entirety.

DETAILED DESCRIPTION OF THE INVENTION

In accordance with the present invention, there is provided compounds of formula

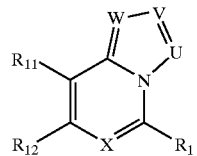

or a pharmaceutically acceptable salt thereof, wherein
X is C—$R_2$ or N;
U, V and W are each independently C—$R_6$ or N, provided when U is N then V is C—$R_6$;
wherein each $R_6$ is independently a hydrogen, halo, alkyl, alkoxy, alkylthio, haloalkyl, haloalkoxy, hydroxy or cyano radical; preferably, each $R_6$ is independently a hydrogen, halo, $C_1$–$C_4$ alkyl, $C_1$–$C_4$ alkoxy, $C_1$–$C_4$ alkylthio, $C_1$–$C_4$ haloalkyl of 1–3 halo radicals, $C_1$–$C_4$ haloalkoxy of 1–3 halo radicals, hydroxy or cyano radical; more preferably, each $R_6$ is independently a hydrogen, $C_1$–$C_4$ alkyl, $C_1$–$C_4$ alkoxy, —$CF_3$, —$OCF_3$ or hydroxy radical; most preferably, each $R_6$ is independently a hydrogen, methyl, methoxy, —$CF_3$, —$OCF_3$ or hydroxy radical;
$R_1$ and $R_2$ are each independently -Z-Y or —Y; provided that the total number of aryl, heteroaryl, cycloalkyl and heterocyclyl radicals in $R_1$ and $R_2$ is 0–3; preferably, $R_1$ is -Z-Y or —Y; provided that the total number of aryl, heteroaryl, cycloalkyl and heterocyclyl radicals in $R_1$ is 0–3; and
preferably, $R_2$ is a radical of hydrogen, $C_1$–$C_4$ alkyl, halo, cyano, hydroxy, $C_1$–$C_4$ alkoxy, $C_1$–$C_2$ haloalkoxy of 1–3 halo radicals, $C_1$–$C_4$ alkylthio, amino, $C_1$–$C_4$ alkylamino, di-($C_1$–$C_4$ alkyl)amino or $C_1$–$C_2$ haloalkyl of 1–3 halo radicals; more preferably, $R_2$ is a radical of hydrogen, $C_1$–$C_4$ alkyl, halo, cyano, hydroxy, $C_1$–$C_4$ alkoxy, trifluoromethoxy or trifluoromethyl; more preferably, $R_2$ is a radical of hydrogen, $C_1$–$C_2$ alkyl, halo, cyano, hydroxy, $C_1$–$C_2$ alkoxy, trifluoromethoxy or trifluoromethyl; more preferably, $R_2$ is a radical of hydrogen, methyl, halo, cyano, hydroxy, methoxy, trifluoromethoxy or trifluoromethyl; most preferably, $R_2$ is a hydrogen radical;
each Z is independently a
(1) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–3 radicals of amino, alkylamino, dialkylamino, alkanoylamino, alkoxycarbonylamino, alkylsulfonylamino, hydroxy, alkoxy, alkylthio, alkyl, arylalkyl, heteroarylalkyl or haloalkyl; and the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;
preferably, each Z is independently a
(1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or $C_1$–$C_4$ haloalkyl of 1–3 halo radicals; and the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;
more preferably, each Z is independently a
(1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or $C_1$–$C_2$ haloalkyl of 1–3 halo radicals; and the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;
more preferably, each Z is independently a
(1) $C_1$–$C_4$ alkyl or $C_2$–$C_5$ alkenyl radical optionally substituted by (a) 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or trifluoromethyl radicals; and the aryl and heteroaryl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;
more preferably, each Z is independently a
(1) $C_1$–$C_4$ alkyl or $C_2$–$C_5$ alkenyl radical optionally substituted by (a) 1–3 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo, and (b) 1–2 radicals of heterocyclyl, aryl or heteroaryl; or
(2) heterocyclyl, aryl or heteroaryl radical;
wherein the heterocyclyl radicals are optionally substituted by 1–2 radicals of $C_1$–$C_4$ alkyl, aryl-$C_1$–$C_2$ alkyl or heteroaryl-$C_1$–$C_2$ alkyl; and wherein the aryl and heteroaryl radicals are optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl;

more preferably, each Z is independently a
(1) $C_1$–$C_4$ alkyl radical optionally substituted by (a) 1–2 radicals of amino, di-($C_1$–$C_2$ alkyl)amino, hydroxy, $C_1$–$C_2$ alkoxy or $C_1$–$C_2$ alkylthio, and (b) a heterocyclyl or aryl radical; or
(2) heterocyclyl radical optionally substituted by 1–2 radicals of $C_1$–$C_4$ alkyl, aryl-$C_1$–$C_2$ alkyl or heteroaryl-$C_1$–$C_2$ alkyl;
wherein the aryl and heteroaryl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl;
more preferably, each Z is independently a
(1) $C_1$–$C_4$ alkyl radical optionally substituted by (a) 1–2 radicals of amino, dimethylamino, hydroxy or methoxy, and (b) a heterocyclyl or phenyl radical; or
(2) heterocyclyl radical;
wherein the heterocyclyl radicals are optionally substituted by 1–2 radicals of $C_1$–$C_4$ alkyl or phenylmethyl; and wherein the phenyl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl;
alternatively more preferably, each Z is independently a (1) $C_1$–$C_4$ alkyl or $C_2$–$C_5$ alkenyl radical optionally substituted by (a) 1–2 radicals of amino, di-($C_1$–$C_2$ alkyl)amino, hydroxy or $C_1$–$C_2$ alkoxy, and (b) a radical of heterocyclyl, aryl or heteroaryl; or
(2) heterocyclyl, aryl or heteroaryl radical;
wherein the heterocyclyl radicals are optionally substituted by 1–2 radicals of amino, di-($C_1$–$C_2$ alkyl)amino, hydroxy, $C_1$–$C_2$ alkoxy, $C_1$–$C_4$ alkyl or trifluoromethyl radicals; and wherein the aryl and heteroaryl radicals are optionally substituted by 1–3 radicals of amino, di-($C_1$–$C_2$ alkyl)amino, acetamido, hydroxy, $C_1$–$C_2$ alkoxy, halo, $C_1$–$C_2$ alkyl or trifluoromethyl;
each Y is independently a
(1) hydrogen radical;
(2) halo or nitro radical;
(3) —C(O)—$R_{20}$, —C(O)—$OR_{21}$, —C(O)—$NR_5R_{21}$ or —C($NR_5$)—$NR_5R_{21}$ radical;
(4) —$OR_{21}$, —O—C(O)—$R_{21}$, —O—C(O)—$NR_5R_{21}$ or —O—C(O)—$NR_{22}$—S(O)$_2$—$R_{20}$ radical;
(5) —$SR_{21}$, —S(O)—$R_{20}$, —S(O)$_2$—$R_{20}$, —S(O)$_2$—$NR_5R_{21}$, —S(O)$_2$—$NR_{22}$—C(O)—$R_{21}$, —S(O)$_2$—$NR_{22}$—C(O)—$OR_{20}$ or —S(O)$_2$—$NR_{22}$—C(O)—$NR_5R_{21}$ radical; or
(6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;
preferably, each Y is independently a
(1) hydrogen or halo radical;
(2) —C(O)—$R_{20}$, —C(O)—$OR_{21}$, —C(O)—$NR_5R_{21}$ or —C($NR_5$)—$NR_5R_{21}$ radical;
(3) —$OR_{21}$, —O—C(O)—$R_{21}$ or —O—C(O)—$NR_5R_{21}$ radical;
(4) —$SR_{21}$, —S(O)—$R_{20}$, —S(O)$_2$—$R_{20}$ or —S(O)$_2$—$NR_5R_{21}$ radical; or
(5) —$NR_5R_{21}$, —$NR_{22}$—C(O)—$R_{21}$, —$NR_{22}$—C(O)—$OR_{20}$ or —$NR_{22}$—C(O)—$NR_5R_{21}$ radical;
more preferably, each Y is independently a
(1) hydrogen radical;
(2) —C(O)—$R_{20}$ or —C(O)—$NR_5R_{21}$ radical;
(3) —$OR_{21}$, —$SR_{21}$, —S(O)—$R_{20}$, —S(O)$_2$—$R_{20}$ or —S(O)$_2$—$NR_5R_{21}$ radical; or
(4) —$NR_5R_{21}$ or —$NR_{22}$—C(O)—$R_{21}$ radical;
more preferably, each Y is independently a hydrogen, —$OR_{21}$, —$SR_{21}$, —S(O)—$R_{20}$, —S(O)$_2$—$R_{20}$ or —$NR_5R_{21}$ radical;
most preferably, each Y is independently a hydrogen, —$OR_{21}$, —$SR_{21}$ or —$NR_5R_{21}$ radical;
each $R_5$ is independently a
(1) hydrogen radical;
(2) alkyl, alkenyl or alkynyl radical optionally substituted by 1–3 radicals of amino, alkylamino, dialkylamino, hydroxy, alkoxy, alkylthio, —SO$_3$H or halo; or
(3) aryl, heteroaryl, arylalkyl, heteroarylalkyl, heterocyclyl, heterocyclylalkyl, cycloalkyl or cycloalkylalkyl radical, wherein the aryl, heteroaryl, heterocyclyl and cycloalkyl radicals are optionally substituted by 1–3 radicals of amino, alkylamino, dialkylamino, hydroxy, alkoxy, alkylthio, alkyl or haloalkyl;
preferably, each $R_5$ is independently a
(1) hydrogen radical;
(2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —SO$_3$H or halo; or
(3) aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical, wherein the aryl, heteroaryl, heterocyclyl and cycloalkyl radicals are optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;
more preferably, each $R_5$ is independently a
(1) hydrogen radical;
(2) $C_1$–$C_4$ alkyl or $C_2$–$C_5$ alkenyl radicals optionally substituted by 1–3 radicals of amino, di-($C_1$–$C_4$-alkyl)amino, hydroxy, $C_1$–$C_4$ alkoxy, $C_1$–$C_4$ alkylthio, —SO$_3$H or halo; or
(3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radical, wherein the cycloalkyl, phenyl, heterocyclyl and heteroaryl radicals are optionally substituted by 1–3 radicals of amino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_2$ haloalkyl of 1–3 halo radicals;
more preferably, each $R_5$ is independently a
(1) hydrogen radical;
(2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or
(3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radical, wherein the phenyl, heteroaryl, heterocyclyl and cycloalkyl radicals are optionally substituted by 1–3 radicals of amino, di-($C_1$–$C_2$-alkyl)amino, hydroxy, $C_1$–$C_2$ alkoxy, $C_1$–$C_2$ alkylthio, $C_1$–$C_4$ alkyl or trifluoromethyl;
more preferably, each $R_5$ is independently a
(1) hydrogen radical;
(2) $C_1$–$C_4$ alkyl radical optionally substituted by 1–3 halo radicals; or
(3) phenyl-$C_1$–$C_2$-alkyl or heteroaryl-$C_1$–$C_2$-alkyl radical, wherein the phenyl and heteroaryl radicals are optionally substituted by 1–3 radicals of amino, dimethylamino, hydroxy, methoxy, methylthio, methyl or trifluoromethyl; most preferably, each $R_5$ is a hydrogen or methyl radical; each $R_{20}$ is independently a (1) alkyl, alkenyl or alkynyl radical optionally substituted by (a) 1–3 radicals of amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl or halo and (b) a radical of aralkoxy, arylalkylthio, arylalkylsulfonyl, cycloalkyl, heterocyclyl, aryl or heteroaryl, wherein the aryl, heteroaryl, heterocyclyl and cycloalkyl radicals are optionally substituted by 1–3 radicals of amino, alkylamino, dialkylamino, alkanoylamino, alkoxycarbonylamino, alkylsulfonylamino, alkanoyl, hydroxy, alkoxy, alkylthio, alkylsulfinyl, alkylsulfonyl, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or (3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;

preferably, each $R_{20}$ is independently a (1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo, and (b) a radical of aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the aryl, heteroaryl, heterocyclyl and cycloalkyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

more preferably, each $R_{20}$ is independently a (1) $C_1$–$C_8$ alkyl or $C_2$–$C_5$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo, and (b) a radical of aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl, wherein the cycloalkyl, aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;

(2) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl; or (3) aryl or heteroaryl radical optionally substituted by 1–2 radicals of amino, $C_1$–$C_4$ alkylamino, di-($C_1$–$C_4$ alkyl)amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl;

more preferably, each $R_{20}$ is independently a (1) $C_1$–$C_8$ alkyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo, and (b) a radical of $C_3$–$C_6$ cycloalkyl, heterocyclyl, aryl or heteroaryl, wherein the cycloalkyl, heterocyclyl, aryl and heteroaryl radicals are optionally substituted by 1–2 radicals of amino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or trifluoromethyl;

(2) heterocyclyl radical optionally substituted by 1–2 radicals of hydroxy, $C_1$–$C_4$ alkoxy, $C_1$–$C_4$ alkylthio or $C_1$–$C_4$ alkyl; or (3) aryl or heteroaryl radical optionally substituted by 1–2 radicals of amino, $C_1$–$C_4$ alkylamino, di-($C_1$–$C_4$ alkyl)amino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl;

more preferably, each $R_{20}$ is independently a (1) $C_1$–$C_6$ alkyl radicals optionally substituted by (a) 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl or halo, and (b) a radical of $C_5$–$C_6$ cycloalkyl, heterocyclyl, phenyl or heteroaryl radical optionally substituted by 1–2 radicals of amino, dimethylamino, acetamino, hydroxy, methoxy, methylthio, halo, methyl or trifluoromethyl radicals;

(2) heterocyclyl radical optionally substituted by 1–2 radicals of hydroxy or $C_1$–$C_4$ alkyl; or (3) aryl or heteroaryl radical optionally substituted by 1–2 radicals of amino, dimethylamino, hydroxy, methoxy, methylthio, halo, methyl or trifluoromethyl;

more preferably, each $R_{20}$ is independently a (1) $C_1$–$C_6$ alkyl radical optionally substituted by (a) 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl or halo, and (b) a radical of $C_5$–$C_6$ cycloalkyl, heterocyclyl, phenyl or heteroaryl optionally substituted by 1–2 radicals of amino, dimethylamino, acetamino, hydroxy, methoxy, methylthio, halo, methyl or trifluoromethyl;

(2) heterocyclyl radical; or
(3) aryl or heteroaryl radical optionally substituted by 1–2 radicals of amino, dimethylamino, hydroxy, methoxy, methylthio, halo, methyl or trifluoromethyl;

more preferably, each $R_{20}$ is independently a
(1) $C_1$–$C_6$ alkyl radical optionally substituted by (a) 1–3 radicals of amino, methylamino, dimethylamino or hydroxy, and (b) a phenyl or heteroaryl radical optionally substituted by 1–2 radicals of amino, dimethylamino, hydroxy, methoxy, methylthio, halo, methyl or trifluoromethyl;
(2) heterocyclyl radical; or
(3) aryl or heteroaryl radicals optionally substituted by 1–2 radicals of amino, dimethylamino, hydroxy, methoxy, methylthio, halo, methyl or trifluoromethyl radicals;

most preferably, each $R_{20}$ is independently a
(1) $C_1$–$C_4$ alkyl radical optionally substituted by 1–2 radicals of amino, $C_1$–$C_2$ alkylamino, di-($C_1$–$C_2$ alkyl)amino, hydroxy or $C_1$–$C_2$ alkoxy; or
(2) trifluoromethyl radical;

each $R_{21}$ is independently a hydrogen radical or $R_{20}$;
each $R_{22}$ is independently a
(1) hydrogen radical;
(2) alkyl radical optionally substituted by a radical of heterocyclyl, aryl or heteroaryl, wherein the heterocyclyl, aryl or heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or
(3) heterocyclyl, aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;

preferably, each $R_{22}$ is independently a
(1) hydrogen radical;
(2) $C_1$–$C_4$ alkyl radical optionally substituted by a radical of heterocyclyl, aryl or heteroaryl, wherein the aryl, heteroaryl and heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or
(3) heterocyclyl, aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

more preferably, each $R_{22}$ is independently a
(1) hydrogen radical; or
(2) $C_1$–$C_4$ alkyl radical optionally substituted by a radical of phenyl or heteroaryl, wherein the phenyl and heteroaryl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

most preferably, each $R_{22}$ is independently a hydrogen or $C_1$–$C_4$ alkyl radical;

$R_{11}$ is an aryl or heteroaryl radical, and $R_{12}$ is an "N"-heteroaryl radical, wherein the aryl, heteroaryl and "N"-heteroaryl radicals are optionally substituted by 1–3 radicals of (1) $R_{30}$;
(2) halo or cyano;
(3) —C(O)—$R_{30}$, —C(O)—O$R_{29}$, —C(O)—N$R_{31}R_{32}$ or —C(N$R_{31}$)—N$R_{31}R_{32}$;
(4) —O$R_{29}$, —O—C(O)—$R_{29}$, —O—C(O)—N$R_{31}R_{32}$ or —O—C(O)—N$R_{33}$—S(O)$_2$—$R_{30}$;
(5) —S$R_{29}$, —S(O)—$R_{30}$, —S(O)$_2$—$R_{30}$, —S(O)$_2$—N$R_{31}R_{32}$, —S(O)$_2$—N$R_{33}$—C(O)—$R_{30}$, —S(O)$_2$—N$R_{33}$—C(O)—O$R_{30}$ or —S(O)$_2$—N$R_{33}$—C(O)—N$R_{31}R_{32}$; or
(6) —N$R_{31}R_{32}$, —N$R_{33}$—C(O)—$R_{29}$, —N$R_{33}$—C(O)—O$R_{30}$, —N$R_{33}$—C(O)—N$R_{31}R_{32}$, —N$R_{33}$—C(N$R_{31}$)—N$R_{31}R_{32}$, —N$R_{33}$—S(O)$_2$—$R_{30}$ or —N$R_{33}$—S(O)$_2$—N$R_{31}R_{32}$;

provided that the total number of aryl, heteroaryl, cycloalkyl and heterocyclyl radicals substituted on each of $R_{11}$ and $R_{12}$ is 0–1;

preferably, $R_{11}$ is an aryl or heteroaryl radical, wherein the aryl and heteroaryl radicals are optionally substituted by 1–2 radicals of
(1) $R_{30}$;
(2) halo or cyano;
(3) —C(O)—$R_{30}$, —C(O)—O$R_{29}$, —C(O)—N$R_{31}R_{32}$ or —C(N$R_{31}$)—N$R_{31}R_{32}$; or
(4) —O$R_{29}$, —S$R_{29}$, —S(O)—$R_{30}$, —S(O)$_2$—$R_{30}$, —S(O)$_2$—N$R_{31}R_{32}$, —N$R_{33}$—S(O)$_2$—$R_{30}$, —N$R_{31}R_{32}$ or —N$R_{33}$—C(O)—$R_{29}$;

more preferably, $R_{11}$ is an aryl or heteroaryl radical, wherein the aryl and heteroaryl radicals are optionally substituted by 1–2 radicals of
(1) $R_{40}$;
(2) halo or cyano; or
(3) —C(O)—N$R_{41}R_{42}$, —O$R_{39}$, —S$R_{39}$, —S(O)—$R_{40}$, —S(O)$_2$—$R_{40}$, —S(O)$_2$—N$R_{41}R_{42}$, —N$R_{41}R_{42}$ or —N$R_{33}$—C(O)—$R_{39}$;

more preferably, $R_{11}$ is an aryl or heteroaryl radical, optionally substituted by 1–2 radicals of (1) $R_{40}$; (2) halo or cyano; or (3) —C(O)—N$R_{41}R_{42}$, —O$R_{39}$, —S$R_{39}$, —S(O)—$R_{40}$, —S(O)$_2$—$R_{40}$, —S(O)$_2$—N$R_{41}R_{42}$, —N$R_{41}R_{42}$ or —N$R_{33}$—C(O)—$R_{39}$; and most preferably, $R_{11}$ is a phenyl, naphthyl, furyl, thienyl, benzofuryl or benzothienyl radical optionally substituted by 1–2 radicals of methyl, amino, dimethylamino, acetamido, hydroxy, halo, cyano, methoxy, methylthio, methylsulfinyl, methylsulfonyl, aminocarbonyl, methyl or trifluoromethyl;

alternatively, preferably, when $R_{11}$ is a heteroaryl radical, the heteroaryl radical is other than a "N"-heteroaryl radical;

preferably, $R_{12}$ is a "N"-heteroaryl radical optionally substituted by 1–2 radicals of
(1) $R_{30}$;
(2) halo or cyano;
(3) —C(O)—$R_{30}$, —C(O)—O$R_{29}$, —C(O)—N$R_{31}R_{32}$ or —C(N$R_{31}$)—N$R_{31}R_{32}$; or
(4) —O$R_{29}$, —S$R_{29}$, —S(O)—$R_{30}$, —S(O)$_2$—$R_{30}$, —S(O)$_2$—N$R_{31}R_{32}$, —N$R_{33}$—S(O)$_2$—$R_{30}$, —N$R_{31}R_{32}$ or —N$R_{33}$—C(O)—$R_{29}$;

more preferably, $R_{12}$ is an "N"-heteroaryl radical optionally substituted by 1–2 radicals of (1) $R_{30}$; (2) halo or cyano; or (3) —C(O)—N$R_{41}R_{42}$, —O$R_{39}$, —S$R_{39}$, —N$R_{41}R_{42}$ or —N$R_{33}$—C(O)—$R_{39}$;

more preferably, $R_{12}$ is a 4-pyridyl, 4-pyrimidyl, 4-quinolinyl, 7-imidazo[4,5-b]pyridinyl, 8-quinazolinyl, 6-(1H)-purinyl or 4-imidazolyl radical optionally substituted by a radical of amino, dimethylamino, acetamido, hydroxy, halo, cyano, methoxy, methyl or trifluoromethyl; and most preferably, $R_{12}$ is a 4-pyridyl or 4-pyrimidyl radical optionally substituted by a radical of amino, dimethylamino, acetamido, hydroxy, halo, cyano, methoxy, methyl or trifluoromethyl;

alternatively more preferably, $R_{12}$ is a pyridyl or pyrimidyl radical optionally substituted by 1–2 radicals of
(1) $R_{30}$;
(2) halo;
(3) —C(O)—$R_{30}$, —C(O)—$OR_{29}$, —C(O)—$NR_{31}R_{32}$ or —C($NR_{31}$)—$NR_{31}R_{32}$; or
(4) —$OR_{29}$, —$SR_{29}$, —S(O)—$R_{30}$, —S(O)$_2$—$R_{30}$, —S(O)$_2$—$NR_{31}R_{32}$, —$NR_{33}$—S(O)$_2$—$R_{30}$, —$NR_{31}R_{32}$ or —$NR_{33}$—C(O)—$R_{29}$; and most preferably, $R_{12}$ is a pyridyl or pyrimidyl radical optionally substituted by 1–2 radicals of
(1) $R_{30}$;
(2) halo;
(3) —C(O)—$NR_{31}R_{32}$ or —C($NR_{31}$)—$NR_{31}R_{32}$; or
(4) —$OR_{29}$, —S(O)$_2$—$NR_{31}R_{32}$, —$NR_{33}$—S(O)$_2$—$R_{30}$, —$NR_{31}R_{32}$ or —$NR_{33}$—C(O)—$R_{29}$;

each $R_{30}$ is independently a
(1) alkyl, alkenyl or alkynyl radical optionally substituted by (a) 1–3 radicals of —$NR_{31}R_{32}$, hydroxy, alkoxy, alkylthio, alkylsulfinyl, alkylsulfonyl, cyano or halo, and (b) a radical of aralkoxy, arylalkylthio, arylalkylsulfonyl, heterocyclyl, aryl or heteroaryl, wherein the heterocyclyl, aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;
(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
(3) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

preferably, each $R_{30}$ is independently a
(1) $C_1$–$C_4$ alkyl, $C_2$–$C_4$ alkenyl or $C_2$–$C_4$ alkynyl radical optionally substituted by (a) 1–3 radicals of —$NR_{31}R_{32}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano or halo, and (b) a radical of aryl-$C_1$–$C_4$-alkoxy, aryl-$C_1$–$C_4$-alkylthio, aryl-$C_1$–$C_4$-alkylsulfonyl, heterocyclyl, aryl or heteroaryl, wherein the heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each $R_{30}$ is independently a
(1) $C_1$–$C_4$ alkyl or $C_2$–$C_5$ alkenyl radical optionally substituted by (a) 1–3 radicals of —$NR_{31}R_{32}$, hydroxy, $C_1$–$C_4$ alkoxy or halo, and (b) a radical of heterocyclyl, aryl or heteroaryl, wherein the heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfonyl, cyano, halo, $C_1$–$C_4$ alkyl or $C_1$–$C_4$ haloalkyl of 1–3 halo radicals;
(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

more preferably, each $R_{30}$ is independently a
(1) $C_1$–$C_4$ alkyl radical optionally substituted by (a) 1–2 radicals of —$NR_{31}R_{32}$, hydroxy or $C_1$–$C_2$ alkoxy, and (b) a radical of aryl or heteroaryl, wherein the aryl and heteroaryl radicals are optionally substituted by 1–2 radicals of amino, $C_1$–$C_2$ alkylamino, di-($C_1$–$C_2$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfonyl, cyano, halo, $C_1$–$C_4$ alkyl or trifluoromethyl; or
(2) aryl or heteroaryl radical optionally substituted by 1–2 radicals of amino, $C_1$–$C_2$ alkylamino, di-($C_1$–$C_2$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfonyl, cyano, halo, $C_1$–$C_4$ alkyl or trifluoromethyl;

more preferably, each $R_{30}$ is independently $R_{40}$;

each $R_{29}$ is independently a hydrogen radical or $R_{30}$;

each $R_{31}$ is independently a
(1) hydrogen radical;
(2) alkyl radical optionally substituted by an cycloalkyl, aryl, heterocyclyl or heteroaryl radical, wherein the cycloalkyl, aryl, heterocyclyl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
(3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{31}$ is independently a
(1) hydrogen radical;
(2) $C_1$–$C_4$ alkyl radical optionally substituted by an $C_3$–$C_8$ cycloalkyl, aryl, heterocyclyl or heteroaryl radical, wherein the cycloalkyl, aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{31}$ is independently a
(1) hydrogen radical; or
(2) $C_1$–$C_4$ alkyl radical optionally substituted by a aryl or heteroaryl radical, wherein the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, $C_1$–$C_4$ alkyl or trifluoromethyl;

more preferably, each $R_{31}$ is independently $R_{41}$;
most preferably, each $R_{31}$ is independently a hydrogen or methyl radical;
each $R_{32}$ is independently a
(1) hydrogen radical;
(2) alkyl radical optionally substituted by a cycloalkyl, aryl, heterocyclyl or heteroaryl radical, wherein the cycloalkyl, aryl, heterocyclyl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or
(3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{32}$ is independently a
(1) hydrogen radical;
(2) $C_1$–$C_4$ alkyl radical optionally substituted by an $C_3$–$C_8$ cycloalkyl, aryl, heterocyclyl or heteroaryl radical, wherein the cycloalkyl, aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or
(3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{32}$ is independently a
(1) hydrogen radical;
(2) $C_1$–$C_4$ alkyl radical optionally substituted by an aryl or heteroaryl radical, wherein the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl; or
(3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl;

more preferably, each $R_{32}$ is independently a
(1) hydrogen radical;
(2) $C_1$–$C_4$ alkyl radical optionally substituted by an aryl or heteroaryl radical, wherein the aryl and heteroaryl radicals are optionally substituted by 1–2 radicals of amino, $C_1$–$C_2$ alkylamino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkyl or trifluoromethyl; or
(3) aryl or heteroaryl radical optionally substituted by 1–2 radicals of amino, $C_1$–$C_2$ alkylamino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkyl or trifluoromethyl;

more preferably, each $R_{32}$ is independently $R_{42}$;
each $R_{33}$ is independently a
(1) hydrogen radical; or
(2) alkyl radical optionally substituted by a radical of heterocyclyl, aryl or heteroaryl, wherein the aryl, heterocyclyl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl;

preferably, each $R_{33}$ is independently a
(1) hydrogen radical; or
(2) $C_1$–$C_4$ alkyl radical optionally substituted by a radical of heterocyclyl, aryl or heteroaryl, wherein the aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

more preferably, each $R_{33}$ is independently a hydrogen or $C_1$–$C_4$ alkyl radical;
most preferably, each $R_{33}$ is independently hydrogen or methyl radical;
each $R_{40}$ is independently a
(1) $C_1$–$C_4$ alkyl radical optionally substituted by a phenyl or heteroaryl radical, wherein the phenyl and heteroaryl radicals are optionally substituted by 1–3 radicals of amino, dimethylamino, acetamido, hydroxy, halo, methoxy, methyl or trifluoromethyl radicals;
(2) trifluoromethyl radical; or
(3) aryl or heteroaryl radical optionally substituted by 1–3 radicals of amino, dimethylamino, acetamido, hydroxy, halo, methoxy, methyl or trifluoromethyl;

preferably, each $R_{40}$ is independently a
(1) $C_1$–$C_4$ alkyl radical optionally substituted by a phenyl radical optionally substituted by 1–3 radicals of amino, dimethylamino, acetamido, hydroxy, halo, methoxy, methyl or trifluoromethyl radicals;
(2) trifluoromethyl radical; or
(3) aryl radical optionally substituted by 1–3 radicals of amino, dimethylamino, acetamido, hydroxy, halo, methoxy, methyl or trifluoromethyl;

each $R_{39}$ is independently a hydrogen radical or $R_{40}$;
each $R_{41}$ is independently a
(1) hydrogen radical; or
(2) $C_1$–$C_4$ alkyl radical optionally substituted by a phenyl or heteroaryl radical, wherein the phenyl and heteroaryl radicals are optionally substituted by 1–3 radicals of amino, $C_1$–$C_2$ alkylamino, di-($C_1$–$C_2$ alkyl)amino, acetamido, hydroxy, $C_1$–$C_2$ alkoxy, $C_1$–$C_2$ alkylthio, cyano, $C_1$–$C_2$ alkyl or trifluoromethyl;

preferably, each $R_{41}$ is independently a hydrogen or $C_1$–$C_4$ alkyl radical;
each $R_{42}$ is independently a
(1) hydrogen radical;
(2) $C_1$–$C_4$ alkyl radical or $C_1$–$C_2$ alkyl radical substituted by an aryl or heteroaryl radical, wherein the aryl and heteroaryl radicals are optionally substituted by 1–3 radicals of amino, dimethylamino, acetamido, hydroxy, methoxy, methyl or trifluoromethyl; or (3) aryl or heteroaryl radical optionally substituted by 1–3 radicals of amino, dimethylamino, acetamido, hydroxy, methoxy, methyl or trifluoromethyl radicals; and preferably, each $R_{42}$ is independently a hydrogen or $C_1$–$C_4$ alkyl radical.

In another embodiment, in conjunction with any one of the above and below embodiments, W is N, V is N, and U is $CR_6$.

In another embodiment, in conjunction with any one of the above and below embodiments, W is N, V is $CR_6$, and U is $CR_6$.

In another embodiment, in conjunction with any one of the above and below embodiments, X is N.

In another embodiment, in conjunction with any one of the above and below embodiments, Z is heterocyclyl.

In another embodiment, in conjunction with any one of the above and below embodiments, Y is $NR_5R_{21}$.

In another embodiment, in conjunction with any one of the above and below embodiments, $R_5$ is hydrogen.

In another embodiment, in conjunction with any one of the above and below embodiments, $R_5$ is:

$C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or aryl, heteroaryl, aryl-$C_1$–$C_4$-alkyl, heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical, wherein the aryl, heteroaryl, heterocyclyl and cycloalkyl radicals are optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals.

In another embodiment, in conjunction with any one of the above and below embodiments, each $R_{20}$ is independently a $C_1$–$C_8$ alkyl, $C_2$–$C_8$ alkenyl or $C_2$–$C_8$ alkynyl radical substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo.

In another embodiment, in conjunction with any one of the above and below embodiments, each $R_{20}$ is independently a radical of aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the aryl, heteroaryl, heterocyclyl and cycloalkyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals.

In another embodiment, in conjunction with any one of the above and below embodiments, each $R_{20}$ is independently a $C_1$–$C_8$ alkyl, $C_2$–$C_8$ alkenyl or $C_2$–$C_8$ alkynyl radical substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo; and $R_{20}$ is also substituted by a radical of aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the aryl, heteroaryl, heterocyclyl and cycloalkyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals.

In another embodiment, the compound is selected from:

5-(3-phenylprop-1-yl)amino-8-(4-fluorophenyl)-7-(4-pyridyl)-1,2,4-triazolo[4,3-c]pyrimidine;

5-(3-phenylprop-1-yl)amino-8-(3-methylphenyl)-7-(4-pyridyl)-1,2,4-triazolo[4,3-c]pyrimidine;

5-(1-piperazinyl)-8-(3-methylphenyl)-7-(2-chloro-4-pyridyl)-1,2,4-triazolo[4,3-c]pyrimidine;

5-(3-phenylprop-1-yl)amino-8-(3-(trifluoromethyl)phenyl)-7-(4-pyridyl)-1,2,4-triazolo[4,3-c]pyrimidine;

5-(2(S)-amino-3-phenylprop-1-yl)amino-8-(3,4-dichlorophenyl)-7-(4-pyridyl)-1,2,4-triazolo[4,3-c]pyrimidine;

5-(piperazin-1-yl)-8-(3-(trifluoromethyl)phenyl)-7-(2-(2-phenylprop-2-yl)amino-4-pyridyl)-1,2,4-triazolo[4,3-c]pyrimidine;

5-(3,5-dimethylpiperazin-1-yl)-8-(3-(trifluoromethyl)phenyl)-7-(2-(1(S)-phenylethyl)amino-4-pyridyl)-1,2,4-triazolo[4,3-c]pyrimidine;

5-(piperazin-1-yl)-8-(3-(trifluoromethyl)phenyl)-7-(2-(1(S)-phenylethyl)amino-4-pyridyl)-1,2,4-triazolo[4,3-c]pyrimidine;

1-(8-(4-fluorophenyl)-7-(4-pyridyl)-1,2,4-triazolo[4,3-c]pyrimidin-5-yl)amino-2(S)-amino-3-phenylpropane;

2-(8-(4-fluorophenyl)-7-(4-pyridyl)-1,2,4-triazolo[4,3-c]pyrimidin-5-yl)amino-2-phenylpropane;

5-(2(S)-amino-2-methyl-3-phenylprop-1-yl)amino-8-(3-(trifluoromethyl)phenyl)-7-(4-pyridyl)-1,2,4-triazolo[4,3-c]pyrimidine;

5-(2,5-diaza-bicyclo[2.2.1]hept-2-yl)-8-(3-(trifluoromethyl)phenyl)-7-(2-(1(S)-phenylethyl)amino-4-pyridyl)-1,2,4-triazolo[4,3-c]pyrimidine;

5-(2(S)-amino-3-phenylprop-1-yl)amino-8-(2-naphthyl)-7-(4-pyridyl)-1,2,4-triazolo[4,3-c]pyrimidine;

5-(3(S)-benzyl-piperazin-1-yl)-8-(2-naphthyl)-7-(4-pyridyl)-1,2,4-triazolo[4,3-c]pyrimidine;

5-(2(S)-amino-3-phenylprop-1-yl)amino-8-(3-chloro-4-fluorophenyl)-7-(4-pyridyl)-1,2,4-triazolo[4,3-c]pyrimidine;

5-(2(S)-pyrrolidinylmethyl)amino-8-(2-naphthyl)-7-(4-pyridyl)-1,2,4-triazolo[4,3-c]pyrimidine;

5-(1-(2-propyl)pyrrolidin-2(S)-ylmethyl)amino-8-(3,4-dichlorophenyl)-7-(4-pyridyl)-1,2,4-triazolo[4,3-c]pyrimidine;

5-(piperazin-1-yl)-8-(3-(trifluoromethyl)phenyl)-7-(2-(cyclopropyl)amino-4-pyridyl)-1,2,4-triazolo[4,3-c]pyrimidine;

5-(1-(2-propyl)piperid-3-yl)amino-8-(3,4-dichlorophenyl)-7-(4-pyridyl)-1,2,4-triazolo[4,3-c]pyrimidine;

5-(1-(2-propyl)pyrrolidin-2(S)-ylmethyl)amino-8-(2-naphthyl)-7-(4-pyridyl)-1,2,4-triazolo[4,3-c]pyrimidine;

2-methyl-$N^2$-(8-naphthalen-2-yl-7-pyridin-4-yl-[1,2,4]triazolo[4,3-c]pyrimidin-5-yl)-propane-1,2-diamine;

$N^1$-isopropyl-2-methyl-$N^2$-(8-naphthalen-2-yl-7-pyridin-4-yl-[1,2,4]triazolo[4,3-c]pyrimidin-5-yl)-propane-1,2-diamine;

$N^1$-cyclopentyl-2-methyl-$N^2$-(8-naphthalen-2-yl-7-pyridin-4-yl-[1,2,4]triazolo[4,3-c]pyrimidin-5-yl)-propane-1,2-diamine;

isopropyl-[1-(8-naphthalen-2-yl-7-pyridin-4-yl-[1,2,4]triazolo[4,3-c]pyrimidin-5-yl)-pyrrolidin-2-ylmethyl]-amine;
[1-(1-isopropyl-piperidin-2-yl)-1-methyl-ethyl]-(8-naphthalen-2-yl-7-pyridin-4-yl-[1,2,4]triazolo[4,3-c]pyrimidin-5-yl)-amine;
(4-methyl-piperidin-4-yl)-(8-naphthalen-2-yl-7-pyridin-4-yl-[1,2,4]triazolo[4,3-c]pyrimidin-5-yl)-amine;
(1-isopropyl-3-methyl-piperidin-3-yl)-(8-naphthalen-2-yl-7-pyridin-4-yl-[1,2,4]triazolo[4,3-c]pyrimidin-5-yl)-amine;
$N^2$-[8-(3,4-dichloro-phenyl)-7-pyridin-4-yl-[1,2,4]triazolo[4,3-c]pyrimidin-5-yl]-$N^1$-isopropyl-2-methyl-propane-1,2-diamine;
[8-(3,4-dichloro-phenyl)-7-pyridin-4-yl-[1,2,4]triazolo[4,3-c]pyrimidin-5-yl]-[1-(1-isopropyl-pyrrolidin-2-yl)-1-methyl-ethyl]-amine;
[8-(3,4-dichloro-phenyl)-7-pyridin-4-yl-[1,2,4]triazolo[4,3-c]pyrimidin-5-yl]-[1-(1-isopropyl-piperidin-2-yl)-1-methyl-ethyl]-amine;
[8-(3,4-dichloro-phenyl)-7-pyridin-4-yl-[1,2,4]triazolo[4,3-c]pyrimidin-5-yl]-(4-methyl-piperidin-4-yl)-amine;
[8-(3,4-dichloro-phenyl)-7-pyridin-4-yl-[1,2,4]triazolo[4,3-c]pyrimidin-5-yl]-(1-isopropyl-3-methyl-piperidin-3-yl)-amine;
isopropyl-[1-(8-naphthalen-2-yl-7-pyridin-4-yl-imidazo[1,2-c]pyrimidin-5-yl)-pyrrolidin-2-ylmethyl]-amine;
{1-[8-(3,4-dichloro-phenyl)-7-pyridin-4-yl-imidazo[1,2-c]pyrimidin-5-yl]-pyrrolidin-2-ylmethyl}-isopropyl-amine;
$N^1$-isopropyl-2-methyl-$N^2$-(8-naphthalen-2-yl-7-pyridin-4-yl-imidazo[1,2-c]pyrimidin-5-yl)-propane-1,2-diamine;
[1-(1-isopropyl-pyrrolidin-2-yl)-1-methyl-ethyl]-(8-naphthalen-2-yl-7-pyridin-4-yl-imidazo[1,2-c]pyrimidin-5-yl)-amine;
[1-(1-isopropyl-piperidin-2-yl)-1-methyl-ethyl]-(8-naphthalen-2-yl-7-pyridin-4-yl-imidazo[1,2-c]pyrimidin-5-yl)-amine;
(4-methyl-piperidin-4-yl)-(8-naphthalen-2-yl-7-pyridin-4-yl-imidazo[1,2-c]pyrimidin-5-yl)-amine;
(1-isopropyl-3-methyl-piperidin-3-yl)-(8-naphthalen-2-yl-7-pyridin-4-yl-imidazo[1,2-c]pyrimidin-5-yl)-amine;
$N^2$-[8-(3,4-dichloro-phenyl)-7-pyridin-4-yl-imidazo[1,2-c]pyrimidin-5-yl]-$N^1$-isopropyl-2-methyl-propane-1,2-diamine;
[8-(3,4-dichloro-phenyl)-7-pyridin-4-yl-imidazo[1,2-c]pyrimidin-5-yl]-[1-(1-isopropyl-pyrrolidin-2-yl)-1-methyl-ethyl]-amine;
[8-(3,4-dichloro-phenyl)-7-pyridin-4-yl-imidazo[1,2-c]pyrimidin-5-yl]-[1-(1-isopropyl-piperidin-2-yl)-1-methyl-ethyl]-amine;
[8-(3,4-dichloro-phenyl)-7-pyridin-4-yl-imidazo[1,2-c]pyrimidin-5-yl]-(4-methyl-piperidin-4-yl)-amine; and
[8-(3,4-Dichloro-phenyl)-7-pyridin-4-yl-imidazo[1,2-c]pyrimidin-5-yl]-(1-isopropyl-3-methyl-piperidin-3-yl)-amine; or a pharmaceutically-acceptable salt thereof.

The compounds of this invention may have in general several asymmetric centers and are typically depicted in the form of racemic mixtures. This invention is intended to encompass racemic mixtures, partially racemic mixtures and separate enantiomers and diasteromers.

Compounds of interest include the following:

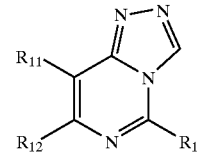

wherein $R_1$, $R_{11}$ and $R_{12}$ are one of the combinations given in the following table:

| $R^{11}$ | $R^{12}$ | $R^1$ |
| --- | --- | --- |
| Phenyl | 4-pyridyl | 3-phenylpropylamino |
| 3-fluorophenyl | 4-pyridyl | 3-phenylpropylamino |
| 4-fluorophenyl | 4-pyridyl | 3-phenylpropylamino |
| 4-fluorophenyl | 4-pyrimidyl | 3-phenylpropylamino |
| 2-naphthyl | 4-pyridyl | 3-phenylpropylamino |
| 3-tolyl | 4-pyrimidyl | 3-phenylpropylamino |
| 3-tolyl | 4-pyridyl | 3-phenylpropylamino |
| 3-$CF_3$-phenyl | 4-pyridyl | 3-phenylpropylamino |
| 2-pyridyl | 4-pyridyl | 3-phenylpropylamino |
| 3,4-dichlorophenyl | 4-pyridyl | 3-phenylpropylamino |
| 3,4-dimethyl phenyl | 4-pyridyl | 3-phenylpropylamino |
| 2-thienyl | 4-pyrimidyl | 3-phenylpropylamino |
| 2-furyl | 4-pyridyl | 3-phenylpropylamino |
| 2-benzothienyl | 4-pyridyl | 3-phenylpropylamino |
| 2-benzofuryl | 4-pyridyl | 3-phenylpropylamino |
| Phenyl | 4-pyridyl | 3-benzyl-1-piperidinyl |
| 3-fluorophenyl | 4-pyridyl | 3-benzyl-1-piperidinyl |
| 4-fluorophenyl | 4-pyridyl | 3-benzyl-1-pyrrolidinyl |
| 1-naphthyl | 4-pyrimidyl | 2-benzyl-4-piperidinyl |
| 2-naphthyl | 4-pyridyl | 3-benzyl-1-piperidinyl |
| 3-$CF_3$-phenyl | 4-pyrimidyl | 3-benzyl-1-piperidinyl |
| 3,4-dimethyl phenyl | 4-pyrimidyl | 3-benzyl-1-piperidinyl |
| 3-tolyl | 4-pyridyl | 3-benzyl-1-piperidinyl |
| 3-$CF_3$-phenyl | 4-pyridyl | 3-benzyl-1-piperidinyl |
| 3,4-dichlorophenyl | 4-pyridyl | 3-benzyl-1-piperidinyl |
| 3,4-dimethyl phenyl | 4-pyridyl | 2-benzyl-4-morpholino |
| 2-thienyl | 4-pyridyl | 3-benzyl-1-piperidinyl |
| 2-furyl | 4-pyridyl | 3-benzyl-1-piperidinyl |
| 2-benzothienyl | 4-pyridyl | 3-benzyl-1-piperidinyl |
| 2-benzofuryl | 4-pyridyl | 3-benzyl-1-piperidinyl |
| Phenyl | 4-pyridyl | 3-benzyl-1-piperazinyl |
| 3-fluorophenyl | 4-pyridyl | 3-benzyl-1-piperazinyl |
| 4-fluorophenyl | 4-pyridyl | 3-benzyl-1-piperazinyl |
| 3-tolyl | 4-pyridyl | 3-benzyl-1-piperazinyl |
| 3-$CF_3$-phenyl | 4-pyridyl | 3-benzyl-1-piperazinyl |
| 3-fluorophenyl | 4-pyrimidyl | 3-benzyl-1-piperazinyl |
| Phenyl | 4-pyrimidyl | 3-benzyl-1-piperazinyl |
| 3,4-dichlorophenyl | 4-pyridyl | 3-benzyl-1-piperazinyl |
| 3,4-dimethyl phenyl | 4-pyridyl | 3-benzyl-1-piperazinyl |
| 2-thienyl | 4-pyridyl | 3-benzyl-1-piperazinyl |
| 2-furyl | 4-pyridyl | 3-benzyl-1-piperazinyl |
| 3-pyridonyl | 4-pyridyl | 3-benzyl-1-piperazinyl |
| 2-benzothienyl | 4-pyrimidyl | 3-benzyl-1-piperazinyl |
| 2-benzofuryl | 4-pyridyl | 3-benzyl-1-piperazinyl |
| 3-fluorophenyl | 2-(benzofur-3-ylamino)-4-pyridyl | 4-piperidinyl |
| 4-fluorophenyl | 3-benzyl amino-4-pyridyl | 3-pyrrolidinylmethyl |
| 1-naphthyl | 3-benzyl amino-4-pyrimidyl | 1-benzyl-4-piperidinyl |
| 2-naphthyl | 4-pyridyl | 1-methyl-4-piperidinyl |
| 3-$CF_3$-phenyl | 6-benzyl amino-4-pyrimidyl | 4-piperidinyl |
| 3,4-dimethyl phenyl | 2-benzyloxy-4-pyrimidyl | 1-piperazinyl |
| 3-tolyl | 2-(phenyl sulfonyl amino)-4-pyridyl | 1-piperazinyl |
| 3-$CF_3$-phenyl | 2-(1-phenyl ethyl)amino-4-pyridyl | 2-aminoethylamino |

-continued

| R¹¹ | R¹² | R¹ |
|---|---|---|
| 3,4-dichlorophenyl | 2-(1-(4-fluorophenyl)ethyl)amino-4-pyridyl | (4-piperidinyl methyl)amino |
| 3,4-dimethyl phenyl | 2-(phenyl amino sulfonyl)-4-pyridyl | 3-aminoprop-1-ylamino |
| Phenyl | 4-pyridyl | 2-amino-3-phenylpropylamino |
| 3-fluorophenyl | 4-pyridyl | 2-amino-3-phenylpropylamino |
| 4-fluorophenyl | 4-pyridyl | 2-amino-3-(4-fluorophenyl)propylamino |
| 3-tolyl | 4-pyridyl | 2-amino-3-phenylpropylamino |
| 3-CF₃-phenyl | 4-pyridyl | 2-amino-3-(3-CF₃-phenyl)propylamino |
| 3,4-dichlorophenyl | 2-amino-4-pyridyl | 2-amino-3-phenylpropylamino |
| 3,4-dimethyl phenyl | 4-pyridyl | 2-amino-3-phenylpropylamino |
| 3-fluorophenyl | 4-pyrimidyl | 2-amino-3-phenylpropylamino |
| 3-tolyl | 4-pyrimidyl | 2-amino-3-phenylpropylamino |
| 2-thienyl | 4-pyridyl | 2-amino-3-phenylpropylamino |
| 2-furyl | 4-pyrimidyl | 2-amino-3-phenylpropylamino |
| 2-benzothienyl | 4-pyridyl | 2-amino-3-phenylpropylamino |
| 2-benzofuryl | 4-pyridyl | 2-amino-3-phenylpropylamino |
| Phenyl | 4-pyridyl | 3-amino-3-phenylpropylamino |
| 4-fluorophenyl | 4-pyridyl | 3-amino-3-phenylpropylamino |
| 3,4-dimethyl phenyl | 4-pyrimidyl | 3-amino-3-phenylpropylamino |
| 3-fluorophenyl | 4-pyrimidyl | 3-amino-3-phenylpropylamino |
| 6-pyridonyl | 4-pyridyl | 3-amino-3-phenylpropylamino |
| 3-tolyl | 4-pyridyl | 3-amino-3-phenylpropylamino |
| 3-CF₃-phenyl | 4-pyridyl | 3-amino-3-phenylpropylamino |
| 2-thienyl | 4-pyridyl | 3-amino-3-phenylpropylamino |
| 2-furyl | 4-pyridyl | 3-amino-3-phenylpropylamino |
| 2-benzothienyl | 4-pyridyl | 3-amino-3-phenylpropylamino |
| 2-benzofuryl | 4-pyrimidyl | 3-amino-3-phenylpropylamino |
| Phenyl | 4-pyridyl | 3-amino-3-phenyl-2,2-dimethylpropylamino |
| 3-fluorophenyl | 4-pyridyl | 3-amino-3-phenyl-2,2-dimethylpropylamino |
| 3-benzoxazolyl | 4-pyridyl | 3-amino-3-phenyl-2,2-dimethylpropylamino |
| 3-tolyl | 4-pyridyl | 3-amino-3-phenyl-2,2-dimethylpropylamino |
| 3-CF₃-phenyl | 4-pyridyl | 3-amino-3-phenyl-2,2-dimethylpropylamino |
| 3,4-dichlorophenyl | 4-pyridyl | 3-amino-3-phenyl-2,2-dimethylpropylamino |
| 3,4-dimethyl phenyl | 4-pyridyl | 3-amino-3-phenyl-2,2-dimethylpropylamino |
| 3-fluorophenyl | 4-pyrimidyl | 3-amino-3-phenyl-2,2-dimethylpropylamino |
| 1-acetyl-2-indolyl | 4-pyrimidyl | 3-amino-3-phenyl-2,2-dimethylpropylamino |
| 3-tolyl | 4-pyrimidyl | 3-amino-3-phenyl-2,2-dimethylpropylamino |
| 2-thienyl | 4-pyridyl | 3-amino-3-phenyl-2,2-dimethylpropylamino |
| 2-furyl | 2-amino-4-pyrimidyl | 3-amino-3-phenyl-2,2-dimethylpropylamino |
| 2-benzothienyl | 4-pyridyl | 3-amino-3-phenyl-2,2-dimethylpropylamino |
| 2-benzofuryl | 4-pyridyl | 3-amino-3-phenyl-2,2-dimethylpropylamino |

Additional preferred compounds are included in the Examples, infra.

As utilized herein, the following terms shall have the following meanings:

"Alkyl", alone or in combination, means a straight-chain or branched-chain alkyl radical containing preferably 1–15 carbon atoms ($C_1$–$C_{15}$), more preferably 1–8 carbon atoms ($C_1$–$C_8$), even more preferably 1–6 carbon atoms ($C_1$–$C_6$), yet more preferably 1–4 carbon atoms ($C_1$–$C_4$), still more preferably 1–3 carbon atoms ($C_1$–$C_3$), and most preferably 1–2 carbon atoms ($C_1$–$C_2$). Examples of such radicals include methyl, ethyl, n-propyl, isopropyl, n-butyl, isobutyl, sec-butyl, tert-butyl, pentyl, iso-amyl, hexyl, octyl and the like.

"Hydroxyalkyl", alone or in combination, means an alkyl radical as defined above wherein at least one hydrogen radical is replaced with a hydroxyl radical, preferably 1–3 hydrogen radicals are replaced by hydroxyl radicals, more preferably 1–2 hydrogen radicals are replaced by hydroxyl radicals, and most preferably one hydrogen radical is replaced by a hydroxyl radical. Examples of such radicals include hydroxymethyl, 1-, 2-hydroxyethyl, 1-, 2-, 3-hydroxypropyl, 1,3-dihydroxy-2-propyl, 1,3-dihydroxybutyl, 1,2,3,4,5,6-hexahydroxy-2-hexyl and the like.

"Alkenyl", alone or in combination, means a straight-chain or branched-chain hydrocarbon radical having one or more double bonds, preferably 1–2 double bonds and more preferably one double bond, and containing preferably 2–15 carbon atoms ($C_2$–$C_{15}$), more preferably 2–8 carbon atoms ($C_2$–$C_8$), even more preferably 2–6 carbon atoms ($C_2$–$C_6$), yet more preferably 2–4 carbon atoms ($C_2$–$C_4$), and still more preferably 2–3 carbon atoms ($C_2$–$C_3$). Examples of such alkenyl radicals include ethenyl, propenyl, 2-methylpropenyl, 1,4-butadienyl and the like.

"Alkoxy", alone or in combination, means a radical of the type "R—O—" wherein "R" is an alkyl radical as defined above and "O" is an oxygen atom. Examples of such alkoxy radicals include methoxy, ethoxy, n-propoxy, isopropoxy, n-butoxy, iso-butoxy, sec-butoxy, tert-butoxy and the like.

"Alkoxycarbonyl", alone or in combination, means a radical of the type "R—O—C(O)—" wherein "R—O—" is an alkoxy radical as defined above and "C(O)" is a carbonyl radical.

"Alkoxycarbonylamino", alone or in combination, means a radical of the type "R—O—C(O)—NH—" wherein "R—O—C(O)" is an alkoxycarbonyl radical as defined above, wherein the amino radical may optionally be substituted, such as with alkyl, aryl, aralkyl, cycloalkyl, cycloalkylalkyl and the like.

"Alkylthio", alone or in combination, means a radical of the type "R—S—" wherein "R" is an alkyl radical as defined above and "S" is a sulfur atom. Examples of such alkylthio radicals include methylthio, ethylthio, n-propylthio, isopropylthio, n-butylthio, iso-butylthio, sec-butylthio, tert-butylthio and the like.

"Alkylsulfinyl", alone or in combination, means a radical of the type "R—S(O)—" wherein "R" is an alkyl radical as defined above and "S(O)" is a mono-oxygenated sulfur atom. Examples of such alkylsulfinyl radicals include methylsulfinyl, ethylsulfinyl, n-propylsulfinyl, isopropylsulfinyl, n-butylsulfinyl, iso-butylsulfinyl, sec-butylsulfinyl, tert-butylsulfinyl and the like.

"Alkylsulfonyl", alone or in combination, means a radical of the type "R—S(O)₂—" wherein "R" is an alkyl radical as defined above and "S(O)₂" is a di-oxygenated sulfur atom. Examples of such alkylsulfonyl radicals include methylsulfonyl, ethylsulfonyl, n-propylsulfonyl, isopropylsulfonyl, n-butylsulfonyl, iso-butylsulfonyl, sec-butylsulfonyl, tert-butylsulfonyl and the like.

"Aryl", alone or in combination, means a phenyl or biphenyl radical, which is optionally benzo fused or heterocyclo fused and which is optionally substituted with one or more substituents selected from alkyl, alkoxy, halogen, hydroxy, amino, azido, nitro, cyano, haloalkyl, carboxy, alkoxycarbonyl, cycloalkyl, alkanoylamino, amido, amidino, alkoxycarbonylamino, N-alkylamidino, alkylamino, dialkylamino, aminoalkyl, alkylaminoalkyl, dialkylaminoalkyl, N-alkylamido, N,N-dialkylamido, aralkoxycarbonylamino, alkylthio, alkylsulfinyl, alkylsulfonyl, oxo and the like. Examples of aryl radicals are phenyl, o-tolyl, 4-methoxyphenyl, 2-(tert-butoxy)phenyl, 3-methyl-4-methoxyphenyl, 2-CF₃-phenyl, 2-fluorophenyl, 2-chlorophenyl, 3-nitrophenyl, 3-aminophenyl, 3-acetamidophenyl, 2-amino-3-(aminomethyl)phenyl, 6-methyl-3-acetamidophenyl, 6-methyl-2-aminophenyl, 6-methyl-2,3-diaminophenyl, 2-amino-3-methylphenyl, 4,6-dimethyl-2-aminophenyl, 4-hydroxyphenyl, 3-methyl-4-hydroxyphenyl, 4-(2-methoxyphenyl)phenyl, 2-amino-1-naphthyl, 2-naphthyl, 3-amino-2-naphthyl, 1-methyl-3-amino-2-naphthyl, 2,3-diamino-1-naphthyl, 4,8-dimethoxy-2-naphthyl and the like.

"Aralkyl" and "arylalkyl", alone or in combination, means an alkyl radical as defined above in which at least one hydrogen atom, preferably 1–2, is replaced by an aryl radical as defined above, such as benzyl, 1-, 2-phenylethyl, dibenzylmethyl, hydroxyphenylmethyl, methylphenylmethyl, diphenylmethyl, dichlorophenylmethyl, 4-methoxyphenylmethyl and the like. For example, phenylmethyl means a methylene diradical substituted with a phenyl radical, i.e., Ph-CH$_2$—, whereas a methylphenyl means a phenylene diradical substituted with a methyl radical, i.e., CH$_3$-Ph-.

"Aralkoxy" and "arylalkoxy", alone or in combination, means an alkoxy radical as defined above in which at least one hydrogen atom, preferably 1–2, is replaced by an aryl radical as defined above, such as benzyloxy, 1-, 2-phenylethoxy, dibenzylmethoxy, hydroxyphenylmethoxy, methylphenylmethoxy, dichlorophenylmethoxy, 4-methoxyphenylmethoxy and the like.

"Aralkoxycarbonyl" and "arylalkoxycarbonyl", alone or in combination, means a radical of the type "R—O—C(O)—" wherein "R—O—" is an aralkoxy radical as defined above and "—C(O)—" is a carbonyl radical.

"Alkanoyl", alone or in combination, means a radical of the type "R—C(O)—" wherein "R" is an alkyl radical as defined above and "—C(O)—" is a carbonyl radical. Examples of such alkanoyl radicals include acetyl, trifluoroacetyl, hydroxyacetyl, propionyl, butyryl, valeryl, 4-methylvaleryl, and the like.

"Alkanoylamino", alone or in combination, means a radical of the type "R—C(O)—NH—" wherein "R—C(O)—" is an alkanoyl radical as defined above, wherein the amino radical may optionally be substituted, such as with alkyl, aryl, aralkyl, cycloalkyl, cycloalkylalkyl and the like.

"Aminocarbonyl", alone or in combination, means an amino substituted carbonyl (carbamoyl) radical, wherein the amino radical may optionally be mono- or di-substituted, such as with alkyl, aryl, aralkyl, cycloalkyl, cycloalkylalkyl, alkanoyl, alkoxycarbonyl, aralkoxycarbonyl and the like.

"Aminosulfonyl", alone or in combination, means an amino substituted sulfonyl radical.

"Benzo", alone or in combination, means the divalent radical C$_6$H$_4$= derived from benzene. "Benzo fused" forms a ring system in which benzene and a cycloalkyl or aryl group have two carbons in common, for example tetrahydronaphthylene and the like.

"Bicyclic" and "tricyclic" as used herein is intended to include both fused ring systems, such as naphthyl and β-carbolinyl, and substituted ring systems, such as biphenyl, phenylpyridyl and diphenylpiperazinyl.

"Cycloalkyl", alone or in combination, means a saturated or partially saturated, preferably one double bond, monocyclic, bicyclic or tricyclic carbocyclic alkyl radical, preferably monocyclic, containing preferably 5–12 carbon atoms (C$_5$–C$_{12}$), more preferably 5–10 carbon atoms (C$_5$–C$_{10}$), even more preferably 5–7 carbon atoms (C$_5$–C$_7$), which is optionally benzo fused or heterocyclo fused and which is optionally substituted as defined herein with respect to the definition of aryl. Examples of such cycloalkyl radicals include cyclopentyl, cyclohexyl, dihydroxycyclohexyl, ethylenedioxycyclohexyl, cycloheptyl, octahydronaphthyl, tetrahydronaphthyl, octahydroquinolinyl, dimethoxytetrahydronaphthyl, 2,3-dihydro-1H-indenyl, azabicyclo[3.2.1]octyl and the like.

"Heteroatoms" means nitrogen, oxygen and sulfur heteroatoms.

"Heterocyclo fused" forms a ring system in which a heterocyclyl or heteroaryl group of 5–6 ring members and a cycloalkyl or aryl group have two carbons in common, for example indole, isoquinoline, tetrahydroquinoline, methylenedioxybenzene and the like.

"Heterocyclyl" means a saturated or partially unsaturated, preferably one double bond, monocyclic or bicyclic, preferably monocyclic, heterocycle radical containing at least one, preferably 1 to 4, more preferably 1 to 3, even more preferably 1–2, nitrogen, oxygen or sulfur atom ring member and having preferably 3–8 ring members in each ring, more preferably 5–8 ring members in each ring and even more preferably 5–6 ring members in each ring. "Heterocyclyl" is intended to include sulfone and sulfoxide derivatives of sulfur ring members and N-oxides of tertiary nitrogen ring members, and carbocyclic fused, preferably 3–6 ring carbon atoms and more preferably 5–6 ring carbon atoms, and benzo fused ring systems. "Heterocyclyl" radicals may optionally be substituted on at least one, preferably 1–4, more preferably 1–3, even more preferably 1–2, carbon atoms by halogen, alkyl, alkoxy, hydroxy, oxo, thioxo, aryl, aralkyl, heteroaryl, heteroaralkyl, amidino, N-alkylamidino, alkoxycarbonylamino, alkylsulfonylamino and the like, and/or on a secondary nitrogen atom by hydroxy, alkyl, aralkoxycarbonyl, alkanoyl, alkoxycarbonyl, heteroaralkyl, aryl or aralkyl radicals. More preferably, "heterocyclyl", alone or in combination, is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals. Examples of such heterocyclyl radicals include pyrrolidinyl, piperidinyl, piperazinyl, morpholinyl, thiamorpholinyl, 4-benzyl-piperazin-1-yl, pyrimidyl, tetrahydrofuryl, pyrazolidonyl, pyrazolinyl, pyridazinonyl, pyrrolidonyl, tetrahydrothienyl and its sulfoxide and sulfone derivatives, 2,3-dihydroindolyl, tetrahydroquinolinyl, 1,2,3,4-tetrahydroisoquinolinyl, 1,2,3, 4-tetrahydro-1-oxo-isoquinolinyl, 2,3-dihydrobenzofuryl, benzopyranyl, methylenedioxyphenyl, ethylenedioxyphenyl and the like.

"Heteroaryl" means a monocyclic or bicyclic, preferably monocyclic, aromatic heterocycle radical, having at least one, preferably 1 to 4, more preferably 1 to 3, even more preferably 1–2, nitrogen, oxygen or sulfur atom ring members and having preferably 5–6 ring members in each ring, which is optionally saturated carbocyclic fused, preferably 3–4 carbon atoms (C$_3$–C$_4$) to form 5–6 ring membered rings and which is optionally substituted as defined above with respect to the definitions of aryl. Examples of such heteroaryl groups include thienyl, furyl oxazolyl, thiazolyl, benzothiazolyl, benzofuryl, benzothienyl, imidazolyl, pyrrolyl, pyrazolyl, pyridyl, 3-(2-methyl)pyridyl, 3-(4-trifluoromethyl)pyridyl, pyrimidyl, 5-(4-trifluoromethyl) pyrimidyl, pyrazinyl, triazolyl, indolyl, quinolinyl, 5,6,7,8-tetrahydroquinolinyl, 5,6,7,8-tetrahydroisoquinolinyl, quinoxalinyl, benzimidazolyl, benzoxazolyl and the like.

""N"-heteroaryl" means an aromatic 5–10 membered monocyclic or bicyclic, preferably a monocyclic, aromatic heterocycle radical containing at least one, preferably 1 to 3, more preferably 1 to 2, even more preferably 1 nitrogen atoms with the remaining atoms being carbon, and having preferably 5–6 ring members in each ring, which is optionally saturated carbocyclic fused, preferably 3–4 carbon atoms ($C_3$–$C_4$) to form 5–6 ring membered rings and which is optionally substituted as defined above with respect to the definitions of aryl. Examples of such "N"-heteroaryl groups include imidazolyl, pyrrolyl, pyrazolyl, pyridyl, 4-(2-amino)pyridyl, 3-(4-trifluoromethyl)pyridyl, pyrimidyl, 5-(4-trifluoromethyl)pyrimidyl, pyrazinyl, triazolyl, indolyl, quinolinyl, imidazopyridine, 5,6,7,8-tetrahydroquinolyl, 5,6,7,8-tetrahydroisoquinolinyl, benzimidazolyl, and the like.

As one skilled in the art will appreciate such heterocycle moieties may exist in several isomeric forms, all of which are to be encompassed by the present invention. For example, a 1,3,5-triazine moiety is isomeric to a 1,2,4-triazine group. Such positional isomers are to be considered within the scope of the present invention. Likewise, the heterocyclyl or heteroaryl groups can be bonded to other moieties in the compounds of the invention. The point(s) of attachment to these other moieties is not to be construed as limiting on the scope of the invention. Thus, by way of example, a pyridyl moiety may be bound to other groups through the 2-, 3-, or 4-position of the pyridyl group and a piperidinyl may be bound to other groups through the nitrogen or carbon atoms of the piperidinyl group. All such configurations are to be construed as within the scope of the present invention.

Examples of heterocyclyl or heteroaryl moieties included in the scope of the present invention may include, but are not limited to, the following:

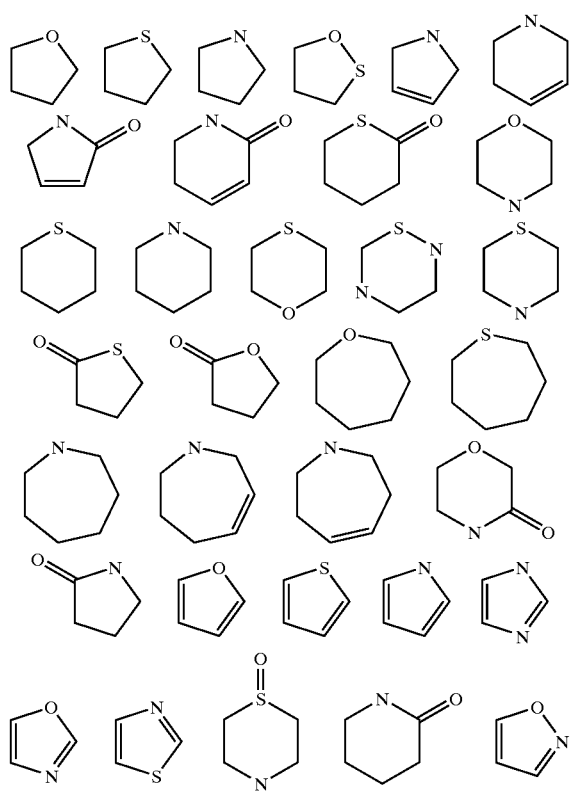

-continued

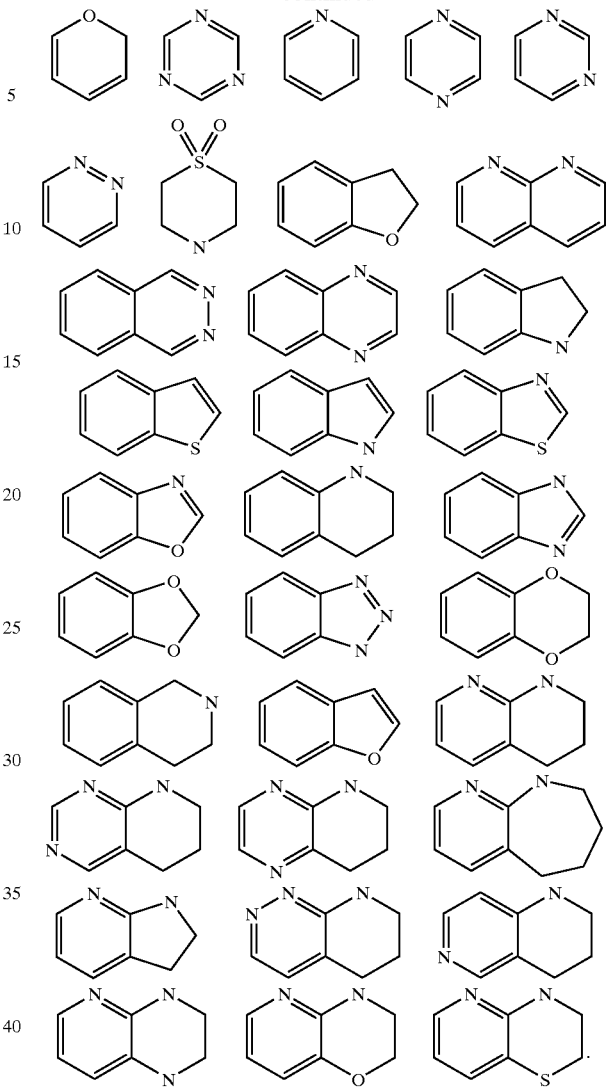

"Heteroaralkyl" and "heteroarylalkyl," alone or in combination, means an alkyl radical as defined above in which at least one hydrogen atom, preferably 1–2, is replaced by a heteroaryl radical as defined above, such as 3-furylpropyl, 2-pyrrolyl propyl, chloroquinolinylmethyl, 2-thienylethyl, pyridylmethyl, 1-imidazolylethyl and the like.

"Halogen" and "halo", alone or in combination, means fluoro, chloro, bromo or iodo radicals.

"Haloalkyl", alone or in combination, means an alkyl radical as defined above in which at least one hydrogen atom, preferably 1–3, is replaced by a halogen radical, more preferably fluoro or chloro radicals. Examples of such haloalkyl radicals include 1,1,1-trifluoroethyl, chloromethyl, 1-bromoethyl, fluoromethyl, difluoromethyl, trifluoromethyl, bis(trifluoromethyl)methyl and the like.

"Pharmacologically acceptable salt" means a salt prepared by conventional means, and are well known by those skilled in the art. The "pharmacologically acceptable salts" include basic salts of inorganic and organic acids, including but not limited to hydrochloric acid, hydrobromic acid, sulphuric acid, phosphoric acid, methanesulphonic acid, ethanesulfonic acid, malic acid, acetic acid, oxalic acid, tartaric acid, citric acid, lactic acid, fumaric acid, succinic acid, maleic acid, salicylic acid, benzoic acid, phenylacetic acid, mandelic acid and the like. When compounds of the invention include an acidic function such as a carboxy group, then suitable pharmaceutically acceptable cation pairs for the carboxy group are well known to those skilled in the art and include alkaline, alkaline earth, ammonium, quaternary ammonium cations and the like. For additional examples of "pharmacologically acceptable salts," see infra and Berge et al, J. Pharm. Sci. 66:1 (1977).

"Indolizine-like compounds" is intended to encompass indolizine compounds as well as mono-, di- and tri-azaindolizine compounds.

"Leaving group" (referred to as "L" in the Schemes) generally refers to groups readily displaceable by a nucleophile, such as an amine, a thiol or an alcohol nucleophile. Such leaving groups are well known in the art. Examples of such leaving groups include, but are not limited to, N-hydroxysuccinimide, N-hydroxybenzotriazole, halides, triflates, tosylates and the like. Preferred leaving groups are indicated herein where appropriate.

"Protecting group" generally refers to groups well known in the art which are used to prevent selected reactive groups, such as carboxy, amino, hydroxy, mercapto and the like, from undergoing undesired reactions, such as nucleophilic, electrophilic, oxidation, reduction and the like. Preferred protecting groups are indicated herein where appropriate. Examples of amino protecting groups include, but are not limited to, aralkyl, substituted aralkyl, cycloalkenylalkyl and substituted cycloalkenyl alkyl, allyl, substituted allyl, acyl, alkoxycarbonyl, aralkoxycarbonyl, silyl and the like. Examples of aralkyl include, but are not limited to, benzyl, ortho-methylbenzyl, trityl and benzhydryl, which can be optionally substituted with halogen, alkyl, alkoxy, hydroxy, nitro, acylamino, acyl and the like, and salts, such as phosphonium and ammonium salts. Examples of aryl groups include phenyl, naphthyl, indanyl, anthracenyl, 9-(9-phenylfluorenyl), phenanthrenyl, durenyl and the like. Examples of cycloalkenylalkyl or substituted cycloalkyle-nylalkyl radicals, preferably have 6–10 carbon atoms, include, but are not limited to, cyclohexenyl methyl and the like. Suitable acyl, alkoxycarbonyl and aralkoxycarbonyl groups include benzyloxycarbonyl, t-butoxycarbonyl, iso-butoxycarbonyl, benzoyl, substituted benzoyl, butyryl, acetyl, tri-fluoroacetyl, tri-chloro acetyl, phthaloyl and the like. A mixture of protecting groups can be used to protect the same amino group, such as a primary amino group can be protected by both an aralkyl group and an aralkoxycarbonyl group. Amino protecting groups can also form a heterocyclic ring with the nitrogen to which they are attached, for example, 1,2-bis(methylene)benzene, phthalimidyl, succinimidyl, maleimidyl and the like and where these heterocyclic groups can further include adjoining aryl and cycloalkyl rings. In addition, the heterocyclic groups can be mono-, di- or tri-substituted, such as nitrophthalimidyl. Amino groups may also be protected against undesired reactions, such as oxidation, through the formation of an addition salt, such as hydrochloride, toluene-sulfonic acid, trifluoroacetic acid and the like. Many of the amino protecting groups are also suitable for protecting carboxy, hydroxy and mercapto groups. For example, aralkyl groups. Alkyl groups are also suitable groups for protecting hydroxy and mercapto groups, such as tert-butyl.

Silyl protecting groups are silicon atoms optionally substituted by one or more alkyl, aryl and aralkyl groups.

Suitable silyl protecting groups include, but are not limited to, trimethylsilyl, triethylsilyl, tri-isopropylsilyl, tert-butyldimethylsilyl, dimethylphenylsilyl, 1,2-bis(dimethylsilyl)benzene, 1,2-bis(dimethylsilyl)ethane and diphenylmethylsilyl. Silylation of an amino groups provide mono- or di-silylamino groups. Silylation of aminoalcohol compounds can lead to a N,N,O-tri-silyl derivative. Removal of the silyl function from a silyl ether function is readily accomplished by treatment with, for example, a metal hydroxide or ammonium fluoride reagent, either as a discrete reaction step or in situ during a reaction with the alcohol group. Suitable silylating agents are, for example, trimethylsilyl chloride, tert-buty-dimethylsilyl chloride, phenyldimethylsilyl chloride, diphenylmethyl silyl chloride or their combination products with imidazole or DMF. Methods for silylation of amines and removal of silyl protecting groups are well known to those skilled in the art. Methods of preparation of these amine derivatives from corresponding amino acids, amino acid amides or amino acid esters are also well known to those skilled in the art of organic chemistry including amino acid/amino acid ester or aminoalcohol chemistry.

Protecting groups are removed under conditions which will not affect the remaining portion of the molecule. These methods are well known in the art and include acid hydrolysis, hydrogenolysis and the like. A preferred method involves removal of a protecting group, such as removal of a benzyloxycarbonyl group by hydrogenolysis utilizing palladium on carbon in a suitable solvent system such as an alcohol, acetic acid, and the like or mixtures thereof. A t-butoxycarbonyl protecting group can be removed utilizing an inorganic or organic acid, such as HCl or trifluoroacetic acid, in a suitable solvent system, such as dioxane or methylene chloride. The resulting amino salt can readily be neutralized to yield the free amine. Carboxy protecting group, such as methyl, ethyl, benzyl, tert-butyl, 4-methoxyphenylmethyl and the like, can be removed under hydrolysis and hydrogenolysis conditions well known to those skilled in the art.

Certain symbols used herein are intended to have the following meanings:

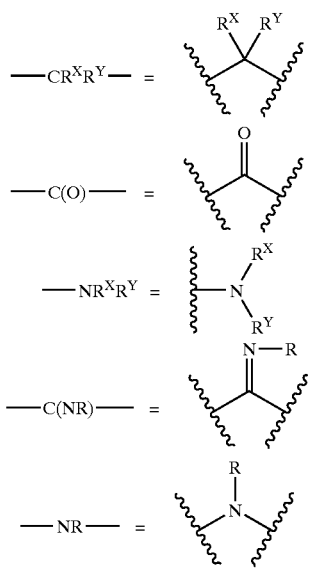

-continued

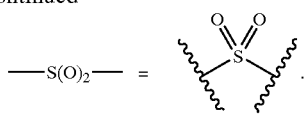

Further, a carbon atom substituted by two hydroxy radicals represents a carbonyl radical. For example, —CR$_2$R$_2$— represents a carbonyl radical when each R$_2$ is a hydroxy radical.

It should be noted that compounds of the invention may contain groups that may exist in tautomeric forms, such as cyclic and acyclic amidine and guanidine groups, heteroatom substituted heteroaryl groups (Y'=O, S, NR), and the like, which are illustrated in the following examples:

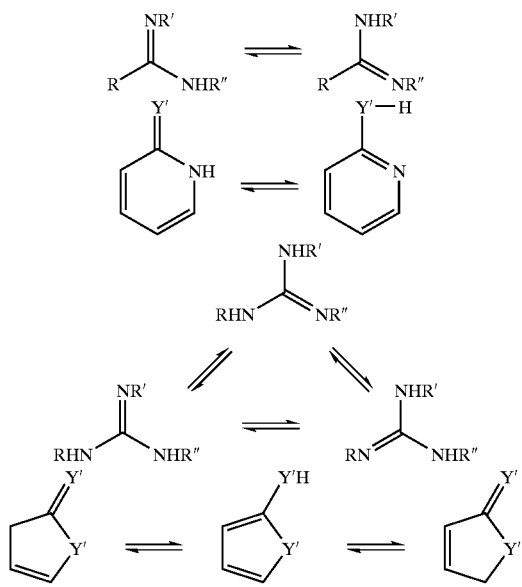

and though one form is named, described, displayed and/or claimed herein, all the tautomeric forms are intended to be inherently included in such name, description, display and/or claim.

Prodrugs of the compounds of this invention are also contemplated by this invention. A prodrug is an active or inactive compound that is modified chemically through in vivo physiological action, such as hydrolysis, metabolism and the like, into a compound of this invention following administration of the prodrug to a patient. The suitability and techniques involved in making and using prodrugs are well known by those skilled in the art. For a general discussion of prodrugs involving esters see Svensson and Tunek Drug Metabolism Reviews 16.5 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use.

Compounds according to the invention can be synthesized according to one or more of the following methods. It should be noted that the general procedures are shown as it relates to preparation of compounds having unspecified stereochemistry. However, such procedures are generally applicable to those compounds of a specific stereochemistry, e.g., where the stereochemistry about a group is (S) or (R). In addition, the compounds having one stereochemistry (e.g., (R)) can often be utilized to produce those having opposite stereochemistry (i.e., (S)) using well-known methods, for example, by inversion.

The invention relates to substituted indolizine-like compounds. Substituted indolizine-like compounds embodied in the current invention may be prepared as described in the following schemes and synthetic examples.

Indolizine-like Compounds:

Substituted indolizine-like compounds I embodied in the current invention (V and W=N; and W=N) may be prepared from substituted 4(3H)-pyrimidinones II or 2(1H)-pyridones III (Scheme 1). II/III carbonyl can be converted into a leaving group (L), such as L=Cl, with POCl$_3$ or the like and heat to form pyrimidine/pyridine IV. Reaction of pyrimidine/pyridine IV with hydrazine in an appropriate solvent, such as ethanol, followed by cyclization with R$_6$—CL$_3$, such as the orthoester R$_6$—C(OCH$_3$)$_3$, can form the substituted indolizine-like compound I (V=N and W=N). Alternatively, reaction of pyrimidine/pyridine IV with a 2-hydroxyethylamine (NH$_2$CHR$_6$CHR$_6$OH) in the presence of base, such as K$_2$CO$_3$ or the like, followed by conversion of the hydroxy group into a leaving group (L), such as L=Cl, with POCl$_3$ or the like, followed by cyclization and oxidation, or oxidation of the hydroxy group to a ketone followed by cyclization to form the substituted indolizine-like compound I (W=N).

Alternatively, reaction of pyrimidine/pyridine IV with an amino acid (NH$_2$CHR$_6$CO$_2$OH) in the presence of base, such as K$_2$CO$_3$ or the like, followed by cyclization can also form the substituted indolizine-like compound I (W=N) which can also serve as an intermediate for substitution at the 3-position (see for example, J. Med. Chem. 31:454–61, 1988; Chem. Pharm. Bull. 33:30–6, 1985; J. Heterocycl. Chem. 28:503–7, 1991). Likewise, conversion of pyrimidine/pyridine IV into amino-pyrimidine/pyridine VI, with AcNHBr and K$_2$CO$_3$ (Synth. Commun. 21:1841–6, 1991), NH$_4$OH (aq) and CuSO$_4$ (Acta Chim. Hung. 127:601–5, 1990) or the like, followed by reaction and cyclization with R$_6$—C(O)—CR$_6$L, wherein L is a leaving group such as Cl, Br or I, can also form the substituted indolizine-like compound I (W=N) (see for example, J. Med. Chem. 35:877–85, 1992; J. Fluorine Chem. 73:83–6, 1995; Chem. Lett. 1317–20, 1993; J. Med. Chem. 32:1686–700, 1989).

Scheme 1

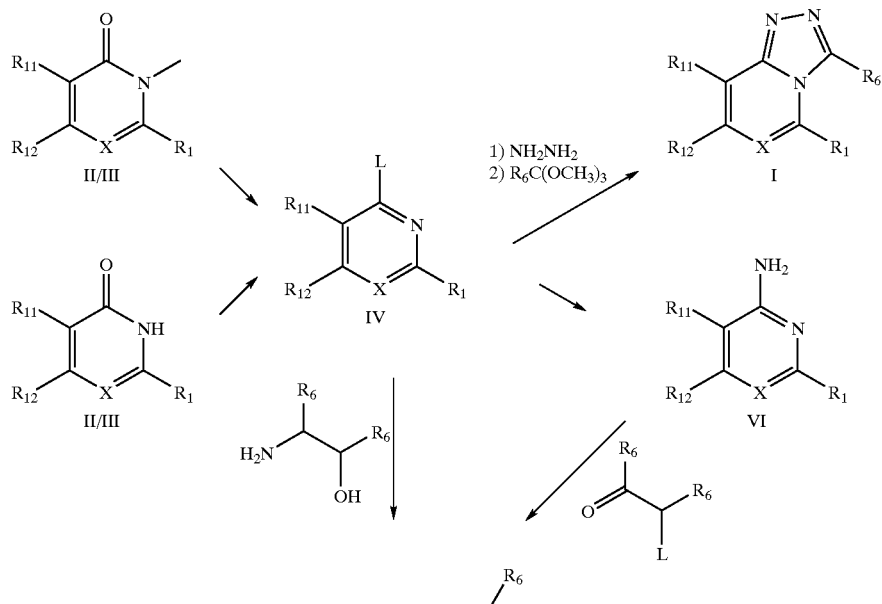

Scheme 2

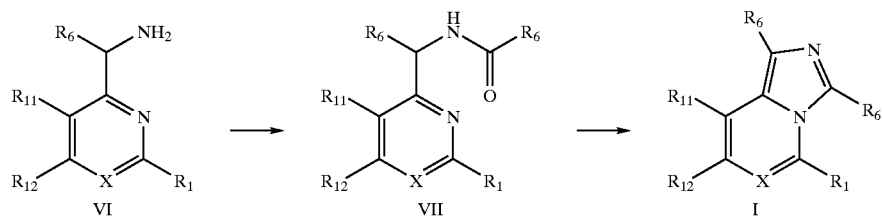

Substituted indolizine-like compounds I embodied in the current invention (V=N) may be prepared from substituted 4(3H)-pyrimidinones VI or 2(1H)-pyridones VI (Scheme 2). The amine VI can be reacted with $R_6C(O)L$ or its equivalent and the resulting amide VII can be cyclized in the presence of $POCl_3$ to form the indolizine-like compounds I (see J. Heterocycl. Chem. 23:981–7, 1986). Alternatively, the amine VI can be reacted with phosgene or its equivalent to form the 3-hydroxy indolizine-like compounds I, which can also serve as an intermediate for substitution at the 3-position.

Amine VI can be prepared by reaction of cyanide ion, such as sodium cyanide or the like, with pyrimidine/pyridine IV in an appropriate solvent, such as dimethylformamide, dimethylsulfoxide or the like, followed by reduction of the cyano group to the aminomethyl group (see Synthesis 961–2, 1989).

4(3H)-Pyrimidines:

For the synthesis of 4(3H)-pyrimidinones II (or its tautomer, 4-hydroxy-pyrimidines), the approach displayed in Scheme 3 may be followed (see WO 98/24782; WO 98/24780; and for a review of synthetic methods see D. J. Brown, *Heterocyclic Compounds: the Pyrimidines*, Chapter 3, 1994, John Wiley & Sons). This approach involves the cyclization reaction between an acrylic acid ester XII and an amidine V followed by oxidation of the resulting dihydropyrimidinone XIII to give II.

Scheme 3

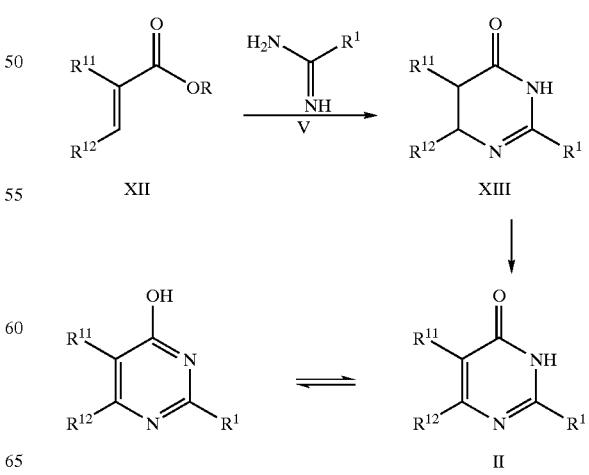

For the synthesis of 2-substituted 5-(4-fluorophenyl)-6-(4-pyridyl)-4-hydroxy-pyrimidines II (Scheme 4), the disubstituted acrylic acid ester XII may be prepared conveniently by condensation of pyridine-4-carboxaldehyde with 4-fluorophenylacetic acid followed by esterification (R=methyl, ethyl, benzyl or the like). XII may be reacted with a variety of amidines V at elevated temperature. As a dehydrogenating agent for the conversion of XIII to II, sodium nitrite/acetic acid is suitable.

6-methylpyrimidine-4-carboxaldehyde, 2-methylpyrimidine-4-carboxaldehyde, 2,6-dimethylpyrimidine-4-carboxalde-hyde (Bredereck et al., Chem. Ber. 97, 3407–3417 (1964)). The use of 2-nitropyridine-4-carboxaldehyde would lead to a derivative of formula II with $R^{12}$ represented by a 2-nitro-4-pyridyl group. Catalytic reduction of the nitro to an amino group would provide the 2-amino-4-pyridyl derivative of II. The approach displayed in Scheme 2 is applicable to the use of

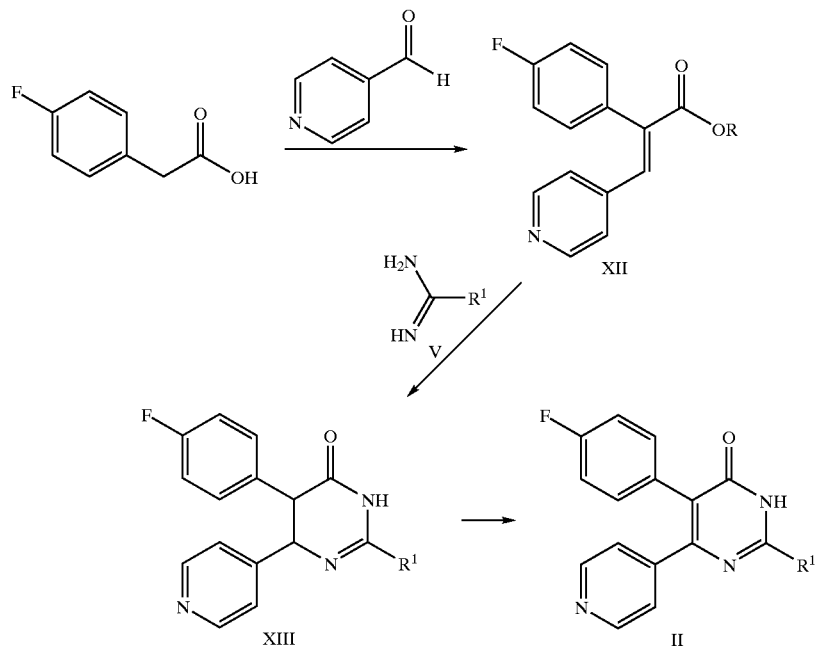

Scheme 4

Accordingly, further compounds of formula II may be obtained in which $R^{12}$ is any other heteroaryl ring within the definition of $R^{12}$ by the appropriate choice of starting material. Such starting materials include but are not limited to 2-methylpyridine-4-carboxaldehyde, 2,6-dimethylpyridine-4-carboxaldehyde (Mathes and Sauermilch, Chem. Ber. 88, 1276–1283 (1955)), quinoline-4-carboxaldehyde, pyrimidine-4-carboxaldehyde, other aryl acetic acids leading to compounds of formula II with different aryl groups as $R^{11}$.

Pyrimidinone II may be substituted at the N-3 position by reaction with e.g. an alkyl halide, such as methyl iodide or ethyl bromide in the presence of an appropriate base such as potassium carbonate and the like.

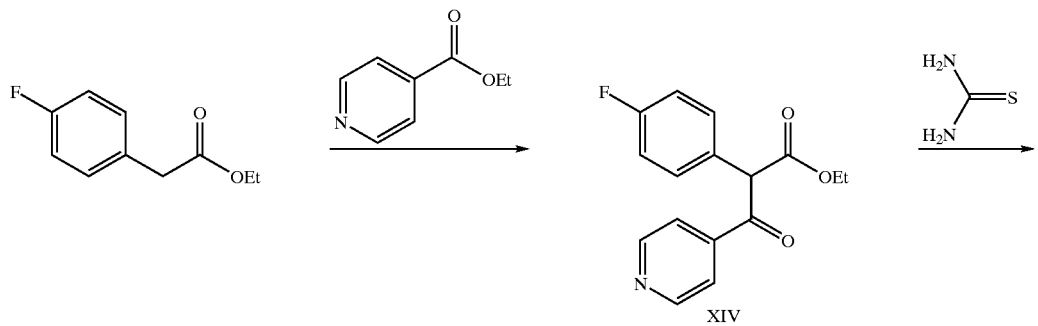

Scheme 5

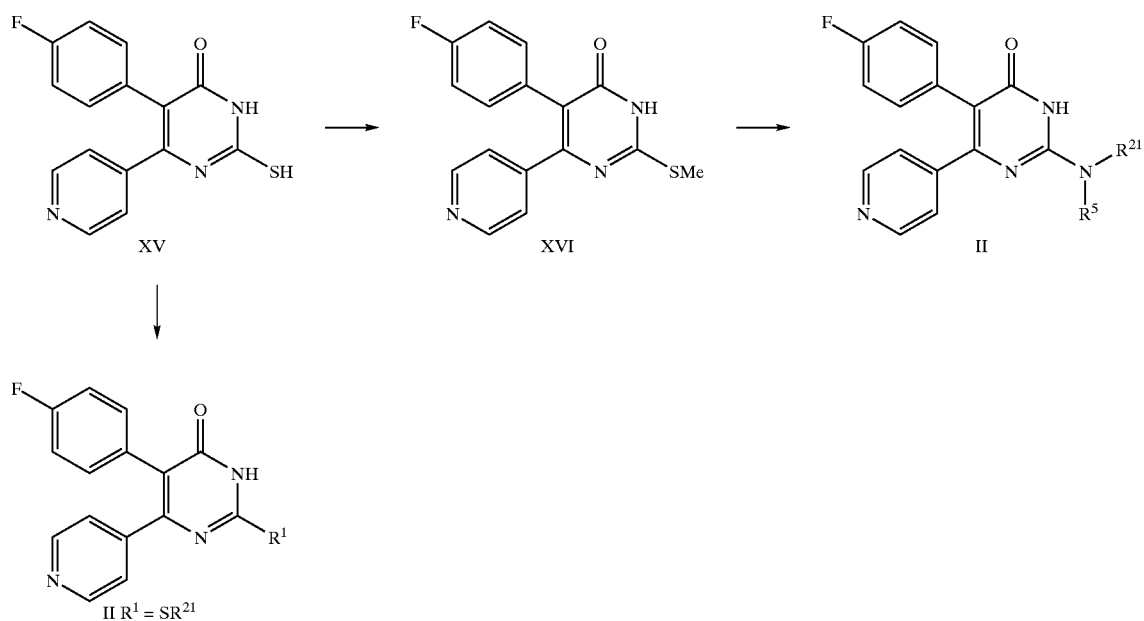

Another approach (Scheme 5) leading to 5,6-disubstituted-4-hydroxy-pyrimidines involves the cyclization of the β-keto ester XIV with thiourea to give the thiouracil derivative XV. XV can be S-monomethylated to XVI. Reaction of XVI with primary and secondary amines leads to 2-amino substituted 4-hydroxy-pyrimidines II. Further 2-thioether derivatives of II with $R^1=SR^{21}$ can be obtained, for example by alkylation of XV with alkyl halides. Treatment of XV or XVI with Raney nickel and $H_2$ provides compounds of structure II wherein $R^1$ is H.

Scheme 6

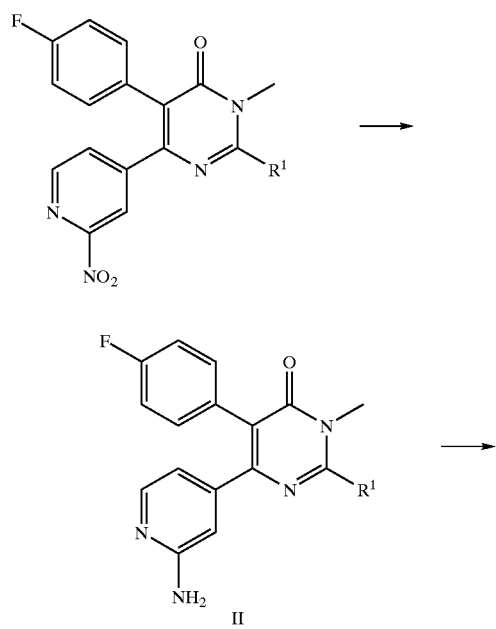

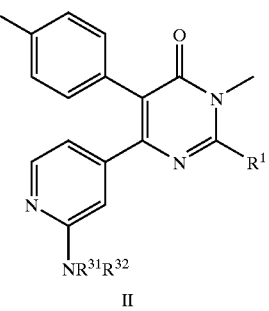

Although Scheme 5 illustrates syntheses in which $R^{12}$ is 4-pyridyl, this approach may be equally applied to any other heteroaryl ring within the definition of $R^{12}$ by the appropriate choice of the starting material. Such starting materials include but are not limited to ethyl 2-methyl isonicotinate (Efimovsky and Rumpf, *Bull. Soc. Chim. FR.* 648–649 (1954)), methyl pyrimidine-4-carboxylate, methyl 2-methylpyrimidine-4-carboxylate, methyl 6-methylpyrimidine-4-carboxylate and methyl 2,6-dimethylpyrimidine-4-carboxylate (Sakasi et al., *Heterocycles* 13, 235 (1978)). Likewise, methyl 2-nitroisonicotinate (Stanonis, *J. Org. Chem.* 22, 475 (1957)) may be reacted with an aryl acetic acid ester followed by cyclization of the resultant β-keto ester with thiourea analogously to Scheme 5. Subsequent catalytic reduction of the nitro group to an amino group would give a pyrimidinone II in which $R^{12}$ is represented by a 2-amino-4-pyridyl group (Scheme 6). The 2-amino group may be subsequently reacted with $R^{31}$-L and $R^{32}$-L to form the N-substituted pyrimidinone II.

Furthermore, methyl 2-acetamido isonicotinate or methyl 2-($R^{32}$HN—)isonicotinate (Scheme 7) may be reacted analogously to Scheme 5 after appropriate protection of the nitrogen with e.g. a tert-butyldimethylsilyloxy methyl group (Benneche et al., *Acta Chem. Scand.* B 42 384–389 (1988)), a tert-butyldimethylsilyl group, a benzyloxymethyl group, a benzyl group or the like (P₁). Alternatively, methyl 2-($R^{31}R^{32}N$—)isonicotinate, wherein $R^{31}$ and $R^{32}$ are each other than hydrogen radical, may also be reacted analogously to Scheme 5.

Alternatively, the halogen derivative of XVIII may be converted into a trialkyltin derivative (L=$Bu_3Sn$) by reaction with e.g. tributylstannyl chloride following lithiation with butyllithium and may then be reacted with an aryl halide or Scheme 7

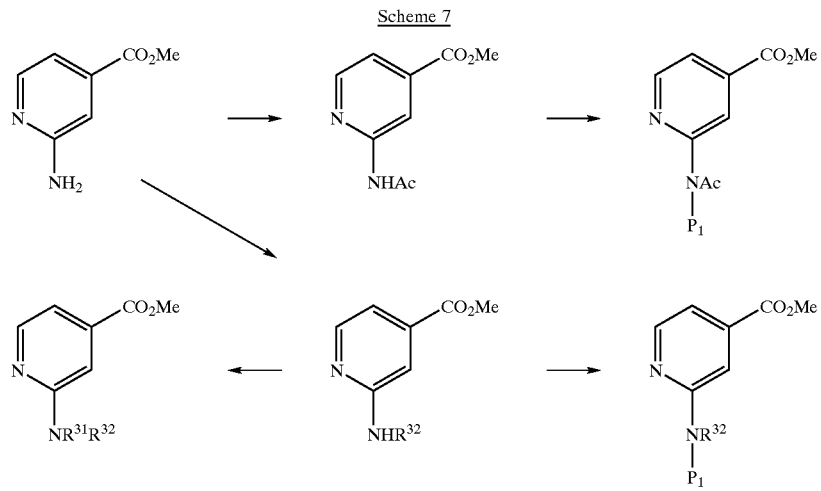

Removal of the protecting group P₁ of the resulting pyrimidine II with a suitable reagent (e.g., tetrabutylammonium fluoride in the case where P₁ is t-butyldimethylsilyloxymethyl) would then lead to a pyrimidinone II with $R^{12}$ represented by a 2-acetamido-4-pyridyl or 2-($R^{32}HN$—)-4-pyridyl group. Needless to say, ethyl p-fluorophenyl acetate may be substituted by any alkyl arylacetate or alkyl heteroarylacetate in the procedure illustrated in Scheme 5 thus providing compounds of formula II with different $R^{11}$ aryl and heteroaryl substituents.

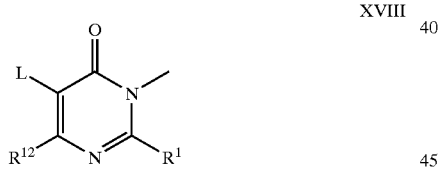

XVIII

In a further process, pyrimidinones II may be prepared by coupling a suitable derivative of XVIII (L is a leaving group, such as halogen radical and the like) with an appropriate aryl or heteroaryl equivalent. Such aryl/heteroaryl couplings are well known to those skilled in the art and involve an organic-metallic component for reaction with a reactive derivative, e.g., a halogeno derivative, of the second compound in the presence of a catalyst. The metallo-organic species may be provided either by the pyrimidinone in which case the $R^{11}$ component provides the reactive halogen equivalent or the pyrimidinone may be in the form of a reactive 5-halogeno derivative for reaction with a metallo organic aryl or heteroaryl compound. Accordingly, 5-bromo and 5-iodo derivatives of XVIII (L=Br, I) may be treated with arylalkyl tin or heteroarylalkyl tin compounds, e.g., trimethylstannylbenzene, in an inert solvent such as tetrahydrofuran in the presence of a palladium catalyst, such as di(triphenylphosphine)palladium(II) dichloride (Peters et al., J. Heterocyclic Chem. 27, 2165–2173, (1990).

heteroaryl halide in the presence of a catalyst. (Sandosham and Undheim, Acta Chem. Scand. 43, 684–689 (1989). Both approaches would lead to pyrimidines II in which $R^{11}$ is represented by aryl and heteroaryl groups.

Scheme 8

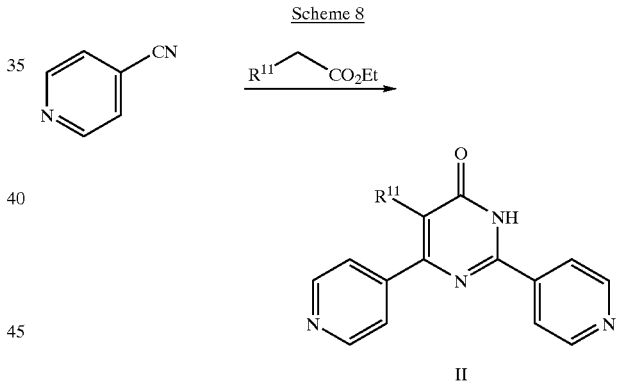

II

As reported in the literature (Kabbe, Lieb. Ann. Chem. 704, 144 (1967); German Patent 1271116 (1968)) and displayed in Scheme 8, 5-$R^{11}$-2,6-dipyridyl-4(3H)-pyrimidinones II may be prepared in a one step synthesis by reaction of the cyanopyridine with an arylacetyl ester, such as ethyl phenylacetate in the presence of sodium methoxide.

In Scheme 9, compounds of the present invention of formula XXX can be readily prepared by reacting the methylthio intermediate XXXI with the amine $NHR^5R^{21}$, for example by heating the mixture preferably at a temperature greater than 100° C., more preferably 150–210° C. Alternatively, compounds of formula XXX can be readily prepared by reacting the methylsulfonyl intermediate XXXII with the amine $NHR^5R^{21}$, for example by heating the mixture preferably at a temperature greater than 40° C., more preferably 50–210° C.

Scheme 9

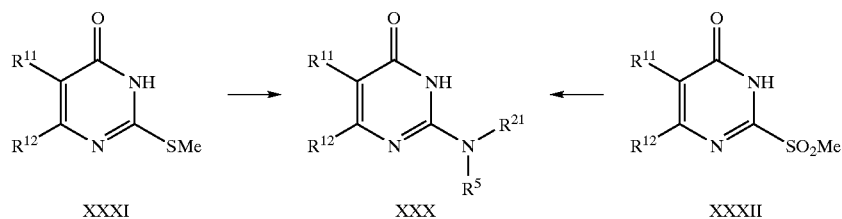

Amines of formula NHR$^5$R$^{21}$ are commercially available or can be readily prepared by those skilled in the art from commercially available starting materials. For example, an amide, nitro or cyano group can be reduced under reducing conditions, such as in the presence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like substituted glycine, β-alanine and the like) using methods well known in the art, such as H. Brunner, P. Hankofer, U. Holzinger, B. Treittinger and H. Schoenenberger, Eur. J. Med. Chem. 25, 35–44, 1990; M. Freiberger and R. B. Hasbrouck, J. Am. Chem. Soc. 82, 696–698, 1960; Dornow and Fust, Chem. Ber. 87, 984, 1954; M. Kojima and J. Fujita, Bull. Chem. Soc. Jpn. 55, 1454–1459, 1982; W. Wheeler and D. O'Bannon, Journal of Labelled Compounds and Radiopharmaceuticals XXXI, 306, 1992; and S. Davies, N. Garrido, O. Ichihara and I. Walters, J. Chem. Soc., Chem. Commun. 1153, 1993.

Scheme 10

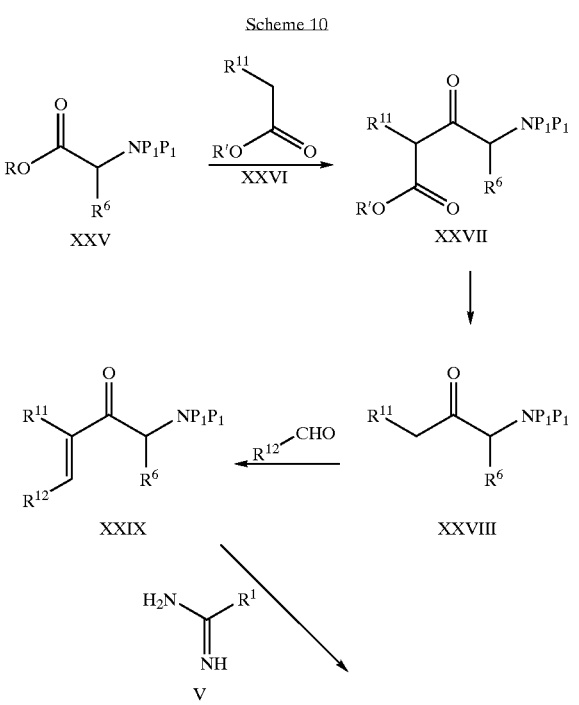

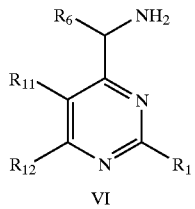

For the synthesis of aminomethyl-4(3H)-pyrimidines VI, the approach displayed in Scheme 10 may be followed. This approach involves the Claisen Condensation of amino ester XXV, wherein —NP$_1$P$_1$ represents an appropriately protected amino group, with the R$^{11}$ substituted acetate XXVI to form the keto ester XXVII which upon hydrolysis and decarboxylation forms the amino ketone XXVIII. The Claisen-Schmidt Condensation of amino ketone XXVIII with the aldehyde R$^{12}$—CHO forms the vinyl ketone XXIX. The Michael Reaction between vinyl ketone XXIX and amidine V in the presence of base followed by cyclization in the presence of POCl$_3$ or the like, followed by oxidation (e.g., MnO$_2$ or the like) and deprotection of the amine can form the 4(3H)-pyrimidine VI (see Synlett 756–758, 1999). Alternatively, condensation and cyclization of vinyl ketone XXIX and the aldehyde R$^1$—CHO in the presence of ammonium acetate followed by oxidation (e.g., MnO$_2$ or the like) can form the 4(3H)-pyrimidine VI (see Pharmazie 53:843–847, 1998; Pharmazie 54:35–41, 1999).

Pyridines:

As displayed in Scheme 11, a suitable route to 2(1H)-pyridones III involves the cyclization reaction between an a,b-unsaturated ketone XXII and a sufficiently reactive, substituted acetamide in the presence of base (El-Rayyes and Al-Hajjar, J. Heterocycl. Chem. 21, 1473 (1984)) and subsequent dehydrogenation.

Scheme 11

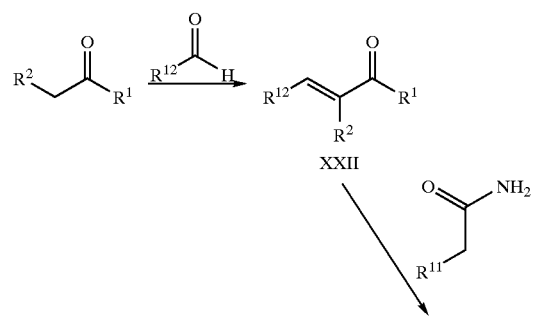

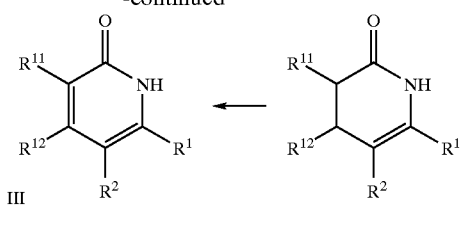

Accordingly (Scheme 12), pyridine-4-carboxaldehyde or other heteroaromatic carboxaldehyde, like pyrimidine-4-carboxaldehydes or quinoline-4-carboxyaldehydes, may be reacted with $R^2CH_2C(O)R^1$ in the presence of piperidine/acetic acid at elevated temperature (Bayer and Hartmann, Arch. Pharm. (Weinheim) 324, 815 (1991)) as well as pinacolone ($CH_3$—CO—$C(CH_3)_3$) in the presence of sodium hydroxide to provide the unsaturated ketone XXII. The reaction of XXII with phenylacetamide in the presence of sodium ethoxide then may lead via the 3,4-dihydropyridone to 6-substituted 3-phenyl-4-(heteroaryl)-2(1H)-pyridones of structure III.

Substituted halopyridines may be readily prepared from the corresponding pyridones using phosphorus oxychloride or pentachloride.

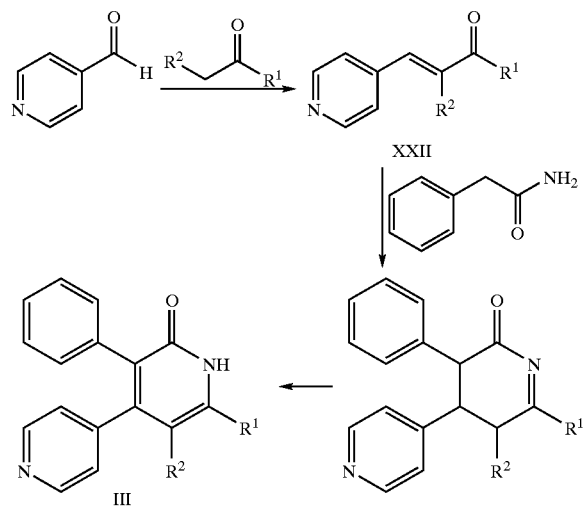

In Scheme 13, a feasible route is illustrated leading to 6-chloro-2(1H)-pyridone XXIV, a versatile intermediate for further modifications at the 6-position. This approach (G. Simchen, Chem. Ber. 103:389–397, 1970) is based on the conversion of the unsaturated cyanocarboxylic acid chloride XXIII into XXIV in the presence of hydrogen chloride.

Reaction of XXIV with ammonia (Katritzky and Rachwal, J. Heterocyclic Chem. 32, 1007 (1995)), primary and secondary amines would lead to 2-amino substituted pyridones III. Furthermore, XXIV may be reacted in a palladium or nickel catalyzed cross-coupling reaction with an alkyl, cycloalkyl, heteroaryl or aryl boronic acid or an alkyl, cycloalkyl, heteroaryl or aryl zinc halide to provide pyridone III wherein $R^3$ is alkyl, cycloalkyl, heteroaryl or aryl.

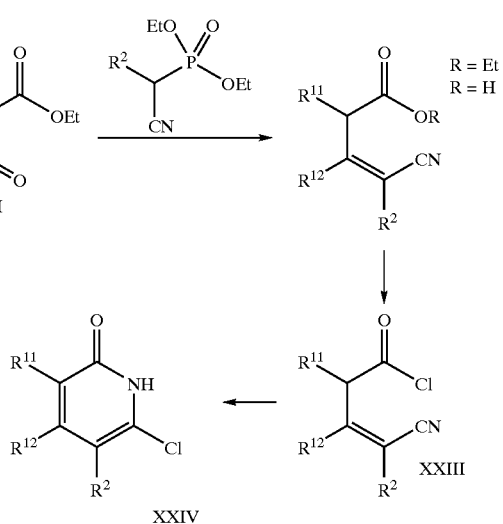

Pyridone III may be substituted at the N-1 position by reaction with, e.g., an alkyl halide in the presence of an appropriate base such as potassium carbonate.

For the synthesis of aminomethyl-pyridines VI, the approach displayed in Scheme 14 may be followed. This approach involves the Claisen Condensation of amino ester XXV, wherein —$NP_1P_1$ represents an appropriately protected amino group, with the $R^{11}$ substituted acetate XXVI to form the keto ester XXVII. The Michael Reaction between the keto ester XXVII and the vinyl ketone $R^{12}CH=C(R^2)$—$C(O)R^1$ in the presence of base, such as methoxide or the like, can form the diketo ester XXXIII (see J. Chem. Soc., Perkin Trans. 1, 3141–3150, 1997; J. Indian Chem. Soc. 67:815–17, 1990). Hydrolysis of the ester followed by decarboxylation can form the diketone XXXIV. Ammonium acetate cyclization reaction of the diketone XXXIV followed by oxidation (e.g., $O_2$, $MnO_2$ or the like) can form pyridine XXXV (see J. Med. Chem. 34:2804–15, 1991; J. Chem. Res. Synop. (4), 180–181, 870–875, 1998; Tetrahedron Lett. 34:5063–6, 1993; Synth. Commun. 22:351–7, 1992). Alternatively, ammonium acetate cyclization reaction of the diketo ester XXXIII followed by ester hydrolysis, decarboxylation and oxidation (e.g., $MnO_2$ or the like) can form pyridine XXXV. Deprotection of the amine of pyridine XXXV then forms aminomethyl-pyridine VI.

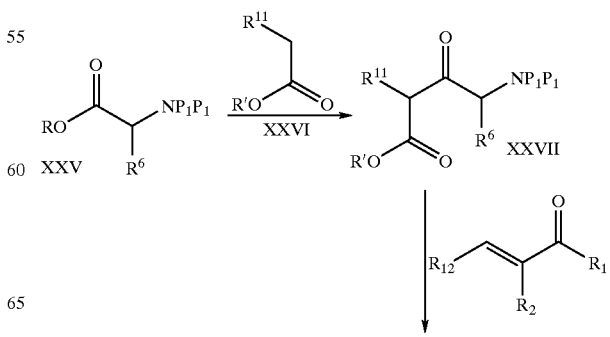

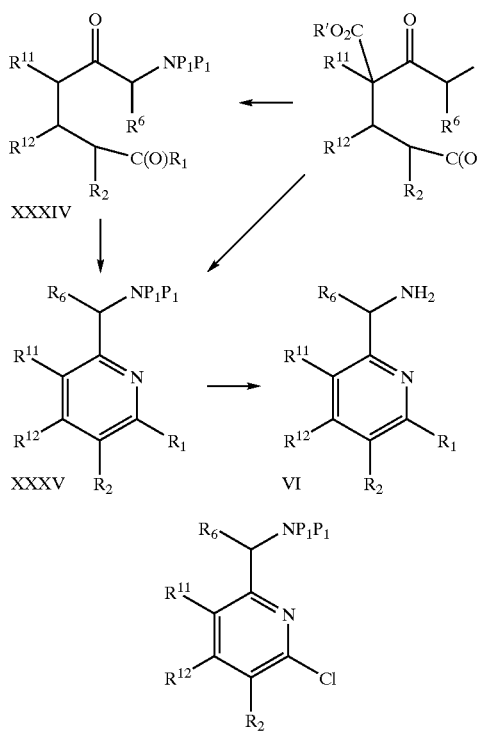

Alternatively, Michael Reaction of keto ester XXVII with $R^{12}CH=C(R^2)CN$ in the presence of base (Tetrahedron Lett. 34:4993–6, 1993; Tetrahedron 54:9079–9088, 1998) followed by cyclization in the presence of POCl₃ (U.S. Pat. No. 5,229,519; Khim. Geterotsikl. Soedin. 514–19, 1989) and oxidation (e.g., $O_2$, $MnO_2$ or the like) can form the intermediate XXXVI which can be reacted to form aminomethyl-pyridine VI as described above for XXIV.

Indolizine-like Compounds:

Alternatively, substituted indolizine-like compounds I embodied in the current invention may be prepared as shown in Schemes 15 and 16.

Scheme 15

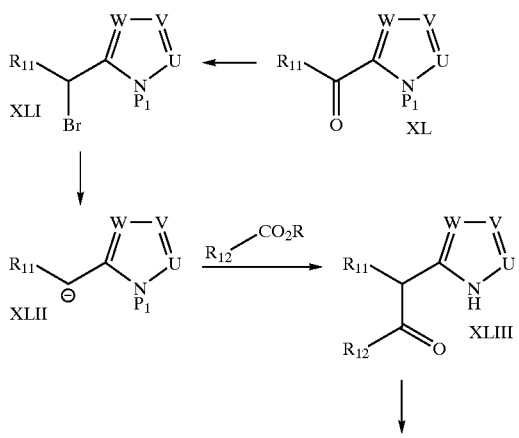

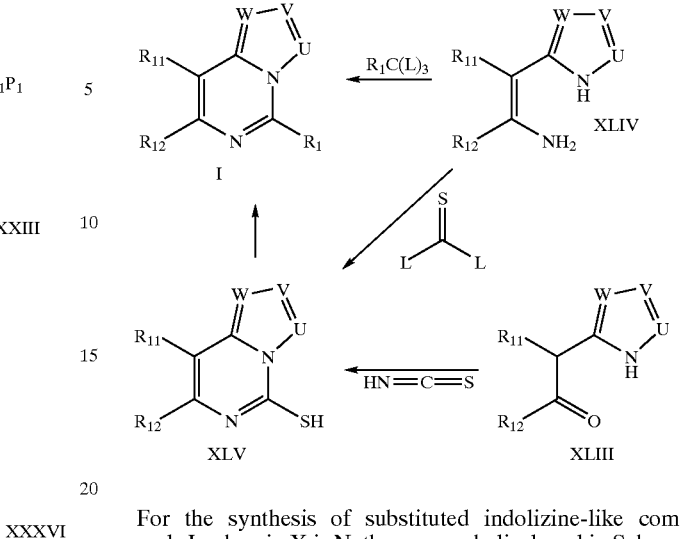

For the synthesis of substituted indolizine-like compounds I, wherein X is N, the approach displayed in Scheme 15 may be followed. This approach involves the conversion of the ketone XL into halo compound XLI (chloro, bromo or iodo) by reduction of ketone XL to a hydroxy group with a reducing agent, such as sodium cyanoborohydride or the like, followed by conversion of the hydroxy group to a halo group, such a bromo or the like, with POCl₃, POBr₃, PBr₅ and the like. Halo compound XLI is converted into an organometallic reagent anion XLII, such as with zinc, copper, magnesium, lithium and the like, which is reacted with $R_{12}$—CO₂R followed by deprotection of the ring nitrogen to form ketone XLIII. Ketone XLIII is converted into enamine XLIV using standard methods well known to those skilled in the art, such as reaction with ammonium acetate and the like. Alternatively, organometallic reagent anion XLII can be reacted with $R_{12}$—CN to form enamine XLIV directly followed by deprotection of the ring nitrogen. Cyclization reaction of enamine XLIV with $R_1C(L)_3$, such as $R_1C(OEt)_3$ and the like, can form substituted indolizine-like compounds I (see Synth. Commun. 29:2617–2624, 1999; J. Heterocycl. Chem. 23:1829–31, 1986; Monatsh. Chem. 127:955–962, 1996; J. Heterocycl. Chem. 26:613–18, 1989; Chem. Heterocycl. Compd. (N.Y.), 1997, 33:854–856, 1998).

Alternatively, enamine XLIV can be reacted with $C(S)L_2$ and the like to form thiol XLV which can be converted into substituted indolizine-like compounds I using the processes and reagents described above. Alternatively, enamine XLIV can be reacted with $C(O)L_2$ and the like to form a hydroxy group in place of the thiol in XLV which can be converted into substituted indolizine-like compounds I using the processes and reagents described above or by first converting the hydroxy group into a leaving group, such as a chloro, bromo or the like group which can be converted into substituted indolizine-like compounds I using the processes and reagents described above. Alternatively, ketone XLIII can be reacted with HN=C=S to form the thiol XLV or with HN=C=O to form the corresponding hydroxy compound.

Ketone XL can be readily prepared by acylation reaction of the five membered ring heteroaryl (with or without the protecting group) with $R_{11}$—C(O)Cl or the like (see Heterocycles 27:1855–60, 1988; J. Org. Chem. 65:7323–7344, 2000; J. Org. Chem. 65:7323–7344, 2000; Synthesis 1291–1294, 2000; J. Heterocycl. Chem. 26:1563–8, 1989; Tetrahedron Lett. 30:2411–12, 1989; J. Heterocycl. Chem.

27:673–8, 1990; Synth. Commun. 20:321–31, 1990; Bioorg. Med. Chem. Lett. 10:1935–1938, 2000; J. Chem. Soc., Perkin Trans. 1, (6), 1139–45, 1989).

Scheme 16

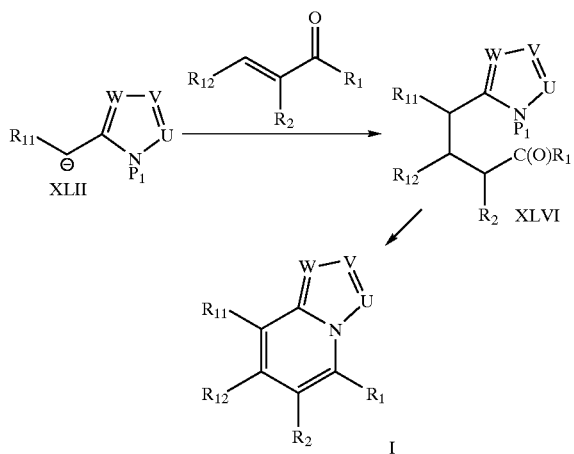

For the synthesis of substituted indolizine-like compounds I, wherein X is C—R$_2$, the approach displayed in Scheme 16 may be followed. This approach involves the Michael Reaction of organometallic reagent anion XLII with R$_{12}$CH═C(R$_2$)—C(O)R$_1$ as described above to from ketone XLVI. Deprotection of the ring nitrogen followed by cyclication and oxidation (e.g., O$_2$, MnO$_2$ or the like) can form substituted indolizine-like compounds I.

Amines of formula NHR$_5$R$_{21}$, NHR$_{31}$R$_{32}$ and NHR$_{41}$R$_{42}$ are commercially available br can be readily prepared by those skilled in the art from commercially available starting materials. For example, an amide, nitro or cyano group can be reduced under reducing conditions, such as in the presence of a reducing agent like lithium aluminum hydride and the like, to form the corresponding amine. Alkylation and acylation of amino groups are well known in the art. Chiral and achiral substituted amines can be prepared from chiral amino acids and amino acid amides (for example, alkyl, aryl, heteroaryl, cycloalkyl, arylalkyl, heteroarylalkyl, cycloalkylalkyl and the like) using methods well known in the art, such as H. Brunner, P. Hankofer, U. Holzinger, B. Treittinger and H. Schoenenberger, Eur. J. Med. Chem. 25, 35–44, 1990; M. Freiberger and R. B. Hasbrouck, J. Am. Chem. Soc. 82, 696–698, 1960; Dornow and Fust, Chem. Ber. 87, 984, 1954; M. Kojima and J. Fujita, Bull. Chem. Soc. Jpn. 55, 1454–1459, 1982; W. Wheeler and D. O'Bannon, Journal of Labelled Compounds and Radiopharmaceuticals XXXI, 306, 1992; and S. Davies, N. Garrido, O. Ichihara and I. Walters, J. Chem. Soc., Chem. Commun. 1153, 1993.

Alkyl sulfonic acids, aryl sulfonic acids, heterocyclyl sulfonic acids, heteroaryl sulfonic acids, alkylmercaptans, arylmercaptans, heterocyclylmercaptans, heteroarylmercaptans, alkylhalides, arylhalides, heterocyclylhalides, heteroarylhalides, and the like are commercially available or can be readily prepared from starting materials commercially available using standard methods well known in the art.

Thioether derivatives can be converted into the corresponding sulfone or sulfoxide by oxidizing the thioether derivative with a suitable oxidation agent in a suitable solvent. Suitable oxidation agents include, for example, hydrogen peroxide, sodium meta-perborate, oxone (potassium peroxy monosulfate), meta-chloroperoxybenzoic acid, periodic acid and the like, including mixtures thereof. Suitable solvents include acetic acid (for sodium meta-perborate) and, for other peracids, ethers such as THF and dioxane, and acetonitrile, DMF and the like, including mixtures thereof.

The chemical reactions described above are generally disclosed in terms of their broadest application to the preparation of the compounds of this invention. Occasionally, the reactions may not be applicable as described to each compound included within the disclosed scope. The compounds for which this occurs will be readily recognized by those skilled in the art. In all such cases, either the reactions can be successfully performed by conventional modifications known to those skilled in the art, e.g., by appropriate protection of interfering groups, by changing to alternative conventional reagents, by routine modification of reaction conditions, and the like, or other reactions disclosed herein or otherwise conventional, will be applicable to the preparation of the corresponding compounds of this invention. In all preparative methods, all starting materials are known or readily prepared from known starting materials.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. The following Examples are presented for illustrative purposes only and are not intended, nor should they be construed, as limiting the invention in any manner. Those skilled in the art will appreciate that modifications and variations of the compounds disclosed herein can be made without violating the spirit or scope of the present invention.

POCl$_3$ is phosphorous oxychloride. TFA is trifluoroacetic acid, DMF is dimethylformide, DCM is dichloromethane, BINAP is rcc-2,2'-bis(diphenylphosphino)-1,1'-binaphthyl, Boc is t-butoxycarbonyl (t-C$_4$H$_9$OCO—), Me is methyl, Et is ethyl, iPr is isopropyl. Heat, as used herein, means elevated temperature, such as 40 to 250° C. Those skilled in the art will recognize that in certain instances it will be necessary to utilize different solvents or reagents to achieve some of the above transformations.

Synthesis of 3-methyl-2-methylsulfanyl-5-naphthalen-2-yl-6-pyridin-4-yl-3H-pyrimidin-4-one

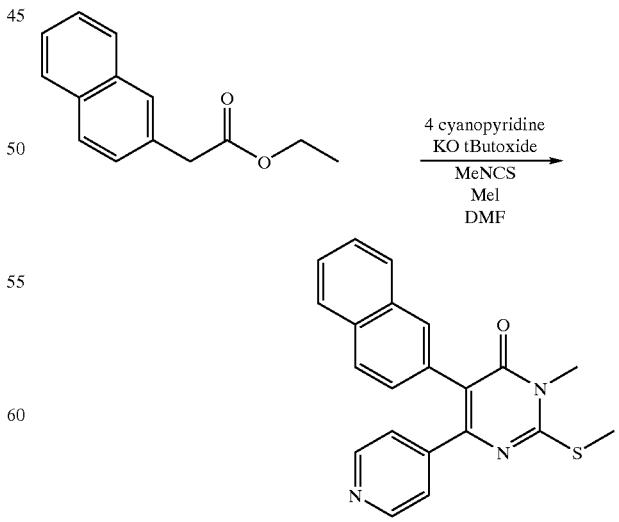

4-Cyanopyridine (83.9 g, 805.5 mmol) was added to a stirring solution of naphthyl acetic acid ethyl ester (172.6 g, 805.5 mmol) in DMF (800 mL) in a 5 L round bottom flask with a stir bar. Using an addition funnel, 1M solution of Potassium t-Butoxide (805.5 mL) is added dropwise. The resulting red/brown solution is stirred at room temperature for 2 hours. A solution of methyl thioisocyanate (58.9 g, 805.5 mmol) in DMF (400 mL) is added to the reaction dropwise. The reaction is then heated to 45° C. for 2 hours. The vessel is then cooled to approximately 0° C. with an ice bath. Upon reaching that temperature ice bath is removed and a dilute solution of methyl iodide (114.3 g, 805.5 mmol) in DMF (300 mL) is added dropwise to the reaction. It is allowed to stir vigorously for 14 h. Workup: The volume is increased 3–4 fold with water and stirred vigorously for 2–4 hours till solids appear. The solids are filtered through a coarse fritted funnel and washed with copious amounts of water. The filtered solids are collected and stirred in ethyl acetate for 1 hour and filtered through a medium fritted funnel. At this time solids are washed with ethyl ether and collected. TLC (4% MeOH/CHCl$_3$) indicated only one compound—3-Methyl-2-methylsulfanyl-5-naphthalen-2-yl-6-pyridin-4-yl-3H-pyrimidin-4-one.

Synthesis of 4-chloro-5-(naphthyl)-2-methylthio-6-(4-pyridyl)pyrimidine

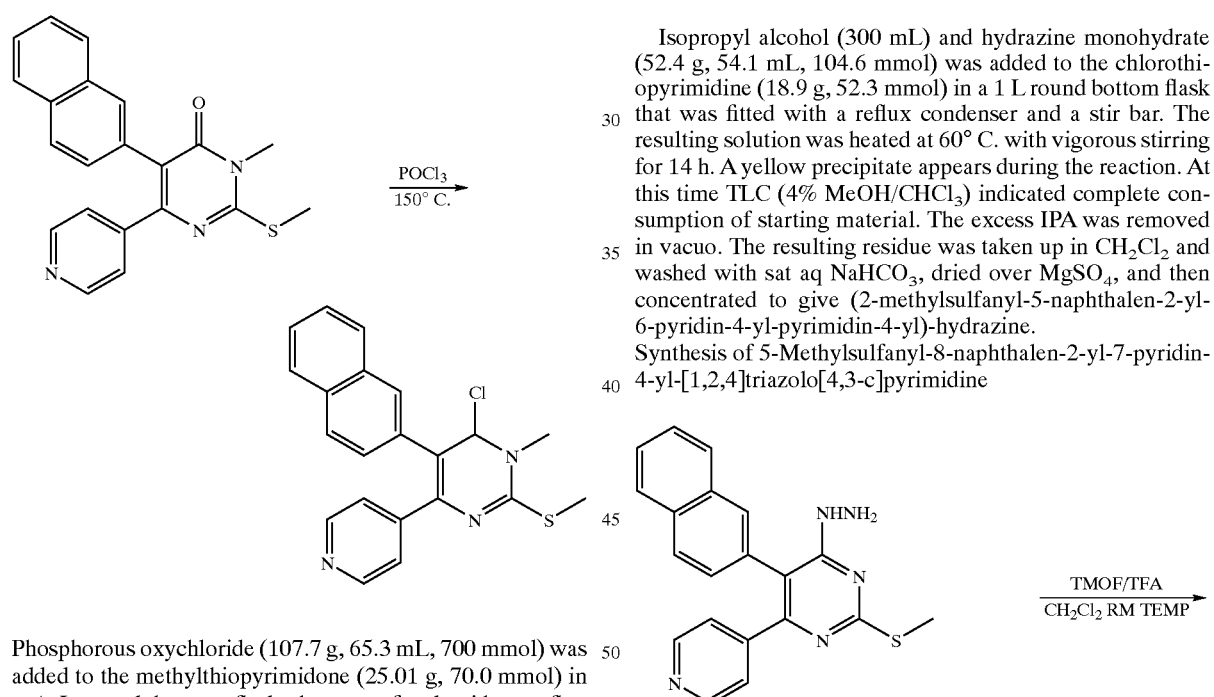

Phosphorous oxychloride (107.7 g, 65.3 mL, 700 mmol) was added to the methylthiopyrimidone (25.01 g, 70.0 mmol) in a 1 L round bottom flask that was fitted with a reflux condenser and a stir bar. The resulting solution was heated at 150° C. with vigorous stirring for 14 h. At this time TLC (4% MeOH/CHCl$_3$) indicated complete consumption of starting material. The mixture was then cooled to room temperature and the excess POCl$_3$ was removed in vacuo. The residue was repeatedly dissolved in toluene and then concentrated (4×50 mL of toluene) to effect azeotropic removal of trace POCl$_3$. The residue was taken up in CH$_2$Cl$_2$ and absorbed onto 30 g silica gel. The resulting slurry was dried in vacuo, loaded onto a short column of silica, then eluted with 2.5% MeOH/CHCl$_3$. The initially eluted fractions contained the desired product (TLC). Product-containing fractions were collected and then concentrated to provide 4-chloro-5-(naphthyl)-2-methylthio-6-(4-pyridyl) pyrimidine as a yellow/brown oil.

Synthesis of (2-methylsulfanyl-5-naphthalen-2-yl-6-pyridin-4-yl-pyrimidin-4-yl)-hydrazine

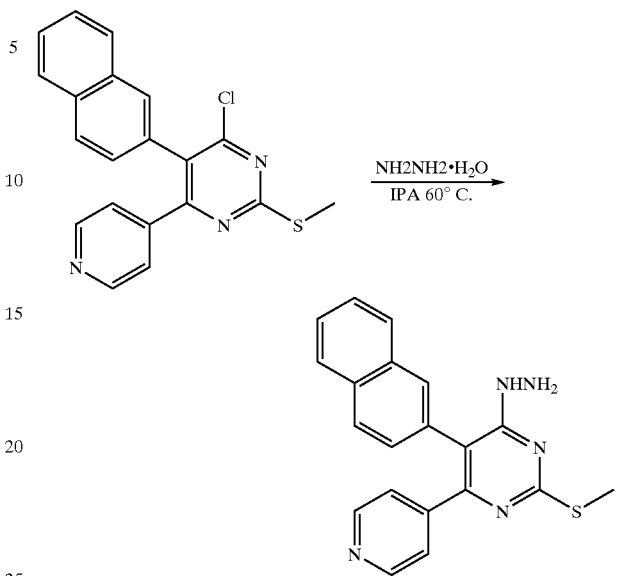

Isopropyl alcohol (300 mL) and hydrazine monohydrate (52.4 g, 54.1 mL, 104.6 mmol) was added to the chlorothiopyrimidine (18.9 g, 52.3 mmol) in a 1 L round bottom flask that was fitted with a reflux condenser and a stir bar. The resulting solution was heated at 60° C. with vigorous stirring for 14 h. A yellow precipitate appears during the reaction. At this time TLC (4% MeOH/CHCl$_3$) indicated complete consumption of starting material. The excess IPA was removed in vacuo. The resulting residue was taken up in CH$_2$Cl$_2$ and washed with sat aq NaHCO$_3$, dried over MgSO$_4$, and then concentrated to give (2-methylsulfanyl-5-naphthalen-2-yl-6-pyridin-4-yl-pyrimidin-4-yl)-hydrazine.

Synthesis of 5-Methylsulfanyl-8-naphthalen-2-yl-7-pyridin-4-yl-[1,2,4]triazolo[4,3-c]pyrimidine Methylene chloride (300 mL) and trimethyl orthoformate (16.7 g, 16.2 mL, 156.9 mmol) was added to the hydrazinethiopyrimidine (18.9 g, 52.3 mmol) in a 1 L round bottom flask and a stir bar. After 1 h, trifluoroacetic acid (5.96 g, 4.02 mL, 52.3 mmol) is added to the stirring solution. A yellow precipitate crashes out overnight. At this time TLC (4% MeOH/CHCl₃) indicated complete consumption of starting material. The resulting solution is poured into sat aq NaHCO₃ to quench the TFA. The organic layer was collected and washed with sat aq NaHCO₃, dried over MgSO₄, and then concentrated. The residue is taken up in a minimal amount of methylene chloride (50–75 mL) and a large amount of ethyl ether (500 mL) is slowly added until an yellow/orange solid precipitates out of the solution. The slurry is filtered and solid collected. The filtrate is concentrated and the previous step is repeated to give 5-methylsulfanyl-8-naphthalen-2-yl-7-pyridin-4-yl-[1,2,4]triazolo[4,3-c]pyrimidine.

EXAMPLE 1

The following amines were prepared as intermediates and may be used to obtain compounds claimed within the scope of this invention.

EXAMPLE 1A

Procedure for the Preparation of 3-phenylbutylamine

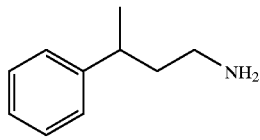

A mixture of 3-phenylbutyraldehyde (3 ml, 20.18 mmol), ammonium acetate (15 g, 195 mmol) and sodium cyanoborohydride (900 mg, 14.32 mmol) in methanol (50 ml) was stirred overnight under an argon atmosphere. The reaction was acidified to pH 2 by the addition of conc. HCl. The solvent was evaporated, dichloromethane and water were added, and the aqueous layer was made basic (pH 12) by the addition of solid potassium hydroxide. Extraction (dichloromethane) and concentration gave the title compound as an oil. ES-MS (m/z): 150.2 (M+H)$^+$; $^1$H NMR (CDCl₃): d 7.40–7.17 (m, 5H, Ph), 2.81 (q, 1H, CH), 2.62 (m, 2H, CH₂), 1.76 (dq, 2H, CH₂), 1.29 (d, 3H, CH₃).

EXAMPLE 1B

Procedure for the Preparation of 3-(2-methylphenyl)propylamine

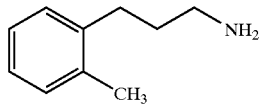

Diethyl cyanomethylphosphonate (5.0 ml, 30.9 mmol) was added to a stirring suspension of sodium hydride (60% oily suspension, 1.24 g, 31 mmol) in tetrahydrofuran (50 ml) under argon. After 30 min, 2-methylbenzaldehyde (3.6 ml, 31.1 mmol) was added and stirring continued for 1 h. The reaction was quenched by the addition of water and extracted with dichloromethane followed by drying and evaporation of the organic solution. Column chromatography (hexane; hexane:ethylacetate=3:1) provided 2-(2-methylphenyl)acrylonitrile as an oil. This material (3.8 g), 10% palladium on carbon (3.8 g) and 12 N hydrochloric acid (11.8 ml, 142 mmol) in methanol (125 ml) were hydrogenated with hydrogen at atmospheric pressure for 2 d. The catalyst was removed by filtration and the solvent was evaporated. The resultant material was partitioned between dichloromethane and water. The aqueous layer was made basic with 10 N sodium hydroxide and extracted with dichloromethane, followed by drying and evaporation. The resultant material was purified on a silica gel column (chloroform:methanol:triethylamine=85:10:5) to provide the title compound as an oil.

EXAMPLE 1C

Procedure for the Preparation of 2-Methyl-3-phenylpropylamine

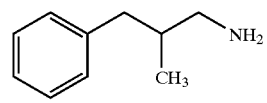

A mixture of commercially available 2-methyl-3-phenylpropylamide (4.32 g, 26.5 mmol) and lithium aluminum hydride (1.3 g, 34.3 mmol) in tetrahydrofuran (184 ml) was stirred at room temperature for 5 h. The reaction mixture was poured into saturated aqueous sodium sulfate and extracted with dichloromethane followed. The combined organic extracts were dried (sodium sulfate) and evaporated to provide the amine as an oil. For alternative preparations see: Dornow and Fust, Chem. Ber. 87, 984 (1954).

EXAMPLE 1D

Procedure for the Preparation of 3-Fluoro-3-phenylpropylamine

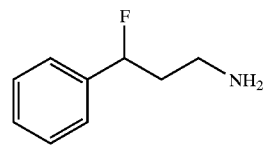

Step A. 3-Hydroxy-3-phenylpropionitrile: Sodium borohydride (1.4 g, 37.00 mmol) was added in portions to a stirring solution of benzoylacetonitrile (10 g, 68.90 mmol) in methanol (200 ml) at ice-bath temperature. After 30 min, the reaction was quenched by the addition of a few drops of acetic acid followed by evaporation. The mixture was partitioned between dichloromethane and water and the combined organic extracts were dried (magnesium, sulfate) and evaporated to provide the Step A compound as a syrup. (cf. Florin, C.; Chantegrel, J.; Charlon, C.; Marsura, A.; Luu-Duc, C. Nouvelle voie de synthese des a-fluorophenylacetonitriles. *Ann. pharmaceuttiques fr.* 1985, 43, 595–599.)

Step B. 3-Fluoro-3-phenylpropionitrile: A solution of 3-hydroxy-3-phenylpropionitrile (3.5 g, 23.8 mmol) in dichloromethane (20 ml) was added at −78° C. to a stirred solution of diethylaminosulfur trifluoride (5 g, 31 mmol) in dichloromethane (23 ml). After 1.5 h, the mixture was allowed to reach room temperature. The reaction was quenched by the addition of water, followed by extraction with dichloromethane, drying of the organic phase and evaporation. Flash chromatography on a column of silica gel (hexane-ethyl acetate=5:1) provided 3-fluoro-3-phenylpropionitrile. $^1$H NMR (CDCl₃): d 7.50–7.29 (m, 5H, Ph), 5.73 (dt, 1H, $J_{H,F}$46.2 Hz, CHF), 3.00 and 2.96 (dd, t, each 1H, CH₂).

Step C. 3-Fluoro-3-phenylpropylamine: A 2N borane-dimethyl sulfide complex solution in tetrahydrofuran (8.8 ml, 17.6 mmol) was added dropwise at room temperature to a stirred solution of 3-fluoro-3-phenylpropionitrile (2 g, 13.41 mmol) in tetrahydrofuran (12 ml). The mixture was warmed to 50° C., the dimethylsulfide was distilled off, and the mixture was then refluxed for 2.5 h. After cooling to 0° C., 1N methanolic hydrogen chloride (20 ml) was added, and the mixture was concentrated. To the resulting concentrate was added dichloromethane and water, and solid potassium hydroxide was added to achieve a pH of approximately 12. Extraction (dichloromethane) and concentration gave the crude product as a mixture of phenylpropylamine and 3-fluoro-3-phenylpropylamine. Column chromatography on a column of Iatrobeads$^R$ (chloroform-methanol-triethylamine=90:7:3) provided the title compound 3-fluoro-3-phenylpropylamine in the first fraction. ES-MS (m/z): 154.0 (M+H)$^+$; $^1$H NMR (CDCl$_3$): d 7.45–7.28 (m, 5H, Ph), 5.60 (ddd, 1H, $J_{H,F}$ 48.2 Hz, CHF), 2.91 (t, 2H, CH$_2$N), 2.15 and 1.96 (2 m, each 1H, CH$_2$).

EXAMPLE 1E

Procedure for the Preparation of 2-Fluoro-3-phenylpropylamine

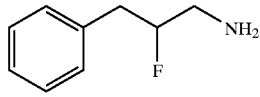

Step A. 1-Azido-2-hydroxy-3-phenylpropane: A mixture of (2,3-epoxypropyl)benzene (9.69 g, 72.22 mmol), sodium azide (16.5 g, 253.8 mmol) and ammonium chloride (6.3 g, 109.5 mmol) in methanol (190 ml) and water (32 ml) was heated at reflux for 1.5 h. The solvent was evaporated, the remainder was partitioned between dichloromethane and water. The organic solution was dried and evaporated to give the Step A compound as an MS (m/z): 178.1 (M+H)$^+$; $^1$H NMR (CDCl$_3$): d 7.43–7.15 (m, 5H, Ph), 4.08 (m, 1H, CH), 3.41 and 3.32 (2 dd, each 1H, CH$_2$), 2.85 and 2.83 (2 d, each 1H, CH$_2$), 1.98 (bs, OH).

Step B. 1-Azido-2-fluoro-3-phenylpropane: A solution of 1-azido-2-hydroxy-3-phenylpropane (3.5 g, 19.75 mmol) in dichloromethane (23 ml) was added at –78° C. to a stirred solution of diethylaminosulfur trifluoride (3.4 ml, 25.74 mmol) in dichloromethane (23 ml). The mixture was slowly warmed to room temperature over 2.5 h. The reaction was quenched by the addition of water, and extracted with dichloromethane. Concentration and purification by flash chromatography on a column of silica gel (hexane-ethyl acetate=8:1 to 6:1:1) provided 1-Azido-2-fluoro-3-phenylpropane as an oil. $^1$H NMR (CDCl$_3$): d 7.46–7.20 (m, 5H, Ph), 4.86 (m, 1H, $J_{H,F}$ 48.2 Hz, CHF), 3.41 (m, 2H, CH$_2$), 3.04 (m, 2H, CH$_2$).

Step C. 2-Fluoro-3-phenylpropylamine: A mixture of 1-azido-2-fluoro-3-phenylpropane (900 mg, 5.0 mmol) and 20% palladium-on-carbon (wet, 50%, 500 mg) in methanol (40 ml) was hydrogenated under a balloon of hydrogen for 2 h. The catalyst was removed by filtration and the solvent was evaporated. The resultant product was purified on a short column of Iatrobeads$^R$ (chloroform-methanol-triethylamine=90:7:1) to provide the title compound as an oil. ES-MS (m/z): 153.9 (M+H)$^+$; $^1$H NMR (CDCl$_3$): d 7.40–7.22 (m, 5H, Ph), 4.68 (m, 1H, $J_{H,F}$ 48.7 Hz, CHF), 3.11–2.83 (m, 4H, 2CH$_2$).

EXAMPLE 1F

Procedure for the Preparation of 2-amino-3-(2-fluorophenyl)-propylamine

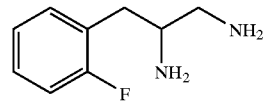

Step A. Methyl 2-amino-3-(2-fluorophenyl)propionate: 5 g (27.3 mmol) of (D,L)-(2-fluoro-phenyl)alanine was suspended in 50 ml methanolic HCl and stirred at room temperature for 3 days. The reaction mixture was concentrated in vacuo and dried to give a yellow oil. MS (m/z): 198 (M+H)$^+$; C$_{10}$H$_{12}$FNO$_2$ requir. 197.2.

Step B. 2-Amino-3-(2-fluorophenyl)propionamide: Methyl 2-amino-3-(2-fluorophenyl)propionate was suspended in 50 ml 30% ammonium hydroxide and stirred at room temperature for 18 hrs. The mixture was filtered, washed with cold water and 2-amino-3-(2-fluorophenyl)propionamide was collected as a white solid. MS (m/z): 183.1 (M+H)$^+$; C$_9$H$_{11}$FN$_2$O requir. 182.2.

Step C. 2-Amino-3-(2-fluorophenyl)-propylamine: 2-Amino-3-(2-fluorophenyl)propionamide was added carefully to a chilled (5°) mixture of LAH (1.0 g, 26.3 mmol) and 20 ml THF under argon. The reaction was then heated at reflux for 10 hrs. The reaction was cooled to 5° C. and carefully treated with Na$_2$SO$_4$.10 H$_2$O. The resulting mixture was stirred for 18 hrs, then filtered to remove the solids. The filtrate was concentrated in vacuo to give an amber oil. MS (m/z): 169 (M+H)$^+$; C$_9$H$_{13}$FN$_2$ requir. 168.19

EXAMPLE 1G

Procedure for the Preparation of 2-Amino-2-methyl-3-phenylpropylamine

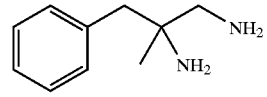

Step A: D,L-α-methyl phenylalanine amide: A solution of commercially available D,L-α-methyl phenylalanine methyl ester (5.0 g, 25.7 mmol) in aqu. 28% ammonium hydroxide (50 ml) was kept at room temperature for 3 d. The resulting white precipitate of D,L-α-methyl phenylalanine amide was filtered and dried.

Step B: 2-Amino-2-methyl-3-phenylpropylamine: D,L-α-methyl phenylalanine amide (2.0 g, 11.22 mmol) was reduced with lithium aluminum hydride (1.3 g, 34.26 mmol) in boiling tetrahydrofuran for 24 h. The reaction was quenched by the addition of sodium sulfate decahydrate at ice-bath temperature. The salts were filtered off, followed by evaporation to leave the title compound as an oil. MS (m/z): 165.1 (M+H)$^+$; C$_{10}$H$_{16}$N$_2$ requir. 164.2. An alternative preparation was reported by M. Freiberger and R. B. Hasbrouck, J. Am. Chem. Soc. 82, 696–698 (1960).

EXAMPLE 1H

Procedure for the Preparation of (S)-1,2-benzylethylenediamine

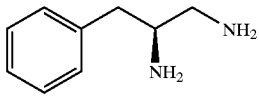

(S)-1,2-Benzylethylendiamine was prepared according to the literature (H. Brunner, P. Hankofer, U. Holzinger, B. Treittinger and H. Schoenenberger, Eur. J. Med. Chem. 25, 35–44, (1990)) by reduction of L-phenylalanine amide with lithium aluminum hydride. The (R)-enantiomer was prepared in the same manner from D-phenylalanine amide.

EXAMPLE 1I

Procedure for the Preparation of (S)-2-N,N-Dimethylamino-3-phenylpropylamine

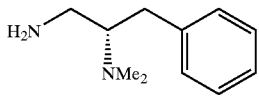

Sodium triacetoxyhydride (13.0 g, 61.3 mmol) was added to a stirring mixture of phenylalanine amide (3.6 g, 21.9 mmol) and 37% formaldehyde solution (4.4 ml, 58.7 mmol) in 1,2-dichloroethane (77 ml). After stirring for 2 h, the reaction was quenched by the addition of sat. aqu. sodium hydrogencarbonate. Then potassium hydroxide pellets were added followed by extraction with dichloromethane, drying of the organic solution and evaporation. The resulting (S)-2-N,N-dimethylamino-3-phenylpropylamide was reduced with lithium aluminum hydride according to the literature (H. Brunner, P. Hankofer, U. Holzinger, B. Treittinger and H. Schoenenberger, Eur. J. Med. Chem. 25, 35–44, (1990)) to provide the title compound.

EXAMPLE 1J

Procedure for the Preparation of (S)-2-N-Ethylamino-3-phenylpropylamine

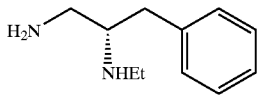

(S)-2-N-Ethylamino-3-phenylpropylamine: Acetic anhydride (1.2 ml, 12.7 mmol) was added to a stirring solution of L-phenylalanine amide (1.0 g, 6.10 mmol) in methanol (25 ml). After 1.5 h at room temperature, it was evaporated followed by drying in an oil pump vacuum. The resultant L-N-ethylphenylalanine amide (6.1 mmol) was reduced with lithium aluminum hydride (570 mg, 15.0 mmol) in tetrahydrofuran (65 mml) at 55° C. for 4 h. The reaction mixture was poured into sat. aqu. sodium hydrogencarbonate followed by extraction with dichloromethane, drying and evaporation. Column chromatography on silica gel (chloroform:methanol:triethylamine=90:7:3) provided the amine as a yellowish oil. MS (m/z): 179.1 (M+H)$^+$; $C_{11}H_{18}N_2$ requir. 178.3.

EXAMPLE 1K

Procedure for the Preparation of (S)-2-Benzylpiperazine

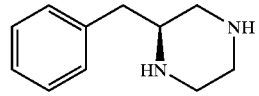

Lithium aluminum hydride (1.6 g, 42.16 mmol) was added in portions to a stirred mixture of (S)-2-benzyl piperazine-3,6-dione (3.0 g, 14.70 mmol) and tetrahydrofuran (80 ml) at 0° C. After 30 min at ice-bath temperature, the mixture was refluxed for 4 h with stirring. The reaction was quenched by the portionwise addition of sodium sulfate decahydrate and some methanol until hydrogen evolution ceased. It was filtered and the solids were washed several times with dichloromethane. The combined filtrates were evaporated to leave a white solid.

MS (m/z): 177.1 (M+H)$^+$; $C_{11}H_{16}N_2$ requir. 176.3.

EXAMPLE 1L

Procedure for the Preparation of ((S)-1,2,3,4-tetrahydroisoquinolin-3-ylmethyl)amine

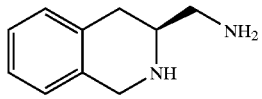

The title compound was obtained from the reduction of (S)-decahydroquinoline-3-carboxamides according to the procedure set forth in Example 1c. Alternatively the title compound may be prepared from (S)-decahydroquinoline-3-carboxylic acid using the procedures described in Example 1f.

EXAMPLE 1M

Procedure for the Preparation of 1-Phenyl-1,3-propanediamine

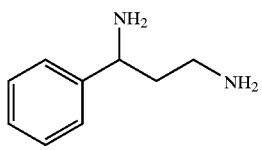

3-Phenyl-3-aminopropionic acid (S. G. Cohen and S. Y. Weinstein, J. Am. Chem. Soc. 86, 725–728, 1964) was converted into 1-phenyl-1,3-propanediamine as reported in the literature (M. Kojima and J. Fujita, Bull. Chem. Soc. Jpn. 55, 1454–1459 (1982)).

"R"=F, or Me, or Cl
Analogously, 1-(2-fluorophenyl)-1,3-propanediamine, 1-(2-methylphenyl)-1,3-propanediamine and 1-(2-chlorophenyl)-

1,3-propanediamine were prepared by using the above procedure and the appropriately substituted 3-phenyl-3-aminopropionic acid.

EXAMPLE 1N

Procedure for the Preparation of (S)-1-Phenyl-1,3-propanediamine

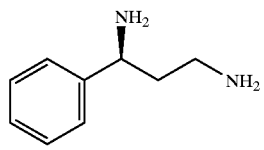

S-3-N-tert.-Butoxycarbonylamino-3-phenylpropionitrile was prepared according to the literature (W. J. Wheeler and D. D. O'Bannon, J. Label. Compds. Radiopharm. XXXI (4), 305–315, 1992) from D-(-)-α-phenylglycinol. For reduction (D. Mitchell and T. M. Koenig, Synth. Comm. 25 (8), 1231–1238, 1995), borane-methyl sulfide complex (2N, 3 ml, 6 mmol) was added dropwise to a solution of the nitrile (1 g, 4.06 mmol) in tetrahydrofuran (6 ml). Methyl sulfide was distilled off and the resulting solution refluxed for 2.5 h. With ice-cooling, methanolic hydrogen chloride (1N, 3 ml) was added followed by evaporation. The remainder was taken up in methanol (10 ml) and 4N hydrogen chloride/dioxane (10 ml) was added. After 1 h at room temperature, it was evaporated and the aqueous solution of the resultant product was washed with dichloromethane. The aqueous solution was made basic by the addition of solid potassium hydroxide followed by repeated dichloromethane extractions. Drying and evaporation of the dichloromethane solution left the crude diamine as an oil. MS (m/z): 150.8 (M+H)$^+$; C$_9$H$_{14}$N$_2$ requir. 150.2.

The enantiomer, (R)-1-phenyl-1,3-propanediamine, was prepared analogously from L-(+)-α-phenylglycinol. MS (m/z): 150.9 (M+H)$^+$; C$_9$H$_{14}$N$_2$ requir. 150.2.

EXAMPLE 1O

Procedure for the Preparation of (1R,2R)-2-methyl-1-phenyl-1,3-propanediamine

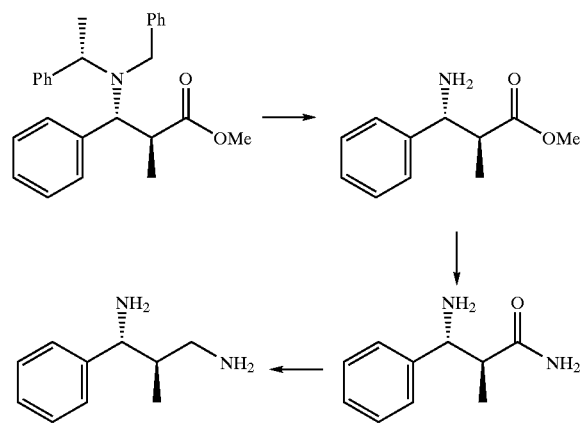

Step A: Methyl (2S,3R,αS)-3-(N-benzyl-N-α-methylbenzylamino)-2-methyl-3-phenylpropionate was prepared as reported for the 2R,3S,αR-enantiomer (S). G. Davies and I. A. S. Walters, J. Chem. Soc. Perkin Trans.1, 1129–1139 (1994).

Step B: Methyl (2S,3R)-3-amino-2-methyl-3-phenylpropionate: A mixture of methyl (2S,3R,αS)-3-(N-benzyl-N-α-methylbenzylamino)-2-methyl-3-phenylpropionate (13.0 g, 33.55 mmol) and 10% palladium-on-carbon (13.0 g) in glacial acetic acid (260 ml) was hydrogenated under a balloon of hydrogen for 24 h. The catalyst was removed by filtration followed by evaporation and co-distillation with toluene to provide the title compound as a white solid. MS (m/z): 194.2 (M+H)$^+$; C$_{11}$H$_{15}$NO$_2$ requir. 193.3.

Step C: (2S,3R)-3-Amino-2-methyl-3-phenylpropionamide: A solution of methyl (2S,3R)-3-amino-2-methyl-3-phenylpropionate (6.3 g, 33 mmol) in 2N methanolic ammonia (20 ml) and ammonium hydroxide (28–30%, 40 ml) was stirred at room temperature. After 4 d, concentration followed by chromatography on a short column of silica gel (dichloromethane-methanol-conc. ammonium hydroxide=93:7:0.7; 90:10:0.8) provided the amide as a white solid. MS (m/z): 179.2 (M+H)$^+$; C$_{10}$H$_{14}$N$_2$O requir. 178.2.

Step D: (1R,2R)-2-methyl-1-phenyl-1,3-propanediamine: Lithium aluminum hydride (2.3 g, 60.60 mmol) was added in portions to a stirring solution of (2S,3R)-3-amino-2-methyl-3-phenylpropionamide (2.6 g, 14.59 mmol) in tetrahydrofuran (54 ml) at ice-bath temperature. After 45 min, the mixture was heated at reflux for 16 h. With ice-bath cooling, the reaction was quenched by the portionwise addition of sodium sulfate decahydrate and some methanol until hydrogen evolution ceased. The solids were removed by filtration and washed with dichloromethane. The combined filtrates were evaporated to provide the title compound. MS (m/z): 165.2 (M+H)$^+$; C$_{10}$H$_{16}$N$_2$ requir. 164.3.

EXAMPLE 1P

Procedure for the Preparation of (1S,2S)-2-methyl-1-phenyl-1,3-propanediamine

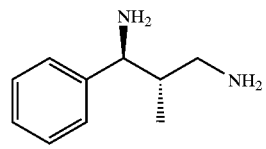

The title compound was prepared as described in the example for the synthesis of the enantiomer, (1R,2R)-2-methyl-1-phenyl-1,3-propanediamine, from methyl (2R,3S,αR)-3-(N-benzyl-N-α-methylbenzylamino)-2-methyl-3-phenylpropionate (Davies et al., J. Chem. Soc. Chem. Commun. 1153–1155, 1993). The title compound was obtained as a crystallizing oil, MS (m/z): 165.3 (M+H)$^+$; C$_{10}$H$_{16}$N$_2$ requir. 164.3.

EXAMPLE 1Q

Procedure for the Preparation of 3-phenyl-2,2-dimethyl-1,3-propanediamine

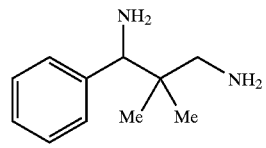

The title compound was prepared according to the procedure described in: W. Ten Hoeve and H. Wynberg, Synth.

Commun. 24 (15), 2215–2221, 1994, MS (m/z): 179.1 (M+H)$^+$; $C_{11}H_{18}N_2$ requir. 168.1

EXAMPLE 1R

Procedure for the Preparation of 3-phenyl-2,2-dimethyl-1-aminopropane

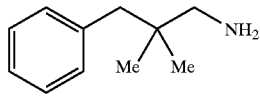

Step A: of 2,2-dimethyl-3-phenyl-1-azidopropane: Diisopropyl azodicarboxylate (19.7 mL, 100 mmol) was added dropwise to a stirred mixture of 2,2-dimethyl-3-phenyl-1-propanol (8.2 gm, 50 mmol), triphenylphosphine (26.2 gm, 100 mmol), and Zn(N$_3$)$_2$.2 pyridine (11.5 gm, 37.5 mmol) in toluene (250 mL) (reference: Synthesis, (1990) page 131). After 2.5 h, celite (25 gm) was added, and the mixture was filtered and concentrated to an oil. Purification (SiO$_2$, 40% EtOAc/hexanes) gave the step A product as an oil.

Step B: of 2,2-dimethyl-3-phenyl-1-aminopropane: A mixture of 2,2-dimethyl-3-phenyl-1-azidopropane (3 gm), 10% Pd—C, methanol (60 mL) and tetrahydrofuran (15 mL) was stirred under 1 atmosphere of hydrogen at RT for 18 h. The mixture was filtered and concentrated to give the title compound as an oil, MS (m/z): 164.1 (M+H)$^+$; $C_{11}H_{17}N$ requir. 163.1.

EXAMPLE 1S

Procedure for the Preparation of 1-(aminomethyl)-2-benzylcyclopentane

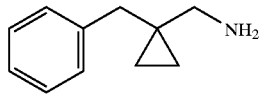

Step A: 1-benzyl-1-cyclopropanecarbonitrile: A solution of cyclopropyl cyanide (3.0 mL, 40 mmol) in 20 mL THF was dropwise added to a stirred, freshly prepared, mixture of lithium diisopropylamide (40 mmol) in THF (100 mL) at −78° C. After 30 min, a solution of benzyl bromide 7.8 mL, 60 mmol) in THF (20 mL) was dropwise added. The resulting mixture was warmed slowly over several hrs and stirred at rt 48 h. The reaction was quenched (250 mL saturated NH$_4$Cl, extracted with ether (3×100 mL) and the combined organic extracts were dried (MgSO$_4$), filtered and concentrated to afford a yellow oil.

Step B: 1-(aminomethyl)-2-benzylcyclopentane: A solution of 1-benzyl-1-cyclopropanecarbonitrile (9.16 gm, 58 mmol), 10% Pd—C (1.5 gm), in MeOH (200 mL), THF (50 mL), and conc. HCl (6 mL) was shaken under a hydrogen atmosphere (50 psi) for 15 h. The mixture was concentrated, water (300 mL0 was added and made basic (pH 10–11) with 2N NaOH. The mixture was extracted with EtOAc (2×100 mL), the combined organic layers were dried (MgSO$_4$), filtered and concentrated to provide the title compound.

EXAMPLE 2

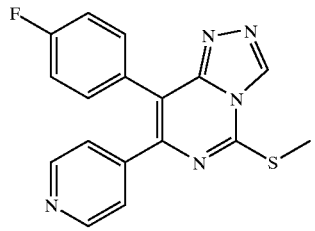

Preparation of 8-(4-fluorophenyl)-5-methylthio-7-(4-pyridyl)-1,2,4-triazolo[4,3-c]pyrimidine Step A: 5-(4-fluorophenyl)-3-methyl-2-methylthio-6-(4-pyridyl)-3H-pyrimidin-4-one A mixture of ethyl 2-(4-fluorophenyl)acetate (273 g, 1.5 mol) and 4-cyanopyridine (156.1 g, 1.5 mol) was dissolved in 1.5 L of DMF in a 12 L, 3-necked r.b.flask equipped with a mechanical stir, temperature probe and 1 L addition funnel. 1.5 L of 1.0M tBuOK/tBuOH (1.5 mol) was added into the solution slowly at RT through a 1L addition funnel. The resulting brown solution was stirred at RT for 1 h. A solution of 109.7 g of MeNCS (1.5 mol) in 750 ml DMF was added into the reaction solution slowly at RT. The temperature of the solution was increased from 26° C. to 33° C. The resulting brown solution was stirred for 1 h. The reaction solution was cooled down to ca. 0° C. using ice-water bath and 93 ml of MeI (1.5 mol) was added into the reaction solution through a 125-ml addition funnel. The reaction solution was stirred at RT and a precipitate formed after 30 min. The suspension was stirred at RT overnight. The solid was filtered off and washed with water (2×200 ml) and dried under vacuum at 50° C. overnight. 5-(4-fluorophenyl)-3-methyl-2-methylthio-6-(4-pyridyl)-3H-pyrimidin-4-one was obtained; MS: m/z (M+H)$^+$ 328; $C_{17}H_{14}FN_3OS$ requir. 327.

Step B: 4-chloro-5-(4-fluorophenyl)-2-methylthio-6-(4-pyridyl)pyrimidine 5-(4-fluorophenyl)-3-methyl-2-methylthio-6-(4-pyridyl)-3H-pyrimidin-4-one (0.327 g, 1 mmol) and 5 ml of POCl$_3$ in a 15-ml r.b.flask with a stir bar was stirred at 120° C. for 16 h. The remaining POCL$_3$ was evaporated in vacuo. The dark brown residue was mixed with ice-water. The resulting acidic dark brown solution was neutralized to pH 7–8 with sat'd NaHCO$_3$ and extracted by EtOAc (2×10 ml). The combined organic layers were washed with brine (10 ml) and dried over Na$_2$SO$_4$. 4-chloro-5-(4-fluorophenyl)-2-methylthio-6-(4-pyridyl)pyrimidine was isolated by flash chromatography with 50% EtOAc in hexane; MS: m/z (M+H)$^+$ 332; $C_{16}H_{11}ClFN_3S$ requir.331.8.

Step C: 8-(4-fluorophenyl)-5-methylthio-7-(4-pyridyl)-1,2,4-triazolo[4,3-c]pyrimidine A solution of 0.28 g of 4-chloro-5-(4-fluoro phenyl)-2-methylthio-6-(4-pyridyl)pyrimidine (0.85 mmol) and 3 ml of NH$_2$NH$_2$—H$_2$O in 20 ml EtOH in a 50-ml r.b.flask with a stir bar was stirred at 70° C. The solvents were evaporated and the residue was mixed with toluene. The residue was dried by removal water with toluene and further dried under vacuum at 50° C. overnight. The resulting light yellow solid was mixed with 40 ml of DCM, 4 ml of CH(OCH$_3$)$_3$, and 2 ml of TFA in a 100-ml r.b.flask with a stir bar. The reaction solution was stirred at RT overnight. The acidic reaction solution was neutralized to pH 8 with sat'd NaHCO$_3$. The DCM layer was washed with brine (10 ml) and dried over Na$_2$SO$_4$. After removal of the DCM in vacuo, 8-(4- fluorophenyl)-5-methylthio-7-(4-pyridyl)-1,2,4-triazolo[4,3-c]pyrimidine was obtained as yellow solid; MS m/z (M+H)$^+$ 338.1; $C_{17}H_{12}FN_5S$ requir. 337.3.

EXAMPLE 3

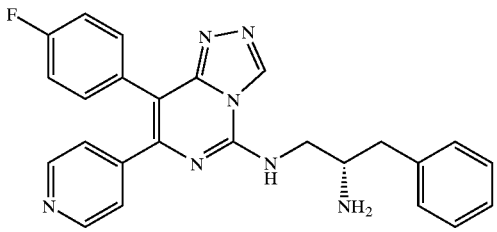

Preparation of 1-(8-(4-fluorophenyl)-7-(4-pyridyl)-1,2,4-triazolo[4,3-c]pyrimidin-5-yl)amino-2(S)-amino-3-phenylpropane A mixture of 8-(4-fluorophenyl)-5-methylthio-7-(4-pyridyl)-1,2,4-triazolo[4,3-c]pyrimidine (1.0 g, 3.0 mmole), potassium carbonate (1.5 g) and (2S)-3-phenylpropane-1,2-diamine (540 mg, 3.6 mmole) in 50 ml of DMF was stirred at room temperature (RT) for 48 hours. The reaction solution was poured into water (200 mL), and the resulting precipitate was filtered and washed with water. The crude product was purified by flash chromatography (3%–15% MeOH/NH$_3$ in DCM) to provide 1-(8-(4-fluorophenyl)-7-(4-pyridyl)-1,2,4-triazolo[4,3-c]pyrimidin-5-yl)amino-2(S)-amino-3-phenylpropane was obtained as white solid; MS: m/z (M+H)$^+$ 440.1; $C_{25}H_{22}FN_7$ requir. 439.5.

EXAMPLE 4

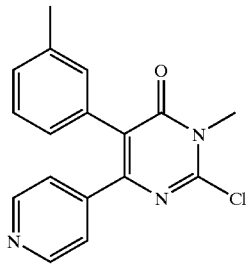

Preparation of 2-Chloro-3-methyl-6-(4-pyridyl)-5-(3-methylphenyl)-4(3H)-pyrimidinone, 2-Chloro-3-methyl-6-(4-pyridyl)-5-(3-trifluoromethylphenyl)-4(3H)-pyrimidinone and 2-Chloro-3-methyl-6-(4-pyridyl)-5-(4-fluorophenyl)-4(3H)-pyrimidinone Step A: 3-Methyl-5-(3-methylphenyl)-6-(4-pyridyl)-(1H,3H)-pyrimidin-2,4-dione and 2,6-bis(2-chloropyrid-4-yl)-3-methyl-5-(3-methylphenyl)-3H-pyrimidin-4-one 10 N Sodium hydroxide (25 ml) and water (50 ml) was added to a solution of 3-methyl-5-(3-methylphenyl)-2-methylthio-6-(4-pyridyl)-4(3H)-pyrimidindione (16.17 g, 0.05 mol) in dioxane (65 ml). The mixture was heated at 80° C. for 16 h. under argon. The mixture was allowed to reach room temperature and the pH value was adjusted to 9 with 1 N hydrochloric acid. The precipitate was filtered, washed with water and dried to give the title compound; MS (m/z): 292 (M−H)$^+$; $C_{17}H_{15}N_3O_2$ requir. 293.3.

The filtrate was extracted with ethyl acetate (100 mL) and dried over Na$_2$SO$_4$. The solution was concentrated under vacuum and flash chromatography (10–30% EtOAc in hexane) of the residue afforded 2,6-bis(2-chloropyrid-4-yl)-3-methyl-5-(3-methylphenyl)-3H-pyrimidin-4-one; MS (m/z) 424.2 (M+H)$^+$; $C_{22}H_{16}Cl_2N_4O$ requir. 423.3.

Step B: 2-Chloro-3-methyl-5-(3-methylphenyl)-6-(4-pyridyl)-4(3H)-pyrimidinone

A mixture of 3-methyl-5-(3-methylphenyl)-6-(4-pyridyl)-(1H,3H)-pyrimidin-2,4-dione (12.5 g, 0.043 mol) and phosphorus oxychloride (65 ml) was refluxed for 16 h. The excess of phosphorus oxychloride was evaporated followed by co-distillation with toluene. The remainder was carefully partitioned between dichloromethane and aqueous sodium hydrogencarbonate. The organic solution was washed with water, dried and evaporated to leave the title compound; MS (m/z): 312 (M+H)$^+$; $C_{17}H_{14}ClN_3O$ requir. 311.8.

2-Chloro-3-methyl-6-(4-pyridyl)-5-(3-trifluoromethylphenyl)-4(3H)-pyrimidinone and 2-Chloro-3-methyl-6-(4-pyridyl)-5-(4-fluorophenyl)-4(3H)-pyrimidinone were prepared according to the same procedure.

EXAMPLE 5

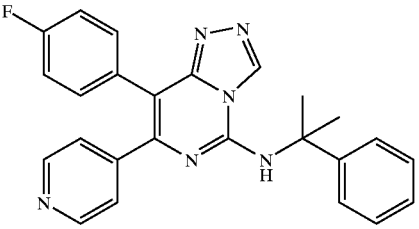

Preparation of 2-(8-(4-fluorophenyl)-7-(4-pyridyl)-1,2,4-triazolo[4,3-c]pyrimidin-5-yl)amino-2-phenylpropane Step A: 5-(4-fluorophenyl)-3-methyl-2-((1-methyl-1-phenylethyl)amino)-6-(4-pyridyl)-(3H)-pyrimidin-4-one 2-Chloro-3-methyl-6-(4-pyridyl)-5-(4-fluorophenyl)-4(3H)-pyrimidinone (5.43 g, 17.2 mmol) and cumyl amine (4.65 g, 34.4 mmol) were combined in dry isopropyl alcohol (ca. 40 mL) and the mixture was heated at reflux for 48 h. The reaction was cooled to RT, the solvent was evaporated in vacuo and the residue was partitioned between sat. aq. NaHCO$_3$ and CHCl$_3$. The organic layer was dried over Na$_2$SO$_4$ and then concentrated. The residue was purified by flash chromatography (1% MeOH/NH$_3$:CHCl$_3$) to provide the product as a tan solid; MS: m/z (M+H)$^+$ 415; $C_{25}H_{23}FN_4O$ requir. 414.5.

Step B: 2-((1-methyl-1-phenylethyl)amino)-4-chloro-5-(4-fluorophenyl)-6-(4-pyridyl)pyrimidine 5-(4-fluorophenyl)-3-methyl-2-((1-methyl-1-phenylethyl)amino)-6-(4-pyridyl)-(3H)-pyrimidin-4-one (1.24 g, 2.99 mmol), benzyltriethylammonium chloride (2.04 g, 8.97 mmol), and diisopropylethylamine (1.16 g, 1.6 mL 8.97 mmol) were combined in phosphorous oxychloride (ca. 20 mL) and the resulting solution was heated at 100° C. for 16 h. The reaction was cooled to RT, the phosphorous oxychloride was evaporated in vacuo and the residue was partitioned between sat. aq. NaHCO$_3$ and CHCl$_3$. The organic layer was dried over Na$_2$SO$_4$ and then concentrated. The residue was purified by flash chromatography (20% EtOAc:CHCl$_3$) to provide the product as a white solid; MS m/z (M+H)$^+$ 419; $C_{24}H_{20}ClFN_4$ requir. 418.8.

Step C: 2-((1-methyl-1-phenylethyl)amino)-4-hydrazino-5-(4-fluorophenyl)-6-(4-pyridyl)pyrimidine 2-((1-methyl-1-phenylethyl)amino)-4-chloro-5-(4-fluorophenyl)-6-(4-pyridyl)pyrimidine (218 mg, 0.52 mmol)

was combined with a solution of hydrazine hydrate (130 mg 2.60 mmol) and isopropylalcohol (ca. 10 mL). The mixture was heated at 70° C. for 4 h. The reaction was cooled to RT, the solvent was evaporated in vacuo and the residue was purified by flash chromatography (2% MeOH:CHCl₃) to provide the product as an off-white solid; MS m/z (M+H)⁺ 415; C₂₄H₂₃FN₆ requir. 414.5.

Step D: 2-(8-(4-fluorophenyl)-7-(4-pyridyl)-1,2,4-triazolo [4,3-c]pyrimidin-5-yl)amino-2-phenylpropane 2-((1-methyl-1-phenylethyl)amino)-4-hydrazino-5-(4-fluorophenyl)-6-(4-pyridyl)pyrimidine (95.1 mg, 0.23 mmol) was combined with trimethylorthoformate (58.4 mg, 0.54 mmol) in CH₂Cl₂ (ca. 5 mL). Trifluoroacetic acid (62.6 mg, 0.54 mmol) was added and the solution was maintained for 1 h. The reaction mixture was washed with saturated NaHCO₃. The organic phase was dried over Na₂SO₄ and concentrated in vacuo. The residue was purified by flash chromatography to provide the product as an off-white solid; MS m/z (M+H)⁺ 425; C₂₅H₂₁FN₆ requir. 424.5.

EXAMPLE 6

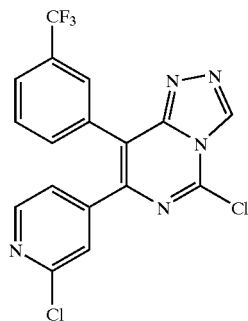

Preparation of 5-chloro-7-(2-chloro-4-pyridyl)-8-(3-(trifluoromethyl)phenyl)-1,2,4-triazolo[4,3-c] pyrimidine Step A: 6-(2-chloro-4-pyridyl)-3-methyl-2-methylthio-5-(3-(trifluoromethyl)phenyl)-(3H)-pyrimidin-4-one 6-(2-chloro-4-pyridyl)-3-methyl-2-methylthio-5-(3-(trifluoromethyl)phenyl)-(3H)-pyrimidin-4-one was prepared in the same manner as 5-(4-fluorophenyl)-3-methyl-2-methylthio-6-(4-pyridyl)-3H-pyrimidin-4-one.

Step B: 4-Chloro-6-(2-chloro-4-pyridyl)-2-methylthio-5-(3-(trifluoromethyl)-phenyl)pyrimidine 6-(2-chloro-4-pyridyl)-3-methyl-2-methylthio-5-(3-(trifluoromethyl)-phenyl)-(3H)-pyrimidin-4-one (2.05 g, 5 mmol), POCl₃ (3.05 g, 20 mmol), and diisopropylethylamine (2.58 g, 20 mmol) in a 50-ml r.b.flask with a stir bar was stirred at 120° C. for 16 h. The reaction was cooled to RT, 20 ml of EtOAc and 5 g of SiO₂ gel were added into the cooled solution, then solvents were evaporated in vacuo at 40° C. The brown solid was placed on a cake of SiO₂ gel (~20 g) and washed by 200 ml of 30% EtOAc in hexane. The brown filtrate was evaporated in vacuo to give an oil product; MS m/z (M+H)⁺ 416.2. The crude intermediate was used in the next step directly.

Step C: 5-methylthio-7-(2-chloro-4-pyridyl)-8-(3-(trifluoromethyl)phenyl)-1,2,4-triazolo[4,3-c]pyrimidine 4-Chloro-6-(2-chloro-4-pyridyl)-2-methylthio-5-(3-(trifluoromethyl)-phenyl)pyrimidine (0.873 g, 2.1 mmol) and 16.5 ml of NH₂NH₂—H₂O in 90 ml EtOH in a 150-ml r.b.flask with a stir bar was stirred at 70° C. The reaction was cooled to room temperature. The solvents were evaporated in vacuo. The residue was dried by addition and removal of toluene in vacuo and further dried under vacuum at 50° C. overnight. The resulting light yellow solid was mixed with 40 ml of DCM, 20 ml of CH(OCH₃)₃, and 10 ml of TFA in a 150-ml r.b.flask with a stir bar. The reaction solution was stirred at RT overnight. The acidic reaction solution was neutralized to pH 8 by sat'd NaHCO₃. The DCM layer was washed with brine (3×20 ml) and dried over Na₂SO₄. After removal of the DCM in vacuo, crude product (MS m/z 421.8 (M+H)⁺) was obtained as a dark brown oil, which was used directly in the next step.

Step D: 5-hydroxy-7-(2-chloro-4-pyridyl)-8-(3-(trifluoromethyl)phenyl)-1,2,4-triazolo[4,3-c]pyrimidine 1 g of crude 5-methylthio-7-(2-chloro-4-pyridyl)-8-(3-(trifluoromethyl)phenyl)-1,2,4-triazolo[4,3-c]pyrimidine and 15 ml of 2M NaOH in 15 ml 1,4-dioxane in a 150-ml r.b.flask with a stir bar was stirred at 80° C. The basic solution was cooled down to room temperature and neutralized to pH 7.5 with 10% HCl. A precipitate was formed, filtered off and washed with water (2×10 ml). The solid was dried under vacuum at 70° C. overnight to give a solid product; MS m/z (M+H)⁺ 392.1.

Step E: 5-chloro-7-(2-chloro-4-pyridyl)-8-(3-(trifluoromethyl)phenyl)-1,2,4-triazolo[4,3-c]pyrimidine 5-hydroxy-7-(2-chloro-4-pyridyl)-8-(3-(trifluoromethyl) phenyl)-1,2,4-triazolo[4,3-c]pyrimidine (0.3 g, 0.76 mmol), POCl₃ (0.459 g, 3 mmol), and diisopropylethylamine (0.387 g, 3 mmol) in a 50-ml r.b.flask with a stir bar was stirred at 120° C. overnight. The reaction solution was cooled to room temperature and 20 ml of EtOAc and 5 g of SiO₂ gel were added into the cooled solution. The solvents were evaporated in vacuo at 40° C. The resulting brown solid was placed on a cake of SiO₂ gel (~20 g) and washed with 250 ml of EtOAc. The brown filtrate was evaporated in vacuo to give 5-chloro-7-(2-chloro-4-pyridyl)-8-(3-(trifluoromethyl) phenyl)-1,2,4-triazolo[4,3-c]pyrimidine; MS m/z (M)⁺ 410; C₁₇H₈Cl₂F₃N₅ requir. 410.2.

EXAMPLE 7

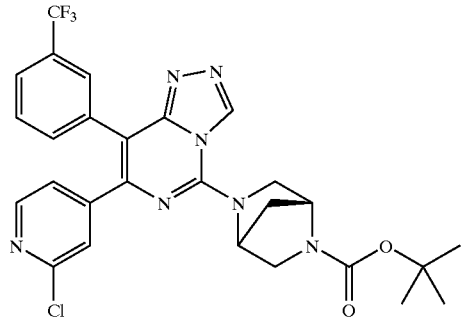

Preparation of 5-{7-(2-chloro-4-pyridyl)-8-(3-(trifluoromethyl)phenyl)-1,2,4-triazolo[4,3-c] pyrimidin-5-yl}-2-(tert-butoxycarbonyl)-(1R)-2,5-diaza-bicyclo[2.2.1]heptane A mixture of 5-chloro-7-(2-chloro-4-pyridyl)-8-(3-(trifluoromethyl)-phenyl)-1,2,4-triazolo[4,3-c]pyrimidine (820 mg, 2.0 mmole), potassium carbonate (ca. 1.0 g) and (−)-2-(tert-butoxycarbonyl)-(1R, 4R)-2,5-diaza-bicyclo [2.2.1]heptane (436 mg, 2.2 mmole) in 10 ml of DMF was stirred at room temperature for 16 hours. The reaction solution was poured into water (50 mL), and precipitate was filtered and washed with water and dried under vacuum to give product as off white solid; MS m/z (M)⁺ 572.3; C₂₇H₂₅ClF₃N₇O₂ requir. 572.

EXAMPLE 8

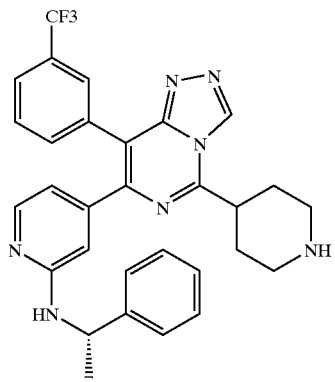

Preparation of 5-(piperidin-4-yl)-7-(2-(1(S)-phenylethyl)amino-4-pyridyl)-8-(3-(trifluoromethyl)phenyl)-1,2,4-triazolo[4,3-c]pyrimidine Step A: 1-(t-butoxycarbonyl)-4-(trifluoromethyl sulfonyloxy)-1,2,3,6-tetrahydropyridine A solution of lithium diisopropylamine (7.3 ml 1.5M, 11 mmol) in 25 ml tetrahydrofuran was cooled to −78° C. and 1-(t-butoxycarbonyl)-4-oxopiperidine (2.0 g, 10.0 mmol) in 25 ml tetrahydrofuran was added and the mixture was stirred for 20 minutes. N-Phenyltrifluoromethane sulfonimide (($CF_3SO_2$)$_2$N—$C_6H_5$; 3.9 g, 11 mmol) was added and the cold bath removed. The mixture was then stirred for 3 hours. At this time the solvent was evaporated and the residue was purified on an alumina neutral column (5% ethyl acetate in hexane) to yield the product; MS m/z (M+H)$^+$ 332.2; $C_{11}H_{16}F_3NO_5S$ require 331.1.

Step B: 5-(1-(t-butoxycarbonyl)-1,2,3,6-tetrahydropyrid-4-yl)-7-(2-chloro-4-pyridyl)-8-(3-(trifluoromethyl)phenyl)-1,2,4-triazolo[4,3-c]pyrimidine 5-Chloro-7-(2-chloro-4-pyridyl)-8-(3-(trifluoromethyl)phenyl)-1,2,4-triazolo[4,3-c]pyrimidine (2.0 g, 5.0 mmol), 1-(t-butoxycarbonyl)-4-(trifluoromethyl sulfonyloxy)-1,2,3,6-tetrahydropyridine (2.0 g, 6.0 mmol), lithium chloride (6.64 g, 15.0 mmol), hexamethylditin (2.0 g, 6.0 mmol) and tetrakistriphenylphosphinopalladium (0.3 g, 0.25 mmol) were combined in dioxane (25 ml) and the resulting solution was heated to 90° C. for 18 hours. The mixture was added to aq. KF and was stirred for 2 hours and then partitioned with methylene chloride. The organic layer was dried over sodium sulfate, filtered and concentrated to a syrup. Purification by column chromatography on silica gel (30% ethyl acetate in hexane) gave the product as a syrup; MS m/z (M+H)$^+$ 557.2; $C_{27}H_{24}F_3ClN_6O_2$ require 556.2.

Step C: 5-(1-(t-butoxycarbonyl)-1,2,3,6-tetrahydropyrid-4-yl)-7-(2-(1(S)-phenylethyl)amino-4-pyridyl)-8-(3-(trifluoromethyl)phenyl)-1,2,4-triazolo[4,3-c]pyrimidine 5-(1-(t-Butoxycarbonyl)-1,2,3,6-tetrahydropyrid-4-yl)-7-(2-chloro-4-pyridyl)-8-(3-(trifluoromethyl)phenyl)-1,2,4-triazolo[4,3-c]pyrimidine (0.93 g, 1.7 mmol), (S)-α-methylbenzylamine (0.48 g, 4 mmol), palladium acetate (0.06 g, 0.26 mmol) and racemic BINAP (0.16 g, 0.26 mmol) were combined in toluene (15 ml) and the resulting solution was degassed with nitrogen. Sodium t-butoxide (0.48 g, 5 mmol) was added and the resulting mixture was heated to 90° C. for 1 hour. The mixture was partitioned between sat. ammonium chloride and ethyl acetate. The organic layer was separated, dried over sodium sulfate, filtered and concentrated to a syrup. The residue was purified by column chromatography on silica gel (30% ethyl acetate in hexane) gave the product as a syrup; MS m/z (M+H)$^+$ 642.4; $C_{35}H_{34}F_3N_7O_2$ require 641.3.

Step D: 5-(1-(t-butoxycarbonyl)piperidin-4-yl)-7-(2-(1(S)-phenylethyl)amino-4-pyridyl)-8-(3-(trifluoromethyl)phenyl)-1,2,4-triazolo[4,3-c]pyrimidine 5-(1-(t-Butoxycarbonyl)-1,2,3,6-tetrahydropyrid-4-yl)-7-(2-(1(S)-phenylethyl)amino-4-pyridyl)-8-(3-(trifluoromethyl)phenyl)-1,2,4-triazolo[4,3-c]pyrimidine (0.12 g, 0.2 mmol) and platinum oxide (0.03 g, 0.13 mmol) were combined in ethanol (5 ml) and maintained at room temperature under an atmosphere of hydrogen for 18 hours. The catalyst was removed by filtration and the filtrate was concentrated to a syrup. The residue was purified by column chromatography on silica gel (30% ethyl acetate in hexane) to give the product as a syrup; MS m/z (M+H)$^+$ 644.5; $C_{35}H_{36}F_3N_7O_2$ require 643.3.

Step E: 5-(piperidin-4-yl)-7-(2-(1(S)-phenylethyl)amino-4-pyridyl)-8-(3-(trifluoromethyl)phenyl)-1,2,4-triazolo[4,3-c]pyrimidine 5-(1-(t-butoxycarbonyl)piperidin-4-yl)-7-(2-(1(S)-phenylethyl)amino-4-pyridyl)-8-(3-(trifluoromethyl)phenyl)-1,2,4-triazolo[4,3-c]pyrimidine (0.03 g, 0.05 mmol) and trifluoroacetic acid (1 ml) were combined in methylene chloride (5 ml) and maintained at room temperature for 24 hours. The solution was concentrated and the residue was partitioned between methylene chloride and 10% sodium carbonate. The organic layer was separated, dried over sodium sulfate, filtered and the solvent evaporated to give the product as a syrup; MS m/z (M+H)$^+$ 544.1; $C_{30}H_{28}F_3N_7$ require 543.2.

EXAMPLE 9

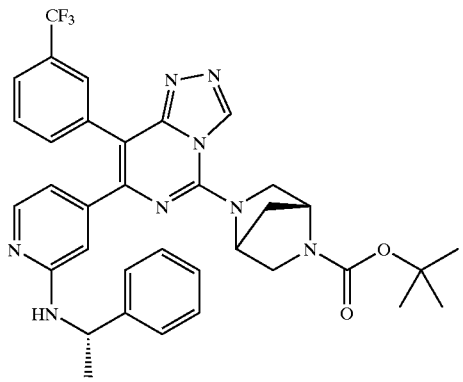

Preparation of 5-{7-(2-(1(S)-phenylethyl)amino-4-pyridyl)-8-(3-(trifluoromethyl)phenyl)-1,2,4-triazolo[4,3-c]pyrimidin-5-yl}-2-(tert-butoxycarbonyl)-(1R)-2,5-diaza-bicyclo[2.2.1]heptane The title compound was synthesized in the same manner as 5-(1-(t-butoxycarbonyl)-1,2,3,6-tetrahydropyrid-4-yl)-7-(2-(1(S)-phenylethyl)amino-4-pyridyl)-8-(3-(trifluoromethyl)phenyl)-1,2,4-triazolo[4,3-c]pyrimidine; MS m/z (M+H)$^+$ 657.4; $C_{35}H_{35}F_3N_8O_2$ requir. 656.7.

EXAMPLE 10

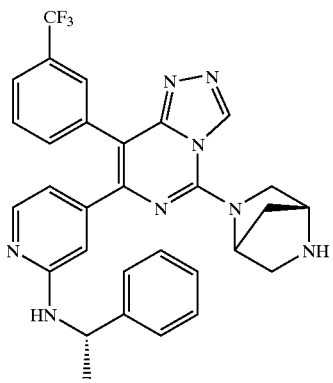

Preparation of 5-(2,5-diaza-bicyclo[2.2.1]hept-2-yl)-8-(3-(trifluoromethyl)phenyl)-7-(2-(1(S)-phenylethyl)amino-4-pyridyl)-1,2,4-triazolo[4,3-c]pyrimidine A solution of 5-{7-(2-(1(S)-phenylethyl)amino-4-pyridyl)-8-(3-(trifluoromethyl)phenyl)-1,2,4-triazolo[4,3-c]pyrimidin-5-yl}-2-(tert-butoxycarbonyl)-(1R)-2,5-diaza-bicyclo[2.2.1]heptane (240 mg, 0.4 mmole) in ethyl acetate (5 mL) was treated with HCl-ether solution (1M, 4 mL) at room temperature. The suspension was stirred at room temperature for 5 minutes. The resulting precipitate was filtered, washed with ether and dried under vacuum to give the product as a light yellowish solid; MS m/z (M)$^+$ 557.3; $C_{30}H_{27}F_3N_8$ requir. 557.4.

EXAMPLE 11

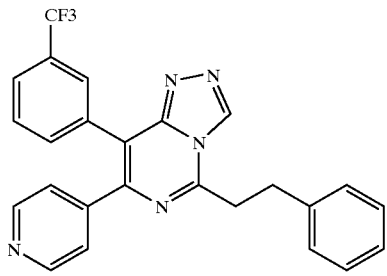

Preparation of 5-(2-phenylethyl)-8-(3-(trifluoromethyl)phenyl)-7-(4-pyridyl)-1,2,4-triazolo[4,3-c]pyrimidine Step A: 3-methyl-4-oxo-6-(4-pyridyl)-5-(3-(trifluoromethyl)phenyl)-3H-pyrimidine-2-carbonitrile To a solution of NaCN (55 mg), water (0.1 ml) in 1-methyl-2-pyrrolidone (50 mL) was added 1,4-diazabicyclo[2,2,2]octane (220 mg, 2 mmole) and a solution of 365 mg of 6-(4-pyridyl)-3-methyl-2-methylthio-5-(3-(trifluoromethyl)phenyl)-(3H)-pyrimidin-4-one in 1-methyl-2-pyrrolidone (2 mL) at room temperature. The resulting mixture was stirred at room temperature for 5 minutes. The reaction mixture was partitioned between water and ethyl acetate. The organic layer was dried over $Na_2SO_4$ and then concentrated. The residue was purified by flash chromatography (20% EtOAc:Hexanes) to provide the product as a colorless oil; MS (m/z) 357 (M+H)$^+$; $C_{18}H_{11}F_3N_4O$ requir. 356.3.

Step B: 3-methyl-2-(2-phenylethyl)-6-(4-pyridyl)-5-(3-(trifluoromethyl)phenyl)-3H-pyrimidin-4-one To a solution of 3-methyl-4-oxo-6-(4-pyridyl)-5-(3-(trifluoromethyl)-phenyl)-3H-pyrimidine-2-carbonitrile (280 mg, 0.79 mmole) in THF (20 mL) was added phenethylene magnesium chloride (1.0M in THF, 1.2 mL) at 0° C. The reaction solution was then stirred at 0° C. for 5 mins. The mixture was partitioned between sat. ammonium chloride and ethyl acetate. The organic layer was separated, dried over sodium sulfate, filtered and concentrated to a syrup. The residue was purified by column chromatography on silica gel (30% ethyl acetate in hexane) to give the product as a syrup; MS (m/z) 436(M+H)$^+$; $C_{25}H_{20}F_3N_3O$ requir. 435.4.

Step C: 4-chloro-2-(2-phenylethyl)-6-(4-pyridyl)-5-(3-(trifluoromethyl)phenyl)pyrimidine The title compound was synthesized in the same manner as 2-((1-methyl-1-phenylethyl)amino)-4-chloro-5-(4-fluorophenyl)-6-(4-pyridyl)pyrimidine; MS m/z (M)$^+$ 440; $C_{24}H_{17}ClF_3N_3$ requir. 439.9.

Step D: 5-(2-phenylethyl)-8-(3-(trifluoromethyl)phenyl)-7-(4-pyridyl)-1,2,4-triazolo[4,3-c]pyrimidine The title compound was synthesized from 4-chloro-2-(2-phenylethyl)-6-(4-pyridyl)-5-(3-(trifluoromethyl)phenyl)pyrimidine in the same manner as 2-(8-(4-fluorophenyl)-7-(4-pyridyl)-1,2,4-triazolo[4,3-c]pyrimidin-5-yl)amino-2-phenylpropane; MS m/z (M+H)$^+$ 446; $C_{25}H_{18}F_3N_5$ requir. 445.4.

EXAMPLE 21

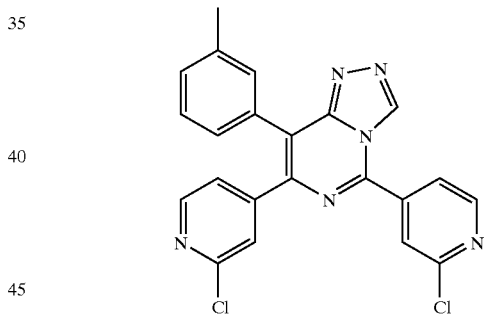

Preparation of 8-(3-methylphenyl)-5,7-bis(2-chloro-4-pyridyl)-1 2,4-triazolo[4,3-c]pyrimidine Step A: 2,6-bis(2-chloro(4-pyridyl))-4-chloro-5-(3-methylphenyl)pyrimidine The title compound was synthesized from 2,6-bis(2-chloropyrid-4-yl)-3-methyl-5-(3-methylphenyl)-3H-pyrimidin-4-one in the same manner as 2-((1-methyl-1-phenylethyl)amino)-4-chloro-5-(4-fluorophenyl)-6-(4-pyridyl)pyrimidine.

Step B: 8-(3-methylphenyl)-5,7-bis(2-chloro-4-pyridyl)-1,2,4-triazolo[4,3-c]pyrimidine The title compound was synthesized from 2,6-bis(2-chloro(4-pyridyl))-4-chloro-5-(3-methylphenyl)pyrimidine in the same manner as 2-(8-(4-fluorophenyl)-7-(4-pyridyl)-1,2,4-triazolo[4,3-c]pyrimidin-5-yl)amino-2-phenylpropane; MS (m/z) 434.9 (M+H)$^+$; $C_{22}H_{14}Cl_2N_6$ requir. 433.29.

EXAMPLE 13

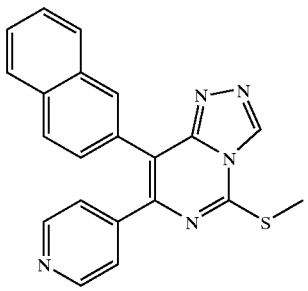

Preparation of 8-(2-naphthyl)-5-methylthio-7-(4-pyridyl)-1,2,4-triazolo[4,3-c]pyrimidine The title compound was synthesized in the same manner as 8-(4-fluorophenyl)-5-methylthio-7-(4-pyridyl)-1,2,4-triazolo[4,3-c]pyrimidine; MS (m/z) 370.1 (M+H)$^+$; $C_{21}H_{15}N_5S$ requir. 369.4.

EXAMPLE 14

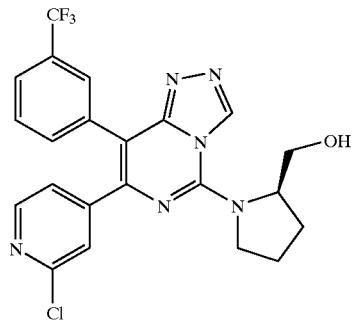

Preparation of 5-(2(R)-(hydroxymethyl)pyrrolidin-1-yl)-7-(2-chloro-4-pyridyl)-8-(3-(trifluoromethyl)phenyl)-1,2,4-triazolo[4,3-c]pyrimidine The title compound was synthesized in the same manner as 5-{7-(2-chloro-4-pyridyl)-8-(3-(trifluoro methyl)phenyl)-1,2,4-triazolo[4,3-c]pyrimidin-5-yl)}-2-(tert-butoxycarbonyl)-(1R)-2,5-diaza-bicyclo[2.2.1]heptane; MS (m/z) 475 (M)$^+$; $C_{22}H_{18}ClF_3N_6O$ requir. 474.87.

EXAMPLE 15

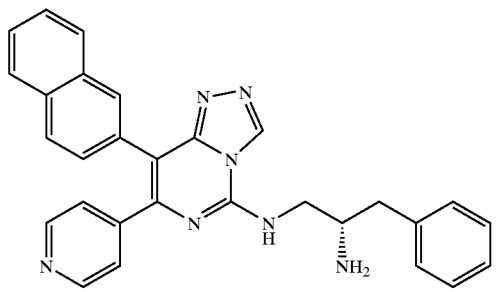

Preparation of 5-(2(S)-amino-3-phenylprop-1-yl)amino-8-(2-naphthyl)-7-(4-pyridyl)-1,2,4-triazolo[4,3-c]pyrimidine 8-(2-naphthyl)-5-methylthio-7-(4-pyridyl)-1,2,4-triazolo[4,3-c]pyrimidine (350 mg, 1 mmol), $K_3CO_3$ (100 mg) and (2S)-3-phenylpropane-1,2-diamine (150 mg, 1 mmol) were combined in dry DMF (ca. 5 mL) and the mixture was stirred at room temperature for 48 h. To the reaction solution was added water (ca. 10 mL) at RT and a precipitate formed. The suspension was stirred at RT for 1 h. The solid was filtered off and washed with water (3×10 ml) and dried under vacuum at 50° C. overnight; MS (m/z) 472.3 (M+H)$^+$; $C_{29}H_{25}N_7$ requir. 471.56.

EXAMPLE 16

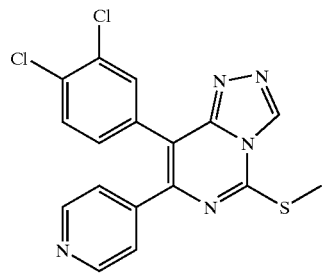

Preparation of 8-(3,4-dichlorophenyl)-5-methylthio-7-(4-pyridyl)-1,2,4-triazolo[4.3-c]pyrimidine The title compound was synthesized in the same manner as 8-(4-fluorophenyl)-5-methylthio-7-(4-pyridyl)-1,2,4-triazolo[4,3-c]pyrimidine; MS (m/z) 388.3 (M)$^+$; $C_{17}H_{11}Cl_2N_5S$ requir. 388.27.

EXAMPLE 17

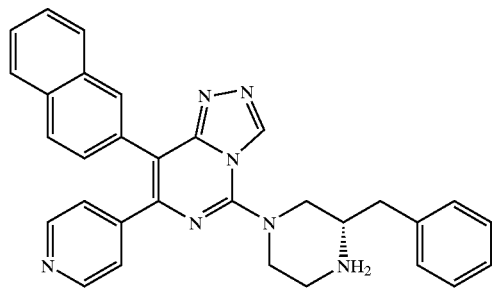

Preparation of 5-(3(S)-benzyl-piperazin-1-yl)-8-(2-naphthyl)-7-(4-pyridyl)-1,2,4-triazolo[4,3-c]pyrimidine 8-(2-naphthyl)-5-methylthio-7-(4-pyridyl)-1,2,4-triazolo[4,3-c]pyrimidine (200 mg, 0.54 mmol), $K_3CO_3$ (100 mg) and (S)-2-benzylpiperazine (170 mg, 0.97 mmol) were combined in dry DMF (ca. 4 mL) and the mixture was heated at 100° C. for 48 h. The reaction was cooled to RT, and partitioned between water and ethyl acetate. The organic layer was dried over $Na_2SO_4$ and then concentrated in vacuo. The residue was purified by flash chromatography (2–8% MeOH/NH$_3$:CH$_2$Cl$_2$) to provide the product as a tan solid; MS (m/z) 498.3 (M+H)$^+$; $C_{31}H_{27}N_7$ requir. 497.59.

EXAMPLE 18

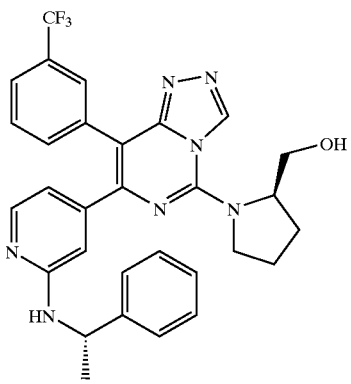

Preparation of 5-(2(R)-(hydroxymethyl)pyrrolidin-1-yl)-7-(2-(1(S)-phenylethyl)amino-4-pyridyl)-8-(3-(trifluoromethyl)phenyl)-1,2,4-triazolo[4,3-c] pyrimidine The title compound was synthesized from 5-(2(R)-(hydroxymethyl)-pyrrolidin-1-yl)-7-(2-chloro-4-pyridyl)-8-(3-(trifluoromethyl)phenyl)-1,2,4-triazolo[4,3-c]pyrimidine in the same manner as 5-(1-(t-butoxycarbonyl)-1,2,3,6-tetrahydropyrid-4-yl)-7-(2-(1(S)-phenylethyl)amino-4-pyridyl)-8-(3-(trifluoromethyl)phenyl)-1,2,4-triazolo[4,3-c] pyrimidine; MS (m/z) 560.4 (M+H)$^+$; $C_{30}H_{28}F_3N_7O$ requir. 559.59.

EXAMPLE 19

Using the procedures of the above general description and the above examples, the compounds of Table 1 were prepared.

| Name | Formula | MS (M + H)$^+$ |
|---|---|---|
| 5-(3-phenylprop-1-yl)amino-8-(4-fluorophenyl)-7-(4-pyridyl)-1,2,4-triazolo[4,3-c]pyrimidine | $C_{25}H_{21}FN_6$ | 425.0 |
| 5-(3-phenylprop-1-yl)amino-8-(3-methylphenyl)-7-(4-pyridyl)-1,2,4-triazolo[4,3-c]pyrimidine | $C_{26}H_{24}N_6$ | 420.51 |
| 8-(3-(trifluoromethyl)phenyl)-7-(4-pyridyl)-1,2,4-triazolo[4,3-c]pyrimidine | $C_{17}H_{10}F_3N_5$ | 342.0 |
| 5-(1-piperazinyl)-8-(3-methylphenyl)-7-(2-chloro-4-pyridyl)-1,2,4-triazolo[4,3-c]pyrimidine | $C_{21}H_{20}ClN_7$ | 406.0 |
| 5-(3-phenylprop-1-yl)amino-8-(3-(trifluoromethyl)phenyl)-7-(4-pyridyl)-1,2,4-triazolo[4,3-c]pyrimidine | $C_{26}H_{21}F_3N_6$ | 475.3 |
| 5-(2(S)-amino-3-phenylprop-1-yl)amino-8-(3,4-dichlorophenyl)-7-(4-pyridyl)-1,2,4-triazolo[4,3-c]pyrimidine | $C_{25}H_{21}Cl_2N_7$ | 491.0 |
| 5-(2(S)-amino-3-phenylprop-1-yl)amino-8-(3-(trifluoromethyl)phenyl)-7-(4-pyridyl)-1,2,4-triazolo[4,3-c]pyrimidine | $C_{26}H_{22}F_3N_7$ | 490.0 |
| 5-(4-(t-butoxycarbonyl)piperazin-1-yl)-8-(3-(trifluoromethyl)phenyl)-7-(2-(2-phenylprop-2-yl)amino-4-pyridyl)-1,2,4-triazolo[4,3-c]pyrimidine | $C_{35}H_{37}F_3N_8O_2$ | 659.5 |
| 5-(piperazin-1-yl)-8-(3-(trifluoromethyl)phenyl)-7-(2-(2-phenylprop-2-yl)amino-4-pyridyl)-1,2,4-triazolo[4,3-c]pyrimidine | $C_{30}H_{29}F_3N_8$ | 559.0 |
| 5-(4-(t-butoxycarbonyl)piperazin-1-yl)-8-(3-methylphenyl)-7-(2-chloro-4-pyridyl)-1,2,4-triazolo[4,3-c]pyrimidine | $C_{26}H_{28}ClN_7O_2$ | 507.0 |
| 5-(piperazin-1-yl)-8-(3-(trifluoromethyl)phenyl)-7-(2-(1(S)-phenylethyl)amino-4-pyridyl)-1,2,4-triazolo[4,3-c]pyrimidine | $C_{29}H_{27}F_3N_8$ | 545.2 |
| 5-(2(S)-amino-2-methyl-3-phenylprop-1-yl)amino-8-(3-(trifluoromethyl)phenyl)-7-(2-chloro-4-pyridyl)-1,2,4-triazolo[4,3-c]pyrimidine | $C_{27}H_{23}ClF_3N_7$ | 538.2 |
| 5-(2(S)-amino-2-methyl-3-phenylprop-1-yl)amino-8-(3-(trifluoromethyl)phenyl)-7-(4-pyridyl)-1,2,4-triazolo[4,3-c]pyrimidine | $C_{27}H_{24}F_3N_7$ | 504.4 |
| 5-(3,5-dimethylpiperazin-1-yl)-8-(3-(trifluoromethyl)phenyl)-7-(2-(1(S)-phenylethyl)amino-4-pyridyl)-1,2,4-triazolo[4,3-c]pyimidine | $C_{31}H_{31}F_3N_8$ | 573.5 |
| 5-(3,5-dimethylpiperazin-1-yl)-8-(3-(trifluoromethyl)phenyl)-7-(2-chloro-4-pyridyl)-1,2,4-triazolo[4,3-c]pyrimidine | $C_{23}H_{21}ClF_3N_7$ | 488.1 |
| 5-(2(S)-amino-3-phenylprop-1-yl)amino-8-(3-(trifluoromethyl)phenyl)-7-(2-chloro-4-pyridyl)-1,2,4-triazolo[4,3-c]pyrimidine | $C_{26}H_{21}ClF_3N_7$ | 524.3 |
| 5-(2(S)-amino-3-phenylprop-1-yl)amino-8-(3-chloro-4-fluorophenyl)-7-(4-pyridyl)-1,2,4-triazolol[4,3-c]pyrimidine | $C_{25}H_{21}ClFN_7$ | 474.3 |
| 5-(2(S)-pyrrolidinylmethyl)amino-8-(3,4-dichlorophenyl)-7-(4-pyridyl)-1,2,4-triazolo[4,3-c]pyrimidine | $C_{21}H_{19}Cl_2N_7$ | 441.3 |
| 5-(2(S)-pyrrolidinylmethyl)amino-8-(2-naphthyl)-7- | $C_{25}H_{23}N_7$ | 422.2 |

| Name | Formula | MS (M + H)+ |
|---|---|---|
| (4-pyridyl)-1,2,4-triazolo[4,3-c]pyrimidine | | |
| 5-(2(S)-(hydroxymethyl)pyrrolidin-1-yl)-8-(3-(trifluoromethyl)phenyl)-7-(2-(1(S)-phenylethyl)amino-4-pyridyl)-1,2,4-triazolo[4,3-c]pyrimidine | $C_{30}H_{28}F_3N_7O$ | 560.5 |
| 5-(1-(2-propyl)pyrrolidin-2(S)-ylmethyl)amino-8-(3,4-dichlorophenyl)-7-(4-pyridyl)-1,2,4-triazolo[4,3-c]pyrimidine | $C_{24}H_{25}Cl_2N_7$ | 483.3 |
| 5-{7-(2-(cyclopropyl)amino-4-pyridyl)-8-(3-(trifluoromethyl)phenyl)-1,2,4-triazolo[4,3-c]pyrimidin-5-yl}-2-(tert-butoxycarbonyl)-(1R)-2,5-diaza-bicyclo[2.2.1]heptane | $C_{30}H_{31}F_3N_8O_2$ | 593.5 |
| 2-{7-(2-(cyclopropyl)amino-4-pyridyl)-8-(3-(trifluoromethyl)phenyl)-1,2,4-triazolo[4,3-c]pyrimidin-5-yl}-(1R)-2,5-diaza-bicyclo[2.2.1]heptane | $C_{25}H_{23}F_3N_8$ | 493.5 |
| 5-(4-(t-butoxycarbonyl)piperazin-1-yl)-8-(3-(trifluoromethyl)phenyl)-7-(2-(cyclopropyl)amino-4-pyridyl)-1,2,4-triazolo[4,3-c]pyrimidine | $C_{29}H_{31}F_3N_8O_2$ | 581.3 |
| 5-(piperazin-1-yl)-8-(3-(trifluoromethyl)phenyl)-7-(2-(cyclopropyl)amino-4-pyridyl)-1,2,4-triazolo[4,3-c]pyrimidine | $C_{24}H_{23}F_3N_8$ | 481.4 |
| 5-(1-(2-propyl)piperid-3-yl)amino-8-(3,4-dichlorophenyl)-7-(4-pyridyl)-1,2,4-triazolo[4,3-c]pyrimidine | $C_{24}H_{25}Cl_2N_7$ | 483.4 |
| 5-(1-(2-propyl)pyrrolidin-2(S)-ylmethyl)amino-8-(2-naphthyl)-7-(4-pyridyl)-1,2,4-triazolo[4,3-c]pyrimidine | $C_{28}H_{29}N_7$ | 464.3 |
| 5-(1-(t-butoxycarbonyl)pyrrolidin-2(S)-ylmethyl)amino-8-(3-(trifluoromethyl)phenyl)-7-(2-chloro-4-pyridyl)-1,2,4-triazolo[4,3-c]pyrimidine | $C_{27}H_{27}ClF_3N_7O_2$ | 574.5 |
| 5-(1-(t-butoxycarbonyl)piperid-3-yl)amino-8-(3-(trifluoromethyl)phenyl)-7-(2-chloro-4-pyridyl)-1,2,4-triazolo[4,3-c]pyrimidine | $C_{27}H_{27}ClF_3N_7O_2$ | 574.4 |
| 5-(piperid-3-yl)amino-8-(3-(trifluoromethyl)phenyl)-7-(2-(cyclopropyl)amino-4-pyridyl)-1,2,4-triazolo[4,3-c]pyrimidine | $C_{25}H_{25}F_3N_8$ | 464.3 |
| 5-(1-(t-butoxycarbonyl)piperid-3-yl)amino-8-(3-(trifluoromethyl)phenyl)-7-(2-(cyclopropyl)amino-4-pyridyl)-1,2,4-triazolo[4,3-c]pyrimidine | $C_{30}H_{33}F_3N_8O_2$ | 483.4 |
| 5-(1-(t-butoxycarbonyl)piperid-3-yl)amino-8-(3,4-dichlorophenyl)-7-(4-pyridyl)-1,2,4-triazolo[4,3-c]pyrimidine | $C_{26}H_{27}Cl_2N_7O_2$ | 541.3 |
| 5-(2(S)-amino-3-(4-fluorophenyl)prop-1-yl)amino-8-(3-chloro-4-fluorophenyl)-7-(4-pyridyl)-1,2,4-triazolo[4,3-c]pyrimidine | $C_{25}H_{20}ClF_2N_7$ | 492.4 |
| 5-(1-(2-propyl)piperid-3-yl)amino-8-(3-trifluoromethylphenyl)-7-(2-(cyclopropyl)amino-4-pyridyl)-1,2,4-triazolo[4,3-c]pyrimidine | $C_{28}H_{31}F_3N_8$ | 537.4 |
| 5-(piperid-3-yl)amino-8-(3-trifluoromethylphenyl)-7-(2-(cyclopropylmethyl)amino-4-pyridyl)-1,2,4-triazolo[4,3-c]pyrimidine | $C_{26}H_{27}F_3N_8$ | 509.5 |
| 5-(1-(t-butoxycarbonyl)piperid-3-yl)amino-8-(3-trifluoromethyl phenyl)-7-(2-(cyclopropylmethyl)amino-4-pyridyl)-1,2,4-triazolo[4,3-c]pyrimidine | $C_{31}H_{35}F_3N_8O_2$ | 609.3 |
| 5-((1-(2-butyl)pyrrolidin-2(S)-yl)methyl)amino-8-(2-naphthyl)-7-(4-pyridyl)-1,2,4-triazolo[4,3-c]pyrimidine | $C_{29}H_{31}N_7$ | 478.4 |
| 5-((1-(1-propyl)pyrrolidin-2(S)-yl)methyl)amino-8-(2-naphthyl)-7-(4-pyridyl)-1,2,4-triazolo[4,3-c]pyrimidine | $C_{28}H_{29}N_7$ | 464.4 |
| 5-((pyrrolidin-2(S)-yl)methyl)amino-8-(3-chloro-4-fluorophenyl)-7-(4-pyridyl)-1,2,4-triazolo[4,3-c]pyrimidine | $C_{21}H_{19}ClFN_7$ | 424.2 |
| 5-methylthio-8-(3-chloro-4-((pyrrolidin-2(S)-yl)methyl)amino phenyl)-7-(4-pyridyl)-1,2,4-triazolo[4,3-c]pyrimidine | $C_{22}H_{22}ClN_7S$ | 452.2 |

EXAMPLE 20

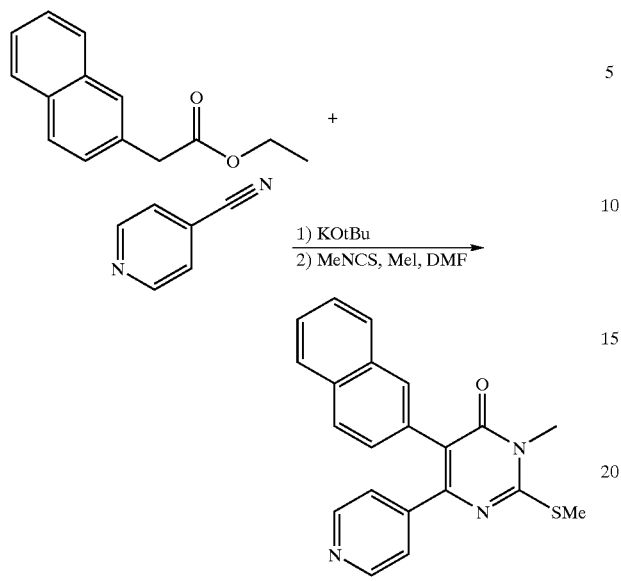

4-Cyanopyridine (83.9 g, 805.5 mmol) was added to a stirred solution of naphthylacetic acid ethyl ester (172.6 g, 805.5 mmol) in DMF (800 mL) in a 5 L round bottom flask fitted with a magnetic stir bar. A solution of potassium tert-butoxide (805.5 mL, 1M solution in tert-butanol) was added dropwise over 1 h via addition funnel. A solution of methyl thioisocyanate (58.9 g, 805.5 mmol) in DMF (400 mL) was added to the reaction dropwise over 30 min. The resulting reddish brown mixture was stirred at RT for 2 h. The mixture was then cooled to 0° C. and then a solution of methyl iodide (114.3 g, 805.5 mmol) in DMF (300 mL) was added dropwise over 30 min. The mixture was stirred vigorously at RT for 14 h. At this time the mixture is diluted with water to increase the volume of solvent four fold. The mixture is stirred vigorously over 4 h and a suspension was formed. The solid is collected by filtration and washed with copious amounts of water. The solid is then stirred as a suspension in ethyl acetate and then collected by filtration, washed with ethyl ether, then dried to provide a light yellow solid. The product was pure by TLC (4% MeOH:CHCl$_3$). MS m/z 360 (MH)$^+$.

EXAMPLE 21

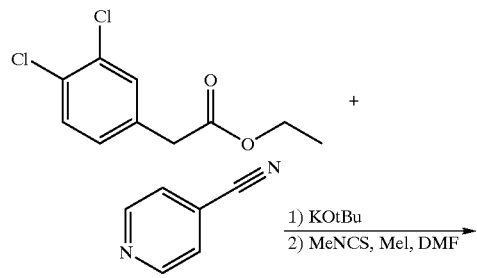

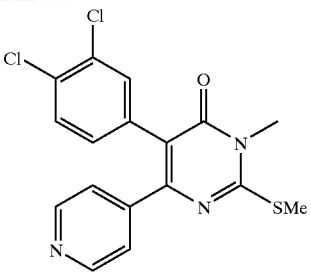

Prepared as in Example 20.

EXAMPLE 22

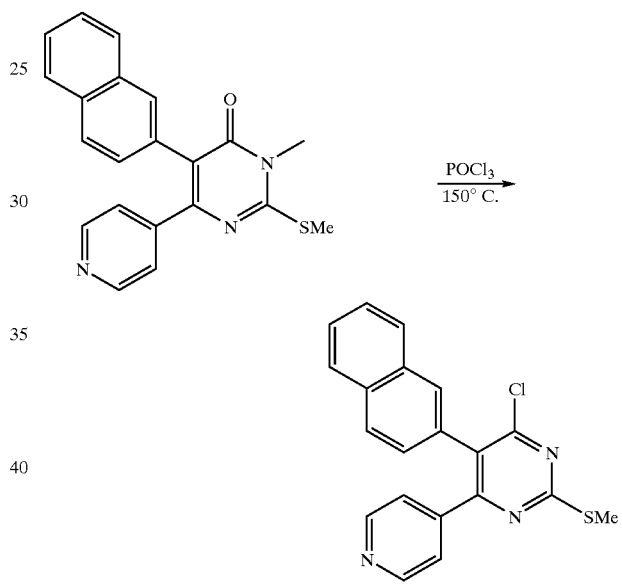

Phosphorous oxychloride (107.7 g, 65.3 mL, 700 mmol) was added to the methylthiopyrimidinone (25.01 g, 70.0 mmol) in a 1 L round bottom flask fitted with a reflux condenser and a magnetic stir bar. The resulting solution was heated at 150° C. and stirred vigorously for 14 h. At this time TLC (4% MeOH:CHCl$_3$) indicated that starting material was consumed. The mixture was allowed to cool to RT and then the POCl$_3$ was removed by in vacuo. The residue was then repeatedly combined with toluene and then concentrated (4×50 mL of toluene) to effect azeotropic removal of trace POCl$_3$. The residue was taken up in CH$_2$Cl$_2$ and then absorbed onto silica gel powder (30 g). The resulting slurry was dried in vacuo then loaded onto a short column of silica and eluted with 2.5% MeOH:CHCl$_3$. The relatively non-polar fractions contain the desired product. These fractions were concentrated to provide a yellow/brown oil. The product was pure by TLC (4% MeOH:CHCl$_3$) and >95% pure by $^1$H NMR. MS m/z 364 (MH)$^+$.

EXAMPLE 23

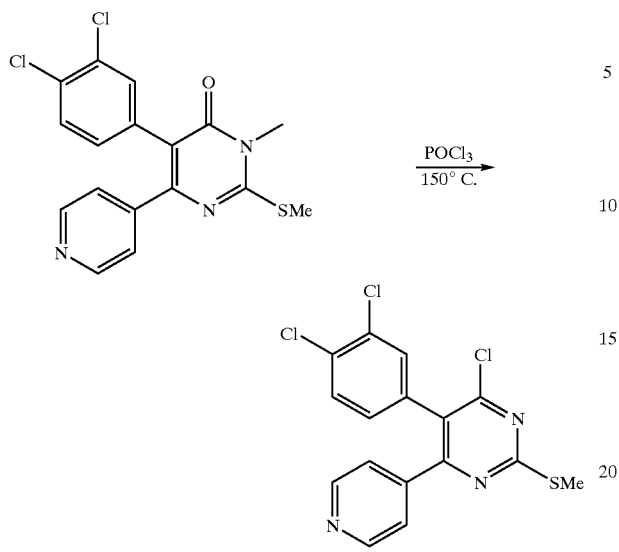

Prepared as in Example 22.

EXAMPLE 24

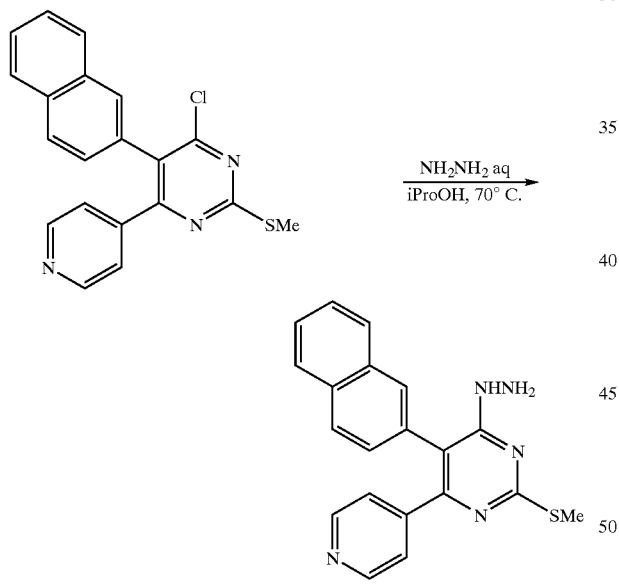

Isopropyl alcohol (300 mL) and hydrazine monohydrate (52.4 g, 54.1 mL, 104.6 mmol) were added to the chloropyrimidine (18.9 g, 52.3 mmol) in a 1 L round bottom flask that was fitted with a reflux condenser and a magnetic stir bar. The resulting solution was heated at 60° C. with vigorous stirring for 14 h. At this time a yellow precipitate had formed and TLC (4% MeOH:CHCl$_3$) indicated complete consumption of starting material. The mixture was concentrated and the residue was partitioned between sat aq NaHCO$_3$ and CH$_2$Cl$_2$. The organic layer was dried over MgSO$_4$ and concentrated to provide the product as a tan solid in purity of >90% by $^1$H NMR. MS m/z 360 (MH)$^+$.

EXAMPLE 25

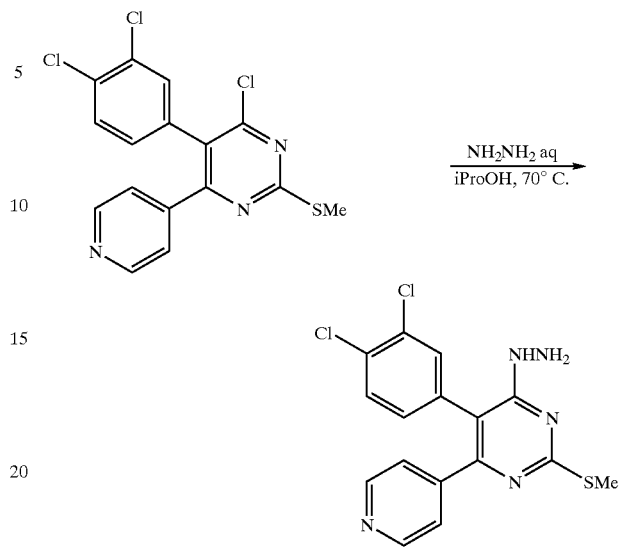

Prepared as in Example 24.

EXAMPLE 26

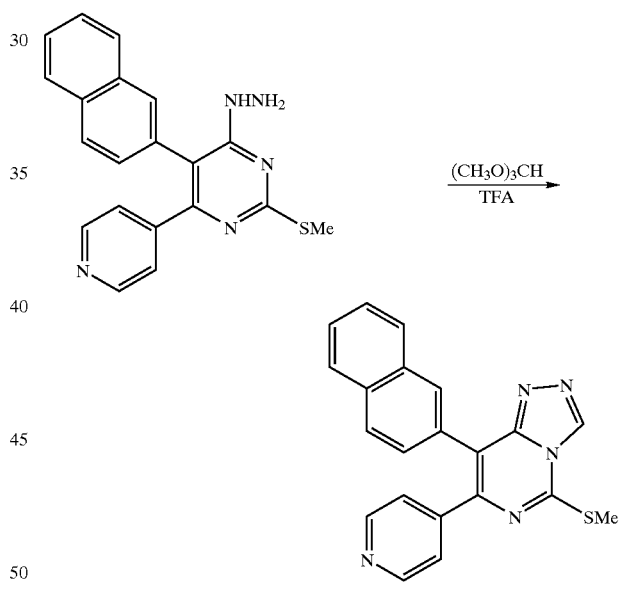

Trimethyl orthoformate (16.7 g, 16.2 mL, 156.9 mmol) and CH$_2$Cl$_2$ (300 mL) were added to the hydrazinopyrimidine (18.9 g, 52.3 mmol) in a 1 L round bottom flask fitted with a stir bar. The mixture was stirred for 1 h at RT and then trifluoroacetic acid (5.96 g, 4.02 mL, 156.9 mmol) was added. The resulting solution was stirred at RT for 16 h. At this time a yellow precipitate had formed and TLC (4% MeOH:CHCl$_3$) indicated complete consumption of starting material. The reaction mixture was washed with sat aq NaHCO$_3$ and the organic layer was dried over MgSO$_4$ and concentrated. The residue was dissolved in a minimum amount of CH$_2$Cl$_2$ (ca. 60 mL) and then ethyl ether (500 mL) was added gradually until a yellow/orange precipitate formed. The solid was collected, the filtrate was concentrated and a second crop of precipitate was collected as in the previous step, to provide a yellow/orange solid. The product was >95% pure by ¹H NMR. MS m/z 370 (MH)⁺.

EXAMPLE 27

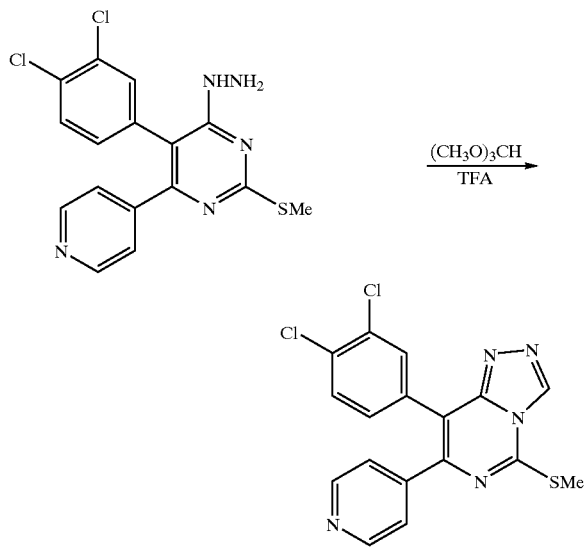

Prepared as in Example 26.

EXAMPLE 28

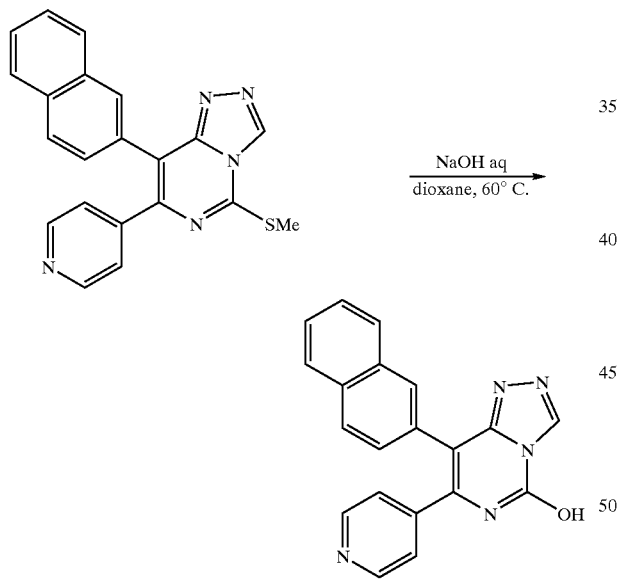

The triazolomethylppyrimidine methylsulfide (from Example 27) (10.3 g, 28.7 mmol) was suspended in dioxane (200 mL) and 2N aq NaOH (100 mL) was added. The mixture was stirred at 70° C. for 2 h and at this time analysis (TLC, 10% MeOH:CHCl₃) indicated starting material to be completely consumed. The reaction mixture was made just acidic by addition of 1N aq HCl, and then neutralized by addition of sat aq NaHCO₃. The resulting mixture was stiffed vigorously and purged with nitrogen gas for 2 h in a fume hood to remove noxious methyl mercaptan gas. The was concentrated and then partitioned between sat aq NaHCO₃ and CHCl₃. The organic layer was dried over Na₂SO₄ and concentrated to provide a yellow semi-solid, which was used without further purification. MS m/z 340 (MH)⁺.

EXAMPLE 29

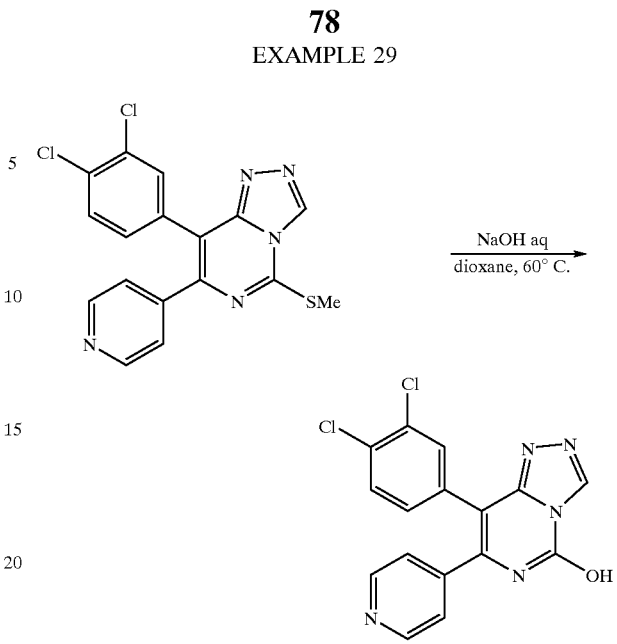

The triazolomethylppyrimidine methylsulfide (from Example 27) (11.62 g, 29.92 mmol) was suspended in dioxane (100 mL) and 2N aq NaOH (100 mL) was added. The mixture was stirred at 60° C. for 2 h and at this time analysis (TLC, 10% MeOH:CHCl₃) indicated starting material to be completely consumed. The reaction mixture was made just acidic by addition of 1N aq HCl, and then neutralized by addition of sat aq NaHCO₃. The resulting mixture was stirred vigorously and purged with nitrogen gas for 2 h in a fume hood to remove noxious methyl mercaptan gas. The mixture was then concentrated to an aqueous suspension. The solid was collected and rinsed with water, then with ether, and then dried in vacuo to provide an off-white solid, which was used without further purification. MS m/z 359 (MH)⁺.

EXAMPLE 30

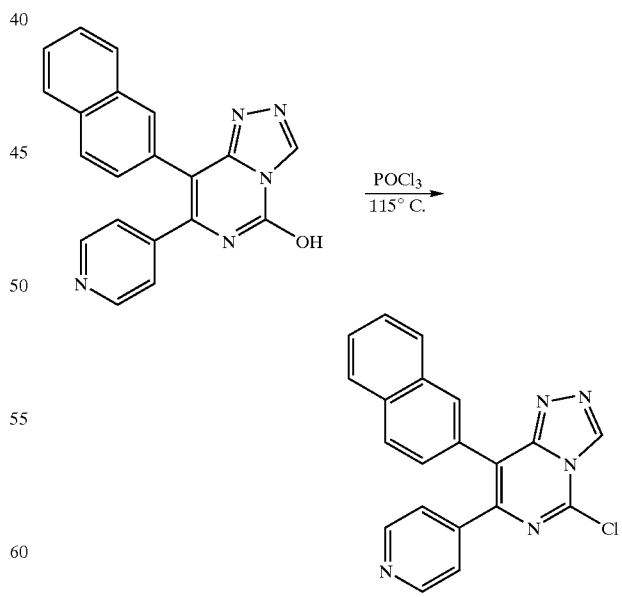

The hydroxy triazololpyrimidine (9.07 g, 27.50 mmol) was combined with POCl₃ (100 mL) and the resulting suspension was heated at 115° C. for 16 h. The resulting dark solution was concentrated and the residue was combined with toluene and concentrated repeatedly (3×50 mL of toluene) to effect azeotropic removal of residual POCl₃. The residue was purified by flash chromatography (3% MeOH:CHCl₃) and the relatively non-polar product fractions were concentrated to provide a reddish brown oil. MS m/z 359 (MH)⁺.

EXAMPLE 31

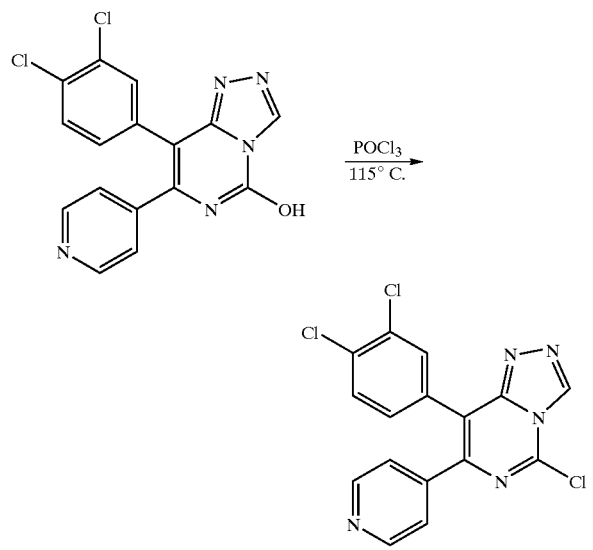

The hydroxytriazolopyrimidine (from Example 29) (10.49 g, 29.3 mmol) was suspended in POCl₃ (ca. 120 mL). The suspension was heated at 115° C. for 16 h. The resulting dark solution was concentrated and the residue was combined with toluene and concentrated repeatedly (3×50 mL of toluene) to effect azeotropic removal of residual POCl₃. The residue was purified by flash chromatography (3% MeOH:CHCl₃) and the relatively non-polar product fractions were concentrated to provide a reddish brown oil. MS m/z 377 (MH)⁺.

EXAMPLE 32a

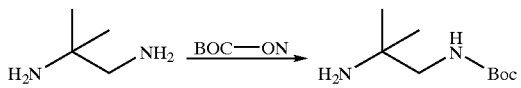

A solution of 1,2-diamino-2-methylpropane (17.6 g, 0.2 mol) in 100 ml dioxane and 100 ml water was cooled to 0° C. The triethylamine (30 g, 0.3 mol) and BOC-ON (54 g, 0.22 mol) were added and stirred 16 hours warming to room temperature. The mixture is concentrated and extracted twice with 100 ml of ethyl acetate. The combined organics are washed with sat. sodium chloride, dried over sodium sulfate, filtered, and concentrated to a syrup. Purification by silica gel chromatography (2% 2M ammonia methanol in dichloromethane) gave a solid. MS m/z (M+H) 189.2; C₉H₂₀N₂O₂ require 188.2.

EXAMPLE 32b

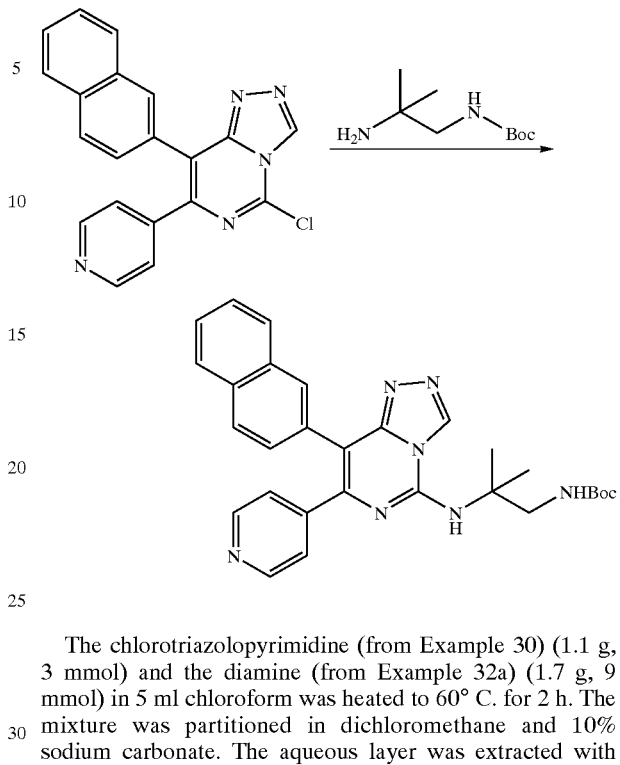

The chlorotriazolopyrimidine (from Example 30) (1.1 g, 3 mmol) and the diamine (from Example 32a) (1.7 g, 9 mmol) in 5 ml chloroform was heated to 60° C. for 2 h. The mixture was partitioned in dichloromethane and 10% sodium carbonate. The aqueous layer was extracted with dichloromethane. The combined organic layers were dried with sodium sulfate, filtered and concentrated to a syrup. Purification by silica gel chromatography (20% ethyl acetate in hexane then 50%) gave a syrup. MS m/z (M+H) 510.4; C₂₉H₃₁N₇O₂ require 509.3

EXAMPLE 32c

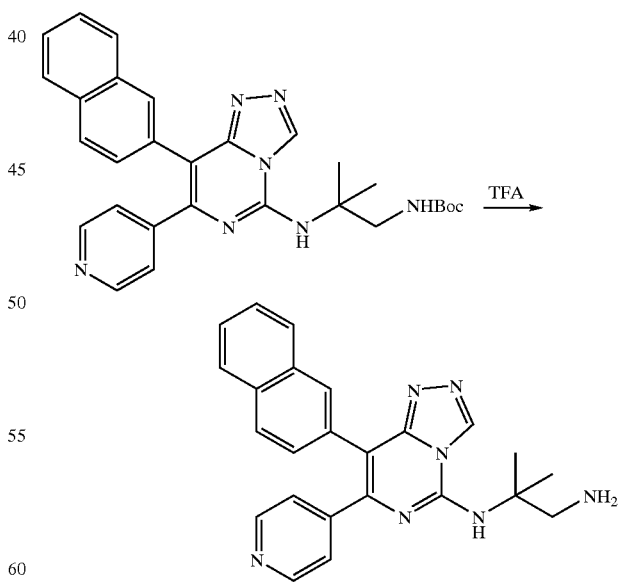

The triazolopyrimidine (from Example 32b) (0.72 g, 1.4 mmol) and 3 ml trifluoroacetic acid in 20 ml dichloromethane was stirred at rt for 3 h. The mixture was partitioned between 10% sodium carbonate and dichloromethane. The organic layer separated and the aqueous layer extracted with dichloromethane. The combined organic layers were dried with sodium sulfate, filtered and the solvent concentrated to a solid. The solid was washed with hot ethyl acetate, filtered and dried. MS m/z (M+H) 410.3; $C_{24}H_{23}N_7$ require 409.2

EXAMPLE 32d

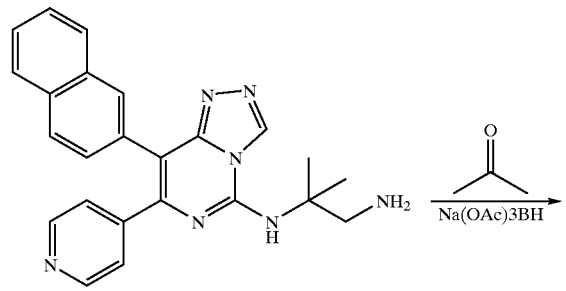

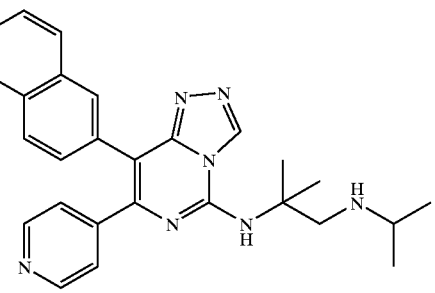

The aminotriazolopyrimidine (from Example 32c) (0.12 g, 0.3 mmol), acetone (0.06 g, 1 mmol) and sodium triacetoxyborohydride (0.21 g, 1 mmol) in 5 ml chloroform was stirred for 3 h at rt. The mixture was partitioned with chloroform and 10% sodium carbonate. The organic layer was separated and the aqueous layer extracted with chloroform. The combined organic layers were dried with sodium sulfate, filtered and the solvent concentrated to give a syrup. Purification by silica gel chromatography (2% 2M ammonia methanol in ethyl acetate) gave 0.12 g of syrup The syrup was dissolved in ethyl acetate and 1 ml 2M HCl in ether was added. The solvent was concentrated to give a solid. MS m/z (M+H) 452.3; $C_{27}H_{29}N_7$ require 451.3

EXAMPLE 32e

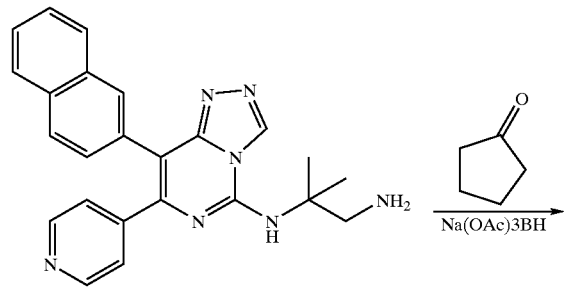

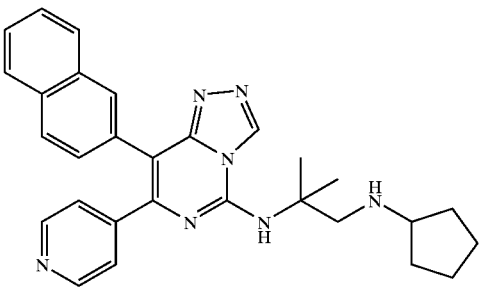

The aminotriazolopyrimidine (from Example 32c) (0.12 g, 0.3 mmol), cyclopentanone (0.08 g, 1 mmol) and sodium triacetoxyborohydride (0.21 g, 1 mmol) in 5 ml chloroform was stirred for 3 h at rt. The mixture was partitioned with chloroform and 10% sodium carbonate. The organic layer was separated and the aqueous layer extracted with chloroform. The combined organic layers were dried with sodium sulfate, filtered and the solvent concentrated to give a syrup. Purification by silica gel chromatography (2% 2M ammonia methanol in ethyl acetate) gave 0.14 g of syrup The syrup was dissolved in ethyl acetate and 1 ml 1M HCl in ether was added. The solvent was concentrated to give a solid. MS m/z (M+H) 478.2; $C_{29}H_{31}N_7$ require 477.3

EXAMPLE 33

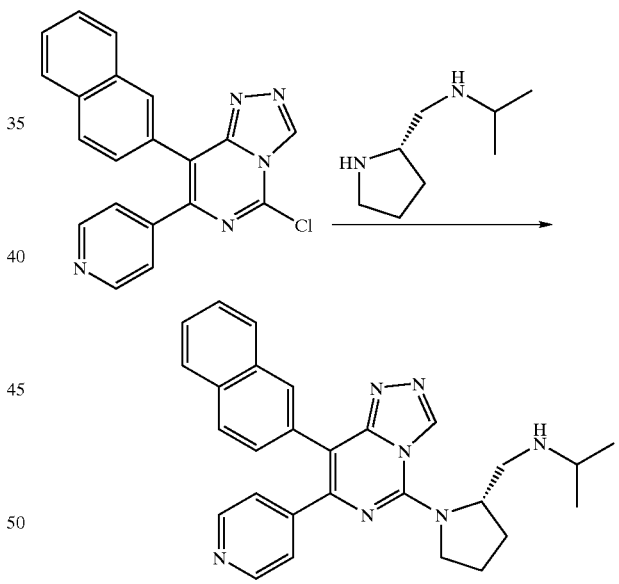

The chloropyrimidine (from Example 30) (0.18 g, 0.5 mmol), amino-pyrrolidine (0.09 g, 0.6 mmol) and diisopropylethylamine (0.13 g, 1 mmol) in 5 ml dichloromethane was stirred at rt for 3 h. The solution was partitioned between dichloromethane and 10% sodium carbonate. The organic layer was separated and the aqueous layer extracted with dichloromethane. The combined organic layers were dried with sodium sulfate, filtered and the solvent concentrated to a syrup. Purification by silica gel chromatography (2% 2M ammonia methanol in ethyl acetate) gave 0.1 g of syrup. The syrup was dissolved in ethyl acetate and 1 ml 1M HCl in ether was added. The solvent was concentrated to a solid. MS m/z (M+H) 464.3; $C_{28}H_{29}N_7$ require 463.3

EXAMPLE 34

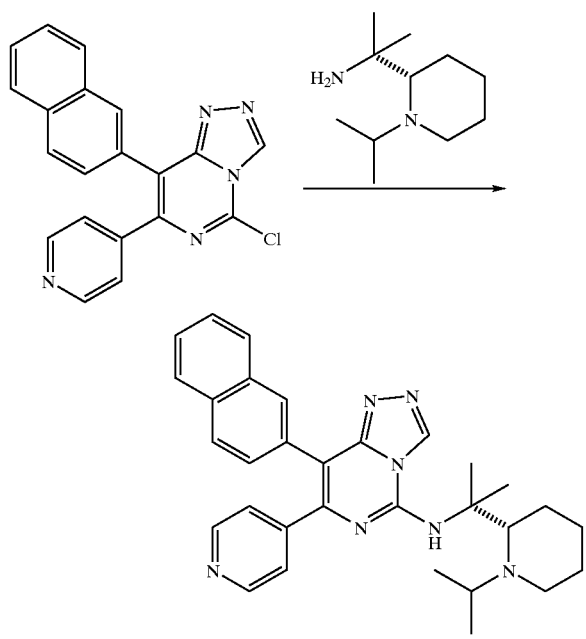

EXAMPLE 35

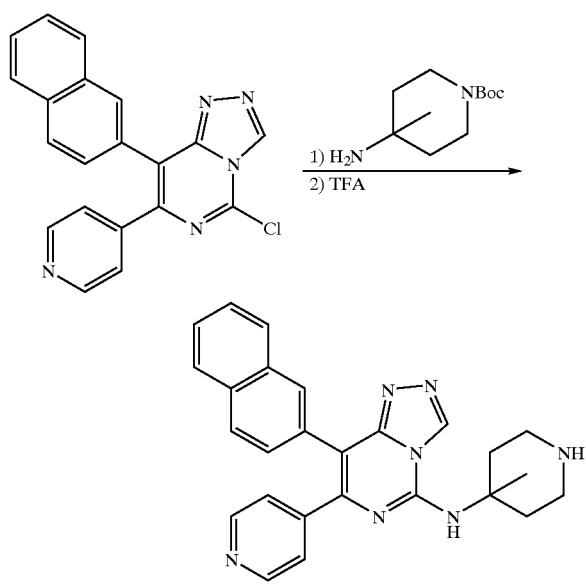

The triazolopyrimidine chloride (from Example 30) (7.84 g, 22.0 mmol) was combined with the Boc-protected amino piperidine (14.9 g, 70.0 mmol) and a minimum amount of CHCl$_3$ (ca. 40 mL) and the resulting solution was heated at 105° C. with evaporation of the CHCl$_3$. The oily residue was heated at 105° C. for an addition 15 min. The residue was partitioned between sat aq Na$_2$CO$_3$ and CHCl$_3$. The organic layer was dried over Na$_2$SO$_4$ and concentrated. The residue was purified by flash chromatography (2% MeOH:CHCl$_3$) to provide the Boc-protected intermediate as a yellow foam (4.67 g). MS m/z 536 (MH)$^+$. This material was dissolved in CHCl$_3$ (20 mL) and trifluoroacetic acid (5 mL) was added. The solution was stirred at RT for 2 h and then was diluted gradually with sat aq Na$_2$CO$_3$. The aqueous mixture was extracted with CHCl$_3$ and the organic layer was dried over Na$_2$SO$_4$ The aqueous mixture was extracted with CHCl$_3$ and the organic layer was dried over Na$_2$SO$_4$ and concentrated and the residue was purified by flash chromatography (20% NH$_3$/MeOH:CHCl$_3$) to provide the deprotected piperidine as a yellow foam. $^1$HNMR δ. MS m/z 436 (MH)$^+$.

EXAMPLE 36a

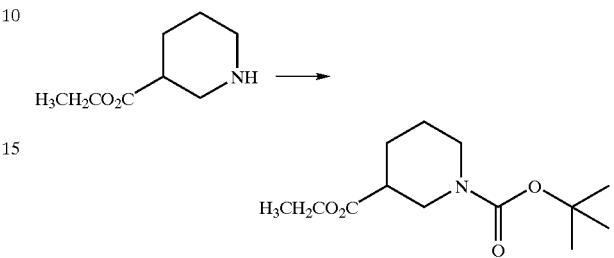

A solution of ethyl nipecotate (15.7 g, 0.1 mol) in 100 ml ethyl acetate and 100 ml 10% sodium carbonate was cooled to 0° C. Di-t-butyldicarbonate (24 g, 0.11 mol) was added and stirred 4 h warming to room temperature. The ethyl acetate layer was separated and the aqueous partitioned with ethyl acetate. The combined layers were washed with sat. sodium chloride, dried with sodium sulfate, filtered and concentrated to a syrup. Purification by silica gel chromatography (10% ethyl acetate in hexane) gave a syrup. MS m/z (M+H) 258.1; C$_{13}$H$_{23}$NO$_4$ require 257.2

EXAMPLE 36b

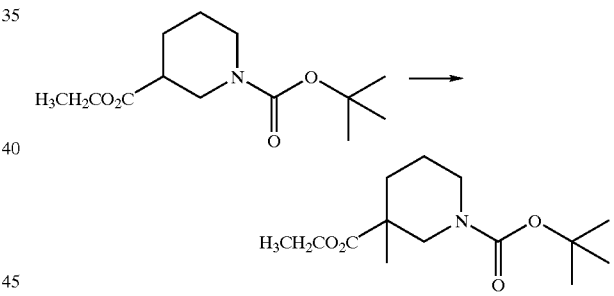

A solution of Example 36a (21.2 g, 0.082 mol) in 100 ml THF was cooled to −70° C. Lithium bis-trimethylsilyl amide (100 ml 1M in ether, 0.1 mol) was added and stirred 15 minutes. Methyl iodide (15.1 g, 0.11 mol) was added and stirred 18 h warming to room temperature. The mixture was poured onto sat. ammonium chloride and extracted twice with ether. The combined ether layers were partitioned with sat sodium chloride, dried with magnesium sulfate, filtered and the solvent concentrated to give a syrup. MS m/z (M+H) 272.1; C$_{14}$H$_{25}$NO$_4$ require 271.2.

EXAMPLE 36c

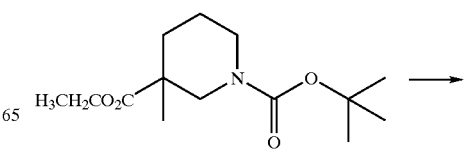

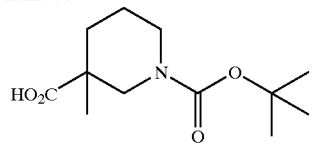

A solution of Example 36b (16.8 g, 0.062 mol), 100 ml 1N sodium hydroxide and 100 ml ethanol was heated to 80° for 18 h. The mixture was concentrated, acidified with 1M phosphoric acid, and extracted twice with dichloromethane. The combined organic layers were dried with sodium sulfate, filtered and concentrated to a solid. MS m/z (M+H) 244.4; $C_{12}H_{21}NO_4$ require 243.2

EXAMPLE 36d

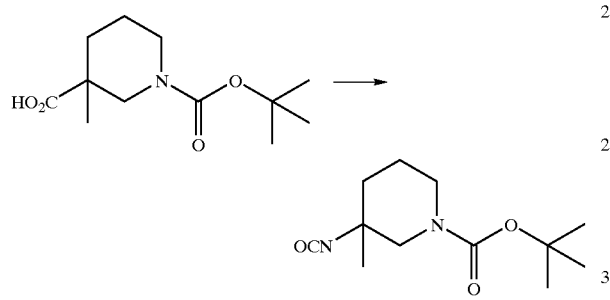

A solution of Example 36c (7.9 g, 0.033 mol), diphenylphosphoryl azide (10.7 g, 0.039 mol), triethylamine (3.9 g, 0.039 mol) in 100 ml toluene was heated to 100° C. for 1 h. The solution was washed with sat. sodium bicarbonate, dried with sodium sulfate and the solvent concentrated to a syrup. Purification by silica gel chromatography (5% ethyl acetate in hexane) gave a syrup. MS m/z (M+H) 241.2; $C_{12}H_{21}N_2O_3$ require 240.2.

EXAMPLE 36e

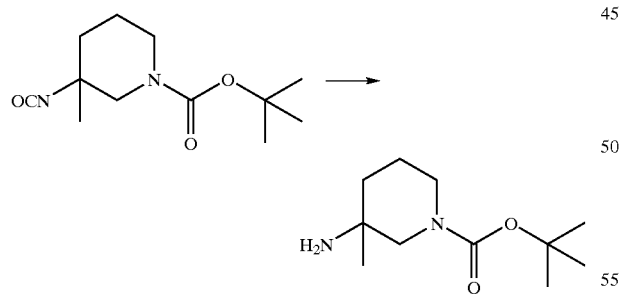

A solution of Example 36d (4 g, 0.017 mol) and potassium trimethyl-silanolate (4.5 g, 0.035 mol) in 50 ml THF was stirred at rt for 18 h. The solvent was concentrated to a syrup. The syrup was partitioned between sat. sodium bicarbonate and dichloromethane. The organic layer was separated and the aqueous extracted with dichloromethane. The combined organic layers were dried with sodium sulfate, filtered and concentrated to a syrup. 3.5 g MS m/z (M+H) 215.3; $C_{11}H_{22}N_2O_2$ require 214.2.

EXAMPLE 36f

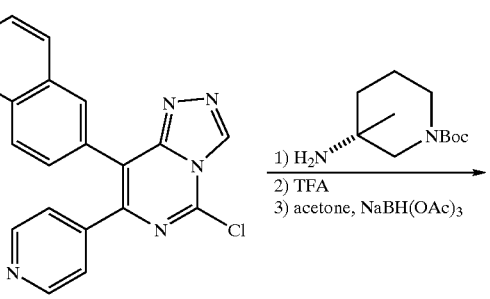

EXAMPLE 37

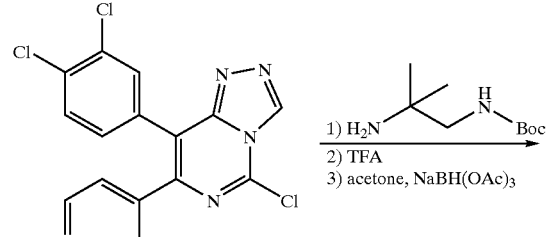

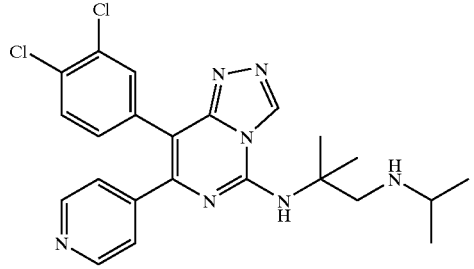

EXAMPLE 38

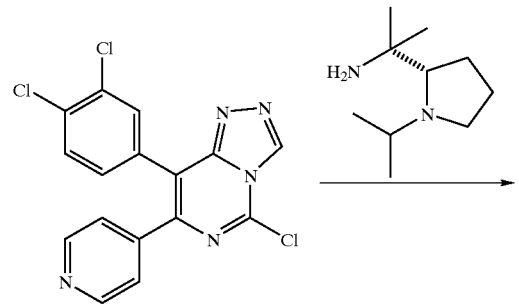

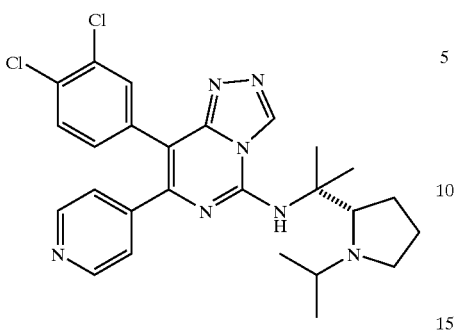

EXAMPLE 39

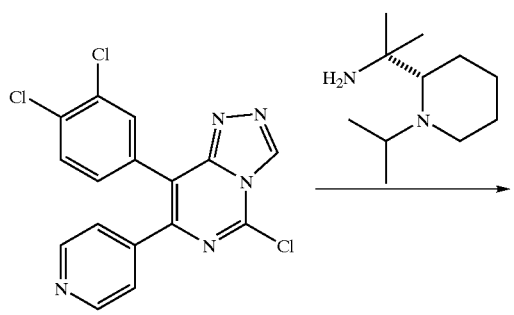

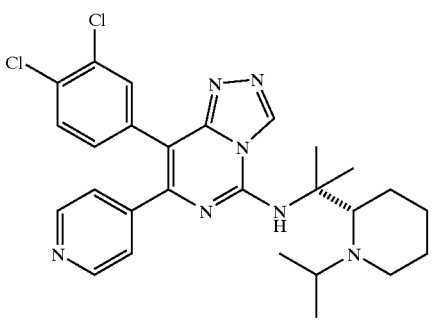

EXAMPLE 40

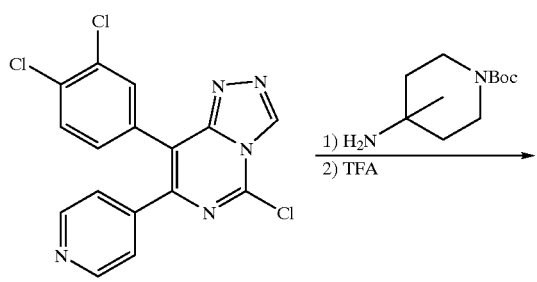

The triazolopyrimidine chloride (from Example 31) (3.27 g, 8.7 mmol) was combined with the Boc-protected amino piperidine (3.73 g, 17.4 mmol) and a minimum amount of $CHCl_3$ (ca. 20 mL) and the resulting solution was heated at 105° C. with evaporation of the $CHCl_3$. The oily residue was heated at 105° C. for an addition 15 min. The residue was partitioned between sat aq $Na_2CO_3$ and $CHCl_3$. The organic layer was dried over $Na_2SO_4$ and concentrated. The residue was purified by flash chromatography (1% $MeOH:CHCl_3$) to provide the Boc-protected intermediate as a yellow foam. MS m/z 554 $(MH)^+$. This material was dissolved in $CHCl_3$ (20 mL) and trifluoroacetic acid (10 mL) was added. The solution was stirred at RT for 2 h and then was diluted gradually with sat aq $Na_2CO_3$. The aqueous mixture was extracted with $CHCl_3$ and the organic layer was dried over $Na_2SO_4$ and concentrated and the residue was purified by flash chromatography (20% $NH_3/MeOH:CHCl_3$) to provide the deprotected piperidine as a yellow foam. MS m/z 454 $(MH)^+$.

EXAMPLE 41

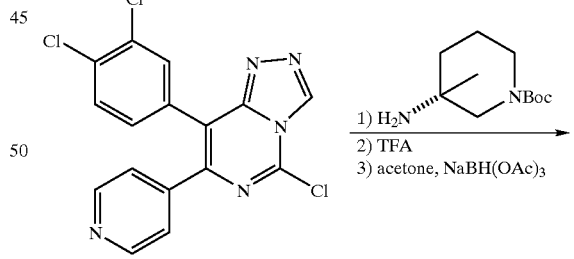

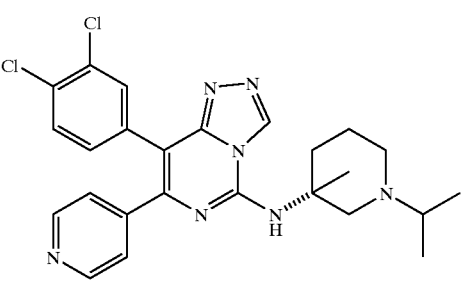

EXAMPLE 42

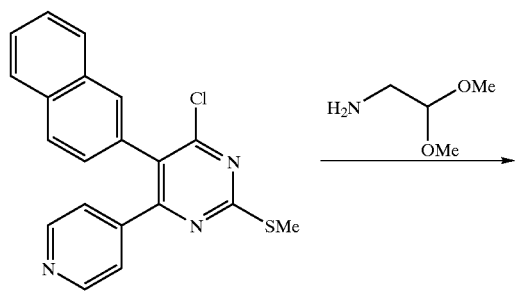

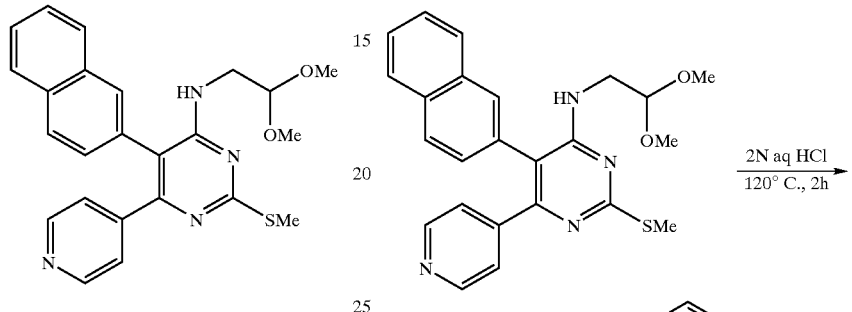

The naphthylchloropyrimidine (from Example 22) (8.95 g, 24.66 mmol) was dissolved in aminoacetaldehyde dimethylactal (5.44 g, 5.64 ml, 51.78 mmol) in a 250 ml round bottom flask fitted with a reflux condenser and a magnetic stir bar. The resulting solution was heated to 140° C. and stirred for 1.5 h. After this time, TLC (10% MeOH:CHCl$_3$) and MS indicated that starting material was consumed. The mixture was allowed to cool to RT, then quenched with H$_2$0, extracted with CHCl$_3$, dried over NaSO$_4$ and concentrated. The residue was purified by flash chromatography in 5–95% gradient of EtOAc/Hex and the product fractions were concentrated to provide a yellowish solid. MS m/z, M+1 433.3, M−1 431.3. C$_{24}$H$_{24}$N$_4$O$_2$S require 432.16

EXAMPLE 43

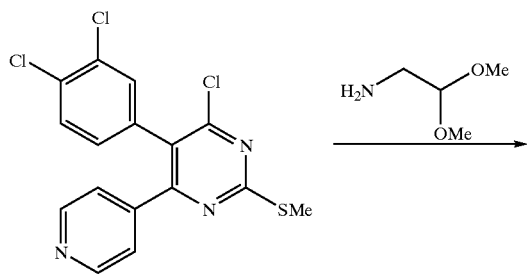

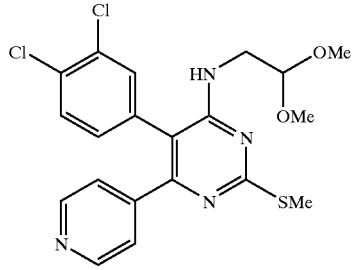

The 3,4-dichloro-chloropyrimidine (from Example 23) (7.0 g, 18.4 mmol) was dissolved in aminoacetaldehyde dimethylactal (4.06 g, 4.2 ml, 38.6 mmol) in a 250 ml round bottom flask fitted with a reflux condenser and a magnetic stir bar. The resulting solution was heated to 140° C. and stirred for 1.5 h. After this time, TLC (10% MeOH:CHCl$_3$) and MS indicated that starting material was consumed. The mixture was allowed to cool to RT, then quenched with H$_2$0, extracted with CHCl$_3$, dried over NaSO$_4$ and concentrated. The residue was purified by flash chromatography in 5–60% gradient of EtOAc/Hex and the product fractions were concentrated to provide a yellowish solid. MS m/z, M+1 451.1, M−1 449.1, C$_{20}$H$_{20}$Cl$_2$N$_4$O$_2$S require 450.07

EXAMPLE 44

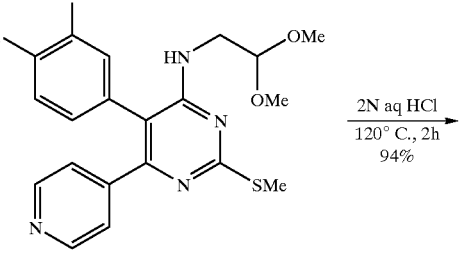

The naphthyldimethylacetal pyrimidine (from Example 42) (3.16 g, 7.32 mmol) was dissolved in 2N HCl aq. (60 ml) in a 150 ml round bottom flask fitted with a reflux condenser and a magnetic stir bar. The resulting solution was heated to 130° C. and stirred for 2 h. After this time, TLC (1:1 EtOAc:Hex) and MS indicated that starting material was consumed. The mixture was allowed to cool to RT, then the HCl solution was slowly poured into a 1 L erlenmeyer flask containing 300 ml of sodium bicarbonate aqueous solution, the pH of solution was checked to be ~8, then extracted with CHCl$_3$, dried over NaSO$_4$, and concentrated. The residue was then repeatedly combine with toluene and concentrated (3×30 ml of toluene) to effect azeotropic removal of trace H$_2$O and dried in the oven at 60° C. overnight. MS m/z, M+1 357.2, M−1 355.2 C$_{21}$H$_{16}$N$_4$O$_2$S require 356.13.

EXAMPLE 45

-continued

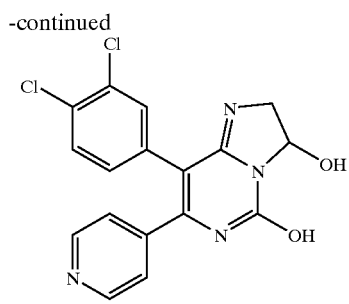

The 3,4-dichlorodimethylacetal pyrimidine (from Example 43) (5.9 g, 13.1 mmol) was dissolved in 2N HCl aq. (110 ml) in a 250 ml round bottom flask fitted with a reflux condenser and a magnetic stir bar. The resulting solution was heated to 130° C. and stirred for 2 hr. After this time, TLC (1:1 EtOAc:Hex) and MS indicated that starting material was consumed. The mixture was allowed to cool to RT, then the HCl solution was slowly poured into a 2 L erlenmeyer flask containing 600 ml of sodium bicarbonate aqueous solution, the pH of solution was checked to be ~8, then extracted with $CHCl_3$, dried over $NaSO_4$, and concentrated. The residue was then repeatedly combine with toluene and concentrated (3×50 ml of toluene) to effect azeotropic removal of trace $H_2O$ and dried in the oven at 60° C. overnight. MS m/z, M+1 375.4, M−1 373.2. $C_{17}H_{12}Cl_2N_4O_2S$ require 374.02.

EXAMPLE 46

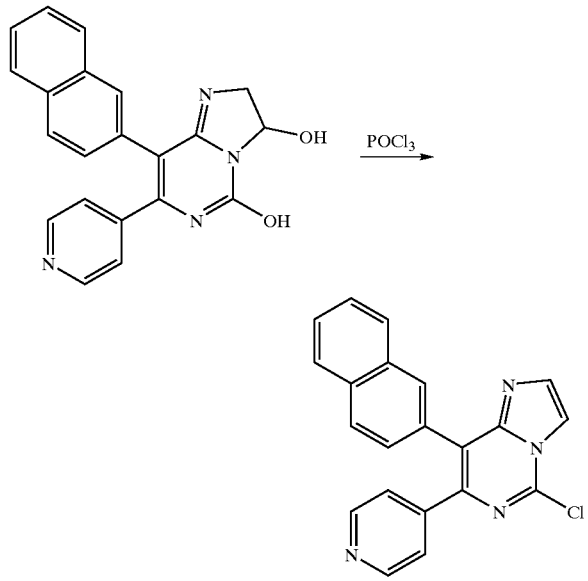

Phosphorous oxychloride (23.3 g, 15 ml, 152 mmol) was added to the Naphthylalcoholpyrimidine (from Example 44) (2.17 g, 6.08 mmol) in a 100 ml round bottom flask fitted with a reflux condenser and a magnetic stir bar. The resulting solution was heated to 150° C. and stirred vigorously for 18 h. At this time TLC (10% MeOH: $CHCl_3$) indicated that starting material was consumed. The mixture was allowed to cool to RT and then the $POCl_3$ was removed by in vacuo. The residue was then repeatedly combined with toluene and then concentrated (4×50 ml) to effect azeotropic removal of trace $POCl_3$. The residue was taken up in 10% MeO- H:$CHCl_3$ and then absorbed onto silica gel powder (40 mg). The resulting slurry was dried in vacuo then loaded onto column of silica and eluted with 5–10% gradient of MeO- H:$CHCl_3$. The product fractions were concentrated to provide a brownish solid. MS m/z M+1 357, $C_{21}H_{13}ClN_4$ require 356.08.

EXAMPLE 47

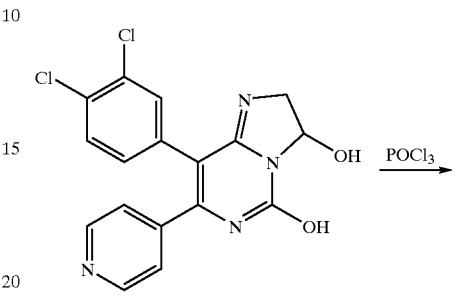

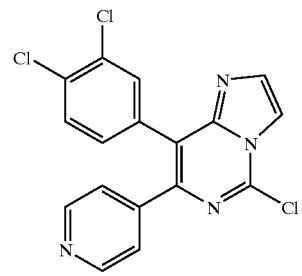

Phosphorous oxychloride (766.65 mg, 5 ml, 5 mmol) was added to the 3,4-dichloroalcoholpyrimidine (from Example 45) (750 mg, 0.2 mmol) in a 25 ml round bottom flask fitted with a reflux condenser and a magnetic stir bar. The resulting solution was heated to 150° C. and stirred vigorously for 18 h. At this time TLC (10% MeOH: $CHCl_3$) indicated that starting material was consumed. The mixture was allowed to cool to RT and then the $POCl_3$ was removed by in vacuo. The residue was then repeatedly combined with toluene and then concentrated (4×10 ml) to effect azeotropic removal of trace $POCl_3$. The residue was taken up in 10% MeO- H:$CHCl_3$ and then absorbed onto silica gel powder (10 mg). The resulting slurry was dried in vacuo then loaded onto column of silica and eluted with 5–10% gradient of MeO- H:$CHCl_3$. The product fractions were concentrated to provide a brownish solid. MS m/z M+1 375.1 $C_{17}H_9Cl_3N_4$ require 373.99

EXAMPLE 48

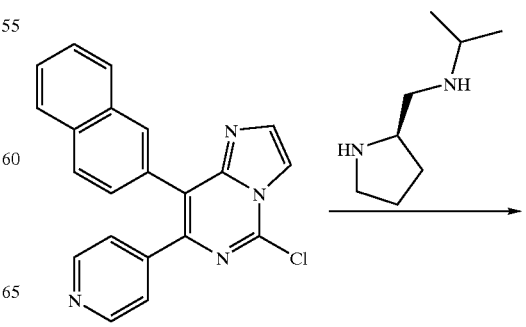

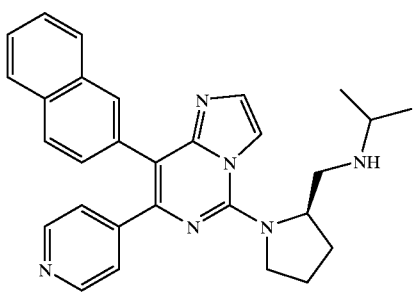

The naphthylbicyclicimizolochloridepyrimidine (from Example 46) (600 mg, 1.69 mmol) was dissolved in DMF (10 ml) and R—N-(2-pyrrolinylmethy)-isopropylamine (502.6 mg, 3.54 mmol) was added in a 50 ml round bottom flask fitted with a magnetic stir bar. The resulting solution was stirred for 1 h at RT. After this time, TLC (10% MeOH/CHCl$_3$) and MS indicated that starting material was consumed. Then quenched with H$_2$O, extracted with CHCl$_3$, dried over NaSO$_4$ and concentrated. The residue was purified by flash chromatography in 3–10% gradient of MeOH/CHCl$_3$ and the product fractions were concentrated to provide a yellowish solid (260 mg). $^1$H NMR, MS m/z M+1 463.4 C$_{29}$H$_{30}$N$_6$ require 462.25.

EXAMPLE 49

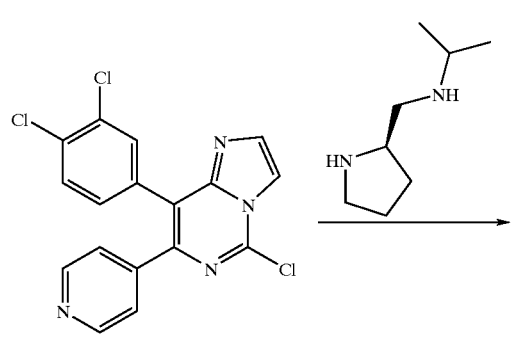

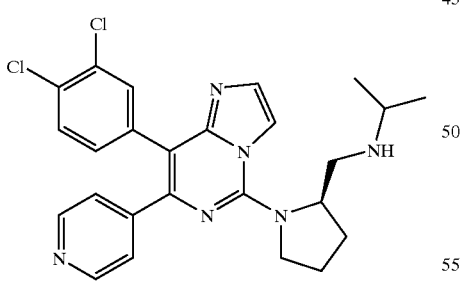

The 3,4-dichlorobicyclicamizolechloridepyrimidine (from Example 47) (1.1 g, 2.94 mmol) was dissolved in DMF (15 ml) and R—N-(2-pyrrolinylmethy) isopropylamine (800 mg, 6.18 mmol) was added in a 50 ml round bottom flask fitted with a magnetic stir bar. The resulting solution was stirred for 1 h at RT. After this time, TLC (10% MeOH/CHCl$_3$) and MS indicated that starting material was consumed. Then quenched with H$_2$O, extracted with EtOAc, dried over NaSO$_4$ and concentrated. The residue was purified by flash chromatography in 70–100% gradient of EtOAc/Hex and the product fractions were concentrated to provide a yellowish solid. MS m/z M+1 481.2, M−1 479.2, C$_{25}$H$_{26}$Cl$_2$N$_6$ require 480.16.

EXAMPLE 50

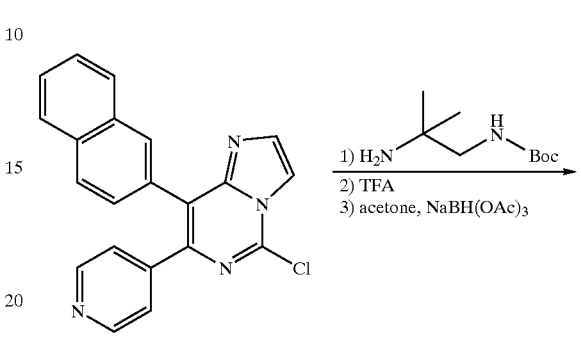

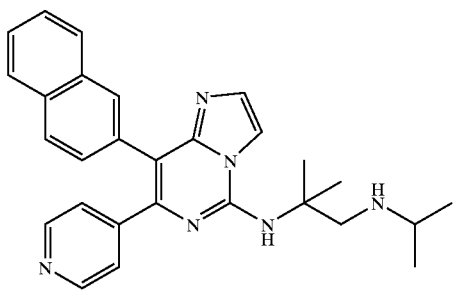

EXAMPLE 51

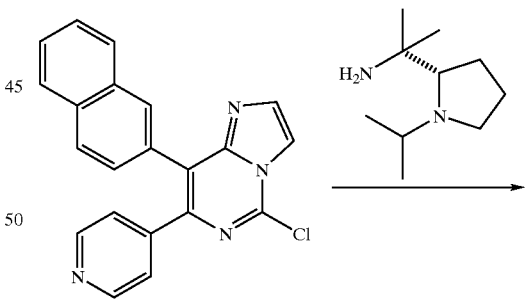

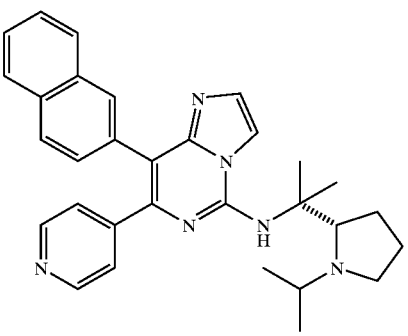

EXAMPLE 52
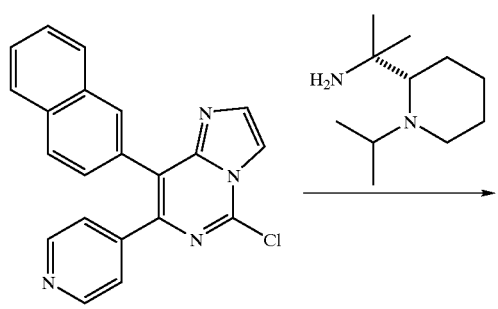
EXAMPLE 53
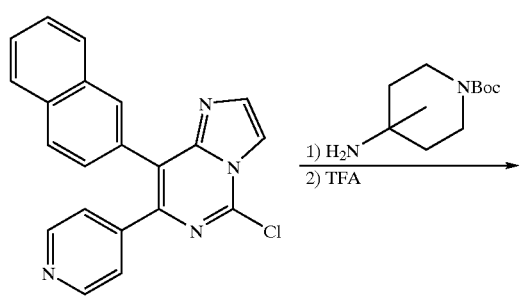
EXAMPLE 54
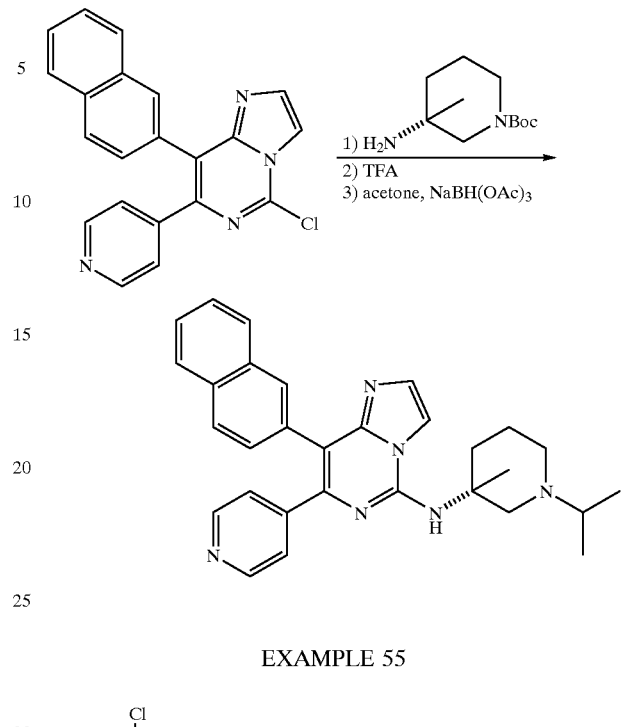
EXAMPLE 55
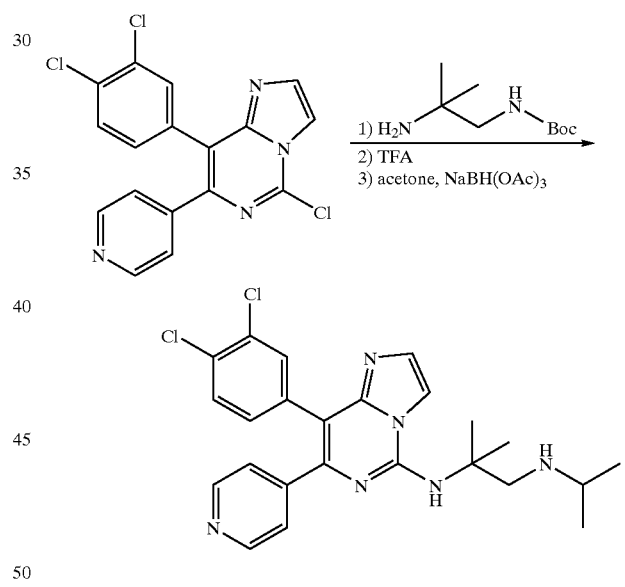
EXAMPLE 56
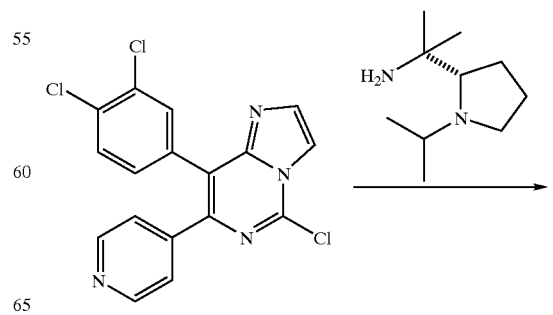

97
-continued
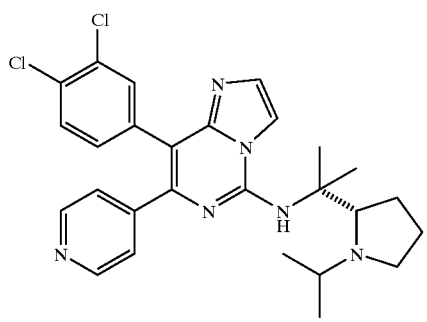
EXAMPLE 57
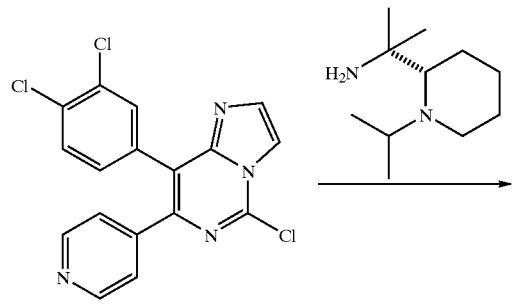
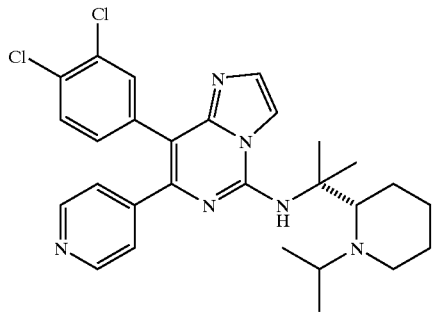
EXAMPLE 58
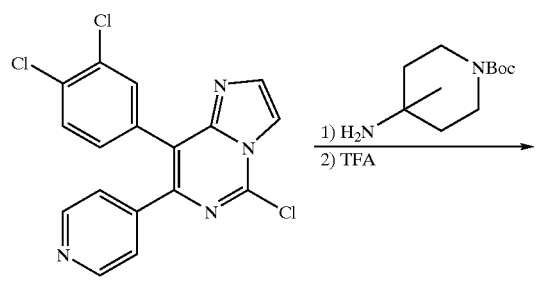
98
-continued
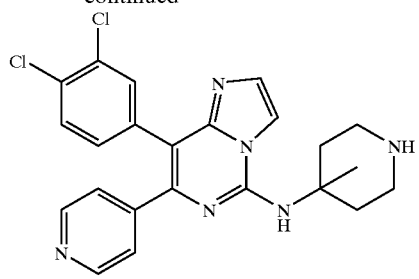
EXAMPLE 59
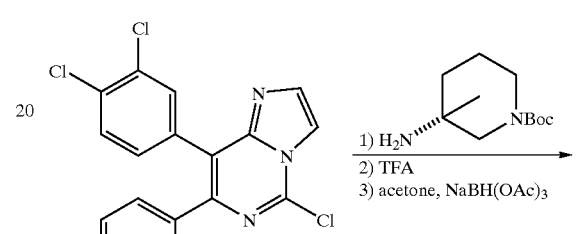
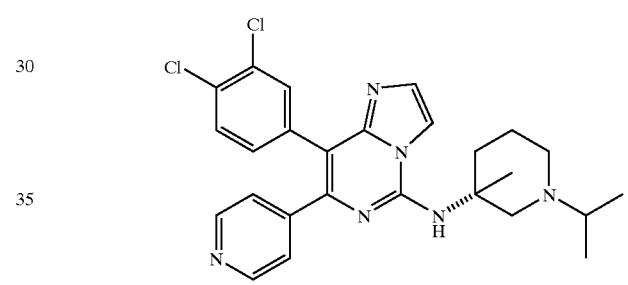
EXAMPLE 60
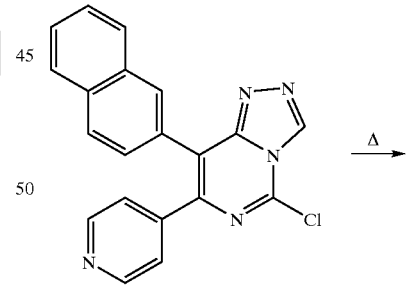
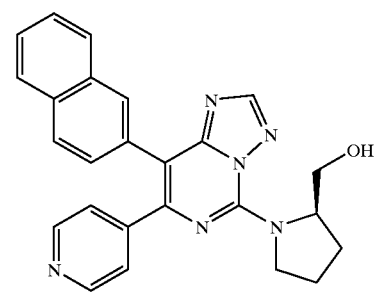

Naphthyltriazolpyrimidine chloride (610 mg, 1.65 mmol) (from Example 30) was dissolved in (R)-(−)-2-pyrrolidinemethanol (500 mg, 4.95 mmol) in a μW sealed tube with a magnetic stir bar. The resulting solution was heated to 120° C. and stirred under microwave conditions for 5 minutes. After this time MS indicated that starting material was consumed. The mixture was quenched with H$_2$O, and resulting product would ppt, collected through fritted funnel and place in the oven to at 60° C. to dried. A yellowish solid product resulted. MS m/z 422.19, $C_{25}H_{22}N_6O$, M+1 423.3, M−1 421.2.

EXAMPLE 60a

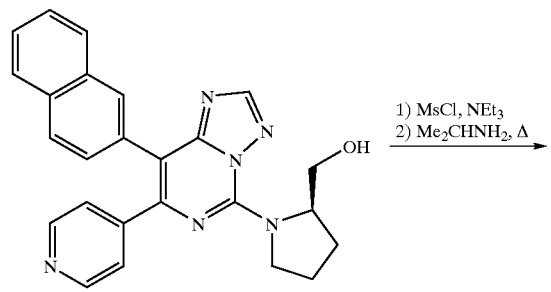

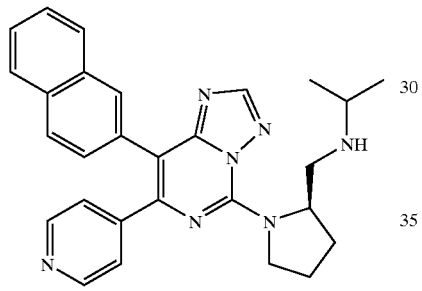

The alcohol (298 mg, 0.70 mmol) (from Example 60) was dissolved in methylene chloride (40 mL) and triethylamine (77.9 mg, 0.77 mmol) was added followed by methanesulfonyl chloride (88.2 mg, 0.77 mmol). The solution was stirred for 4 hr. At this time isopropylamine (207 mg, 3.5 mmol) was added and the resulting solution was heated at reflux for 16 hr. At this time the mixture was partitioned between methylene chloride and sat. aq sodium carbonate. The organic phase was dried over Na$_2$SO$_4$ and then concentrated. The residue was purified by flash chromatography (20% NH$_3$/MeOH:CHCl$_3$) to provide the product as a yellow foam. MS m/z 464 (MH)$^+$.

EXAMPLE 60b

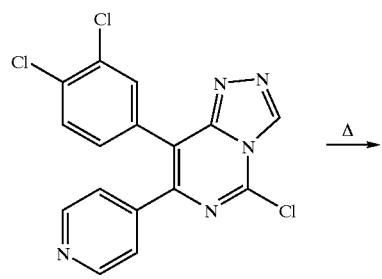

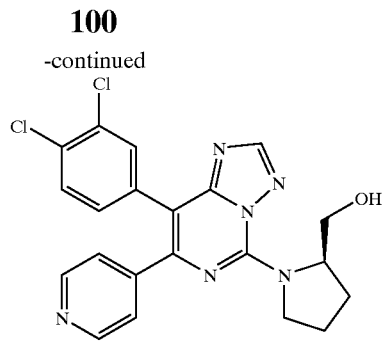

3,4-Dichlorotriazolpyrimidine chloride (500 mg, 1.29 mmol) (from Example 31) was dissolved in (R)-(−)-2-pyrrolidinemethanol (391 mg, 3.88 mmol) in a μW sealed tube with a magnetic stir bar. The resulting solution was heated to 120° C. and stirred under microwave conditions for 5 minutes. After this time MS indicated that starting material was consumed. The mixture was quenched with H$_2$O, and resulting product would ppt, collected through a fritted funnel and place in the oven at 60° C. to be dried. A yellowish solid product resulted. MS m/z 440.09, $C_{21}H_{18}Cl_2N_6O$, M+1 441.2, M−1 439.0.

EXAMPLE 60c

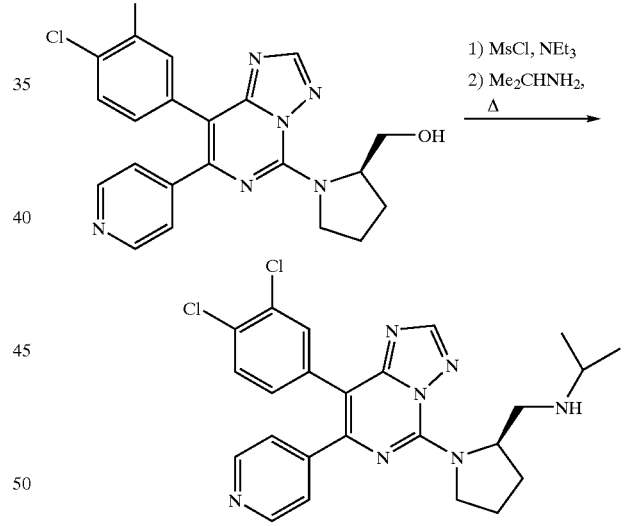

The alcohol (322 mg, 0.73 mmol) (from Example 60b) was dissolved in methylene chloride (40 mL) and triethylamine (80.9 mg, 0.80 mmol) was added followed by methanesulfonyl chloride (91.6 mg, 0.80 mmol). The solution was stirred for 4 hr. At this time isopropylamine (207 mg, 3.5 mmol) was added and the resulting solution was heated at reflux for 16 hr. At this time the mixture was partitioned between methylene chloride and sat. aq sodium carbonate. The organic phase was dried over Na$_2$SO$_4$ and then concentrated. The residue was purified by flash chromatography (20% NH$_3$/MeOH:CHCl$_3$) to provide the product as a yellow foam. MS m/z 483 (MH)$^+$.

EXAMPLE 61

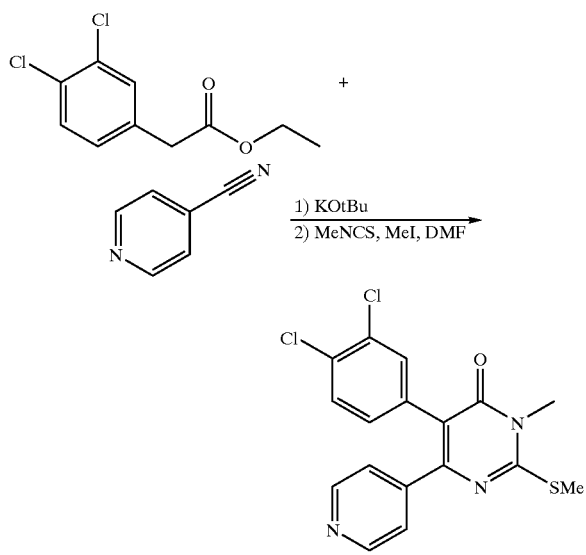

4-Cyanopyridine (38.08 g, 366.0 mmol) was added to a stirred solution of 3,4-dichlorophenylacetic acid ethyl ester (85.26 g, 366.0 mmol) in DMF (360 mL) in a 5 L round bottom flask fitted with a magnetic stir bar. A solution of potassium tert-butoxide (366.0 mL, 1M solution in tert-butanol) was added dropwise over 1 h via addition funnel. A solution of methyl thioisocyanate (26.77 g, 366.0 mmol) in DMF (180 mL) was added to the reaction dropwise over 30 min. The resulting reddish brown mixture was stirred at RT for 2 h. The mixture was then cooled to 0° C. and then a solution of methyl iodide (22.7 g, 366.0 mmol) in DMF (100 mL) was added dropwise over 30 min. The mixture was stirred vigorously at RT for 14 h. At this time the mixture is diluted with water to increase the volume of solvent four fold. The mixture is stirred vigorously over 4 h and a suspension was formed. The solid is collected by filtration and washed with copious amounts of water. The solid is then stirred as a suspension in ethyl acetate and then collected by filtration, washed with ethyl ether, then dried to provide a off-white solid. The product was pure by TLC (4% MeOH:CHCl$_3$). MS m/z 379.3 (MH)$^+$.

EXAMPLE 62

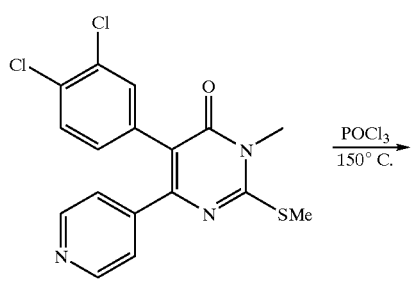

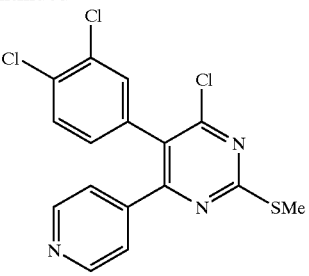

Phosphorous oxychloride (107.7 g, 65.3 mL, 700 mmol) was added to the methylthiopyrimidinone (26.5 g, 70.0 mmol) in a 1 L round bottom flask fitted with a reflux condenser and a magnetic stir bar. The resulting solution was heated at 150° C. and stirred vigorously for 14 h. At this time TLC (4% MeOH:CHCl$_3$) indicated that starting material was consumed. The mixture was allowed to cool to RT and then the POCl$_3$ was removed by in vacuo. The residue was then repeatedly combined with toluene and then concentrated (4×50 mL of toluene) to effect azeotropic removal of trace POCl$_3$. The residue was taken up in CH$_2$Cl$_2$ and then absorbed onto silica gel powder (30 g). The resulting slurry was dried in vacuo then loaded onto a short column of silica and eluted with 2.5% MeOH:CHCl$_3$. The relatively non-polar fractions contain the desired product. These fractions were concentrated to provide a yellow/brown oil. The product was pure by TLC (4% MeOH:CHCl$_3$) and >95% pure by $^1$H NMR. MS m/z 383.7 (MH)$^+$.

EXAMPLE 63

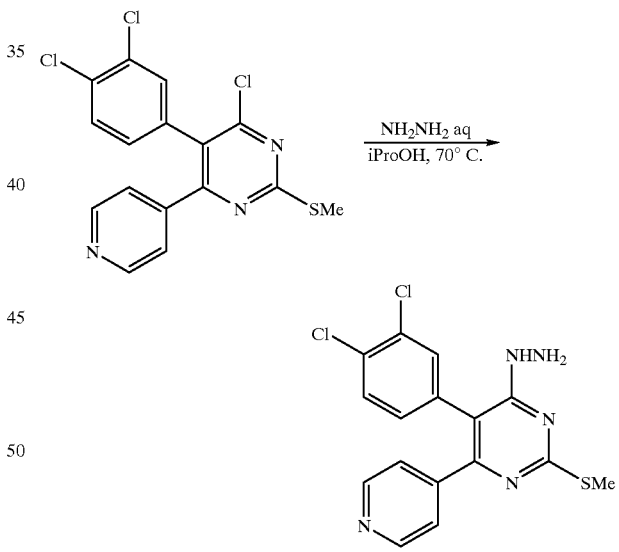

Isopropyl alcohol (300 mL) and hydrazine monohydrate (52.4 g, 54.1 mL, 104.6 mmol) were added to the chloropyrimidine (20.1 g, 52.3 mmol) in a 1 L round bottom flask that was fitted with a reflux condenser and a magnetic stir bar. The resulting solution was heated at 60° C. with vigorous stirring for 14 h. At this time a yellow precipitate had formed and TLC (4% MeOH:CHCl$_3$) indicated complete consumption of starting material. The mixture was concentrated and the residue was partitioned between sat aq NaHCO$_3$ and CH$_2$Cl$_2$. The organic layer was dried over MgSO$_4$ and concentrated to provide the product as a tan solid in purity of >90% by $^1$H NMR. MS m/z 379.3 (MH)$^+$.

EXAMPLE 64

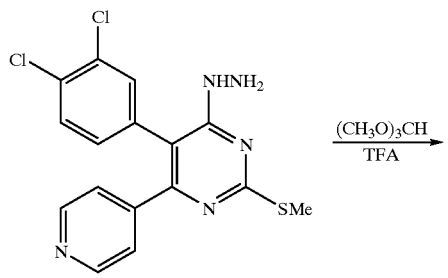

Trimethyl orthoformate (16.7 g, 16.2 mL, 156.9 mmol) and CH$_2$Cl$_2$ (300 mL) were added to the hydrazinopyrimidine (19.8 g, 52.3 mmol) in a 1 L round bottom flask fitted with a stir bar. The mixture was stirred for 1 h at RT and then trifluoroacetic acid (5.96 g, 4.02 mL, 156.9 mmol) was added. The resulting solution was stirred at RT for 16 h. At this time a yellow precipitate had formed and TLC (4% MeOH:CHCl$_3$) indicated complete consumption of starting material. The reaction mixture was washed with sat aq NaHCO$_3$ and the organic layer was dried over MgSO$_4$ and concentrated. The residue was dissolved in a minimum amount of CH$_2$Cl$_2$ (ca. 60 mL) and then ethyl ether (500 mL) was added gradually until a yellow/orange precipitate formed. The solid was collected, the filtrate was concentrated and a second crop of precipitate was collected as in the previous step, to provide a light yellow/white solid. The product was >95% pure by $^1$H NMR. MS m/z 389 (MH)$^+$.

EXAMPLE 65

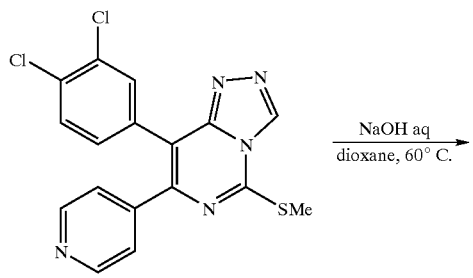

The triazolomethylppyrimidine methylsulfide (from Example 64) (11.62 g, 29.92 mmol) was suspended in dioxane (100 mL) and 2N aq NaOH (100 mL) was added. The mixture was stirred at 60° C. for 2 h and at this time analysis (TLC, 10% MeOH:CHCl$_3$) indicated starting material to be completely consumed. The reaction mixture was made just acidic by addition of 1N aq HCl, and then neutralized by addition of sat aq NaHCO$_3$. The resulting mixture was stirred vigorously and purged with nitrogen gas for 2 h in a fume hood to remove noxious methyl mercaptan gas. The mixture was then concentrated to an aqueous suspension. The solid was collected and rinsed with water, then with ether, and then dried in vacuo to provide an off-white solid, which was used without further purification. MS m/z 359 (MH)$^+$.

EXAMPLE xx

Using the procedures of the above general description and the above examples, the compounds of Tables 2–6 can be prepared.

TABLE 2

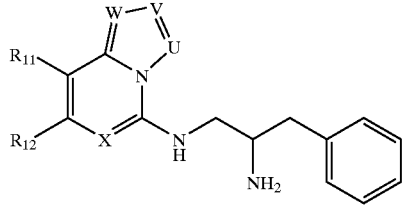

| U | V | W | X | R$^{11}$ | R$^{12}$ |
|---|---|---|---|---|---|
| C—H | N | N | C—H | 3-CF$_3$-phenyl | 4-pyridyl |
| C—H | N | N | C—H | 4-F-phenyl | 4-quinolyl |
| C—H | N | N | C—H | 3-Me-4-F-phenyl | 4-pyrimidyl |
| C—H | N | N | C—H | 3-Cl-4-F-phenyl | 2-Me-4-pyridyl |
| C—H | N | N | C—H | 3,4-di-Cl-phenyl | 2-NH$_2$-4-pyrimidyl |
| C—H | N | N | C—H | 3-cyclopropyl-4-F-phenyl | 4-pyridyl |
| C—H | C—H | N | N | 3-CF$_3$-phenyl | 4-quinolyl |
| C—H | C—H | N | N | 4-F-phenyl | 4-pyrimidyl |
| C—H | C—H | N | N | 3-Me-4-F-phenyl | 2-NH$_2$-4-pyridyl |
| C—H | C—H | N | N | 3-Cl-4-F-phenyl | 2-Me-4-pyrimidyl |
| C—H | C—H | N | N | 3,4-di-Cl-phenyl | 4-pyridyl |
| C—H | C—H | N | N | 3-cyclopropyl-4-F-phenyl | 4-pyridyl |
| C—H | C—H | N | C—H | 3-CF$_3$-phenyl | 4-pyridyl |
| C—H | C—H | N | C—H | 4-F-phenyl | 4-pyridyl |
| C—H | C—H | N | C—H | 3-Me-4-F-phenyl | 4-quinolyl |
| C—H | C—H | N | C—H | 3-Cl-4-F-phenyl | 4-pyrimidyl |
| C—H | C—H | N | C—H | 3,4-di-Cl-phenyl | 2-Me-4-pyridyl |
| C—H | C—H | N | C—H | 3-cyclopropyl-4-F-phenyl | 2-NH$_2$-4-pyrimidyl |
| N | C—CH$_3$ | N | C—H | 3-CF$_3$-phenyl | 4-pyridyl |
| N | C—H | N | C—H | 4-F-phenyl | 4-quinolyl |
| N | C—OH | N | C—H | 3-Me-4-F-phenyl | 4-pyrimidyl |
| N | C—CF$_3$ | N | C—H | 3-Cl-4-F-phenyl | 2-Me-4-pyridyl |
| N | C—H | N | C—H | 3,4-di-Cl-phenyl | 2-NH$_2$-4-pyrimidyl |
| N | C—H | N | C—H | 3-cyclopropyl-4-F-phenyl | 4-pyridyl |
| N | C—H | C—H | N | 3-CF$_3$-phenyl | 4-quinolyl |
| N | C—H | C—H | N | 4-F-phenyl | 4-pyrimidyl |
| N | C—H | C—H | N | 3-Me-4-F-phenyl | 2-NH$_2$-4-pyridyl |
| N | C—H | C—H | N | 3-Cl-4-F-phenyl | 2-Me-4-pyrimidyl |
| N | C—H | C—H | N | 3,4-di-Cl-phenyl | 4-pyridyl |
| N | C—H | C—H | N | 3-cyclopropyl-4-F-phenyl | 4-pyridyl |
| N | C—H | N | N | 3-CF$_3$-phenyl | 4-pyridyl |
| N | C—H | N | N | 4-F-phenyl | 4-pyridyl |
| N | C—OH | N | N | 3-Me-4-F-phenyl | 4-quinolyl |
| N | C—H | N | N | 3-Cl-4-F-phenyl | 4-pyrimidyl |
| N | C—H | N | N | 3,4-di-Cl-phenyl | 2-Me-4-pyridyl |
| N | C—CH$_3$ | N | N | 3-cyclopropyl-4-F-phenyl | 2-NH$_2$-4-pyrimidyl |
| C—H | N | N | C—H | 6-F-2-naphthyl | 4-pyridyl |
| C—H | N | N | C—H | 6-quinolyl | 4-pyridyl |
| C—H | N | N | C—H | 3-isoquinolyl | 4-pyrimidyl |
| C—H | N | N | C—H | 7-isoquinolyl | 2-NH$_2$-4-pyridyl |

TABLE 2-continued

| U | V | W | X | R¹¹ | R¹² |
|---|---|---|---|---|---|
| C—H | N | N | C—H | 7-quinolyl | 2-Me-4-pyrimidyl |
| C—H | C—H | N | N | 2-naphthyl | 4-pyrimidyl |
| C—H | C—H | N | N | 6-quinolyl | 2-NH₂-4-pyridyl |
| C—H | C—H | N | N | 6-isoquinolyl | 2-Me-4-pyrimidyl |
| C—H | C—H | N | N | 7-isoquinolyl | 4-pyridyl |
| C—H | C—H | N | N | 7-quinolyl | 4-pyridyl |
| C—H | C—H | N | C—H | 5-indolyl | 4-pyridyl |
| C—H | C—H | N | C—H | 6-quinolyl | 4-pyrimidyl |
| C—H | C—H | N | C—H | 6-benzimidazolyl | 2-NH₂-4-pyridyl |
| C—H | C—H | N | C—H | 7-isoquinolyl | 2-Me-4-pyrimidyl |
| C—H | C—H | N | C—H | 7-quinolyl | 4-pyridyl |
| N | C—CH₃ | N | C—H | 6-CF₃-fur-2-yl | 4-pyridyl |
| N | C—H | N | C—H | 6-benzofuryl | 4-quinolyl |
| N | C—OH | N | C—H | 6-benzothienyl | 4-pyrimidyl |
| N | C—CF₃ | N | C—H | 2-benzothienyl | 2-Me-4-pyridyl |
| N | C—H | N | C—H | 5-benzothiazolyl | 2-NH₂-4-pyrimidyl |
| N | C—H | N | C—H | 6-benzoxazolyl | 4-pyridyl |
| N | C—H | C—H | N | 2-thienyl | 4-quinolyl |
| N | C—H | C—H | N | 1-Me-6-indazolyl | 4-pyrimidyl |
| N | C—H | C—H | N | 1-Me-6-indolyl | 2-NH₂-4-pyridyl |
| N | C—H | C—H | N | 3-furyl | 2-Me-4-pyrimidyl |
| N | C—H | C—H | N | 5-benzofuryl | 4-pyridyl |
| N | C—H | C—H | N | 5-benzothienyl | 4-pyridyl |
| N | C—H | N | N | 2-benzofuryl | 4-pyridyl |
| N | C—H | N | N | 6-benzothiazolyl | 4-pyridyl |
| N | C—OH | N | N | 5-benzoxazolyl | 4-quinolyl |
| N | C—H | N | N | 2-naphthyl | 4-pyrimidyl |
| N | C—H | N | N | 2-quinolyl | 2-Me-4-pyridyl |
| N | C—CH₃ | N | N | 6-F-2-naphthyl | 2-NH₂-4-pyrimidyl |

TABLE 3

| U | V | W | X | R¹¹ | R¹² |
|---|---|---|---|---|---|
| C—H | N | N | C—H | 3-CF₃-phenyl | 4-pyridyl |
| C—H | N | N | C—H | 3-isopropyl-4-F-phenyl | 4-quinolyl |
| C—H | N | N | C—H | 3-Me-4-F-phenyl | 4-pyrimidyl |
| C—H | N | N | C—H | 3-Cl-4-F-phenyl | 2-Me-4-pyridyl |
| C—H | N | N | C—H | 3,4-di-Cl-phenyl | 2-NH₂-4-pyrimidyl |
| C—H | N | N | C—H | 3-cyclopropyl-4-F-phenyl | 4-pyridyl |
| C—H | C—H | N | N | 3-CF₃-phenyl | 4-quinolyl |
| C—H | C—H | N | N | 3-isopropyl-4-F-phenyl | 4-pyrimidyl |
| C—H | C—H | N | N | 3-Me-4-F-phenyl | 2-NH₂-4-pyridyl |
| C—H | C—H | N | N | 3-Cl-4-F-phenyl | 2-Me-4-pyrimidyl |
| C—H | C—H | N | N | 3,4-di-Cl-phenyl | 4-pyridyl |
| C—H | C—H | N | N | 3-cyclopropyl-4-F-phenyl | 4-pyridyl |
| C—H | C—H | N | C—H | 3-CF₃-phenyl | 4-pyridyl |
| C—H | C—H | N | C—H | 3-isopropyl-4-F-phenyl | 4-pyridyl |
| C—H | C—H | N | C—H | 3-Me-4-F-phenyl | 4-pyridyl |
| C—H | C—H | N | C—H | 3-Cl-4-F-phenyl | 4-pyridyl |
| C—H | C—H | N | C—H | 3,4-di-Cl-phenyl | 2-Me-4-pyridyl |
| C—H | C—H | N | C—H | 3-cyclopropyl-4-F-phenyl | 2-NH₂-4-pyrimidyl |
| N | C—CH₃ | N | C—H | 3-CF₃-phenyl | 4-pyridyl |
| N | C—H | N | C—H | 3-isopropyl-4-F-phenyl | 4-quinolyl |
| N | C—OH | N | C—H | 3-Me-4-F-phenyl | 4-pyrimidyl |
| N | C—CF₃ | N | C—H | 3-Cl-4-F-phenyl | 2-Me-4-pyridyl |
| N | C—H | N | C—H | 3,4-di-Cl-phenyl | 2-NH₂-4-pyrimidyl |
| N | C—H | N | C—H | 3-cyclopropyl-4-F-phenyl | 4-pyridyl |
| N | C—H | C—H | N | 3-CF₃-phenyl | 4-quinolyl |
| N | C—H | C—H | N | 3-isopropyl-4-F-phenyl | 4-pyrimidyl |
| N | C—H | C—H | N | 3-Me-4-F-phenyl | 2-NH₂-4-pyridyl |
| N | C—H | C—H | N | 3-Cl-4-F-phenyl | 2-Me-4-pyrimidyl |
| N | C—H | C—H | N | 3,4-di-Cl-phenyl | 4-pyridyl |
| N | C—H | C—H | N | 3-cyclopropyl-4-F-phenyl | 4-pyridyl |
| N | C—H | N | N | 3-CF₃-phenyl | 4-pyridyl |
| N | C—H | N | N | 4-F-phenyl | 4-pyridyl |
| N | C-OH | N | N | 3-Me-4-F-phenyl | 4-quinolyl |
| N | C—H | N | N | 3-Cl-4-F-phenyl | 4-pyrimidyl |
| N | C—H | N | N | 3,4-di-Ci-phenyl | 2-Me-4-pyridyl |
| N | C—CH₃ | N | N | 3-cyclopropyl-4-F-phenyl | 2-NH₂-4-pyrimidyl |
| C—H | N | N | C—H | 6-F-2-naphthyl | 4-pyridyl |
| C—H | N | N | C—H | 6-quinolyl | 4-pyridyl |
| C—H | N | N | C—H | 3-isoquinolyl | 4-pyridyl |
| C—H | N | N | C—H | 7-isoquinolyl | 2-NH₂-4-pyridyl |
| C—H | N | N | C—H | 7-quinolyl | 2-Me-4-pyridyl |
| C—H | C—H | N | N | 2-naphthyl | 4-pyrimidyl |
| C—H | C—H | N | N | 6-quinolyl | 2-NH₂-4-pyridyl |
| C—H | C—H | N | N | 6-isoquinolyl | 2-Me-4-pyrimidyl |
| C—H | C—H | N | N | 7-isoquinolyl | 4-pyridyl |
| C—H | C—H | N | N | 7-quinolyl | 4-pyridyl |
| C—H | C—H | N | C—H | 5-indolyl | 4-pyridyl |
| C—H | C—H | N | C—H | 6-quinolyl | 4-pyrimidyl |
| C—H | C—H | N | C—H | 6-benzimidazolyl | 2-NH₂-4-pyridyl |
| C—H | C—H | N | C—H | 7-isoquinolyl | 2-Me-4-pyrimidyl |
| C—H | C—H | N | C—H | 7-quinolyl | 4-pyridyl |
| N | C—CH₃ | N | C—H | 6-CF₃-fur-2-yl | 4-pyridyl |
| N | C—H | N | C—H | 6-benzofuryl | 4-quinolyl |
| N | C—OH | N | C—H | 6-benzothienyl | 4-pyrimidyl |
| N | C—CF₃ | N | C—H | 2-benzothienyl | 2-Me-4-pyridyl |
| N | C—H | N | C—H | 5-benzothiazolyl | 2-NH₂-4-pyrimidyl |
| N | C—H | N | C—H | 6-benzoxazolyl | 4-pyridyl |
| N | C—H | C—H | N | 2-thienyl | 4-quinolyl |
| N | C—H | C—H | N | 1-Me-6-indazolyl | 4-pyrimidyl |
| N | C—H | C—H | N | 1-Me-6-indolyl | 2-NH₂-4-pyridyl |
| N | C—H | C—H | N | 3-furyl | 2-Me-4-pyrimidyl |
| N | C—H | C—H | N | 5-benzofuryl | 4-pyridyl |
| N | C—H | C—H | N | 5-benzothienyl | 4-pyridyl |
| N | C—H | N | N | 2-benzofuryl | 4-pyridyl |
| N | C—H | N | N | 6-benzothiazolyl | 4-pyridyl |
| N | C—OH | N | N | 5-benzoxazolyl | 4-quinolyl |
| N | C—H | N | N | 2-naphthyl | 4-pyrimidyl |
| N | C—H | N | N | 2-quinolyl | 2-Me-4-pyridyl |
| N | C—CH₃ | N | N | 6-F-2-naphthyl | 2-NH₂-4-pyrimidyl |

TABLE 4

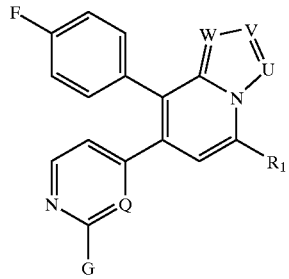

| U | V | W | Q | G | R¹ |
|---|---|---|---|---|---|
| C—H | N | N | C—H | H | (1,1-di-Me-2-NH$_2$-3-(4-Cl-phenyl)propyl)amino |
| C—H | N | N | C—H | H | (2-Me-2-NH$_2$-3-(4-F-phenyl)propyl)amino |
| C—H | N | N | C—H | H | (2-Me-2-NH$_2$-3-cyclohexyl-propyl)amino |
| C—H | N | N | C—H | H | (3-pyrid-4-yl-propyl)amino |
| C—H | N | N | C—H | H | (1,1-di-Me-2-imidazol-4-yl-ethyl)amino |
| C—H | N | N | C—H | H | 3-benzyl-piperazin-1-yl |
| C—H | N | N | C—H | H | (1-isopropyl-piperid-3-yl)amino |
| C—H | N | N | C—H | 1(R)-pheneth-1-ylamino | 1-piperazinyl |
| C—H | N | N | C—H | phenylethynyl | 1-piperazinyl |
| C—H | N | N | C—H | 1(R)-pheneth-1-ylamino | 4-piperidyl |
| C—H | N | N | C—H | ethoxy | (3-phenyl-2-NH$_2$-propyl)amino |
| C—H | N | N | C—H | (cyclopropyl methyl)amino | 3,5-di-Me-piperazin-1-yl |
| C—H | N | N | C—H | (4-piperidyl methyl)amino | H |
| C—H | N | N | C—H | (cyclohexyl methyl)amino | 4-piperidyl |
| C—H | N | N | N | H | (1,1-di-Me-2-NH$_2$-3-(4-Cl-phenyl)propyl)amino |
| C—H | N | N | N | H | (2-Me-2-NH$_2$-3-(4-F-phenyl)propyl)amino |
| C—H | N | N | N | H | (2-Me-2-NH$_2$-3-cyclohexyl-propyl)amino |
| C—H | N | N | N | H | (3-pyrid-4-yl-propyl)amino |
| C—H | N | N | N | H | (1,1-di-Me-2-imidazol-4-yl-ethyl)amino |
| C—H | N | N | N | H | 3-benzyl-piperazin-1-yl |
| C—H | N | N | N | H | (1-isopropyl-piperid-3-yl)amino |
| C—H | N | N | N | 1(R)-pheneth-1-ylamino | 1-piperazinyl |
| C—H | N | N | N | phenylethynyl | 1-piperazinyl |
| C—H | N | N | N | 1(R)-pheneth-1-ylamino | 4-piperidyl |
| C—H | N | N | N | ethoxy | (3-phenyl-2-NH$_2$-propyl)amino |
| C—H | N | N | N | (cyclopropyl methyl)amino | 3,5-di-Me-piperazin-1-yl |
| C—H | N | N | N | (4-piperidyl methyl)amino | H |
| C—H | N | N | N | (cyclohexyl methyl)amino | 4-piperidyl |

TABLE 4-continued

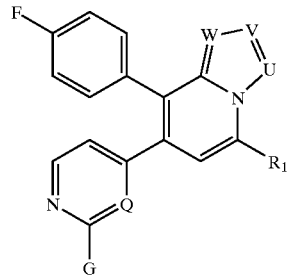

| U | V | W | Q | G | R¹ |
|---|---|---|---|---|---|
| C—H | C—H | N | C—H | H | (1,1-di-Me-2-NH$_2$-3-(4-Cl-phenyl)propyl)amino |
| C—H | C—H | N | C—H | H | (2-Me-2-NH$_2$-3-(4-F-phenyl)propyl)amino |
| C—H | C—H | N | C—H | H | (2-Me-2-NH$_2$-3-cyclohexyl-propyl)amino |
| C—H | C—H | N | C—H | H | (3-pyrid-4-yl-propyl)amino |
| C—H | C—H | N | C—H | H | (1,1-di-Me-2-imidazol-4-yl-ethyl)amino |
| C—H | C—H | N | C—H | H | 3-benzyl-piperazin-1-yl |
| C—H | C—H | N | C—H | H | (1-isopropyl-piperid-3-yl)amino |
| C—H | C—H | N | C—H | 1(R)-pheneth-1-ylamino | 1-piperazinyl |
| C—H | C—H | N | C—H | phenylethynyl | 1-piperazinyl |
| C—H | C—H | N | C—H | 1(R)-pheneth-1-ylamino | 4-piperidyl |
| C—H | C—H | N | C—H | ethoxy | (3-phenyl-2-NH$_2$-propyl)amino |
| C—H | C—H | N | C—H | (cyclopropyl methyl)amino | 3,5-di-Me-piperazin-1-yl |
| C—H | C—H | N | C—H | (4-piperidyl methyl)amino | H |
| C—H | C—H | N | C—H | (cyclohexyl methyl)amino | 4-piperidyl |

TABLE 5

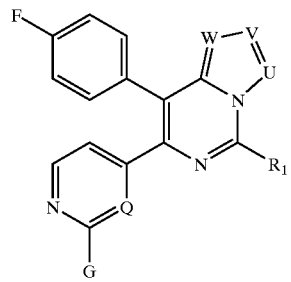

| U | V | W | Q | G | R¹ |
|---|---|---|---|---|---|
| C—H | N | N | C—H | H | (1,1-di-Me-2-NH$_2$-3-(4-Cl-phenyl)propyl)amino |
| C—H | N | N | C—H | H | (2-Me-2-NH$_2$-3-(4-F-phenyl)propyl)amino |
| C—H | N | N | C—H | H | (2-Me-2-NH$_2$-3-cyclohexyl-propyl)amino |
| C—H | N | N | C—H | H | (3-pyrid-4-yl-propyl)amino |

TABLE 5-continued

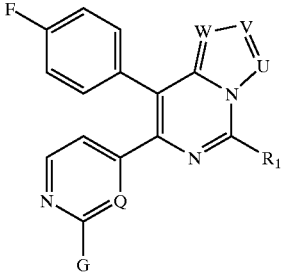

| U | V | W | Q | G | R¹ |
|---|---|---|---|---|---|
| C—H | N | N | C—H | H | (1,1-di-Me-2-imidazol-4-yl-ethyl)amino |
| C—H | N | N | C—H | H | 3-benzyl-piperazin-1-yl |
| C—H | N | N | C—H | H | (1-isopropyl-piperid-3-yl)amino |
| C—H | N | N | C—H | 1(R)-pheneth-1-ylamino | 1-piperazinyl |
| C—H | N | N | C—H | phenylethynyl | 1-piperazinyl |
| C—H | N | N | C—H | 1(R)-pheneth-1-ylamino | 4-piperidyl |
| C—H | N | N | C—H | ethoxy | (3-phenyl-2-$NH_2$-propyl)amino |
| C—H | N | N | C—H | (cyclopropyl methyl)amino | 3,5-di-Me-piperazin-1-yl |
| C—H | N | N | C—H | (4-piperidyl methyl)amino | H |
| C—H | N | N | C—H | (cyclohexyl methyl)amino | 4-piperidyl |
| C—H | N | N | N | H | (1,1-di-Me-2-$NH_2$-3-(4-Cl-phenyl)propyl)amino |
| C—H | N | N | N | H | (2-Me-2-$NH_2$-3-(4-F-phenyl)propyl)amino |
| C—H | N | N | N | H | (2-Me-2-$NH_2$-3-cyclohexyl-propyl)amino |
| C—H | N | N | N | H | (3-pyrid-4-yl-propyl)amino |
| C—H | N | N | N | H | (1,1-di-Me-2-imidazol-4-yl-ethyl)amino |
| C—H | N | N | N | H | 3-benzyl-piperazin-1-yl |
| C—H | N | N | N | H | (1-isopropyl-piperid-3-yl)amino |
| C—H | N | N | N | 1(R)-pheneth-1-ylamino | 1-piperazinyl |
| C—H | N | N | N | phenylethynyl | 1-piperazinyl |
| C—H | N | N | N | 1(R)-pheneth-1-ylamino | 4-piperidyl |
| C—H | N | N | N | ethoxy | (3-phenyl-2-$NH_2$-propyl)amino |
| C—H | N | N | N | (cyclopropyl methyl)amino | 3,5-di-Me-piperazin-1-yl |
| C—H | N | N | N | (4-piperidyl methyl)amino | H |
| C—H | N | N | N | (cyclohexyl methyl)amino | 4-piperidyl |

TABLE 6

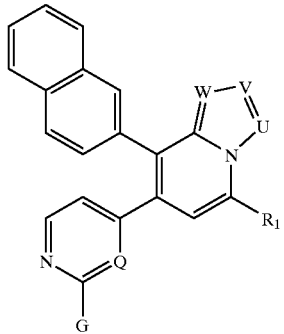

| U | V | W | Q | G | R¹ |
|---|---|---|---|---|---|
| C—H | N | N | C—H | H | (2-$NH_2$-3-phenyl-propyl)amino |
| C—H | N | N | C—H | H | (2-Me-2-$NH_2$-3-(4-F-phenyl)propyl)amino |
| C—H | N | N | C—H | H | (2-Me-2-$NH_2$-3-cyclohexyl-propyl)amino |
| C—H | N | N | C—H | H | (3-piperid-1-yl-1-phenyl-3-oxo-propyl)amino |
| C—H | N | N | C—H | H | (1,1-di-Me-2-imidazol-4-yl-ethyl)amino |
| C—H | N | N | C—H | H | 3-benzyl-piperazin-1-yl |
| C—H | N | N | C—H | 1(R)-pheneth-1-ylamino | 1-piperazinyl |
| C—H | N | N | C—H | phenylethynyl | 1-piperazinyl |
| C—H | N | N | C—H | 1(R)-pheneth-1-ylamino | 4-piperidyl |
| C—H | N | N | C—H | ethoxy | (3-phenyl-2-$NH_2$-propyl)amino |
| C—H | N | N | C—H | (cyclopropyl methyl)amino | 3,5-di-Me-piperazin-1-yl |
| C—H | N | N | C—H | (4-piperidyl methyl)amino | H |
| C—H | N | N | N | H | (2-$NH_2$-3-phenyl-propyl)amino |
| C—H | N | N | N | H | (2-Me-2-$NH_2$-3-(4-F-phenyl)propyl)amino |
| C—H | N | N | N | H | (2-Me-2-$NH_2$-3-cyclohexyl-propyl)amino |
| C—H | N | N | N | H | (3-piperid-1-yl-1-phenyl-3-oxo-propyl)amino |
| C—H | N | N | N | H | (1,1-di-Me-2-imidazol-4-yl-ethyl)amino |
| C—H | N | N | N | H | 3-benzyl-piperazin-1-yl |
| C—H | N | N | N | 1(R)-pheneth-1-ylamino | 1-piperazinyl |
| C—H | N | N | N | phenylethynyl | 1-piperazinyl |
| C—H | N | N | N | 1(R)-pheneth-1-ylamino | 4-piperidyl |
| C—H | N | N | N | ethoxy | (3-phenyl-2-$NH_2$-propyl)amino |
| C—H | N | N | N | (cyclopropyl methyl)amino | 3,5-di-Me-piperazin-1-yl |
| C—H | N | N | N | (4-piperidyl methyl)amino | H |
| C—H | C—H | N | C—H | H | (2-$NH_2$-3-phenyl-propyl)amino |
| C—H | C—H | N | C—H | H | (2-Me-2-$NH_2$-3-(4-F-phenyl)propyl)amino |
| C—H | C—H | N | C—H | H | (2-Me-2-$NH_2$-3-cyclohexyl-propyl)amino |

TABLE 6-continued

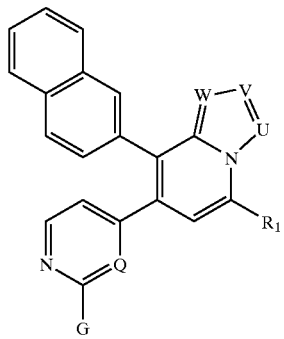

| U | V | W | Q | G | R¹ |
|---|---|---|---|---|---|
| C—H | C—H | N | C—H | H | (3-piperid-1-yl-1-phenyl-3-oxo-propyl)amino |
| C—H | C—H | N | C—H | H | (1,1-di-Me-2-imidazol-4-yl-ethyl)amino |
| C—H | C—H | N | C—H | H | 3-benzyl-piperazin-1-yl |
| C—H | C—H | N | C—H | 1(R)-pheneth-1-ylamino | 1-piperazinyl |
| C—H | C—H | N | C—H | phenylethynyl | 1-piperazinyl |
| C—H | C—H | N | C—H | 1(R)-pheneth-1-ylamino | 4-piperidyl |
| C—H | C—H | N | C—H | ethoxy | (3-phenyl-2-NH$_2$-propyl)amino |
| C—H | C—H | N | C—H | (cyclopropyl methyl)amino | 3,5-di-Me-piperazin-1-yl |
| C—H | C—H | N | C—H | (4-piperidyl methyl)amino | H |
| C—H | C—H | N | N | H | (2-NH$_2$-3-phenyl-propyl)amino |
| C—H | C—H | N | N | H | (2-Me-2-NH$_2$-3-(4-F-phenyl)propyl)amino |
| C—H | C—H | N | N | H | (2-Me-2-NH$_2$-3-cyclohexyl-propyl)amino |
| C—H | C—H | N | N | H | (3-piperid-1-yl-1-phenyl-3-oxo-propyl)amino |
| C—H | C—H | N | N | H | (1,1-di-Me-2-imidazol-4-yl-ethyl)amino |
| C—H | C—H | N | N | H | 3-benzyl-piperazin-1-yl |
| C—H | C—H | N | N | 1(R)-pheneth-1-ylamino | 1-piperazinyl |
| C—H | C—H | N | N | phenylethynyl | 1-piperazinyl |
| C—H | C—H | N | N | 1(R)-pheneth-1-ylamino | 4-piperidyl |
| C—H | C—H | N | N | ethoxy | (3-phenyl-2-NH$_2$-propyl)amino |
| C—H | C—H | N | N | (cyclopropyl methyl)amino | 3,5-di-Me-piperazin-1-yl |
| C—H | C—H | N | N | (4-piperidyl methyl)amino | H |

Biological Assays

The following assays were used to characterize the ability of compounds of the invention to inhibit the production of TNF-α and IL-1-β. The second assay can be used to measure the inhibition of TNF-α and/or IL-1-β in mice after oral administration of the test compounds. The third assay, a glucagon binding inhibition in vitro assay, can be used to characterize the ability of compounds of the invention to inhibit glucagon binding. The fourth assay, a Cyclooxygenase enzyme (COX-1 and COX-2) inhibition activity in vitro assay, can be used to characterize the ability of compounds of the invention to inhibit COX-1 and/or COX-2. The fifth assay, a Raf-kinase inhibition assay, can be used to characterize the compounds of the invention to inhibit phosphorylation of MEK by activated Raf-kinase.

Lipopolysaccharide-activated Monocyte TNF Production Assay

Isolation of Monocytes

Test compounds were evaluated in vitro for the ability to inhibit the production of TNF by monocytes activated with bacterial lipopolysaccharide (LPS). Fresh residual source leukocytes (a byproduct of plateletpheresis) were obtained from a local blood bank, and peripheral blood mononuclear cells (PBMCs) were isolated by density gradient centrifugation on Ficol-Paque Plus (Pharmacia). PBMCs were suspended at $2\times10^6$/ml in DMEM supplemented to contain 2% FCS, 10 mM, 0.3 mg/ml glutamate, 100 U/ml penicillin G and 100 mg/ml streptomycin sulfate (complete media). Cells were plated into Falcon flat bottom, 96 well culture plates (200 μl/well) and cultured overnight at 37° C. and 6% $CO_2$. Non-adherent cells were removed by washing with 200 μl/well of fresh medium. Wells containing adherent cells (~70% monocytes) were replenished with 100 μl of fresh medium.

Preparation of Test Compound Stock Solutions

Test compounds were dissolved in DMZ. Compound stock solutions were prepared to an initial concentration of 10–50 μM. Stocks were diluted initially to 20–200 μM in complete media. Nine two-fold serial dilutions of each compound were then prepared in complete medium.

Treatment of Cells with Test Compounds and Activation of TNF Production with Lipopolysaccharide One hundred microliters of each test compound dilution were added to microtiter wells containing adherent monocytes and 100 μl complete medium. Monocytes were cultured with test compounds for 60 min at which time 25 μl of complete medium containing 30 ng/ml lipopolysaccharide from E. coli K532 were added to each well. Cells were cultured an additional 4 hrs. Culture supernatants were then removed and TNF presence in the supernatants was quantified using an ELISA.

TNF ELISA

Flat bottom, 96 well Corning High Binding ELISA plates were coated overnight (4° C.) with 150 μL/well of 3 μg/ml murine anti-human TNF-α MAb (R&D Systems #MAB210). Wells were then blocked for 1 hr at room temperature with 200 μL/well of $CaCl_2$-free ELISA buffer supplemented to contain 20 mg/ml BSA (standard ELISA buffer: 20 mM, 150 mM NaCl, 2 mM $CaCl_2$, 0.15 mM thimerosal, pH 7.4). Plates were washed and replenished with 100 μl of test supernatants (diluted 1:3) or standards. Standards consisted of eleven 1.5-fold serial dilutions from a stock of 1 ng/ml recombinant human TNF (R&D Systems). Plates were incubated at room temperature for 1 hr on orbital shaker (300 rpm), washed and replenished with 100 μl/well of 0.5 μg/ml goat anti-human TNF-α (R&D systems #AB-210-NA) biotinylated at a 4:1 ratio. Plates were incubated for 40 min, washed and replenished with 100 μl/well of alkaline phosphatase-conjugated streptavidin (Jackson ImmunoResearch #016-050-084) at 0.02 μg/ml. Plates were incubated 30 min, washed and replenished with 200 μl/well of 1 mg/ml of p-nitrophenyl phosphate. After 30 min, plates were read at 405 nm on a $V_{max}$ plate reader.

Data Analysis

Standard curve data were fit to a second order polynomial and unknown TNF-α concentrations determined from their OD by solving this equation for concentration. TNF concentrations were then plotted vs. test compound concentration using a second order polynomial. This equation was then used to calculate the concentration of test compounds causing a 50% reduction in TNF production.

Compounds of the invention can also be shown to inhibit LPS-induced release of IL-1β, IL-6 and/or IL-8 from monocytes by measuring concentrations of IL-1β, IL-6 and/or IL-8 by methods well known to those skilled in the art. In a similar manner to the above described assay involving the LPS induced release of TNF?? from monocytes, compounds of this invention can also be shown to inhibit LPS induced release of IL-1β, IL-6 and/or IL-8 from monocytes by measuring concentrations of IL-1β, IL-6 and/or IL-8 by methods well known to those skilled in the art. Thus, the compounds of the invention may lower elevated levels of TNF-α, IL-1, IL-6, and IL-8 levels. Reducing elevated levels of these inflammatory cytokines to basal levels or below is favorable in controlling, slowing progression, and alleviating many disease states. All of the compounds are useful in the methods of treating disease states in which TNF-α, IL-1β, IL-6, and IL-8 play a role to the full extent of the definition of TNF-α-mediated diseases described herein.

Lipopolysaccharide-activated THP1 Cell TNF Production Assay

THP1 cells are resuspended in fresh THP1 media (RPMI 1640, 10% heat-inactivated FBS, 1×PGS, 1×NEAA, plus 30 μM βME) at a concentration of 1E6/mL. One hundred microliters of cells per well are plated in a polystyrene 96-well tissue culture. One microgram per mL of bacterial LPS is prepared in THP1 media and is transferred to the wells. Test compounds are dissolved in 100% DMSO and are serially diluted 3 fold in a polypropylene 96-well microtiter plate (drug plate). HI control and LO control wells contain only DMSO. One microliter of test compound from the drug plate followed by 10 μL of LPS are transferred to the cell plate. The treated cells are induced to synthesize and secrete TNF-α at 37° C. for 3 hr. Forty microliters of conditioned media are transferred to a 96-well polypropylene plate containing 110 μL of ECL buffer (50 mM Tris-HCl pH 8.0, 100 mM NaCl, 0.05% Tween 20, 0.05% NaN$_3$ and 1% FBS) supplemented with 0.44 nM MAB610 monoclonal Ab (R&D Systems), 0.34 nM ruthenylated AF210NA polyclonal Ab (R&D Systems) and 44 μg/mL sheep anti-mouse M280 Dynabeads (Dynal). After a 2 hr. incubation at room temperature with shaking, the reaction is read on the ECL M8 Instrument (IGEN Inc.). A low voltage is applied to the ruthenylated TNF-α immune complexes, which in the presence of TPA (the active component in Origlo), results in a cyclical redox reaction generating light at 620 nM. The amount of secreted TNF-α in the presence of compound compared with that in the presence of DMSO vehicle alone (HI control) is calculated using the formula: % control (POC)=(cpd−average LO)/(average HI−average LO)*100. Data (consisting of POC and inhibitor concentration in μM) is fitted to a 4-parameter equation (y=A+((B−A)/(1+((x/C)^D))), where A is the minimum y (POC) value, B is the maximum y (POC), C is the x (cpd concentration) at the point of inflection and D is the slope factor) using a Levenburg-Marquardt non-linear regression algorithm.

The following compounds exhibit activities in the THP1 cell assay (LPS induced TNF release) with IC$_{50}$ values of 20 μM or less:

5-(3-phenylprop-1-yl)amino-8-(4-fluorophenyl)-7-(4-pyridyl)-1,2,4-triazolo[4,3-c]pyrimidine;
5-(3-phenylprop-1-yl)amino-8-(3-methylphenyl)-7-(4-pyridyl)-1,2,4-triazolo[4,3-c]pyrimidine;
5-(1-piperazinyl)-8-(3-methylphenyl)-7-(2-chloro-4-pyridyl)-1,2,4-triazolo[4,3-c]pyrimidine;
5-(3-phenylprop-1-yl)amino-8-(3-(trifluoromethyl)phenyl)-7-(4-pyridyl)-1,2,4-triazolo[4,3-c]pyrimidine;
5-(2(S)-amino-3-phenylprop-1-yl)amino-8-(3,4-dichlorophenyl)-7-(4-pyridyl)-1,2,4-triazolo[4,3-c]pyrimidine;
5-(piperazin-1-yl)-8-(3-(trifluoromethyl)phenyl)-7-(2-(2-phenylprop-2-yl)amino-4-pyridyl)-1,2,4-triazolo[4,3-c]pyrimidine;
5-(3,5-dimethylpiperazin-1-yl)-8-(3-(trifluoromethyl)phenyl)-7-(2-(1(S)-phenylethyl)amino-4-pyridyl)-1,2,4-triazolo[4,3-c]pyrimidine;
5-(piperazin-1-yl)-8-(3-(trifluoromethyl)phenyl)-7-(2-(1(S)-phenylethyl)amino-4-pyridyl)-1,2,4-triazolo[4,3-c]pyrimidine;
1-(8-(4-fluorophenyl)-7-(4-pyridyl)-1,2,4-triazolo[4,3-c]pyrimidin-5-yl)amino-2(S)-amino-3-phenylpropane;
2-(8-(4-fluorophenyl)-7-(4-pyridyl)-1,2,4-triazolo[4,3-c]pyrimidin-5-yl)amino-2-phenylpropane;
5-(2(S)-amino-2-methyl-3-phenylprop-1-yl)amino-8-(3-(trifluoromethyl)phenyl)-7-(4-pyridyl)-1,2,4-triazolo[4,3-c]pyrimidine;
5-(2,5-diaza-bicyclo[2.2.1]hept-2-yl)-8-(3-(trifluoromethyl)phenyl)-7-(2-(1(S)-phenylethyl) amino-4-pyridyl)-1,2,4-triazolo[4,3-c]pyrimidine;
5-(2(S)-amino-3-phenylprop-1-yl)amino-8-(2-naphthyl)-7-(4-pyridyl)-1,2,4-triazolo[4,3-c]pyrimidine;
5-(3(S)-benzyl-piperazin-1-yl)-8-(2-naphthyl)-7-(4-pyridyl)-1,2,4-triazolo[4,3-c]pyrimidine;
5-(2(S)-amino-3-phenylprop-1-yl)amino-8-(3-chloro-4-fluorophenyl)-7-(4-pyridyl)-1,2,4-triazolo[4,3-c]pyrimidine;
5-(2(S)-pyrrolidinylmethyl)amino-8-(2-naphthyl)-7-(4-pyridyl)-1,2,4-triazolo[4,3-c]pyrimidine;
5-(1-(2-propyl)pyrrolidin-2(S)-ylmethyl)amino-8-(3,4-dichlorophenyl)-7-(4-pyridyl)-1,2,4-triazolo[4,3-c]pyrimidine;
5-(piperazin-1-yl)-8-(3-(trifluoromethyl)phenyl)-7-(2-(cyclopropyl)amino-4-pyridyl)-1,2,4-triazolo[4,3-c]pyrimidine;
5-(1-(2-propyl)piperid-3-yl)amino-8-(3,4-dichlorophenyl)-7-(4-pyridyl)-1,2,4-triazolo[4,3-c]pyrimidine; and
5-(1-(2-propyl)pyrrolidin-2(S)-ylmethyl)amino-8-(2-naphthyl)-7-(4-pyridyl)-1,2,4-triazolo[4,3-c]pyrimidine.

The following compounds exhibit activities in the THP1 cell assay (LPS induced TNF release) with IC$_{50}$ values of 5 μM or less:

5-(3-phenylprop-1-yl)amino-8-(4-fluorophenyl)-7-(4-pyridyl)-1,2,4-triazolo[4,3-c]pyrimidine;
5-(3-phenylprop-1-yl)amino-8-(3-methylphenyl)-7-(4-pyridyl)-1,2,4-triazolo[4,3-c]pyrimidine;
5-(1-piperazinyl)-8-(3-methylphenyl)-7-(2-chloro-4-pyridyl)-1,2,4-triazolo [4,3-c]pyrimidine;
5-(3-phenylprop-1-yl)amino-8-(3-(trifluoromethyl)phenyl)-7-(4-pyridyl)-1,2,4-triazolo[4,3-c]pyrimidine;
5-(2(S)-amino-3-phenylprop-1-yl)amino-8-(3,4-dichlorophenyl)-7-(4-pyridyl)-1,2,4-triazolo[4,3-c]pyrimidine;
5-(piperazin-1-yl)-8-(3-(trifluoromethyl)phenyl)-7-(2-(2-phenylprop-2-yl)amino-4-pyridyl)-1,2,4-triazolo[4,3-c]pyrimidine;
5-(3,5-dimethylpiperazin-1-yl)-8-(3-(trifluoromethyl)phenyl)-7-(2-(1(S)-phenylethyl)amino-4-pyridyl)-1,2,4-triazolo[4,3-c]pyrimidine;
5-(piperazin-1-yl)-8-(3-(trifluoromethyl)phenyl)-7-(2-(1(S)-phenylethyl)amino-4-pyridyl)-1,2,4-triazolo[4,3-c]pyrimidine;
1-(8-(4-fluorophenyl)-7-(4-pyridyl)-1,2,4-triazolo[4,3-c]pyrimidin-5-yl)amino-2(S)-amino-3-phenylpropane;

2-(8-(4-fluorophenyl)-7-(4-pyridyl)-1,2,4-triazolo [4,3-c] pyrimidin-5-yl)amino-2-phenylpropane;

5-(2(S)-amino-2-methyl-3-phenylprop-1-yl)amino-8-(3-(trifluoromethyl)phenyl)-7-(4-pyridyl)-1,2,4-triazolo[4,3-c]pyrimidine;

5-(2,5-diaza-bicyclo[2.2.1]hept-2-yl)-8-(3-(trifluoromethyl)phenyl)-7-(2-(1(S)-phenylethyl) amino-4-pyridyl)-1,2,4-triazolo[4,3-c]pyrimidine;

5-(2(S)-amino-3-phenylprop-1-yl)amino-8-(2-naphthyl)-7-(4-pyridyl)-1,2,4-triazolo[4,3-c]pyrimidine;

5-(3(S)-benzyl-piperazin-1-yl)-8-(2-naphthyl)-7-(4-pyridyl)-1,2,4-triazolo[4,3-c]pyrimidine;

5-(2(S)-amino-3-phenylprop-1-yl)amino-8-(3-chloro-4-fluorophenyl)-7-(4-pyridyl)-1,2,4-triazolo[4,3-c] pyrimidine;

5-(2(S)-pyrrolidinylmethyl)amino-8-(2-naphthyl)-7-(4-pyridyl)-1,2,4-triazolo[4,3-c]pyrimidine;

5-(1-(2-propyl)pyrrolidin-2(S)-ylmethyl)amino-8-(3,4-dichlorophenyl)-7-(4-pyridyl)-1,2,4-triazolo[4,3-c] pyrimidine;

5-(piperazin-1-yl)-8-(3-(trifluoromethyl)phenyl)-7-(2-(cyclopropyl)amino-4-pyridyl)-1,2,4-triazolo[4,3-c] pyrimidine;

5-(1-(2-propyl)piperid-3-yl)amino-8-(3,4-dichlorophenyl)-7-(4-pyridyl)-1,2,4-triazolo[4,3-c]pyrimidine; and 5-(1-(2-propyl)pyrrolidin-2(S)-ylmethyl)amino-8-(2-naphthyl)-7-(4-pyridyl)-1,2,4-triazolo[4,3-c]pyrimidine.

Inhibition of LPS-Induced TNF-α Production in Mice

Male DBA/1 LACJ mice are dosed with vehicle or test compounds in a vehicle (the vehicle consisting of 0.5% tragacanth in 0.03 N HCl) 30 minutes prior to lipopolysaccharide (2 mg/kg, I.V.) injection. Ninety minutes after LPS injection, blood is collected and the serum is analyzed by ELISA for TNF-α levels.

Compounds of the invention may be shown to have anti-inflammatory properties in animal models of inflammation, including carrageenan paw edema, collagen induced arthritis and adjuvant arthritis, such as the carrageenan paw edema model (C. A. Winter et al Proc. Soc. Exp. Biol. Med. (1962) vol 111, p 544; K. F. Swingle, in R. A. Scherrer and M. W. Whitehouse, Eds., Antiinflammatory Agents, Chemistry and Pharmacology, Vol. 13-II, Academic, New York, 1974, p. 33) and collagen induced arthritis (D. E. Trentham et al J. Exp. Med. (1977) vol. 146, p 857; J. S. Courtenay, Nature (New Biol.) (1980), Vol 283, p 666).

$^{125}$I-Glucagon Binding Screen with CHO/hGLUR Cells

The assay is described in WO 97/16442, which is incorporated herein by reference in its entirety.

Reagents

The reagents can be prepared as follows: (a) prepare fresh 1M o-Phenanthroline (Aldrich) (198.2 mg/ml ethanol); (b) prepare fresh 0.5M DTT (Sigma); (c) Protease Inhibitor Mix (1000×): 5 mg leupeptin, 10 mg benzamidine, 40 mg bacitracin and 5 mg soybean trypsin inhibitor per ml DMSO and store aliquots at −20° C.; (d) 250 µM human glucagon (Peninsula): solubilize 0.5 mg vial in 575 µl 0.1N acetic acid (1 µl yields 1 µM final concentration in assay for non-specific binding) and store in aliquots at −20° C.; (e) Assay Buffer: 20 mM Tris (pH 7.8), 1 mM DTT and 3 mM o-phenanthroline; (f) Assay Buffer with 0.1% BSA (for dilution of label only; 0.01% final in assay): 10 µl 10% BSA (heat-inactivated) and 990 µl Assay Buffer; (g) $^{125}$I-Glucagon (NEN, receptor-grade, 2200 Ci/mmol): dilute to 50,000 cpm/25 µl in assay buffer with BSA (about 50 pM final concentration in assay).

Harvesting of CHO/hGLUR Cells for Assay

1. Remove media from confluent flask then rinse once each with PBS (Ca, Mg-free) and Enzyme-free Dissociation Fluid (Specialty Media, Inc.).

2. Add 10 ml Enzyme-free Dissoc. Fluid and hold for about 4 min. at 37° C.

3. Gently tap cells free, triturate, take aliquot for counting and centrifuge remainder for 5 min. at 1000 rpm.

4. Resuspend pellet in Assay Buffer at 75000 cells per 100 µl.

Membrane preparations of CHO/hGLUR cells can be used in place of whole cells at the same assay volume. Final protein concentration of a membrane preparation is determined on a per batch basis.

Assay

The determination of inhibition of glucagon binding can be carried out by measuring the reduction of $I^{125}$-glucagon binding in the presence of compounds of Formula I. The reagents are combined as follows:

|  | Compound/Vehicle | 250 µM Glucagon | $^{125}$I-Glucagon | CHO/hGLUR Cells |
|---|---|---|---|---|
| Total Binding | —/5 µl | — | 25 µl | 100 µl |
| + Compound | 5 µl/— | — | 25 µl | 100 µl |
| Nonspecific Binding | —/5 µl | 1 µl | 25 µl | 100 µl |

The mixture is incubated for 60 min. at 22° C. on a shaker at 275 rpm. The mixture is filtered over pre-soaked (0.5% polyethylimine (PEI)) GF/C filtermat using an Innotech Harvester or Tomtec Harvester with four washes of ice-cold 20 mM Tris buffer (pH 7.8). The radioactivity in the filters is determined by a gamma-scintillation counter.

Thus, compounds of the invention may also be shown to inhibit the binding of glucagon to glucagon receptors.

Cyclooxygenase Enzyme Activity Assay

The human monocytic leukemia cell line, THP-1, differentiated by exposure to phorbol esters expresses only COX-1; the human osteosarcoma cell line 143B expresses predominantly COX-2. THP-1 cells are routinely cultured in RPMI complete media supplemented with 10% FBS and human osteosarcoma cells (HOSC) are cultured in minimal essential media supplemented with 10% fetal bovine serum (MEM-10% FBS); all cell incubations are at 37° C. in a humidified environment containing 5% $CO_2$.

COX-1 Assay

In preparation for the COX-1 assay, THP-1 cells are grown to confluency, split 1:3 into RPMI containing 2% FBS and 10 mM phorbol 12-myristate 13-acetate (TPA), and incubated for 48 hours on a shaker to prevent attachment. Cells are pelleted and resuspended in Hank's Buffered Saline (HBS) at a concentration of $2.5\times10^6$ cells/mL and plated in 96-well culture plates at a density of $5\times10^5$ cells/mL. Test compounds are diluted in HBS and added to the desired final concentration and the cells are incubated for an additional 4 hours. Arachidonic acid is added to a final concentration of 30 mM, the cells incubated for 20 minutes at 37° C., and enzyme activity determined as described below.

COX-2 Assay

For the COX-2 assay, subconfluent HOSC are trypsinized and resuspended at $3\times10^6$ cells/mL in MEM-FBS containing 1 ng human IL-1b/mL, plated in 96-well tissue culture plates at a density of $3\times10^4$ cells per well, incubated on a shaker for 1 hour to evenly distribute cells, followed by an additional 2 hour static incubation to allow attachment. The media is then replaced with MEM containing 2% FBS (MEM-2% FBS) and 1 ng human IL-1b/mL, and the cells incubated for 18–22 hours. Following replacement of media with 190 mL MEM, 10 mL of test compound diluted in HBS is added to achieve the desired concentration and the cells incubated for 4 hours. The supernatants are removed and replaced with MEM containing 30 mM arachidonic acid, the cells incubated for 20 minutes at 37° C., and enzyme activity determined as described below.

COX Activity Determined

After incubation with arachidonic acid, the reactions are stopped by the addition of 1 N HCl, followed by neutralization with 1 N NaOH and centrifugation to pellet cell debris. Cyclooxygenase enzyme activity in both HOSC and THP-1 cell supernatants is determined by measuring the concentration of $PGE_2$ using a commercially available ELISA (Neogen #404110). A standard curve of $PGE_2$ is used for calibration, and commercially available COX-1 and COX-2 inhibitors are included as standard controls.

Raf Kinase Assay

In vitro Raf kinase activity is measured by the extent of phosphorylation of the substrate MEK (Map kinase/ERK kinase) by activated Raf kinase, as described in GB 1,238,959 (incorporated herein by reference in its entirety). Phosphorylated MEK is trapped on a filter and incorporation of radiolabeled phosphate is quantified by scintillation counting.

Materials:

Activated Raf is produced by triple transfection of Sf9 cells with baculoviruses expressing "Glu-Glu"-epitope tagged Raf,$val^{12}$-H-Ras, and Lck. The "Glu-Glu"-epitope, Glu-Try-Met-Pro-Met-Glu, was fused to the carboxy-terminus of full length c-Raf.

Catalytically inactive MEK (K97A mutation) is produced in Sf9 cells transfected with a baculovirus expressing c-terminus "3Glu-Glu" epitope-tagged K97A MEK1.

Anti "Glu-Glu" antibody was purified from cells grown as described in: Grussenmeyer, et al., Proceedings of the National Academy of Science, U.S.A. pp 7952–7954, 1985.

Column buffer: 20 mM Tris pH=8, 100 mM NaCl, 1 mM EDTA, 2.5 mM EGTA, 10 mM $MgCl_2$, 2 mM DTT, 0.4 mM AEBSF, 0.1% n-octylglucopyranoside, 1 nM okadeic acid, and 10 μg/mL each of benzamidine, leupeptin, pepstatin, and aprotinin.

5× Reaction buffer: 125 mM HEPES pH=8, 25 mM $MgCl_2$, 5 mM EDTA, 5 mM $Na_3VO_4$, 100 μg/mL BSA.

Enzyme dilution buffer: 25 mM HEPES pH=8, 1 mM EDTA, 1 mM $Na_3VO_4$, 400 μg/mL BSA.

Stop solution: 100 mM EDTA, 80 mM sodium pyrophosphate.

Filter plates: Milipore multiscreen #SE3MO78E3, Immobilon-P (PVDF).

Methods:

Protein purification: Sf9 cells were infected with baculovirus and grown as described in Williams, et al., Proceedings of the National Academy of Science, U.S.A. pp 2922–2926, 1992. All subsequent steps were preformed on ice or at 4° C. Cells were pelleted and lysed by sonication in column buffer. Lysates were spun at 17,000×g for 20 min, followed by 0.22 μm filtration. Epitope tagged proteins were purified by chromatography over GammaBind Plus affinity column to which the "Glu-Glu" antibody was coupled. Proteins were loaded on the column followed by sequential washes with two column volumes of column buffer, and eluted with 50 μg/mL Glu-Tyr-Met-Pro-Met-Glu in column buffer.

Raf kinase assay: Test compounds were evaluated using ten 3-fold serial dilutions starting at 10–100 μM. 10 μL of the test inhibitor or control, dissolved in 10% DMSO, was added to the assay plate followed by the addition of 30 μL of the a mixture containing 10 μL 5× reaction buffer, 1 mM $^{33}$P-γ-ATP (20 μCi/mL), 0.5 μL MEK (2.5 mg/mL), 1 μL 50 mM β-mercaptoethanol. The reaction was started by the addition of 10 μL of enzyme dilution buffer containing 1 mM DTT and an amount of activated Raf that produces linear kinetics over the reaction time course. The reaction was mixed and incubated at room temperature for 90 min. and stopped by the addition of 50 μL stop solution. 90 μL aliquots of this stopped solution were transferred onto GFP-30 cellulose microtiter filter plates (Polyfiltronics), the filter plates washed in four well volumes of 5% phosphoric acid, allowed to dry, and then replenished with 25 μl scintillation cocktail. The plates were counted for $^{33}$P gamma emission using a TopCount Scintillation Reader.

Accordingly, the compounds of the invention or a pharmaceutical composition thereof are useful for treatment of rheumatoid arthritis; Pagets disease; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; bone resorption diseases; graft vs. host reaction; ischemia reperfusion injury; atherosclerosis; brain trauma; Alzheimer's disease; stroke; myocardial infarction; multiple sclerosis; cerebral malaria; sepsis; septic shock; toxic shock syndrome; fever, and myalgias due to infection. HIV-1, HIV-2, HIV-3, cytomegalovirus (CMV), influenza, adenovirus, the herpes viruses (including HSV-1, HSV-2), and herpes zoster, all of which are sensitive to TNF-α and/or IL-1 inhibition or glucagon antagonism, will also be positively effected by the compounds and methods of the invention.

The compounds of the present invention may also possess oncolytic characteristics and may be useful for the treatment of cancer. The compounds of the present invention may also block signal transduction by extracellular mitogenic stimuli and oncoproteins through inhibition of Raf kinase. Thus the compounds of the present invention, a pharmaceutical salt thereof, or a pharmaceutical composition of either, may also be useful in the treatment of cancers which are mediated by Raf and Raf-inducible proteins, such as cancers where Raf kinase is implicated by overexpression and cancers involving overexpression of upstream activators of Raf or Raf-activating oncogenes. Examples of cancers where Raf kinase is implicated by overexpression include cancers of the brain, larynx, lung, lymphatic system, urinary tract and stomach, including hystocytic lymphoma, lung adenocarcinoma, small cell lung cancers and the like. Examples of cancers involving overexpression of upstream activators of Raf or Raf-activating oncogenes, include pancreatic carcinoma, breast carcinoma and the like.

The compounds of the present invention also may possess analgesic properties and may be useful for the treatment of pain disorders, such as hyperalgesia due to excessive IL-1. The compounds of the present invention may also prevent the production of prostaglandins by inhibition of enzymes in the human arachidonic acid/prostaglandin pathway, including cyclooxygenase (WO 96/03387, incorporated herein by reference in its entirety).

Because of their ability to lower TNF-α and IL-1 concentrations or inhibit glucagon binding to its receptor, the compounds of the invention are also useful research tools for studying the physiology associated with blocking these effects.

The methods of the invention comprise administering an effective dose of a compound of the invention, a pharmaceutical salt thereof, or a pharmaceutical composition of either, to a subject (i.e., an animal, preferably a mammal, most preferably a human) in need of a reduction in the level of TNF-α, IL-1, IL-6, and/or IL-8 levels and/or reduction in plasma glucose levels and/or which subject may be suffering from rheumatoid arthritis; Pagets disease; osteoporosis; multiple myeloma; uveititis; acute and chronic myelogenous leukemia; pancreatic β cell destruction; osteoarthritis; rheumatoid spondylitis; gouty arthritis; inflammatory bowel disease; adult respiratory distress syndrome (ARDS); psoriasis; Crohn's disease; allergic rhinitis; ulcerative colitis; anaphylaxis; contact dermatitis; asthma; muscle degeneration; cachexia; Reiter's syndrome; type I and type II diabetes; cancer; bone resorption diseases; graft vs. host reaction; Alzheimer's disease; stroke; myocardial infarction; ischemia reperfusion injury; atherosclerosis; brain trauma; multiple sclerosis; cerebral malaria; sepsis; septic shock; toxic shock syndrome; fever, and myalgias due to infection, or which subject is infected by HIV-1, HIV-2, HIV-3, cytomegalovirus (CMV), influenza, adenovirus, the herpes viruses (including HSV-1, HSV-2), or herpes zoster.

In another aspect, this invention comprises the use of a compound of the invention, or pharmaceutically acceptable salts thereof, in the manufacture of a medicament for the treatment either acutely or chronically of a TNF-α, IL-1β, IL-6, and/or IL-8 mediated disease state, including those described previously. The compounds of the present are also useful in the manufacture of an anti-cancer medicament. The compounds of the present invention are also useful in the manufacture of a medicament to attenuate or prevent signal transduction by extracellular mitogenic stimuli and oncoproteins through inhibition of Raf kinase. Also, the compounds of this invention are useful in the manufacture of a analgesic medicament and a medicament for treating pain disorders, such as hyperalgesia. The compounds of the present invention also are useful in the manufacture of a medicament to prevent the production of prostaglandins by inhibition of enzymes in the human arachidonic acid/prostaglandin pathway.

A further method of the invention comprises administering an effective dose of a compound of the invention, a pharmaceutical salt thereof, or a pharmaceutical composition of either, to a subject (i.e., an animal, preferably a mammal, most preferably a human) in need of treatment of a cancer(s) which is mediated by Raf, Raf-inducible proteins and/or activators of Raf or Raf-activating oncogenes, and/or which subject may be suffering from cancers of the brain, larynx, lung, lymphatic system, urinary tract and stomach, including hystocytic lymphoma, lung adenocarcinoma, small cell lung cancers, pancreatic carcinoma, breast carcinoma and the like. Further, the compounds of this invention may be useful in the manufacture of a medicament for treating cancers, such as cancers of the brain, larynx, lung, lymphatic system, urinary tract and stomach, including hystocytic lymphoma, lung adenocarcinoma, small cell lung cancers, pancreatic carcinoma, breast carcinoma and the like.

In still another aspect, this invention provides a pharmaceutical composition comprising an effective TNF-α, IL-1β, IL-6, and/or IL-8 lowering amount and/or effective plasma glucose level lowering amount and/or effective tumor suppressing amount of a compound of the invention and a pharmaceutically acceptable carrier or diluent, and if desired other active ingredients. The compounds of the invention are administered by any suitable route, preferably in the form of a pharmaceutical composition adapted to such a route, and in a dose effective for the treatment intended. Therapeutically effective doses of the compounds of the present invention required to arrest the progress or prevent tissue damage associated with the disease are readily ascertained by one of ordinary skill in the art using standard methods.

For the treatment of TNF-α, IL-1β, IL-6, and IL-8 mediated diseases, cancer, and/or hyperglycemia, the compounds of the present invention may be administered orally, parentally, by inhalation spray, rectally, or topically in dosage unit formulations containing conventional pharmaceutically acceptable carriers, adjuvants, and vehicles. The term parenteral as used herein includes, subcutaneous, intravenous, intramuscular, intrasternal, infusion techniques or intraperitoneally.

Treatment of diseases and disorders herein is intended to also include the prophylactic administration of a compound of the invention, a pharmaceutical salt thereof, or a pharmaceutical composition of either to a subject (i.e., an animal, preferably a mammal, most preferably a human) believed to be in need of preventative treatment, such as, for example, pain, inflammation and the like.

The dosage regimen for treating a TNF-α, IL-1, IL-6, and IL-8 mediated diseases, cancer, and/or hyperglycemia with the compounds of this invention and/or compositions of this invention is based on a variety of factors, including the type of disease, the age, weight, sex, medical condition of the patient, the severity of the condition, the route of administration, and the particular compound employed. Thus, the dosage regimen may vary widely, but can be determined routinely using standard methods. Dosage levels of the order from about 0.01 mg to 30 mg per kilogram of body weight per day, preferably from about 0.1 mg to 10 mg/kg, more preferably from about 0.25 mg to 1 mg/kg are useful for all methods of use disclosed herein.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a capsule, a tablet, a suspension, or liquid. The pharmaceutical composition is preferably made in the form of a dosage unit containing a given amount of the active ingredient. For example, these may contain an amount of active ingredient from about 1 to 2000 mg, preferably from about 1 to 500 mg, more preferably from about 5 to 150 mg. A suitable daily dose for a human or other mammal may vary widely depending on the condition of the patient and other factors, but, once again, can be determined using routine methods.

The active ingredient may also be administered by injection as a composition with suitable carriers including saline, dextrose, or water. The daily parenteral dosage regimen will be from about 0.1 to about 30 mg/kg of total body weight, preferably from about 0.1 to about 10 mg/kg, and more preferably from about 0.25 mg to 1 mg/kg.

Injectable preparations, such as sterile injectable aqueous or oleaginous suspensions, may be formulated according to the known are using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

Suppositories for rectal administration of the drug can be prepared by mixing the drug with a suitable non-irritating excipient such as cocoa butter and polyethylene glycols that are solid at ordinary temperatures but liquid at the rectal temperature and will therefore melt in the rectum and release the drug.

A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

Formulations suitable for topical administration include liquid or semi-liquid preparations suitable for penetration through the skin (e.g., liniments, lotions, ointments, creams, or pastes) and drops suitable for administration to the eye, ear, or nose.

For administration, the compounds of this invention are ordinarily combined with one or more adjuvants appropriate for the indicated route of administration. The compounds may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinyl-pyrrolidine, and/or polyvinyl alcohol, and tableted or encapsulated for conventional administration. Alternatively, the compounds of this invention may be dissolved in saline, water, polyethylene glycol, propylene glycol, ethanol, corn oil, peanut oil, cottonseed oil, sesame oil, tragacanth gum, and/or various buffers. Other adjuvants and modes of administration are well known in the pharmaceutical art. The carrier or diluent may include time delay material, such as glyceryl monostearate or glyceryl distearate alone or with a wax, or other materials well known in the art.

The pharmaceutical compositions may be made up in a solid form (including granules, powders or suppositories) or in a liquid form (e.g., solutions, suspensions, or emulsions). The pharmaceutical compositions may be subjected to conventional pharmaceutical operations such as sterilization and/or may contain conventional adjuvants, such as preservatives, stabilizers, wetting agents, emulsifiers, buffers etc.

Solid dosage forms for oral administration may include capsules, tablets, pills, powders, and granules. In such solid dosage forms, the active compound may be admixed with at least one inert diluent such as sucrose, lactose, or starch. Such dosage forms may also comprise, as in normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, solutions, suspensions, syrups, and elixirs containing inert diluents commonly used in the art, such as water. Such compositions may also comprise adjuvants, such as wetting, sweetening, flavoring, and perfuming agents.

Compounds of the present invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, e.g., by formation of diastereoisomeric salts, by treatment with an optically active acid or base. Examples of appropriate acids are tartaric, diacetyltartaric, dibenzoyltartaric, ditoluoyltartaric, and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of the invention with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active compounds of the invention can likewise be obtained by using active starting materials. These isomers may be in the form of a free acid, a free base, an ester or a salt.

Likewise, the compounds of this invention may exist as isomers, that is compounds of the same molecular formula but in which the atoms, relative to one another, are arranged differently. In particular, the alkylene substituents of the compounds of this invention, are normally and preferably arranged and inserted into the molecules as indicated in the definitions for each of these groups, being read from left to right. However, in certain cases, one skilled in the art will appreciate that it is possible to prepare compounds of this invention in which these substituents are reversed in orientation relative to the other atoms in the molecule. That is, the substituent to be inserted may be the same as that noted above except that it is inserted into the molecule in the reverse orientation. One skilled in the art will appreciate that these isomeric forms of the compounds of this invention are to be construed as encompassed within the scope of the present invention.

The compounds of the present invention can be used in the form of salts derived from inorganic or organic acids. The salts include, but are not limited to, the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemisulfate, heptanoate, hexanoate, fumarate, hydrochloride, hydrobromide, hydroiodide, 2-hyroxy-ethanesulfonate, lactate, maleate, methansulfonate, nicotinate, 2-naphthalenesulfonate, oxalate, palmoate, pectinate, persulfate, 2-phenylpropionate, picrate, pivalate, propionate, succinate, tartrate, thiocyanate, tosylate, mesylate, and undecanoate. Also, the basic nitrogen-containing groups can be quaternized with such agents as lower alkyl halides, such as methyl, ethyl, propyl, and butyl chloride, bromides and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water or oil-soluble or dispersible products are thereby obtained.

Examples of acids that may be employed to from pharmaceutically acceptable acid addition salts include such inorganic acids as hydrochloric acid, sulphuric acid and phosphoric acid and such organic acids as oxalic acid, maleic acid, succinic acid and citric acid. Other examples include salts with alkali metals or alkaline earth metals, such as sodium, potassium, calcium or magnesium or with organic bases.

Also encompassed in the scope of the present invention are pharmaceutically acceptable esters of a carboxylic acid or hydroxyl containing group, including a metabolically labile ester or a prodrug form of a compound of this invention. A metabolically labile ester is one which may produce, for example, an increase in blood levels and prolong the efficacy of the corresponding non-esterified form of the compound. A prodrug form is one which is not in an active form of the molecule as administered but which becomes therapeutically active after some in vivo activity or biotransformation, such as metabolism, for example, enzymatic or hydrolytic cleavage. For a general discussion of prodrugs involving esters see Svensson and Tunek Drug Metabolism Reviews 165 (1988) and Bundgaard Design of Prodrugs, Elsevier (1985). Examples of a masked carboxylate anion include a variety of esters, such as alkyl (for example, methyl, ethyl), cycloalkyl (for example, cyclohexyl), aralkyl (for example, benzyl, p-methoxybenzyl), and alkylcarbonyloxyalkyl (for example, pivaloyloxymethyl). Amines have been masked as arylcarbonyloxymethyl substituted derivatives which are cleaved by esterases in vivo releasing the free drug and formaldehyde (Bungaard J. Med. Chem. 2503 (1989)). Also, drugs containing an acidic NH group, such as imidazole, imide, indole and the like, have been masked with N-acyloxymethyl groups (Bundgaard Design of Prodrugs, Elsevier (1985)). Hydroxy groups have been masked as esters and ethers. EP 039,051 (Sloan and Little, Apr. 11, 1981) discloses Mannich-base hydroxamic acid prodrugs, their preparation and use. Esters of a compound of this invention, may include, for example, the methyl, ethyl, propyl, and butyl esters, as well as other suitable esters formed between an acidic moiety and a hydroxyl containing moiety. Metabolically labile esters, may include, for example, methoxymethyl, ethoxymethyl, isopropoxymethyl, α-methoxyethyl, groups such as α-(($C_1$–$C_4$)alkyloxy)ethyl; for example, methoxyethyl, ethoxyethyl, propoxyethyl, iso-propoxyethyl, etc.; 2-oxo-1,3-dioxolen-4-ylmethyl groups, such as 5-methyl-2-oxo-1,3, dioxolen-4-ylmethyl, etc.; $C_1$–$C_3$ alkylthiomethyl groups, for example, methylthiomethyl, ethylthiomethyl, isopropylthiomethyl, etc.; acyloxymethyl groups, for example, pivaloyloxymethyl, α-acetoxymethyl, etc.; ethoxycarbonyl-1-methyl; or α-acyloxy-α-substituted methyl groups, for example α-acetoxyethyl.

Further, the compounds of the invention may exist as crystalline solids which can be crystallized from common solvents such as ethanol, N,N-dimethyl-formamide, water, or the like. Thus, crystalline forms of the compounds of the invention may exist as solvates and/or hydrates of the parent compounds or their pharmaceutically acceptable salts. All of such forms likewise are to be construed as falling within the scope of the invention.

While the compounds of the invention can be administered as the sole active pharmaceutical agent, they can also be used in combination with one or more compounds of the invention or other agents. When administered as a combination, the therapeutic agents can be formulated as separate compositions that are given at the same time or different times, or the therapeutic agents can be given as a single composition.

The foregoing is merely illustrative of the invention and is not intended to limit the invention to the disclosed compounds. Variations and changes which are obvious to one skilled in the art are intended to be within the scope and nature of the invention which are defined in the appended claims.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A compound of formula

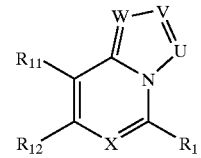

or a pharmaceutically acceptable salt thereof, wherein
$R_1$-Z-Y or —Y; provided that the total number of aryl, heteroaryl, cycloalkyl and heterocyclyl radicals in $R_1$ is 0–3;

U, V and W are each independently C—$R_6$ or N, provided when U is N then V is C—$R_6$;

each $R_6$ is independently a hydrogen, halo, alkyl, alkoxy, alkylthio, haloalkyl, haloalkoxy, hydroxy or cyano radical;

each Z is independently a (1) alkyl, alkenyl or alkynyl radical optionally substituted by (a) 1–3 radicals of amino, alkylamino, dialkylamino, alkanoylamino, alkoxycarbonylamino, alkylsulfonylamino, hydroxy, alkoxy, alkylthio or halo, and (b) 1–2 radicals of heterocyclyl, aryl or heteroaryl; or (2) heterocyclyl, aryl or heteroaryl radical;

wherein the heterocyclyl radicals are optionally substituted by 1–3 radicals of amino, alkylamino, dialkylamino, alkanoylamino, alkoxycarbonylamino, alkylsulfonylamino, hydroxy, alkoxy, alkylthio, alkyl, arylalkyl, heteroarylalkyl or haloalkyl; and the aryl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

each Y is independently a (1) hydrogen radical;

(2) halo or nitro radical;

(3) —C(O)—$R_{20}$, —C(O)—$OR_{21}$, —C(O)—$NR_5R_{21}$ or —C($NR_5$)—$NR_5R_{21}$ radical;

(4) —$OR_{21}$, —O—C(O)—$R_{21}$, —C(O)—$NR_5R_{21}$ or —C(O)—$NR_{22}$—S(O)$_2$—$R_{20}$ radical;

(5) —$SR_{21}$, —S(O)—$R_{20}$, —S(O)$_2$—$R_{20}$, —S(O)$_2$—$NR_5R_{21}$, —S(O)$_2$—$NR_{22}$—C(O)—$R_{21}$, —S(O)$_2$—$NR_{22}$—C(O)—$OR_{20}$ or —S(O)$_2$—$NR_{22}$—C(O)—$NR_5R_{21}$ radical; or (6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—S(O)$_2$—$R_{20}$ or —$NR_{22}$—S(O)$_2$—$NR_5R_{21}$ radical;

each $R_5$ is independently a (1) hydrogen radical;

(2) alkyl, alkenyl or alkynyl radical optionally substituted by 1–3 radicals of amino, alkylamino, dialkylamino, hydroxy, alkoxy, alkylthio, —$SO_3H$ or halo; or (3) aryl, heteroaryl, arylalkyl, heteroarylalkyl, heterocyclyl, heterocyclylalkyl, cycloalkyl or cycloalkylalkyl radical, wherein the aryl, heteroaryl, heterocyclyl and cycloalkyl radicals are optionally substituted by 1–3 radicals of amino, alkylamino, dialkylamino, hydroxy, alkoxy, alkylthio, alkyl or haloalkyl;

each $R_{20}$ is independently a (1) alkyl, alkenyl or alkynyl radical optionally substituted by (a) 1–3 radicals of amino, alkylamino, dialkylamino, alkanoylamino, alkoxycarbonylamino, N-(alkoxycarbonyl)-N-(alkyl)amino, aminocarbonylamino, alkylsulfonylamino, hydroxy, alkoxy, alkylthio, alkylsulfinyl, alkylsulfonyl or halo and (b) a radical of aralkoxy, arylalkylthio, arylalkylsulfonyl, cycloalkyl, heterocyclyl, aryl or heteroaryl, wherein the aryl, heteroaryl, heterocyclyl and cycloalkyl radicals are optionally substituted by 1–3 radicals of amino, alkylamino, dialkylamino, alkanoylamino, alkoxycarbonylamino, alkylsulfonylamino, alkanoyl, hydroxy, alkoxy, alkylthio, alkylsulfinyl, alkylsulfonyl, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, alkyl or haloalkyl; or (3) aryl or heteroaryl radicals optionally substituted by 1–3 radicals of amino, alkylamino, dialkylamino, alkanoylamino, alkoxycarbonylamino, alkylsulfonylamino, alkoxycarbonyl, hydroxy, alkoxy, alkylthio, cyano, halo, azido, alkyl or haloalkyl;

each $R_{21}$ is independently a hydrogen radical or $R_{20}$;

each $R_{22}$ is independently a (1) hydrogen radical;

(2) alkyl radical optionally substituted by a radical of heterocyclyl, aryl or heteroaryl, wherein the heterocyclyl, aryl or heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl; or (3) heterocyclyl, aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, alkylsulfinyl, alkylsulfonyl, cyano, halo, alkyl or haloalkyl;

$R_{11}$ is an aryl or heteroaryl radical, and $R_{12}$ is an "N"-heteroaxyl radical, wherein the aryl, heteroaryl and "N"-heteroaryl radicals are optionally substituted by 1–3 radicals of (1) $R_{30}$;

(2) halo or cyano;

(3) —C(O)—$R_{30}$, —C(O)—$OR_{29}$, —C(O)—$NR_{31}R_{32}$ or —C($NR_{31}$)—$NR_{31}R_{32}$;

(4) —$OR_{29}$, —O—C(O)—$R_{29}$, —O—C(O)—$NR_{31}R_{32}$ or —O—C(O)—$NR_{33}$—S(O)$_2$—$R_{30}$;

(5) —$SR_{29}$, —S(O)—$R_{30}$, —S(O)$_2$—$R_{30}$, —S(O)$_2$—$NR_{31}R_{32}$, —S(O)$_2$—$NR_{33}$—C(O)—$R_{30}$, —S(O)$_2$—$NR_{33}$—C(O)—$OR_{30}$ or —S(O)$_2$—$NR_{33}$—C(O)—$NR_{31}R_{32}$; or (6) —$NR_{31}$, $R_{32}$, —$NR_{33}$—C(O)—$R_{29}$, —$NR_{33}$—C(O)—$OR_{30}$, —$NR_{33}$—C(O)—$NR_{31}R_{32}$, —$NR_{33}$—C(O)—($NR_{31}$)—$NR_{31}R_{32}$, —$NR_{33}$—S(O)$_2$—$R_{30}$ or —$NR_{33}$—S(O)$_2$—$NR_{31}R_{32}$;

provided that the total number of aryl, heteroaryl, cycloalkyl and heterocyclyl radicals substituted on each of $R_{11}$ and $R_{12}$ is 0–1;

each $R_{30}$ is independently a (1) alkyl, alkenyl or alkynyl radical optionally substituted by (a) 1–3 radicals of —$NR_{31}R_{32}$, hydroxy, alkoxy, alkylthio, alkylsulfinyl, alkylsulfonyl, cyano or halo, and (b) a radical of aralkoxy, arylalkylthio, arylalkylsulfonyl, heterocyclyl, aryl or heteroaryl, wherein the heterocyclyl, aryl and heteroaryl radicals are optionally substituted by 1–3 radicals of amino, alkylamino, dialkylamino, alkanoylamino, alkoxycarbonylamino alkylsulfonylamino, hydroxy, alkoxy, alkylthio, alkylsulfinyl, alkylsulfonyl, cyano, halo, alkyl or haloalkyl;

(2) heterocyclyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl or heteroaryl radical optionally substituted by 1–3 radicals of amino, alkylamino, dialkylamino, alkanoylamino, alkoxycarbonylamino, alkylsulfonylamino, hydroxy, alkoxy, alkylthio, cyano, halo, alkyl or haloalkyl;

each $R_{29}$ is independently a hydrogen radical or $R_{30}$;

each $R_{31}$ is independently a (1) hydrogen radical;

(2) alkyl radical optionally substituted by an cycloalkyl, aryl, heterocyclyl or heteroaryl radical, wherein the cycloalkyl, aryl, heterocyclyl and heteroaryl radicals are optionally substituted by 1–3 radicals of amino, alkylamino, dialkylamino, alkanoylamino, alkoxycarbonylamino alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino alkylsulfonylamino, hydroxy, alkoxy, alkylthio, cyano, alkyl or haloalkyl;

each $R_{32}$ is independently a (1) hydrogen radical;

(2) alkyl radical optionally substituted by a cycloalkyl, aryl, heterocyclyl or heteroaryl radical, wherein the cycloalkyl, aryl, heterocyclyl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; or (3) aryl, heteroaryl, heterocyclyl or cycloalkyl radical optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl; and each $R_{33}$ is independently a (1) hydrogen radical; or (2) alkyl radical optionally substituted by a radical of heterocyclyl, aryl or heteroaryl, wherein the aryl, heterocyclyl and heteroaryl radicals are optionally substituted by 1–3 radicals of amino, alkylamino, dialkylamino, alkanoylamino, alkoxycarbonylamino, alkylsulfonylamino, hydroxy, alkoxy, alkylthio, cyano, alkyl or haloalkyl.

2. The compound of claim 1 or a pharmaceutically acceptable salt thereof, wherein $R_1$-Z-Y or —Y; provided that the total number of aryl, heteroaryl, cycloalkyl and heterocyclyl radicals in $R_1$ is 0–3;

U, V and W are each independently C—$R_6$ or N, provided when U is N then V is C—$R_6$;

each $R_6$ is independently a hydrogen, halo, $C_1$–$C_4$ alkyl, $C_1$–$C_4$ alkoxy, $C_1$–$C_4$ alkylthio, $C_1$–$C_4$ haloalkyl of 1–3 halo radicals, $C_1$–$C_4$ haloalkoxy of 1–3 halo radicals, hydroxy or cyano radical;

each Z is independently a (1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio or halo, and (b) 1–2 radicals of heterocyclyl, aryl or heteroaryl; or (2) heterocyclyl, aryl or heteroaryl radical;

wherein the heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or $C_1$–$C_4$ haloalkyl of 1–3 halo radicals; and the aryl and heteroaxyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each Y is independently a (1) hydrogen radical;

(2) halo or nitro radical;

(3) —C(O)—$R_{20}$, —C(O)—$OR_{21}$, —C(O)—$NR_5R_{21}$ or —C($NR_5$)—$NR_5R_{21}$ radical;

(4) —$OR_{21}$, —O—C(O)—$R_{21}$, —O—C(O)—$NR_5R_{21}$ or —O—C(O)—$NR_{22}$—$S(O)_2$—$R_{20}$ radical;

(5) —$SR_{21}$, —S(O)—$R_{20}$, —$S(O)_2$—$R_{20}$, —$S(O)_2$—$NR_5R_{21}$, —$S(O)_2$—$NR_{22}$—C(O)—$R_{21}$, —$S(O)_2$—$NR_{22}$—C(O)—$OR_{20}$ or —$S(O)_2$—$NR_{22}$—C(O)—$NR_5R_{21}$ radical; or (6) —$NR_5R_{21}$, —$NR_{22}$—C(O)—$R_{21}$, —$NR_{22}$—C(O)—$OR_{20}$, —$NR_{22}$—C(O)—$NR_5R_{21}$, —$NR_{22}$—C($NR_5$)—$NR_5R_{21}$, —$NR_{22}$—$S(O)_2$—$R_{20}$ or —$NR_{22}$—$S(O)_2$—$NR_5R_{21}$ radical;

each $R_5$ is independently a (1) hydrogen radical;

(2) $C_1$–$C_8$ alkyl, $C_2$–$C_8$ alkenyl or $C_2$–$C_8$ alkynyl radical optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, —$SO_3H$ or halo; or (3) aryl, heteroaryl, aryl-$C_1$–$C_4$-alkyl heteroaryl-$C_1$–$C_4$-alkyl, heterocyclyl, heterocyclyl-$C_1$–$C_4$-alkyl, $C_3$–$C_8$ cycloalkyl or $C_3$–$C_8$-cycloalkyl-$C_1$–$C_4$-alkyl radical, wherein the aryl, heteroaryl, heterocyclyl and cycloalkyl radicals are optionally substituted by 1–3 radicals of amino, $C_1$–$C_4$ alkylamino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_4$ haloalkyl of 1–3 halo radicals;

each $R_{20}$ is independently a (1) $C_1$–$C_8$ alkyl, $C_2$–$C_8$ alkenyl or $C_2$–$C_8$ alkynyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo, and (b) a radical of aryl-$C_1$–$C_4$-alkoxy, aryl-$C_1$–$C_4$-alkylthio, aryl-$C_1$–$C_4$-alkylsulfonyl, $C_3$–$C_8$ cycloalkyl, heterocyclyl, aryl or heteroaryl radicals, wherein the aryl, heteroaryl, heterocyclyl and cycloalkyl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, $C_1$–$C_4$ alkylsulfinyl, $C_1$–$C_4$ alkylsulfonyl, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino hydroxy, $C_1$–$C_4$ alkoxy, $C_1$–$C_4$ alkylthio, $C_1$–$C_4$ alkyl or $C_1$–$C_4$ haloalkyl of 1–3 halo radicals; or (3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or $C_1$–$C_4$ haloalkyl of 1–3 halo radicals;

each $R_{21}$ is independently a hydrogen radical or $R_{20}$;

each $R_{22}$ is independently a (1) hydrogen radical;

(2) $C_1$–$C_4$ alkyl radical optionally substituted by a radical of heterocyclyl, aryl or heteroaryl, wherein the aryl, heteroaryl and heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino hydroxy, $C_1$–$C_4$ alkoxy, $C_1$–$C_4$ alkylthio, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals; or (3) heterocyclyl, aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

$R_{11}$ is an aryl or heteroaryl radical, and $R_{12}$ is a "N"-heteroaryl radical, wherein the aryl, heteroaryl and "N"-heteroaryl radicals are optionally substituted by 1–2 radicals of (1) $R_{30}$;

(2) halo or cyano;

(3) —C(O)—$R_{30}$, —C(O)—$OR_{29}$, —C(O)—$NR_{31}R_{32}$ or —C($NR_{31}$)—$NR_{31}R_{32}$;

(4) —$OR_{29}$, —O—C(O)—$R_{29}$, —O—C(O)—$NR_{31}R_{32}$ or —O—C(O)—$NR_{33}$—$S(O)_2$—$R_{30}$;

(5) —$SR_{29}$, —S(O)—$R_{30}$, —$S(O)_2$—$R_{30}$, —$S(O)_2$—$NR_{31}R_{32}$, —$S(O)_2$—$NR_{33}$—C(O)—$R_{30}$, —$S(O)_2$—$NR_{33}$—C(O)—$OR_{30}$ or —$S(O)_2$—$NR_{33}$—C(O)—$NR_{31}R_{32}$; or (6) —$NR_{31}R_{32}$, —$NR_{33}$—$C(O)$—$R_{29}$, —$NR_{33}$—$C(O)$—$OR_{30}$, —$NR_{33}$—$C(O)$—$NR_{31}R_{32}$, —$NR_{33}$—$C(NR_{31})$—$NR_{31}R_{32}$, —$NR_{33}$—$S(O)_2$—$R_{30}$ or —$NR_{33}$—$S(O)_2$—$NR_{31}R_{32}$;

provided that the total number of aryl, heteroaryl, cycloalkyl and heterocyclyl radicals substituted on each of $R_{11}$ and $R_{12}$ is 0–1;

each $R_{30}$ is independently a (1) $C_1$–$C_4$ alkyl, $C_2$–$C_4$ alkenyl or $C_2$–$C_4$ alkynyl radical optionally substituted by (a) 1–3 radicals of —$NR_{31}R_{32}$, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano or halo, and (b) a radical of aryl-$C_1$–$C_4$-alkoxy, aryl-$C_1$–$C_4$-alkylthio, aryl-$C_1$–$C_4$-alkylsulfonyl, heterocyclyl, aryl or heteroaryl, wherein the heterocyclyl, aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl, cyano, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl or heteroaryl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or haloalkyl of 1–3 halo radicals;

each $R_{29}$ is independently a hydrogen radical or $R_{30}$;

each $R_{31}$ is independently a (1) hydrogen radical;

(2) $C_1$–$C_4$ alkyl radical optionally substituted by an $C_3$–$C_8$ cycloalkyl, aryl, heterocyclyl or heteroaryl radical, wherein the cycloalkyl, aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals;

each $R_{32}$ is independently a (1) hydrogen radical;

(2) $C_1$–$C_4$ alkyl radical optionally substituted by an $C_3$–$C_8$ cycloalkyl, aryl, heterocyclyl or heteroaryl radical, wherein the cycloalkyl, aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ al $C_1$–$C_4$ alkylthio, cyano, $C_1$–$C_4$ alkyl or $C_1$–$C_4$ haloalkyl of 1–3 halo radicals; or (3) aryl, heteroaryl, heterocyclyl or $C_3$–$C_8$ cycloalkyl radical optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and each $R_{33}$ is independently a (1) hydrogen radical; or (2) $C_1$–$C_4$ alkyl radical optionally substituted by a radical of heterocyclyl, aryl or heteroaryl, wherein the aryl, heterocyclyl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; and wherein heterocyclyl is a radical of a monocyclic or bicyclic saturated heterocyclic ring system having 5–8 ring members per ring, wherein 1–3 ring members are oxygen, sulfur or nitrogen heteroatoms, which is optionally partially unsaturated or benzo-fused and optionally substituted by 1–2 oxo or thioxo radicals; aryl is a phenyl or naphthyl radical; and heteroaryl is radical of a monocyclic or bicyclic aromatic heterocyclic ring system having 5–6 ring members per ring, wherein 1–3 ring members are oxygen, sulfur or nitrogen heteroatoms, which is optionally benzo-fused or saturated $C_3$–$C_4$-carbocyclic-fused.

3. The compound of claim 2 or a pharmaceutically acceptable salt thereof, wherein each Z is independently a (1) $C_1$–$C_8$ alkyl or $C_2$–$C_8$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio or halo, and (b) 1–2 radicals of heterocyclyl, aryl or heteroaryl; or (2) heterocyclyl, aryl or heteroaryl radical;

wherein the heterocyclyl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or $C_1$–$C_2$ haloalkyl of 1–3 halo radicals; and the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

each Y is independently a (1) hydrogen or halo radical;

(2) —$C(O)$—$R_{20}$, —$C(O)$—$OR_{21}$, —$C(O)$—$NR_5R_{21}$ or —$C(NR_5)$—$NR_5R_{21}$ radical;

(3) —$OR_{21}$, —$O$—$C(O)$—$R_{21}$ or —$O$—$C(O)$—$NR_5R_{21}$ radical;

(4) —$SR_{21}$, —$S(O)$—$R_{20}$, —$S(O)_2$—$R_{20}$ or —$S(O)_2$—$NR_5R_{21}$ radical; or (5) —$NR_5R_{21}$, —$NR_{22}$—$C(O)$—$R_{21}$, —$NR_{22}$—$C(O)$—$OR_{20}$ or —$NR_{22}$—$C(O)$—$NR_5R_{21}$ radical;

each $R_5$ is independently a (1) hydrogen radical;

(2) $C_1$–$C_4$ alkyl or $C_2$–$C_5$ alkenyl radicals optionally substituted by 1–3 radicals of amino, di-($C_1$–$C_4$-alkyl)

amino, hydroxy, $C_1$–$C_4$ alkoxy, $C_1$–$C_4$ alkylthio, —$SO_3H$ or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_2$-alkyl radical, wherein the cycloalkyl, phenyl, heterocyclyl and heteroaryl radicals are optionally substituted by 1–3 radicals of amino, di-($C_1$–$C_4$-alkyl)amino, hydroxy, $C_1$–$C_4$ alkoxy, $C_1$–$C_4$ alkylthio, $C_1$–$C_4$ alkyl or $C_1$–$C_2$ haloalkyl of 1–3 halo radicals;

each $R_{20}$ is independently a (1) $C_1$–$C_8$ alkyl or $C_2$–$C_5$ alkenyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl) amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo, and (b) a radical of aryl-$C_1$–$C_4$-alkoxy, aryl-$C_1$–$C_4$-alkylthio, aryl-$C_1$–$C_4$-alkylsulfonyl, $C_3$–$C_6$ cycloalkyl, heterocyclyl, aryl or heteroaryl, wherein the cycloalkyl, aryl, heterocyclyl and heteroaryl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, $C_1$–$C_5$ alkanoyl, hydroxy, $C_1$–$C_4$ alkoxy, $C_1$–$C_4$ alkylthio, halo, $C_1$–$C_4$ alkyl or $C_1$–$C_2$ haloalkyl of 1–3 halo radicals;

(2) heterocyclyl radical optionally substituted by 1–2 radicals of amino, di-($C_1$–$C_4$ alkyl)amino, ($C_1$–$C_4$ alkoxy)carbonylamino, hydroxy, $C_1$–$C_4$ alkoxy, $C_1$–$C_4$ alkylthio or $C_1$–$C_4$ alkyl; or (3) aryl or heteroaryl radical optionally substituted by 1–2 radicals of amino, $C_1$–$C_4$ alkylamino, di-($C_1$–$C_4$ alkyl) amino, acetamido, ($C_1$–$C_4$ alkoxy)carbonylamino, $C_1$–$C_4$ alkylsulfonylamino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl;

each $R_{21}$ is independently a hydrogen radical or $R_{20}$;

each $R_{22}$ is independently a (1) hydrogen radical; or (2) $C_1$–$C_4$ alkyl radical optionally substituted by a radical of phenyl or heteroaryl, wherein the phenyl and heteroaryl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or $C_1$–$C_2$ haloalkyl of 1–3 halo radicals;

$R_{11}$ is an aryl or heteroaryl radical, and $R_{12}$ is a "N"-heteroaryl radical, wherein the aryl, heteroaryl and "N"-heteroaryl radicals are optionally substituted by 1–2 radicals of (1)$R_{30}$;

(2) halo or cyano;

(3) —C(O)—$R_{30}$, —C(O)—$OR_{29}$, —C(O)—$NR_{31}R_{32}$ or —C($NR_{31}$)—$NR_{31}$)—$NR_{31}R_{32}$; or (4) —$OR_{29}$, —$SR_{29}$, —S(O)—$R_{30}$, —$S(O)_2$—$R_{30}$, —$S(O)_2$—$NR_{31}R_{32}$, —$NR_{33}$—$S(O)_2$—$R_{30}$, —$NR_{31}R_{32}$ or —$NR_{33}$—C(O)—$R_{29}$;

each $R_{30}$ is independently a (1) $C_1$–$C_4$ alkyl or $C_2$–$C_5$ alkenyl radical optionally substituted by (a) 1–3 radicals of —$NR_{31}R_{32}$, hydroxy, $C_1$–$C_4$ alkoxy or halo, and (b) a radical of heterocyclyl, aryl or heteroaryl, wherein the heterocyclyl, aryl and heteroaryl radicals are optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfonyl, cyano, halo, $C_1$–$C_4$ alkyl or $C_1$–$C_4$ haloalkyl of 1–3 halo radicals;

(2) heterocyclyl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, $C_1$–$C_4$ alkylylsufonylamino hydroxy, $C_1$–$C_4$ alkoxy, $C_1$–$C_4$ alkylthio, cyano, $C_1$–$C_4$ alkyl or $C_1$–$C_4$ haloalkyl of 1–3 halo radicals; or (3) aryl or heteroaryl radical optionally substituted by 1–3 radicals of amino, $C_1$–$C_4$ alkylamino, di-($C_1$–$C_4$ alky) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, cyano, halo, $C_1$–$C_4$ alkyl or $C_1$–$C_4$ haloalkyl of 1–3 halo radicals;

each $R_{29}$ is independently a hydrogen radical or each $R_{31}$ is independently a (1) hydrogen radical; or (2) $C_1$–$C_4$ alkyl radical optionally substituted by a aryl or heteroaryl radical, wherein the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, $C_1$–$C_4$ alkyl or trifluoromethyl;

each $R_{32}$ is independently a (1) hydrogen radical;

(2) $C_1$–$C_4$ alkyl radical optionally substituted by an aryl or heteroaryl radical, wherein the aryl and heteroaryl radicals are optionally substituted by 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkyl or trifluoromethyl; or (3) aryl or heteroaryl radical optionally substituted by 1–3 radicals of amino, $C_1$–$C_4$ alkylamino, di-($C_1$–$C_4$ alkyl) amino, $C_1$–$C_5$ alkanoylamino, ($C_1$–$C_4$ alkoxy) carbonylamino, hydroxy, $C_1$–$C_4$ alkoxy, $C_1$–$C_4$ alkyl or trifluoromethyl; and each $R_{33}$ is independently a hydrogen or $C_1$–$C_4$ alkyl radical.

4. The compound of claim 3 or a pharmaceutically acceptable salt thereof, wherein $R_1$ is -Z-Y or —Y; provided that the total number of aryl, heteroaryl, cycloalkyl and heterocyclyl radicals in $R_1$ is 0–2;

each Z is independently a (1) $C_1$–$C_4$ alkyl or $C_2$–$C_5$ alkenyl radical optionally substituted by (a) 1–3 radicals of amino, di-($C_1$–$C_2$ alkyl)amino, $C_1$–$C_5$ alkanoylamino, ($C_1$–$C_4$ alkoxy) carbonylamino, hydroxy, $C_1$–$C_2$ alkoxy, $C_1$–$C_2$ alkylthio or halo, and (b) 1–2 radicals of heterocyclyl, aryl or heteroaryl; or (2) heterocyclyl, aryl or heteroaryl radical; wherein the heterocyclyl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, $C_1$–$C_4$ alkyl, aryl-$C_1$–$C_4$ alkyl, heteroaryl-$C_1$–$C_4$ alkyl or trifluoromethyl radicals; and the aryl and heteroaryl radicals are optionally substituted by 1–3 radicals of amino, di-($C_1$–$C_2$ alkyl)amino, $C_1$–$C_5$ alkanoylamino, ($C_1$–$C_4$ alkoxy)carbonylamino, hydroxy, $C_1$–$C_4$ alkoxy, $C_1$–$C_4$ alkylthio, cyano, halo, $C_1$–$C_4$ alkyl or trifluoromethyl radicals;

each Y is independently a (1) hydrogen radical;

(2) —C(O)—$R_{20}$ or —C(O)—$NR_5R_{21}$ radical;

(3) —$OR_{21}$, —$SR_{21}$, —S(O)—$R_{20}$, —S(O)$_2$—$R_{20}$ or —S(O)$_2$—$NR_5R_{21}$ radical; or (4) —$NR_5R_{21}$ or —$NR_{22}$—C(O)—$R_{21}$ radical;

each $R_5$ is independently a (1) hydrogen radical;

(2) $C_1$–$C_4$ alkyl radical optionally substituted by 1–3 radicals of amino, di-($C_1$–$C_2$-alkyl)amino, hydroxy, $C_1$–$C_2$ alkoxy, $C_1$–$C_2$ alkylthio or halo; or (3) phenyl-$C_1$–$C_2$-alkyl, heteroaryl-$C_1$–$C_2$-alkyl, heterocyclyl-$C_1$–$C_2$-alkyl or $C_3$–$C_6$-cycloalkyl-$C_1$–$C_2$-alkyl radical, wherein the phenyl, heteroaryl, heterocyclyl and cycloalkyl radicals are optionally substituted by 1–3 radicals of amino, di-($C_1$–$C_2$-alkyl)amino, hydroxy, $C_1$–$C_2$ alkoxy, $C_1$–$C_2$ alkylthio, $C_1$–$C_4$ alkyl or trifluoromethyl;

each $R_{20}$ is independently a (1) $C_1$–$C_8$ alkyl radical optionally substituted by (a) 1–3 radicals of amino, $C_1$–$C_4$ alkylamino, di-($C_1$–$C_4$ alkyl)amino, $C_1$–$C_5$ alkanoylamino, ($C_1$–$C_4$ alkoxy)carbonylamino, N—(($C_1$–$C_4$ alkoxy)carbonyl)-N—($C_1$–$C_4$ alkyl)amino, aminocarbonylamino, hydroxy, $C_1$–$C_4$ alkoxy, $C_1$–$C_4$ alkylthio, $C_1$–$C_4$ alkylsulfinyl, $C_1$–$C_4$ alkylsulfonyl or halo, and (b) a radical of $C_3$–$C_6$ cycloalkyl, heterocyclyl, aryl or heteroaryl, wherein the cycloalkyl, heterocyclyl, aryl and heteroaryl radicals are optionally substituted by 1–2 radicals of amino, di-($C_1$–$C_4$ alkyl)amino, $C_1$–$C_5$ alkanoylamino, ($C_1$–$C_4$ alkoxy)carbonylamino, $C_1$–$C_4$ alkylsulfonylamino, hydroxy, $C_1$–$C_4$ alkoxy, $C_1$–$C_4$ alkylthio, halo, $C_1$–$C_4$ alkyl or trifluoromethyl;

(2) heterocyclyl radical optionally substituted by 1–2 radicals of hydroxy, $C_1$–$C_4$ alkoxy, $C_1$–$C_4$ alkylthio or $C_1$–$C_4$ alkyl; or (3) aryl or heteroaryl radical optionally substituted by 1–2 radicals of amino, $C_1$–$C_4$ alkylamino, di-($C_1$–$C_4$ alkyl)amino, ($C_1$–$C_4$ alkoxy)carbonyl, hydroxy, $C_1$–$C_4$ alkoxy, $C_1$–$C_4$ alkylthio, cyano, halo, azido, $C_1$–$C_4$ alkyl or trifluoromethyl;

each $R_{21}$ is independently a hydrogen radical or $R_{20}$;

each $R_{22}$ is independently a hydrogen or $C_1$–$C_4$ alkyl radical;

$R_{11}$ is an aryl or heteroaryl radical, wherein the aryl and heteroaryl radicals are optionally substituted by 1–2 radicals of (1) $R_{40}$;

(2) halo or cyano; or (3) —C(O)—$NR_{41}R_{42}$, —$OR_{39}$, —$SR_{39}$, —S(O)—$R_{40}$, —S(O)$_2$—$R_{40}$, —S(O)$_2$—$NR_{41}R_{42}$, —$NR_{33}$—C(O)—$R_{39}$;

each $R_{40}$ is independently a (1) $C_1$–$C_4$ alkyl radical optionally substituted by a phenyl or heteroaryl radical, wherein the phenyl and heteroaryl radicals are optionally substituted by 1–3 radicals of amino, dimethylamino, acetamido, hydroxy, halo, methoxy, methyl or trifluoromethyl radicals;

(2) trifluoromethyl radical; or (3) aryl or heteroaryl radical optionally substituted by 1–3 radicals of amino, dimethylamino, acetamido, hydroxy, halo, methoxy, methyl or trifluoromethyl;

each $R_{39}$ is independently a hydrogen radical or $R_{40}$;

each $R_{41}$ is independently a (1) hydrogen radical; or (2) $C_1$–$C_4$ alkyl radical optionally substituted by a phenyl or heteroaryl radical, wherein the phenyl and heteroaryl radicals are optionally substituted by 1–3 radicals of amino, $C_1$–$C_2$ alkylamino, di-($C_1$–$C_2$ alkyl)amino, acetamido, hydroxy, $C_1$–$C_2$ alkoxy, $C_1$–$C_2$ alkylthio, cyano, $C_1$–$C_2$ alkyl or trifluoromethyl;

each $R_{42}$ is independently a (1) hydrogen radical;

(2) $C_1$–$C_4$ alkyl radical or $C_1$–$C_2$ alkyl radical substituted by an aryl or heteroaryl radical, wherein the aryl and heteroaryl radicals are optionally substituted by 1–3 radicals of amino, dimethylamino, acetamido, hydroxy, methoxy, methyl or trifluoromethyl; or (3) aryl or heteroaryl radical optionally substituted by 1–3 radicals of amino, dimethylamino, acetamido, hydroxy, methoxy, methyl or trifluoromethyl radicals;

each $R_{33}$ is independently a hydrogen or methyl radical; and wherein heterocyclyl is a radical of a monocyclic saturated heterocyclic ring system having 5–6 ring members, wherein 1–3 ring members are oxygen, sulfur or nitrogen heteroatoms, which is optionally benzo-fused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–3 ring members are oxygen, sulfur or nitrogen heteroatoms, which is optionally benzo-fused or saturated $C_3$–$C_4$-carbocyclic-fused.

5. The compound of claim 4 or a pharmaceutically acceptable salt thereof, wherein each $R_6$ is independently a hydrogen, $C_1$–$C_4$ alkyl, $C_1$–$C_4$ alkoxy, —$CF_3$, —$OCF_3$ or hydroxy radical;

each Z is independently a (1) $C_1$–$C_4$ alkyl or $C_2$–$C_5$ alkenyl radical optionally substituted by (a) 1–3 radicals of amino, di-($C_1$–$C_2$ alkyl)amino, ($C_1$–$C_4$ alkoxy)carbonylamino, hydroxy, $C_1$–$C_2$ alkoxy, $C_1$–$C_2$ alkylthio or halo, and (b) 1–2 radicals of heterocyclyl, aryl or heteroaryl; or (2) heterocyclyl, aryl or heteroaryl radical;

wherein the heterocyclyl radicals are optionally substituted by 1–2 radicals of $C_1$–$C_4$ alkyl, aryl-$C_1$–$C_2$ alkyl or heteroaryl-$C_1$–$C_2$ alkyl; and wherein the aryl and heteroaryl radicals are optionally substituted by 1–3 radicals of amino, di-($C_1$–$C_2$ alkyl)amino, acetamido, ($C_1$–$C_4$ alkoxy)carbonylamino, hydroxy, $C_1$–$C_2$ alkoxy, $C_1$–$C_2$ alkylthio, cyano, halo, $C_1$–$C_4$ alkyl or trifluoromethyl;

each Y is independently a hydrogen, —$OR_{21}$, —$SR_{21}$, —S(O)—$R_{20}$, —S(O)$_2$—$R_{20}$ or —$NR_5R_{21}$ radical;

each $R_5$ is independently a (1) hydrogen radical;

(2) $C_1$–$C_4$ alkyl radical optionally substituted by 1–3 halo radicals; or (3) phenyl-$C_1$–$C_2$-alkyl or heteroaryl-$C_1$–$C_2$-alkyl radical, wherein the phenyl and heteroaryl radicals are optionally substituted by 1–3 radicals of amino, dimethylamino, hydroxy, methoxy, methylthio, methyl or trifluoromethyl;

each $R_{20}$ is independently a (1) $C_1$–$C_6$ alkyl radicals optionally substituted by (a) 1–3 radicals of amino, methylamino, dimethylamino, t-butoxycarbonylamino, N-((t-butoxy)carbonyl)-N-(methyl)amino, aminocarbonylamino, hydroxy, butoxy, methoxy, butylthio, methylthio, methylsulfinyl, methylsulfonyl or halo, and (b) a radical of $C_5$–$C_6$ cycloalkyl, heterocyclyl, phenyl or heteroaryl radical optionally substituted by 1–2 radicals of amino, dimethylamino, acetamino, hydroxy, methoxy, methylthio, halo, methyl or trifluoromethyl radicals;

(2) heterocyclyl radical optionally substituted by 1–2 radicals of hydroxy or $C_1$–$C_4$ alkyl; or (3) aryl or heteroaryl radical optionally substituted by 1–2 radicals of amino, dimethylamino, hydroxy, methoxy, methylthio, halo, methyl or trifluoromethyl;

each $R_{21}$ is independently a hydrogen radical or $R_{20}$;

$R_{11}$ is an aryl or heteroaryl radical, optionally substituted by 1–2 radicals of (1) $R_{40}$; (2) halo or cyano; or (3) —C(O)—$NR_{41}R_{42}$, —$OR_{39}$, —$SR_{39}$, —S(O)—$R_{40}$, —$S(O)_2$—$R_{40}$, —$S(O)_2$—$NR_{41}R_{42}$, —$NR_{41}R_{42}$ or —$NR_{33}$—C(O)—$R_{39}$;

$R_{12}$ is an "N"-heteroaryl radical optionally substituted by 1–2 radicals of (1) $R_{30}$; (2) halo or cyano; or (3) —C(O)—$NR_{41}R_{42}$, —$OR_{39}$, —$SR_{39}$, —$NR_{41}R_{42}$ or —$NR_{33}$—C(O)—$R_{39}$;

$R_{40}$ is independently a (1) $C_1$–$C_4$ alkyl radical optionally substituted by a phenyl or heteroaryl radical, wherein the phenyl and heteroaryl radicals are optionally substituted by 1–2 radicals of amino, dimethylamino, acetamido, hydroxy, halo, methoxy, methyl or trifluoromethyl;

(2) trifluoromethyl radical; or (3) aryl or heteroaryl radical optionally substituted by 1–3 radicals of amino, dimethylamino, acetamido, hydroxy, halo, methoxy, methyl or trifluoromethyl;

each $R_{39}$ is independently a hydrogen radical or $R_{40}$;

each $R_{41}$ is independently a hydrogen or $C_1$–$C_4$ alkyl radical;

each $R_{42}$ is independently a hydrogen or $C_1$–$C_4$ alkyl radical; and wherein hererocyclyl is a radical of a monocyclic saturated heterocyclic ring system having 5–6 ring members, wherein 1–2 ring members are oxygen, sulfur or nitrogen heteroatoms, which is optionally benzofused and optionally substituted by 1–2 oxo or thioxo radicals; aryl is a phenyl or naphthyl radical; and heteroaryl is radical of a monocyclic aromatic heterocyclic ring system having 5–6 ring members, wherein 1–2 ring members are oxygen, sulfur or nitrogen heteroatoms, which is optionally benzo-fused.

6. The compound of claim 5 or a pharmaceutically acceptable salt thereof, wherein each Z is independently a (1) $C_1$–$C_4$ alkyl radical optionally substituted by (a) 1–2 radicals of amino, di-($C_1$–$C_2$ alkyl)amino, hydroxy, $C_1$–$C_2$ alkoxy or $C_1$–$C_2$ alkylthio, and (b) a heterocyclyl or aryl radical; or (2) heterocyclyl radical optionally substituted by 1–2 radicals of $C_1$–$C_4$ alkyl, aryl-$C_1$–$C_2$ alkyl or heteroaryl-$C_1$–$C_2$ alkyl;

wherein the aryl and heteroaryl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl;

each Y is independently a hydrogen, —$OR_{21}$, —$SR_{21}$ or —$NR_5R_{21}$ radical;

each $R_5$ is independently a hydrogen or $C_1$–$C_4$ alkyl radical;

each $R_{20}$ is independently a (1) $C_1$–$C_6$ alkyl radical optionally substituted by (a) 1–3 radicals of amino, methylamino, dimethylamino, t-butoxycarbonylamino no, N-((t-butoxy)carbonyl)-N-(methyl)amino, aminocarbonylamino, hydroxy, butoxy, methoxy, butylthio, methylthio, methylsulfinyl, methylsulfonyl or halo, and (b) a radical of $C_5$–$C_6$ cycloalkyl, heterocyclyl, phenyl or heteroaryl optionally substituted by 1–2 radicals of amino, dimethylamino, acetamino, hydroxy, methoxy, methylthio, halo, methyl or trifluoromethyl;

(2) heterocyclyl radical; or (3) aryl or heteroaryl radical optionally substituted by 1–2 radicals of amino, dimethylamino, hydroxy, methoxy, methylthio, halo, methyl or trifluoromethyl;

each $R_{21}$ is independently a hydrogen radical or $R_{20}$;

$R_{11}$ is a phenyl, naphthyl, furyl, thienyl, benzofuryl or benzothienyl radical optionally substituted by 1–2 radicals of methyl, amino, dimethylamino, acetamido, hydroxy, halo, cyano, methoxy, methylthio, methylsulfinyl, methylsulfonyl, aminocarbonyl, methyl or trifluoromethyl; and $R_{12}$ is a 4-pyridyl, 4-pyrimidyl, 4-quinolinyl, 7-imidazo[4,5-b]pyridinyl, 8-quinazolinyl, 6-(1H)-purinyl or 4-imidazolyl radical optionally substituted by a radical of amino, dimethylamino, acetamido, hydroxy, halo, cyano, methoxy, methyl or trifluoromethyl.

7. The compound of claim 6 or a pharmaceutically acceptable salt thereof, wherein each $R_6$ is independently a hydrogen, methyl, methoxy, —$CF_3$, —$OCF_3$ or hydroxy radical;

each Z is independently a (1) $C_1$–$C_4$ alkyl radical optionally substituted by (a) 1–2 radicals of amino, dimethylamino, hydroxy or methoxy, and (b) a heterocyclyl or phenyl radical; or (2) heterocyclyl radical;

wherein the heterocyclyl radicals are optionally substituted by 1–2 radicals of $C_1$–$C_4$ alkyl or phenylmethyl; and wherein the phenyl radicals are optionally substituted by 1–2 radicals of amino, di-($C_1$–$C_2$ alkyl)amino, hydroxy, $C_1$–$C_2$ alkoxy, $C_1$–$C_2$ alkylthio, cyano, halo, $C_1$–$C_2$ alkyl or trifluoromethyl;

each $R_5$ is a hydrogen or methyl radical;

each $R_{20}$ is independently a (1) $C_1$–$C_6$ alkyl radical optionally substituted by (a) 1–3 radicals of amino, methylamino, dimethylamino or hydroxy, and (b) a phenyl or heteroaryl radical optionally substituted by 1–2 radicals of amino, dimethylamino, hydroxy, methoxy, methylthio, halo, methyl or trifluoromethyl;

(2) heterocyclyl radical; or (3) aryl or heteroaryl radicals optionally substituted by 1–2 radicals of amino, dimethylamino, hydroxy, methoxy, methylthio, halo, methyl or trifluoromethyl radicals;

each $R_{21}$ is independently a hydrogen radical or $R_{20}$; and $R_{12}$ is a 4-pyridyl or 4-pyrimidyl radical optionally substituted by a radical of amino, dimethylamino, acetamido, hydroxy, halo, cyano, methoxy, methyl or trifluoromethyl.

8. The compound of claim 4 or a pharmaceutically acceptable salt thereof, wherein each Z is independently a (1) $C_1$–$C_4$ alkyl or $C_2$–$C_5$ alkenyl radical optionally substituted by (a) 1–2 radicals of amino, di-($C_1$–$C_2$ alkyl)amino, hydroxy or $C_1$–$C_2$ alkoxy, and (b) a radical of heterocyclyl, aryl or heteroaryl; or (2) heterocyclyl, aryl or heteroaryl radical;

wherein the heterocyclyl radicals are optionally substituted by 1–2 radicals of amino, di-($C_1$–$C_2$ alkyl)amino, hydroxy, $C_1$–$C_2$ alkoxy, $C_1$–$C_4$ alkyl or trifluoromethyl radicals; and wherein the aryl and heteroaryl radicals are optionally substituted by 1–3 radicals of amino, di-($C_1$–$C_2$ alkyl)amino, acetamido, hydroxy, $C_1$–$C_2$ alkoxy, halo, $C_1$–$C_2$ alkyl or trifluoromethyl;

each Y is independently a (1) hydrogen radical;

(2) —C(O)—$R_{20}$ or —C(O)—$NR_5R_{21}$ radical;

(3) —$OR_{21}$, —$SR_{21}$, —S(O)—$R_{20}$, —S(O)$_2$—$R_{20}$ or —S(O)$_2$—$NR_5R_{21}$ radical; or (4) —$NR_5R_{21}$ or —$NR_{22}$—C(O)—$R_{21}$, radical;

each $R_5$ is a hydrogen or methyl radical;

each $R_{20}$ is independently a (1) $C_1$–$C_4$ alkyl radical optionally substituted by 1–2 radicals of amino, $C_1$–$C_2$ alkylamino, di-($C_1$–$C_2$ alkyl)amino, hydroxy or $C_1$–$C_2$ alkoxy; or (2) trifluoromethyl radical;

each $R_{21}$ is independently hydrogen radical or $R_{20}$;

$R_{12}$ is a pyridyl or pyrimidyl radical optionally substituted by 1–2 radicals of (1) $R_{30}$;

(2) halo;

(3) —C(O)—$R_{30}$, —C(O)—$OR_{29}$, —C(O)—$NR_{31}R_{32}$ or —C($NR_{31}$)—$NR_{31}R_{32}$; or (4) —$OR_{29}$, —$SR_{29}$, —S(O)—$R_{30}$, —S(O)$_2$—$R_{30}$, —S(O)$_2$—$NR_{31}R_{32}$, —$NR_{33}$—S(O)$_2$—$R_{30}$, —$NR_{31}R_{32}$ or —$NR_{33}$— each $R_{30}$ is independently a (1) $C_1$–$C_4$ alkyl radical optionally substituted by (a) 1–2 radicals of —$NR_{31}R_{32}$, hydroxy or $C_1$–$C_2$ alkoxy, and (b) a radical of aryl or heteroaryl, wherein the aryl and heteroaryl radicals are optionally substituted by 1–2 radicals of amino, $C_1$–$C_2$ alkylamino, di-($C_1$–$C_2$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfonyl, cyano, halo, $C_1$–$C_4$ alkyl or trifluoromethyl; or (2) aryl or heteroaryl radical optionally substituted by 1–2 radicals of amino, $C_1$–$C_2$ alkylamino, di-($C_1$–$C_2$ alkyl) amino, $C_1$–$C_5$ alkanoylamino, ($C_1$–$C_4$ alkoxy) carbonylamino, $C_1$–$C_4$ alkylsulfonylamino, hydroxy, $C_1$–$C_4$ alkoxy, $C_1$–$C_4$ alkylthio, $C_1$–$C_4$ alkylsulfonyl, cyano, halo, $C_1$–$C_4$ alkyl or trifluoromethyl;

each $R_{29}$ is independently a hydrogen radical or $R_{30}$;

each $R_{31}$ is independently a hydrogen or methyl radical;

each $R_{32}$ is independently a (1) hydrogen radical;

(2) $C_1$–$C_4$ alkyl radical optionally substituted by an aryl or heteroaryl radical, wherein the aryl and heteroaryl radicals are optionally substituted by 1–2 radicals of amino, $C_1$–$C_2$ alkylamino, di-($C_1$–$C_2$ alkyl)amino, $C_1$–$C_5$ alkanoylamino, ($C_1$–$C_4$ alkoxy)carbonylamino, hydroxy, $C_1$–$C_2$ alkoxy, $C_1$–$C_2$ alkyl or trifluoromethyl; or (3) aryl or heteroaryl radical optionally substituted by 1–2 radicals of amino, $C_1$–$C_2$ alkylamino, di-($C_1$–$C_2$ alkyl) amino, $C_1$–$C_5$ alkanoylamino, ($C_1$–$C_4$ alkoxy) carbonylamino, hydroxy, $C_1$–$C_2$ alkoxy, $C_1$–$C_2$ alkyl or trifluoromethyl; and each $R_{33}$ is independently hydrogen or methyl radical.

9. The compound of claim 8 or a pharmaceutically acceptable salt thereof, wherein $R_{12}$ is a pyridyl or pyrimidyl radical optionally substituted by 1–2 radicals of (1) $R_{30}$;

(2) halo;

(3) —C(O)—$NR_{31}R_{32}$ or —C($NR_{31}$)—$NR_{31}R_{32}$; or (4) —$OR_{29}$, —S(O)$_2$—$NR_{31}R_{32}$, —$NR_{33}$—S(O)$_2$—$R_{30}$, —$NR_{31}R_{32}$ or —$NR_{33}$—C(O)—$R_{29}$.

10. The compound of claim 1 which is:

5-(3-phenylprop-1-yl)amino-8-(4-fluorophenyl)-7-(4-pyridyl)-1,2,4-triazolo[4,3-c]pyrimidine;

5-(3-phenylprop-1-yl)amino-8-(3-methylphenyl)-7-(4-pyridyl)-1,2,4-triazolo[4,3-c]pyrimidine;

5-(1-piperazinyl)-8-(3-methylphenyl)-7-(2-chloro-4-pyridyl)-1,2,4-triazolo[4,3-c]pyrimidine;

5-(3-phenylprop-1-yl)amino-8-(3-(trifluoromethyl) phenyl)-7-(4-pyridyl)-1,2,4-triazolo[4,3-c]pyrimidine;

5-(2(S)-amino-3-phenylprop-1-yl)amino-8-(3,4-dichlorophenyl)-7-(4-pyridyl)-1,2,4-triazolo[4,3-c] pyrimidine;

5-(piperazin-1-yl)-8-(3-(trifluoromethyl)phenyl)-7-(2-(2-phenylprop-2-yl)amino-4-pyridyl)-1,2,4-triazolo[4,3-c]pyrimidine;

5-(3,5-dimethylpiperazin-1-yl)-8-(3-(trifluoromethyl) phenyl)-7-(2-(1(S)-phenylethyl)amino-4-pyridyl)-1,2,4-triazolo[4,3-c]pyrimidine;

5-(piperazin-1-yl)-8-(3-(trifluoromethyl)phenyl)-7-(2-(1(S)-phenylethyl)amino-4-pyridyl)-1,2,4-triazolo[4,3-c] pyrimidine;

1-(8-(4-fluorophenyl)-7-(4-pyridyl)-1,2,4-triazolo[4,3-c] pyrimidin-5-yl)amino-2(S)-amino-3-phenylpropane;

2-(8-(4-fluorophenyl)-7-(4-pyridyl)-1,2,4-triazolo[4,3-c] pyrimidin-5-yl)amino-2-phenylpropane;

5-(2(S)-amino-2-methyl-3-phenylprop-1-yl)amino-8-(3-(trifluoromethyl)phenyl)-7-(4-pyridyl)-1,2,4-triazolo [4,3-c]pyrimidine;

5-(2,5-diaza-bicyclo[2.2.1]hept-2-yl)-8-(3-(trifluoromethyl)phenyl)-7-(2-(1(S)-phenylethyl) amino-4-pyridyl)-1,2,4-triazolo[4,3-c]pyrimidine;

5-(2(S)-amino-3-phenylprop-1-yl)amino-8-(2-naphthyl)-7-(4-pyridyl)-1,2,4-triazolo[4,3-c]pyrimidine;

5-(3(S)-benzyl-piperazin-1-yl)-8-(2-naphthyl)-7-(4-pyridyl)-1,2,4-triazolo[4,3-c]pyrimidine;

5-(2(S)-amino-3-phenylprop-1-yl)amino-8-(3-chloro-4-fluorophenyl)-7-(4-pyridyl)-1,2,4-triazolo[4,3-c] pyrimidine;

5-(2(S)-pyrrolidinylmethyl)amino-8-(2-naphthyl)-7-(4-pyridyl)-1,2,4-triazolo[4,3-c]pyrimidine;

5-(1-(2-propyl)pyrrolidin-2(S)-ylmethyl)amino-8-(3,4-dichlorophenyl)-7-(4-pyridyl)-1,2,4-triazolo[4,3-c] pyrimidine;

5-(piperazin-1-yl)-8-(3-(trifluoromethyl)phenyl)-7-(2-(cyclopropyl)amino-4-pyridyl)-1,2,4-triazolo[4,3-c]pyrimidine;

5-(1-(2-propyl)piperid-3-yl)amino-8-(3,4-dichlorophenyl)-7-(4-pyridyl)-1,2,4-triazolo[4,3-c]pyrimidine;

5-(1-(2-propyl)pyrrolidin-2(S)-ylmethyl)amino-8-(2-naphthyl)-7-(4-pyridyl)-1,2,4-trizolo[4,3-c]pyrimidine;

2-methyl-$N^2$-(8-naphthalen-2-yl-7-pyridin-4-yl-[1,2,4]triazolo[4,3-c]pyrimidin-5-yl)-propane-1,2-diamine;

$N^1$-isopropyl-2-methyl-$N^2$-(8-naphthalen-2-yl-7-pyridin-4-yl-[1,2,4]triazolo[4,3-c]pyrimidin-5-yl)-propane-1,2-diamine;

$N^1$-cyclopentyl-2-methyl-$N^2$-(8-naphthalen-2-yl-7-pyridin-4-yl-[1,2,4]triazolo[4,3-c]pyrimidin-5-yl)-propane-1,2-diamine;

isopropyl-[1-(8-naphthalen-2-yl-7-pyridin-4-yl-[1,2,4]triazolo[4,3-c]pyrimidin-5-yl)-pyrrolidin-2-ylmethyl)-amine;

[1-(1-isopropyl-piperidin-2-yl)-1-methyl-ethyl]-(8-naphthalen-2-yl-7-pyridin-4-yl-[1,2,4]triazolo[4,3-c]pyrimidin-5-yl)-amine;

(4-methyl-piperidin-4-yl)-(8-naphthalen-2-yl-7-pyridin-4-yl-[1,2,4]triazolo[4,3-c]pyrimidin-5-yl)-amine;

(1-isopropy-3-methyl-piperidin-3-yl)-(8-naphthalen-2-yl-7-pyridin-4-yl-[1,2,4]triazolo[4,3-c]pyrimidin-5-yl)-amine;

$N^2$-[8-(3,4-dichloro-phenyl)-7-pyridin-4-yl-[1,2,4]triazolo[4,3-c]pyrimidin-5-yl]-$N^1$-isopropyl-2-methyl-propane-1,2-diamine;

[8-(3,4-dichloro-phenyl)-7-pyridin-4-yl-[1,2,4]triazolo[4,3-c]pyrimidin-5-yl]-[1-(1-(1-isopropyl-pyrrolidin-2-yl)-1-methyl-ethyl]-amine;

[8-(3,4-dichloro-phenyl)-7-pyridin-4-yl-[1,2,4]triazolo[4,3-c]pyrimidin-5-yl]-[1-(1-isopropyl-pipendin-2-yl)-1-methyl-ethyl]-amine;

[8-(3,4-dichloro-phenyl)-7-pyridin-4-yl-[1,2,4]triazolo[4,3-c]pyrimidin-5-yl]-(4-methyl-piperidin-4-yl)-amine;

[8-(3,4-dichloro-phenyl)-7-pyridin-4-yl-[1,2,4]triazolo[4,3-c]pyrimidin-5-yl]-(1-isopropyl-3-methyl-piperidin-3-yl)-amine;

isopropyl-[1-(8-naphthalen-2-yl-7-pyridin-4-yl-imidazo[1,2-c]pyrimidin-5-yl)-pyrrolidin-2-ylmethyl]-amine;

{1-[8-(3,4-dichloro-phenyl)-7-pyridin-4-yl-imidazo[1,2-c]pyrimidin-5-yl]-pyrrolidin-2-ylmethyl}-isopropyl-amine;

$N^1$-isopropyl-2-methyl-$N^2$-(8-naphthalen-2-yl-7-pyridin-4-yl imidazo[1,2-c]pyrimidin-5-yl)-propane-1,2-diamine;

[1-(1-isopropyl-pyrrolidin-2-yl)-1-methyl-ethyl]-(8-naphthalen-2-yl-7-pyridin-4-yl-imidazo[1,2-c]pyrimidin-5-yl)-amine;

[1-(1-isopropyl-pyrrolidin-2-yl)-1-methyl-ethyl]-(8-naphthalen-2-yl-7-pyridin-4-yl-imidazo[1,2-c]pyrimidin-5-yl)-amine;

(4-methyl-piperidin-4-yl)-(8-naphthalen-2-yl-7-pyridin4-yl-imidazo[1,2-c]pyrimidin-5-yl)-amine;

(1-isopropyl-3-methyl-piperidin-3-yl)-(8-naphthalen-2-yl-7-pyridin-4-yl-imidazo[1,2-c]pyrimidin-5-yl)-amine;

$N^2$-[8-(3,4-dichloro-phenyl)-7-pyridin-4-yl-imidazo[1,2-c]pyrimidin-5-yl]-$N^1$-isopropyl-2-methyl-propane-1,2-diamine;

[8-(3,4-dichloro-phenyl)-7-pyridin-4-yl-imidazo[1,2-c]pyrimidin-5-yl]-[1-(1-isopropyl-pyrrolidin-2-yl)-1-methyl-ethyl]-amine;

[8-(3,4-dichloro-phenyl)-7-pyridin-4-yl-imidazo[1,2-c]pyrimidin-5-yl]-[1-(1-isopropyl-piperidin-2-yl)-1-methyl-ethyl]-amine;

[8-(3,4-dichloro-phenyl)-7-pyridin-4-yl-imidazo[1,2-c]pyrimidin-5-yl]-(4-methyl-piperidin-4-amine; or

[8-(3,4-Dichloro-phenyl)-7-pyridin-4-yl-imidazo[1,2-c]pyrimidin-5-yl]-(1-isopropyl-3-methyl-piperidin-3-yl)-amine;

or a pharmaceutically acceptable salt thereof.

11. A pharmaceutical composition comprising a compound of claim 1 and a pharmaceutically acceptable carrier.

12. A method of treatment of inflammation comprising administering an effective amount of a compound of claim 1.

13. A method of treatment of inflammation comprising administering an effective amount of a composition of claim 11.

14. A method of treatment of rheumatoid arthritis or psoriasis in a mammal comprising administering an effective amount of a compound of claim 1.

15. A method of treatment of rheumatoid arthritis or psoriasis, in a mammal comprising administering an effective amount of a composition of claim 11.

16. A method of lowering plasma concentrations of either or both TNF-α and IL-1 comprising administering an effective amount of a compound of claim 1.

17. A method of lowering plasma concentrations of either or both TNF-α and IL-1 comprising administering an effective amount of a composition of claim 11.

18. A method of decreasing cyclooxygenase enzyme activity in a mammal comprising administering an effective amount of a compound according to claim 1.

19. The method of claim 18 wherein the cyclooxygenase enzyme is COX-2.

20. A method of decreasing cyclooxygenase enzyme activity in a mammal comprising administering an effective amount of a pharmaceutical composition according to claim 11.

21. The method of claim 20 wherein the cyclooxygenase enzyme is COX-2.

* * * * *

UNITED STATES PATENT AND TRADEMARK OFFICE
CERTIFICATE OF CORRECTION

PATENT NO. : 6,921,762 B2
DATED : July 26, 2005
INVENTOR(S) : Cai et al.

It is certified that error appears in the above-identified patent and that said Letters Patent is hereby corrected as shown below:

Column 124,
Lines 50 and 51, change "-C(O)" to read -- -O-C(O) --.

Column 131,
Line 59, change "-C($NR_{31}$)- $NR_{31}$)-$NR_{31}R_{32}$;" to read -- -C($NR_{31}$)-$NR_{31}R_{32}$; --.

Column 133,
Line 60, change "-$NR_{41}R_{42}$-" to read -- -$NR_{41}R_{42}$, -$NR_{41}R_{42}$ or --.

Column 137,
Line 44, change "-$NR_{33}$-" to read -- -$NR_{33}$-C(O)-$R_{29}$ --.

Signed and Sealed this

Seventh Day of February, 2006

JON W. DUDAS
*Director of the United States Patent and Trademark Office*